(12) United States Patent
Wood et al.

(10) Patent No.: US 7,906,282 B2
(45) Date of Patent: Mar. 15, 2011

(54) SYNTHETIC NUCLEIC ACID MOLECULE COMPOSITIONS AND METHODS OF PREPARATION

(75) Inventors: Keith V. Wood, Madison, WI (US); Monika G. Gruber, Madison, WI (US); Yao Zhuang, Madison, WI (US); Aileen Paguio, Madison, WI (US)

(73) Assignee: Promega Corporation, Madison, WI (US)

( * ) Notice: Subject to any disclaimer, the term of this patent is extended or adjusted under 35 U.S.C. 154(b) by 412 days.

(21) Appl. No.: 11/786,785

(22) Filed: Apr. 12, 2007

(65) Prior Publication Data
US 2008/0090291 A1    Apr. 17, 2008

Related U.S. Application Data

(62) Division of application No. 09/645,706, filed on Aug. 24, 2000.

(51) Int. Cl.
*C12N 15/53*   (2006.01)
*C12N 5/10*    (2006.01)
*C12N 15/63*   (2006.01)

(52) U.S. Cl. ........ 435/6; 536/23.2; 435/189; 435/252.3; 435/325; 435/320.1

(58) Field of Classification Search ............ None
See application file for complete search history.

(56) References Cited

U.S. PATENT DOCUMENTS

| | | | |
|---|---|---|---|
| 4,246,340 A | 1/1981 | Lundin et al. |
| 4,412,001 A | 10/1983 | Baldwin et al. |
| 4,503,142 A | 3/1985 | Berman et al. |
| 4,581,335 A | 4/1986 | Baldwin et al. |
| 4,968,613 A | 11/1990 | Masuda et al. |
| 5,096,825 A | 3/1992 | Barr et al. |
| 5,106,732 A | 4/1992 | Kondo et al. |
| 5,168,062 A | 12/1992 | Stinski |
| 5,182,202 A | 1/1993 | Kajiyama et al. |
| 5,196,524 A | 3/1993 | Gustafson et al. |
| 5,219,737 A | 6/1993 | Kajiyama et al. |
| 5,221,623 A | 6/1993 | Legocki et al. |
| 5,229,285 A | 7/1993 | Kajiyama et al. |
| 5,283,179 A | 2/1994 | Wood |
| 5,292,658 A | 3/1994 | Cormier et al. |
| 5,330,906 A | 7/1994 | Kajiyama et al. |
| 5,352,598 A | 10/1994 | Kajiyama et al. |
| 5,418,155 A | 5/1995 | Cormier et al. |
| 5,567,862 A | 10/1996 | Adang et al. |
| 5,583,024 A | 12/1996 | McElroy et al. |
| 5,604,123 A | 2/1997 | Kazami et al. |
| 5,605,793 A | 2/1997 | Stemmer |
| 5,618,682 A | 4/1997 | Scheirer |
| 5,629,168 A | 5/1997 | Kricka |
| 5,641,641 A | 6/1997 | Wood |
| 5,650,289 A | 7/1997 | Wood |
| 5,670,356 A | 9/1997 | Sherf et al. |
| 5,674,713 A | 10/1997 | McElroy et al. |
| 5,700,673 A | 12/1997 | McElroy et al. |
| 5,744,307 A | 4/1998 | Kuroda et al. |
| 5,744,320 A | 4/1998 | Sherf et al. |
| 5,786,464 A | 7/1998 | Seed |
| 5,795,737 A | 8/1998 | Seed et al. |
| 5,814,471 A | 9/1998 | Wood |
| 5,874,304 A | 2/1999 | Zolotukhin et al. |
| 5,952,547 A | 9/1999 | Cornelissen et al. |
| 5,968,750 A | 10/1999 | Zolotukhin et al. |
| 5,976,796 A | 11/1999 | Szalay et al. |
| 6,020,192 A | 2/2000 | Muzyczka et al. |
| 6,074,859 A | 6/2000 | Hirokawa et al. |
| 6,114,148 A | 9/2000 | Seed et al. |
| 6,130,313 A | 10/2000 | Li et al. |
| 6,169,232 B1 | 1/2001 | Hey et al. |
| 6,306,600 B1 | 10/2001 | Kain et al. |
| 6,602,677 B1 | 8/2003 | Wood et al. |
| 6,700,038 B1 | 3/2004 | Dasgputa et al. |
| 6,878,531 B1 | 4/2005 | Seyfang |
| 7,728,118 B2 | 6/2010 | Wood et al. |
| 2002/0100076 A1 | 7/2002 | Garcon et al. |
| 2003/0157643 A1 | 8/2003 | Almond et al. |
| 2004/0146987 A1 | 7/2004 | Zdanovsky et al. |
| 2005/0032085 A1 | 2/2005 | Labas et al. |
| 2006/0127988 A1 | 6/2006 | Wood et al. |
| 2006/0183212 A1 | 8/2006 | Wood et al. |
| 2008/0070299 A1 | 3/2008 | Wood et al. |
| 2009/0191622 A1 | 7/2009 | Almond et al. |

FOREIGN PATENT DOCUMENTS

| | | |
|---|---|---|
| EP | 0337349 | 10/1989 |
| EP | 0364707 A1 | 4/1990 |
| EP | 0437013 | 7/1991 |
| EP | 0449621 | 10/1991 |
| EP | 0524448 | 1/1993 |
| EP | 0353464 B1 | 10/1993 |
| JP | 3-167288 | 7/1991 |
| JP | 07-067696 | 3/1995 |
| JP | 8-510837 | 12/1996 |
| JP | 9-294600 | 11/1997 |
| JP | 10-87621 | 4/1998 |

(Continued)

OTHER PUBLICATIONS

Kappel et al. "Regulating Gene Expression in Transgenic Animals", Current Opinion in Biotechnology 3:548-553, 1992.*

Mullins et al. "Trangenesis in Nonmurine Species", Hypertension 22(4):630-633, 1993.*

Mullins et al. "Trangenesis in the Rat and Larger Mammals", J. Clin. Invest. 97(7):1557-1560, 1996.*

(Continued)

*Primary Examiner* — Rebecca Prouty

(74) *Attorney, Agent, or Firm* — Michael Best & Friedrich LLP

(57) ABSTRACT

A method to prepare synthetic nucleic acid molecules having reduced inappropriate or unintended transcriptional characteristics when expressed in a particular host cell.

38 Claims, 63 Drawing Sheets

FOREIGN PATENT DOCUMENTS

| | | |
|---|---|---|
| JP | 2000-503536 | 3/2000 |
| JP | 2004-180561 | 2/2004 |
| WO | WO-9001542 A1 | 2/1990 |
| WO | WO-9116432 A1 | 10/1991 |
| WO | WO-9215673 A1 | 9/1992 |
| WO | WO-95/18853 | 7/1995 |
| WO | WO-95/25798 | 9/1995 |
| WO | WO-96/22376 | 7/1996 |
| WO | 97/08320 | 3/1997 |
| WO | WO-97/26366 | 7/1997 |
| WO | WO-9726333 | 7/1997 |
| WO | WO-98/13487 | 4/1998 |
| WO | WO-98/46729 | 10/1998 |
| WO | WO-99/14336 | 3/1999 |
| WO | WO-9914336 A2 | 3/1999 |
| WO | 01/23541 | 4/2001 |
| WO | 01/27150 | 4/2001 |
| WO | 02/16944 | 2/2002 |
| WO | 02/090535 | 11/2002 |
| WO | 02/094992 | 11/2002 |
| WO | 03/042401 | 5/2003 |
| WO | 2004/025264 | 3/2004 |
| WO | 2004/042010 | 5/2004 |
| WO | 2006/034061 | 3/2006 |

OTHER PUBLICATIONS

Wigley et al. "site-pecific Trangene Insertion: an Approach", Reprod. Pert. Dev. 6:585-588, 1994.*

Cameron, "Recent Advances in Transgenic Technology", Molecular Biotechnology 7:253-265, 1997.*

"Dual-Luciferase tm Reporter Assay System", (1998),2 pgs.

"Luciferase Reporter Gene Technology", (1996),4 pgs.

"Promega Technical Bulletin No. 161—Luciferase Assay System With Reporter Lysis Buffer", (Mar. 1998),9 pgs.

"Promega Technical Bulletin No. 101—Luciferase Assay System", (Mar. 1998),9 pgs.

"Promega Technical Manual—Dual-Luciferase tm Reporter Assay System", (Feb. 1999),26 pgs.

"Promega Technical Manual—Steady-Glo tm Luciferase Assay System", (Oct. 1998),19 pgs.

"Steady-Glo tm Luciferase Assay System", (1998),2 pgs.

"TESS—Filtered String Search Page", http://www.cbil.upenn.edu/cgi-bin/tess/tess?RQ=SEA-FR-QueryF,(Jun. 2006),6 pgs.

Alam, J., et al., "Reporter Genes: Application to the Study of Mammalian Gene Transcription", *Analytical Biochemistry*, 188(2), (1990),245-254.

Andrews, E. M., et al., "Hierarchy of Polyadenylation Site Usage by Bovine Papillomavirus in Transformed Mouse Cells", *Journal of Virology*, 67(12), (1993),7705-7710.

Aota, S., "Codon Usage Tabulated from the GenBank Genetic Sequence Data", *Nucleic Acids Research*, 16, A Supplement to Nucleic Acids Research vol. 16,(1988),r315-r402.

Arnold, F. H., "Directed Evolution: Creating Biocatalysts for the Future", *Chemical Engineering Science*, 51, (1996),5091-5102.

Bachmair, A., "In vivo Half-Life of a Protein is a Function of its Amino Terminal Residue", *Science*, 234(4773), (1986),179-186.

Batt, David B., "Polyadenylation and Transcription Termination in Gene Constructs Containing Multiple Tandem Polyadenylation Signals", *Nucleic Acids Research*, 22(14), (Jul. 15, 1994),2811-2816.

Benzakour, O., "Evaluation of the Use of the Luciferase-Reporter-Gene System for Gene-Regulation Studies Involving Cyclic AMP-Elevating Agents.", *Biochem. J*, 309 (Pt 2), (Jul. 15, 1995),385-387.

Bernardi, G., "Codon Usage and Genome Composition", *J. Mol. Evol.*, 22(4), (1985),363-365.

Bonin, A. L., "*Photinus pyralis* Luciferase: Vectors that Contain a Modified luc Coding Sequence Allowing Convenient Transfer into Other Systems", *Gene*, 141(1), (1994),75-77.

Borovkov, A. Y., et al., "Xcm-I-Containing Vector for Direct Cloning of PCR Products", *BioTechniques*, 22(5), (1997),812-814.

Bothwell, A. L., et al., "Heavy Chain Variable Region Contribution to the NP b Family of Antibodies: Somatic Mutation Evident in a y2a Variable Region", *Cell*, 24(3), (Jun. 1981),625-637.

Bouthors, A.-T., et al., "Site-Directed Mutagenesis of Residues 164, 170, 171, 179, 220, 237 and 242 in PER-1 beta-Lactamase Hydrolysing Expanded-Spectrum Cephalosporins", *Protein Engineering*, 12(4), (Apr. 1999),313-318.

Bronstein, Irena, et al., "Chemiluminescent and Bioluminescent Reporter Gene Assays", *Analytical Biochemistry*, 219(2), (1994),169-181.

Bulmer, M, "Codon usage and secondary structure of MS2 phage RNA", *Nucleic Acids Res.*, 17(5), (Mar. 11, 1989),1839-1843.

Bulmer, M, "Coevolution of codon usage and transfer RNA abundance", *Nature*, 325(6106), (1987),728-730.

Cadwell, R. C., et al., "Randomization of Genes by PCR Mutagenesis", *PCR Methods and Applications*, 2, (1992),28-33.

Carswell, S., et al., "Efficiency of Utilization of the Simian Virus 40 Late Polyadenylation Site: Effects of Upsteam Sequences", *Molecular and Cellular Biology*, 9(10), (1989),4248-4258.

Chen, H., "Gene transfer and expression in oligodendrocytes under the control of myelin basic protein transcriptional control region mediated by adeno-associated virus", *Gene Therapy*, 5, (Jan. 14, 1998),50-58.

Chen, C.-Y., et al., "Interplay of Two Functionally and Structurally Distinct Domains of the c-fos Au-Rich Element Specifies Its mRNA-Destabilizing Function", *Molecular and Cellular Biology*, 14(1), (Jan. 1994),416-426.

Cheng, X., et al., "Agrobacterium-transformed Rice Plants Expressing Synthetic crylA(b) and CrylA(c) Genes are Highly Toxic to Striped Stem Borer and Yellow Stem Borer", *Proceedings of the National Academy of Sciences of the USA*, 95(6), (Mar. 17, 1998),2767-2772.

Coker, G T., "8-Br-cAMP Inhibits the Transient Expression of Firefly Luciferase", *FEBS Letters*, 249, (1989),183-185.

De Wet, Jeffrey R., "Cloning of Firefly Luciferase cDNA and the Expression of Active Luciferase in *Escherichia coli*", *Proc. Natl. Acad. Sci. USA*, 82, (1985),7870-7873.

De Wet, J. R., "Firefly Luciferase Gene: Structure and Expression in Mammalian Cells", *Molecular and Cellular Bioiogy*, 7(2), (1987),725-737.

Dean, Caroline, "mRNA Transcripts of Several Plant Genes are Polyadenylated at multiple sites in vivo", *Nucleic Acids Research*, vol. 14(5), (1986),2229-2240.

Deluca, M., et al., "The Role of 1,N6-Ethenoadenosine Triphosphate and 1,N6-Ethenoadenosine", *Proc. Nat. Acad. Sci. USA*, 70(6), (1973),1664-1666.

Dementieva, E. I., "Physicochemical Properties of Recombinant *Luciolo mingrelica* luciferase and its Mutant Forms", *Biochemistry*, 61 (1), (1996),115-119.

Faisst, S, "Compilation of Vertebrate-Encoded Transcription Factors", *Nucleic Acids Research*, 20(1), (Jan. 11, 1992),3-26.

Farr, A., et al., "A Pitfall of Using a Second Plasmid to Determine Transfection Efficiency", *Nucleic Acids Research*, 20(4), (Feb. 25, 1992),p. 920.

Ferbitz, L., et al., "A Synthetic Gene Coding for *Renilla* Luciferase is a Versatile Expression Marker in Green Algae", http://getentry.ddbj.nig.ac.jp/cgi-bin/qetentry-j.pl, NCBI Sequence Accession No. AY004213,(Aug. 8, 2000),1 pg.

Fiers, W, et al., "On Codon Usage (letter)", *Nature*, 277(5694), (1979),328.

Fleer, R., "High-Level Secretion of Correctly Processed Recombinant Human interleukin-1 beta in *Kluyveromyces lactis*", *Gene*, 107(2), (1991),285-295.

Ford, S. R., et al., "Enhancement of Firefly Luciferase Activity by Cytidine Nucleotides", *Analytical Biochemistry*, 204(2), (1992),283-291.

Frampton, J., et al., "Synergy Between the NF-E1 Erythroid-Specific Transcription Factor and the CACCC Factor in the Erythroid-Specific Promoter of the Human Porphobilinogen Deaminase Gene", *Molecular and Cellular Biology*, 10(7), (1990),3838-3842.

Fromant, M, et al., "Direct Random Mutagenesis of Gene-Sized DNA Fragments Using Polymerase Chain Reactio", *Analytical Biochemistry*, 224, (1995),347-353.

Fuerst, Thomas R., "Structure and stability of mRNA synthesized by vaccinia virus-encoded bacteriophage T7 RNA polymerase in mammalian cells Importance of teh 5' untranslated leader", *J. Mol. Biol.*, 206, (1989),333-348.

Gluzman, Y. , "SV40-Transformed Cells Support the Replication of Early SV40 Mutants", *Cell*, 23(1), (Jan. 1981),175-182.

Gould, S. J., "A Conserved Tripeptide Sorts Proteins to Peroxisomes", *The Journal of Cell Biology*, 108, (1989),1657-1664.

Gould, S. J., "Antibodies Directed Against the Peroxisomal Targeting Signal of Firefly Luciferase Recognize Multiple Mammalian Peroxisomal Proteins", *The Journal of Cell Biology*, 110, (1990),27-34.

Gould, S. J., et al., "Firefly Luciferase as a Tool in Molecular and Cell Biology", *Analytical Biochemistry*, 175, (1988),5-13.

Gould, S. J., "Identification and Characterization of a Peroxisomal Targeting Signal", *Dissertation Abstracts International*, vol. 50/07-B, (1989),2 pgs.

Gouy, M , "Codon usage in bacteria: correlation with gene expressivity", *Nucleic Acids Res.*, 10(22), (1982),7055-7074.

Green, Pamela J., "Control of mRNA Stability in Higher Plants", *Plant Physiol.*, vol. 102, (1993),1065-1070.

Gruber, M G., "Design Strategy for Synthetic Luciferase Reporter Genes", *11th International Symposium on Bioluminescence and Chemiluminescence*, An abstract,(May 2000).

Hanahan, D. , "Chapter 4—Techniques for Transformation of *E. coli*", In: *DNA Cloning: A Practical Approach*, vol. 1, Chapter 6, Glover, D.W., (editor), IRL Press, Oxford,(1985),109-135.

Hastings, J. W., "Biological Diversity, Chemical Mechanisms, and the Evolutionary Origins of Bioluminescent Systems", *Journal of Molecular Evolution*, 19(3/4), (1983),309-321.

Henning, K. A., "Humanizing the yeast telomerase template", *Proceedings of the National Academy of Sciences of USA*, 95(10), (May 12, 1998),5667-5671.

Hofte, H. , et al., "Structural and Functional Analysis of a Cloned Delta Endotoxin of *Bacillus thuringiensis* berliner 1715", *European Journal of Biochemistry*, 161, (1986)273-280.

Holcik, M. , et al., "Four Highly Stable Eukaryotic mRNAs Assemble 3' Untranslated Region RNA-protein Complexes Sharing cis and trans Ccomponents", *Proc. Natl.Acad.Sci. USA*, 94(6), (1997),2410-2414.

Holm, L , "Codon usage and gene expression", *Nucleic Acids Res.*, 14(7), (1986),3075-3087.

Hsieh, C. J., et al., "Nucleotide Sequence, Transcriptional Analysis, and Glucose Regulation of the Phenoxazinone Synthase Gene (phsA) from *Streptomyces antibioticus*", *Journal of Bacteriology*, 177(20), (1995),5740-5747.

Iannacone, Rina , "Specific sequence modifications os a cry3B endotoxin gene result in high levels of expression and insect resistance", *Plant Melecular Biology* 34, (Jun. 1997),485-496.

Ikemura, T , "Codon usage and tRNA content in unicellular and multicellular organisms", *Molecular Biology and Evolution*, 2(1), (1985),13-34.

Janowski, M. , "Ras Proteins and the Ras-Related Signal Transduction Pathway", *Radiation and Environmental Biophysics*, 30(3), (1991),185-189.

Jensen, P. R., et al., "The Sequence of Spacers Between the Consensus Sequences Modulates the Strength of Prokaryotic Promoters", *Applied and Environmental Microbiology*, 64(1), (1998),82-87.

Johnson, L R., "Role of the transcription factor Sox-2 in the expression of the FGF-4 gene in embryonal carcinoma cells", *Molecular Reproduction and Development.*, 50(4), (1998),377-386.

Jones, P L., "Tumor Necrosis Factor Alpha and Iinterleukin-1beta Regulate the Murine Manganese Superoxide Dismurtase Gene Through a Complex Intronic Enhancer Involving C/EBP-Beta and NF-KappaB", *Mol. Cell. Biol.*, 17(12), (1997),6970-6981.

Kajiyama, N. , et al., "Enhancement of Thermostability of Firefly Luciferase from *Luciola lateralis* by a Single Amino Acid Substitution", *Biosci Biotechnol Biochem.*, 58(6), (Jun. 1994),1170-1171.

Kajiyama, N. , et al., "Isolation and Characterization of Mutants of Firefly Luciferase Which Produce Different Colors of Light", *Protein Engineering*, vol. 4, No. 6, (Aug. 1991),691-693.

Kajiyama, N , et al., "Thermostabilization of firefly luciferase by a single amino acid substitution at position 217", *Biochemistry*, 32(50), (Dec. 21, 1993),13795-13799.

Kao, R. , et al., "Single Amino Acid Substitutions Affecting the Specificity of the Fungal Ribotoxin Mitogillin", *FEBS Letters*, 466(1), (Jan. 21, 2001),87-90.

Kay, S. A., et al., "Video Imaging of Regulated Firefly Luciferase Activity in Transgenic Plants and *Drosophila*", *Promega Notes Magine*, No. 49, (1994),7 pgs.

Kim, C. H., et al., "Codon Optimization for High-level Expression of Human Erythropoietin (EPO) in Mammalian Cells", *Gene*, vol. 199, No. 1-2, XP004126394, (Oct. 15, 1997),293-301.

Kimura, A , et al., "Detailed analysis of the mouse H-2Kb promoter: enhancer-like sequences and their role in the regulation of class I gene expression", *Cell*, 44(2), (Jan. 31, 1986),261-272.

Kuprash, D.V., "Conserved kappa B Element Located Downstream of the Tumor Necrosis Factor alpha Gene: Distinct NF-kappa B Binding Pattern and Enhancer Activity in LPS Activated Murine Macrophages", *Oncogene*, 11(1), (1995),97-106.

Kutuzova, Galina D., et al., "Bioluminescence Color Variation and Kinetic Behavior Relationships Among Beetle Luciferases", *Bioluminescence and Chemiluminescence, Molecular Reporting with Photons*, J W Hastings et al., (editors), John Wiley & Sons, Chinchester, England,(1996),248-252.

Lamb, K A., "Effects of Differentiation on the Transcriptional Regulation of the FGF-4 Gene: Critical Roles Played by a Distal Enhancer", *Molecular Reproduction and Development*, 51(2), (1998),218-224.

Lathe, R. , "Synthetic Oligonucleotide Probes Deduced From Amino Acid Sequence Data Theoretical and Practical Considerations", *Journal of Molecular Biology*, 183(1), (1985),1-12.

Lee, Reiko T., "Substrate-Binding Properties of Firefly Luciferase", *Archives of Biochemistry and Biophysics*, 141(1), (1970),38-52.

Lewis, M. K., et al., "Efficient Site Directed in vitro Mutagenesis Using Ampicillin Selection",*Nucleic Acids Research*, 18(12), (1990),3439-3443.

Liljenstrom, H , "Translation rate modification by preferential codon usage: intragenic position effects", *J. Theor. Biol.*, 124(1), (1987),43-55.

Liu, J. , "Improved assay sensitivity of an engineered secreted *Renilla* luciferase", *Gene*, 237(1), (Sep. 3, 1999),153-159.

Lorenz, W. W., et al., "Isolation and expression of a cDNA encoding *Renilla reniformis* luciferase", *Proc. Natl. Acad. Sci. USA*, 88(10), (May 15, 1991),4438-4442.

Lucas, M. , et al., "Coelenterazine Is a Superoxide Anion-Sensitive Chemiluminescent Probe: Its Usefulness in the Assay of Respiratory Burst in Neutrophils", *Analytical Biochemistry*, 206(2), (Nov. 1, 1992),273-277.

Magari, S. R., "Pharmacologic Control of a Humanized Gene Therapy System Implanted into Nude Mice", *Journal of Clinical Investigation*, 100(11), (Dec. 1, 1997),2865-2872.

Malter, James S., "Identification of an AUUUA-Specific Messenger RNA Binding Protein", *Science*, vol. 246, (1989),664-666.

Manukhov, I. V., et al., "Cloning of the *Vibrio harveyi* luxA and luxB Genes and the Expression of Bioluminescence in *Escherichia coli* and *Bacillus subtilis*", *Russian Biotechnology*, 1, (1996),1-6.

Maranville, E. , et al., "Assessment of Amino-Acid Substutions at Tryptophan 16 in alpha-galactosidase", *European Journal of Biochemistry*, 267(5), (2000),1495-1501.

Matsumura, I. , et al., "Directed Evolution of the surface Chemistry of the Reporter Enzyme Beta-glucuronidase", *Nature Biotechnology*, 17(7), (1999),696-701.

Matthews, J , "Purification and properties of *Renilla reniformis* luciferase.", *Biochemistry*, 16(1), (Jan. 11, 1977),85-91.

McElroy, William D., "Factors Influencing the Response of the Bioluminescent Reaction to Adenosine Triphosphate", *Archives of Biochemistry and Biophysics*, 22, (1949),420-433.

McElroy, W. D., et al., "Function of Adenosine Triphosphate in the Activation of Luciferin", *Archives of Biochemistry and Biophysics*, 64, (1956),257-271.

McElroy, W. D., et al., "Mechanisms of Bioluminescent Reactions", In: *A Symposium on Light and Life*, Edited by W. D. McElroy and B. Glass (John Hopkins Press, 1961),219-257.

McWherter, C. A., et al., "Scanning Alanine Mutagenesis and De-Peptidization of a *Candate albicans* myristoyl-CoA: Protein N-myristoyltransferase Octapeptide Substrate Reveals Three Elements Critical for Molecular Recognition", *Journal of Biological Chemistry*, 272(18), (1997),11874-11880.

Mount, S. M., "Genomic Sequence, Splicing, and Gene Annotation", *American Journal of Human Genetics*, 67(4), (2000),788-792.

Moyer, J. D., et al., "Nucleoside Triphosphate Specificity of Firefly Luciferase", *Analytical Biochemistry*, 131(1), (1983),187-189.

Murakami, S, et al., "Bioluminescent Enzyme Immunoassay Using Thermostable Mutant Luciferase and Acetate Kinase as a Labelled Enzyme", *Analytica Chimica*, 361, (1998),19-26.

Murray, E. E., "Codon Usage in Plant Genes", *Nucleic Acids Research*, 17(2), (Jan. 25, 1989),477-498.

Murray, I. A., et al., "Steroid Recognition by Chloramphenicol Acetyltransferase: Engineering and Structural Analysis of a High Affinity Fusidic Acid Binding Site", *Journal of Molecular Biology*, 254, (1995),993-1005.

Nibu, Y, "A Cell Type-Dependent Enhancer Core Element is Located in Exon 5 of the Human Angiotensinogen Gene", *Biochemical Biophysical Research Communications*, 205(2), (1994),1102-1108.

Ow, D. W., "Transient and Stable Expression of the Firefly Luciferase Gene in Plant Cells and Transgenic Plants", *Science*, 234(4778), (Nov. 14, 1986),856-859.

Pan, W., et al., "Vaccine Candidate MSP-1 from *Plasmodium falciparum*: a Redesigned 4917 bp polynucleotide enables ynthesis and isolation of full-length Protein from *Escherichia coli* and Mammalian cells", *Nucleic Acids Research*, 27(4), DDBJ/EMBL/GenBank accession No. AJ131294,(Feb. 15, 1999),1094-1103.

Peers, B, "Regulatory Elements Controlling Pituitary-Specific Expression of the Human Prolactin Gene", *Molecular and Cellular Biology*, 10(9), (Sep. 1990),4690-4700.

Perlak, Frederick J., "Modification of the coding sequence enhances plant expression of insect control protein genes", *Proc. Natl. Acad. Sci.*, 88, (1991),3324-3328.

Petit, T., et al., "A Mutation Ser 213/Asn in the Hexokinase 1 from *Schizosaccharomyces pombe* Increases Its Affinity for Glucoses", *Biochemical and Biophysical Research Communications*, 251(3), (Oct. 29, 1998),714-719.

Pinto, M., et al., "Denaturation of Proteins During Heat Shock", *The Journal of Biological Chemistry*, 266(21), (1991),13941-13946.

Purdy, D, et al., "Heterologous Gene Expression in *Campylobacter coli*: The Use of Bacterial Luciferase in a Promoter Probe Vector", *FEMS Microbiology Letters*, 111(2-3), (Aug. 1, 1993),233-237.

Reese, M G., "Large Scale Sequencing Specific Neural Networks for Promoter and Splice Site Recognition", *Biocomputing: Proceedings of the 1996 Pacific Symposium*, Hunter et al., ed., World Publishing Co., Singapore, Abstract Only,(1996),1 pg.

Reese, M G., et al., "New Neural Network Algorithms for Improved Eukaryotic Promoter Site Recognition", *The Seventh International Genome Sequencing and Analysis Conference*, Hilton Head Island, South Carolina, (Abstract Only),(1995),1 pg.

Rhodes, W. C., "The Synthesis and Function of Luciferyl-adenylate and Oxyluciferyl-adenylate", *J. Biol. Chem.*, 233(6), (1958),1528-1537.

Riggs, J., et al., "Common Factor 1 Is a Transcriptional Activator Which Binds in the c-myc Promoter, the Skeletal alpha-Actin Provider, and the Immunoglobulin Heavy-Chain Enhancer", *Molecular and Cellular Biologry*, 11(3), (1991),1765-1769.

Rommens, J. M., et al., "cAMP-inducible chloride conductance in mouse fibroblast lines stably expressing the human cystic fibrosis transmembrance conductance regulator", *Proc. Natl. Acad. Sci.*, 88, (1991),7500-7504.

Rosendahl, M. S., et al., "Dimensional Probing of the ATP Binding Site on Firefly Luciferase", *Photochemistry and Photobiology*, 35(6), (1982),857-861.

Saiki, R. K., et al., "Primer-Directed Enzymatic Amplification of DNA with a Thermostable DNA Polymerase", *Science*, 239(4839), (Jan. 29, 1988),487-491.

Saisanit, S, "A Novel Enhancer, the Pro-B Enhancer, Regulates Id1 Gene Expression in Progenitor B Cells", *Mol. Cell. Biol.*, 15(3), (1995),1513-1521.

Sala-Newby, G., et al., "Engineering a bioluminescent indicator for cyclic AMP-dependent protein kinase", *Biochem. J.*,279 (Pt 3), (1991),727-732.

Sala-Newby, G., "Engineering firefly luciferase as an indicator of cyclic AMP-dependent protein kinase in living cells", *FEBS Letters*, 307 (2), (Jul. 1992),pp. 241-244.

Sala-Newby, G. B., et al., "Expression of Recombinant Firefly Luciferase in Prokaryotic and Eukaryotic Cells", *Biochemical Society Transactions*, 20, (1992),p. 143S.

Sala-Newby, G. B., "Stepwise Removal of the C-Terminal 12 Amino Acids of Firefly Luciferase Results in Graded Loss of Activity", *Biochimica et Biophysica Acta (BBA)—Protein Structure and Molecular Enzymology*, 1206(1), (1994),155-160.

Schatt, M D., "A Single DNA-Binding Transcription Factor is Sufficient for Activation from a Distant Enhancer and/or from a Promoter Position", *The EMBO Journal*, 9(2), (Feb. 1990),481-487.

Schmidt, E. V., et al., "The Cytomegalovirus Enhancer: A Pan-Active Control Element in Transgenic Mice", *Molecular and Cellular Biology*, 10(8), (1990),4406-4411.

Schutte, B. C., "Optimized Conditions for Cloning PCR Products Into an Xcml T-vector", *BioTechniques*, 22(1), (1997),40-43.

Seliger, H. H., "The Colors of Firefly Bioluminescence: Enzyme Configuration and Species Specificity", *Proc. Natl. Acad. Sci., USA*, 52(1), (1964),75-81.

Senapathy, P., et al., "Splice Junctions, Branch Point Sites, and Exons: Sequence Statistics, Identification, and Applications to Genome Project", *Methods in Enzymology*, 183, (1990),252.

Seol, J. H., et al., "Site-Directed Mutagenesis of the Cys Residues in ClpA, the ATPase Component of Protease Ti (SlpAP) in *Escherichia coil"*, *Biological Chemistry*, 378(10), (Abstract Only),(1997),1205-1209.

Sharp, P. M., "Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity", *Nucleic Acids Research*, 16(17), (Sep. 12, 1988),8207-8211.

Sharp, P. M., "The Codon Adaptation Index—A Measure of Directional Synonymous Codon Usage Bias, and Its Potential Applications", *Nucleic Acids Research*, 15(3), (Feb. 11, 1987),1281-95.

Shaw, Gray, "A Conserved AU Sequence from the 3' Untranslated Region of GM-CSF mRNA Mediates Selective mRNA Degradation", *Cell*, vol. 46, (1986),659-667.

Sherf, B. A., et al., "Dual-Luciferase tm Reporter Assay: An Advanced Co-Reporter Technology Integrating Firefly and *Renilla* Luciferase Assays", *Promega Notes Magazine*, No. 57, (1996),7 pgs.

Sherf, B. A., "Firefly Luciferase Engineered for Improved Genetic Reporting", *Promega Notes Magazine* No. 49, (1994),8 pgs.

Simpson, Craig G., "Efficient Splicing of an AU-Rich Antisense Intron Sequence", *Plant Molecular Biology*, vol. 21, (1993),205-211.

Sirot, D., et al., "A Complex Mutant of TEM-1 Beta-Lactamase With Mutations Encountered in Both IRT-4 and Extended-Spectrum TEM-15, Produced by *Escherichia coli* Clnical Isolate", *Antimicrobial Agents and Chemotherapy*, 41(6), (Jun. 1997),1322-1325.

Sommer, Jurg M., "In vivo import of firefly luciferase into the glycosomes of *Trypanosoma brucei* and mutational analysis of the C-terminal targeting signal", *Mol. Biol. of the Cell*, 3, (1992),749-759.

Sorensen, M A., "Codon usage determines translatin rate in *Escherichia coli"*, *J. Mol. Biol.*, 207(2), (1989),365-377.

Stapleton, P. D., et al., "Construction and Characterization of Mutants of the TEM-1 beta-Lactamase Containing Amino Acid Substitutions Associated With Both Extended=Spectrum Resistance and Resistance to beta-Lactamase Inhibitors", *Antimicrobial Agents and Chemotherapy*, 43(8), (Aug. 1999),1881-1887.

Stemmer, W. P., et al., "DNA Shuffling by Random Fragmentation and Reassembly: In vitro Recombination for Molecular Evolution", *Proceedings of the National Academy of Sciences of USA*, 91(22), (Oct. 25, 1994), 10747-10751.

Stewart, C. L., et al., "Expression of Retroviral Vectors in Transgenic Mice Obtain by Embryo Infection", *The EMBO Journal*, 6(2), (Feb. 1987),383-388.

Strauss, E. C., et al., "In Vivo Protein-DNA Interactions of Hypersensitive Site 3 of the Human Beta-Globin Locus Control Region", *Proc. Natl. Acad. Sci. USA*, 89(13), (Jul. 1992),5809-5813.

Szittner, R., et al., "Nucleotide Sequence, Expression, and Properties of Luciferase Coded by lux Genes from a Terrestrial Bacterium", *The Journal of Biological Chemistry*, 265(27), (Sep. 25, 1990),16581-16587.

Tanaka, M, "Synonymous codon usage and cost of genetic information", *Bull. Osaka Med. Coll.*, 34(1-2), (3-12),1988.

Tarpey, M. M., et al., "Chemiluminescent detection of oxidants in vascular tissue. Lucigenin but not coelenterazine enhances superoxide formation", *Circulation Research*, 84(10), (May 28, 1999),1203-1211.

Teranishi, K., "Coelenterazine analogs as chemiluminescent probe for superoxide anion", *Analytical Biochemistry*, 249(1), (Jun. 15, 1997),37-43.

Ticher, A, "Nucleic acid compositions, codon usage, and the rate of synonymous substitution in protein-coding genes", *J. Mol. Evol.*, 28(4), (1989),286-298.

Van Aarssen, Roel, et al., "cry IA(b) Transcript Formation in Tobacco is Inefficient", *Plant Molecular Biology*, vol. 28, (1995),513-524.

Voladri, R. K., et al., "Structure-Function Relationships Among Wild-Type Variants of *Staphylococcus aureu* beta-Lactamase: Importance of Amino Acids 128 and 216", *Journal of Bacteriology*, 178(24), (Dec. 1996),7248-7253.

Wada, Ken-Nosuke, "Codon Usage Tabulated from GenBank Genetic Sequence Data", *Nucleic Acids Research*, 18 Suppl, (Apr. 25, 1990),2367-2411.

Wada, K.-N., et al., "Codon Usuage Tabulated From the GenBank Genetic Sequence Data", *Nucleic Acids Research*, 20(Suppl,), (1992),2111-2118.

Wagner, E. F., et al., "Transfer of Genes Into Embryonal Carcimona Cells by Retrovirus Infection: Efficient Expression From an Internal Promoter", *The EMBO Journal*, 4(3), (Mar. 1985),663-666.

Wain-Hobson, S, "Preferential codon usage in genes", *Gene*, 13(4), (1981),355-364.

Walker, D. E., et al., "An Aspartic Acid at Amino Acid 108 Is Required to Rescue Infectious Virus After Transfection of a Poliovirus cDNA Containing a CGDD but Not SGDD Amino Acid Motif in 3D pol", *Journal of Virology*, 69(12), (1995),8173-8177.

White, P J., et al., "Generation and Characterisation of a Thermostable Mutant of Luciferase from *Photinus pyralis*", in Bioluminescence and Chemiluminescence, Fundamentals and Applied Aspects", *Proceedings of the 8th International Symposium on Bioluminescence and Chemiluminescence*, John Wiley & Sons, Cambridge,(Sep. 1994),419-422.

White, Peter J., et al., "Improved thermostability of the North American firefly luciferase: saturation mutagenesis at position 354", *Biochemical Journal*, 319 (Pt 2), (Oct. 15, 1996),343-350.

Wilson, Tim, "Removal of poly(A) and Consequence Degradation of c-fos mRNA Facilitated by 3' AU-Rich Sequences", *Nature*, vol. 336, (1988),396-399.

Wood, Keith V., "Bioluminescent click beetles revisited", *Journal of Bioluminescence and Chemiluminescence*, 4(1), (Jul. 1989),31-39.

Wood, K., et al., "Bioluminescent click beetle revisited", *J.Bioluminescence and Chemiluminescence*,4(1), (1989),31-39.

Wood, K. V., et al., "Complementary DNA coding click beetle luciferases can elicit bioluminescence of different colors", *Science*, 244(4905), (May 12, 1989),700-702.

Wood, Keith V., "Introduction to beetle luciferases and their applications", *Journal of Bioluminescence and Chemiluminescence*, 4, (Jul. 1989),289-301.

Wood, K V., "Luc Genes: Introduction of Colour Into Bioluminescence Assays", *Journal of Bioluminescence and Chemiluminescence*, vol. 5, (Apr. 1990),107-114.

Wood, K. V., "Photographic Detection of Luminescence in *Escherichia coli* Containing the Gene for Firefly Luciferase", *Analytical Biochemistry*, 161(2), (Mar. 1987),501-507.

Wood, K.V., et al., "Synthesis of Active Firefly Luciferase by In Vitro Translation of RNA Obtained From Adult Lanterns", *Biochemical and Biophysical Research Communications*, 124(2), (Oct. 30, 1984),592-596.

Wood, K. V., "The Chemical Mechanism and Evolutionary Development of Beetle Bioluminescence", *Photochemistry and Photobiology*, 62 (4), (1995),662-673.

Yanai, K, et al., "A cis-acting DNA element located between TATA box and transcription initiation site is critical in response to regulatory sequences in human angiotensinogen gene", *J. Biol. Chem.*, 271(27), (1996),15981-15986.

Yang, J K., "Human Dihydrofolate Reductase Gene Organization. Extensive Conservation of the G+C-rich 5' Non-Coding Sequence and Strong Intron Size Divergence From Homologous Mammalian Genes", *Journal of Molecular Biology*, 176(2), (Jun. 25, 1984),169-187.

Ye, Li, "Cloning and Sequencing of a cDNA for Firefly Luciferase from *Photuris pennsylvanica*", *Biochimica et Biophvsica Acta*, 1339 (1), (Apr. 25, 1997),39-52.

Zhang, J.-H., et al., "Directed Evolution of a Fucosidase From a Galactosidase by DNA Shuffling and Screening", *Proc.Natl. Acad. Sci. USA*, 94(9), (Apr. 29, 1997),4504-4509.

Zhao, H., et al., "Functional and Nonfunctional Mutations Distinguished by Random Recombination of Homologous Genes", *Proc. Natl. Acad. Sci. USA*, 94(15), (Jul. 22, 1997),7997-8000.

"BIOBASE" [online] [retrieved Jul. 31, 2007 from Internet: www.gene-regulation.com/pub/databases/html>, (2007) 8 pages.

BLAST 2 sequences - aminoglycoside 3'-phosphotransferase mutant [synthetic construct], http://www.ncbi.nlm.nih.gov/blast/b12seq/wblast2.cgi.?o, (2007) 3 pages.

"Cloning vector PGFP-1 green fluorescent protein, complete cds" GenBank Accession No. U19276.1 (Jul. 1995) 2 pages.

"Cloning Vector psiSTRIKE Puromycin, complete sequence," NCBI Sequence Accession No. AY497507 (Jan. 2004) 2 pages.

"Sequence of pcdna3.1/Hygro," [Retrieved from the Internet http://www.invitrogen.com/content/sfs/vectors/pcdna3.1hygro_seq.txt] (2005) 2 pages).

Alberts, "Intron sequences are removed as lariat-shaped RNA molecules," Mol. Cell Biol. (1994) 3:373-374.

Bowie, J.U. et al., "Deciphering the message in protein sequences: tolerance to amino acid substitutions," Science (1990) 247(4948):1306-1310.

Branchini, B.R., "Naphtyl- and quinolylluciferin: green and red light emitting firefly luciferin analogues," Photochem. Photobiol. (1989) 49(5):689-695.

CloneTech Laboratories, Inc., Document PT2038-5 (1998) 2 pages, pGFP-1 Vector Information.

ClonTech Catalog (1996/97) 2 pages, p. 96.

Corish, P. et al., "Attenuation of green fluorescent protein half-life in mammalian cells," Protein Engin. (1999) 12(12):1035-1040.

Deluca, M. et al., "Role of sulfhydryl groups in firefly luciferase," Biochem. (1964) 3(7):935-939.

Deluca, M. et al., "The hydrolase properties of firefly luciferase," Biochem. Biophys. Res. Comm (1965) 18(5-6):836-842.

Devine, J.H. et al., "Luciferase from the East European firefly *luciola mingrelica*: cloning and nucleotide sequence of the cDNA, overexpression in *escherichia coli* and purification of the enzyme," Biochim. et Biophys. Acta (1993) 1173:121-132.

Dorsky, R.I. et al., "A transgenic Lefl/beta-catenin-dependent reporter is expressed in spatially restricted domains throughout zebrafish development," Dev. Biol. (2002) 241:229-237.

Egly, J. et al., "Sequence 1 from Patent WO 95/29245," NCBI Sequence Accession No. A47120 (Mar. 1997) 2 pages.

Franklin, S. et al., "Development of a GFP reporter gene for *chlamydomonas reinhardtii* chloroplast," The Plant Journal (2002) 30(6):733-744.

Genbank Deposit Accession No. AF384683, "*Montastraea cavernosa* green fluorescent protein mRNA," Complete cds, Version AF384683.2 GI: 15298095, Aug. 2001, 1 page.

Genbank Deposit Accession No. AY037770, "*Montastraea cavernosa* meavFP_7.5 mRNA," Complete cds, Version AY037770.1 GI:19982596, Apr. 2002, 1 page.

Genbank Deposit Accession No. AY056460, "*Montastraea cavernosa* cyan fluorescent protein mRNA," Complete cds, Version AY056460.1 GI:16508124, Oct. 2001, 1 page.

Gilon, T. et al., "Degradation signals for ubiquitin system proteolysis in *Saccharomyces cerevisiae*," Embo J. (1998) 17(10):2759-2766.

Glass, R.E. et al., "Gene function: *E.coli* and its heritable elements," University of California Press (1982) 95.
Keller, G-A. et al., "Firefly luciferase is targeted to peroxisomes in mammalian cells," Proc. Natl. Acad. Sci. USA (1987) 84:3264-3268.
Kitts, P.A., "Neomycin phosphotransferase," GenBank Accession No. AAA69543 (Jul. 1995) 2 pages.
Kozak, M., "An analysis of 5'-noncoding sequences from 699 vertebrate messenger RNAs," Nucl. Acids Res. (1987) 15(20):8125-8132.
Leclerc, G.M. et al., "Development of a destabilized firefly luciferase enzyme for measurement of gene expression," Biotechniques (2000) 29(3):590-601.
Lesser, M.P. et al., "*Montastraea cavernosa* green fluorescent protein mRNA, complete cds," GenBank Accession No. AF406766 (Sep. 2, 2001) 2 pages.
Lesser, M.P. et al., "*Montastraea faveolata* green fluorescent protein mRNA, complete cds," GenBank Accession No. AF401282 (Aug. 5, 2001) 2 pages.
Lisser, S. et al., "Compilation of *E.coli* MRNA promoter sequences," Nucl. Acids Res. (1993) 21(7):1507-1516.
Lodish et al., "Splicesomes, assembled from snRNPs and a pre-mRNA, carry out splicing," Chapter 11, RNA Processing, Nuclear Transport, and Post-Transcriptional Control, Mol. Cell Biol. (2000) 4:416-418.
Matz, "Amplification of representative cDNA samples from microscopic amounts of invertebrate tissue to search for new genes," Institute of Bioorganic Chemistry RAS (2002) 1-21.
Matz, M.V. et al., "Fluorescent proteins from nonbioluminescent anthozoa species," Nat. Biotech. (1999) 17(10):969-973.
Matz, M.V. et al., "*Montastraea cavernosa* clone 7.7 green fluorescent protein-like protein mRNA, complete cds," GenBank Accession No. AY037768 (May 31, 2001) 2 pages.
Petit, T. et al., "A mutation Ser 213/Asn in the hexokinase 1 from schizosaccharomyces pombe increases its affinity for cluesses," Biochem. Biophys. Res. Comm (1998) 251(3):714-719.
Quandt, K. et al., "MatInd and MatInspector: new fast and versatile tools for detection of consensus matches in nucleotide sequence data," Nucl. Acids Res. (1995) 23(23):4878-4884.
Ringquist, S. et al., "Translation initiation in *escherichia coli*: sequences within the ribosome-binding site," Mol. Microbiol. (1992) 1219-1229.
Robinson, M. et al., "Codon usage can affect efficiency of translation of genes in *escherichia coli*," Nuc. Acids Res. (1984) 12(17):6663-6671.
Shim, J. et al., "Canonical 3'-deoxyribonucleotides as a chain terminator for HCV NS5B RNA-dependent RNA polymerase," Antiviral Research (2003) 58:243-251.
Tabaska, J.E. et al., "Detection of polyadenylation signals in human DNA sequences," Gene (1999) 77-86.
Turkel, S. et al., "GCR-1 dependent transcriptional activation of yeast retrotransposon Ty2-917," Yeast (1997) 13(1):917-930.
Viviani, V.R. et al., "Bioluminescence color determinants of phrixothrix railroad-worm luciferases: chimeric luciferases, site-directed mutagenesis of Arg 215 and guanidine effect," Photochem. Photobiol. (2000) 72(2):267-271.
Voss, S.D. et al., "The role of enhancers in the regulation of cell-type-specific transcriptional control," Trends Biochem. Sci. (1986) 11:287-289.
Wells, K.D. et al., "Codon optimization, genetic insulation, and an ηTA reporter improve performance of the tetracycline switch," Trans. Res. (1999) 8:371-381.
Wood, K.V., "Luciferases of luminous beetles: evolution, color variation, and applications," Dissertation (1989), submitted as two parts, Part 1 and Part 2.
Yang, F. et al., "The molecular structure of green fluorescent protein," Nature Biotech. (1996) 14(10):1246-1251.
Yotov, W.V. et al., "Synthetic construct aminoglycoside 3'-phosphotransferase mutant (mNeo) gene, complete cds," GenBank Accession No. AF081957.1 (Aug. 1999) 2 pages.
Yotov, W.V. et al., GenBank Accession No. AAD50549 (Aug. 1999) 2 pages.
Zhuang, Y. et al., "Co-reporter vector phRG-b, complete sequence," Database EMBL (Accession No. EMBL:AF362550) (May 15, 2001) 4 pages.

Australian Patent Office Action for Application No. 2001285278 dated Dec. 19, 2007 (2 pages).
Australian Patent Office Action for Application No. 2001285278 dated Oct. 16, 2006 (2 pages).
Australian Patent Office Action for Application No. 2003297293 dated Jun. 18, 2006 (2 pages).
Australian Patent Office Action for Application No. 2003297293 dated Oct. 5, 2006 (2 pages).
Canadian Patent Office Action for Application No. 2,420,328 dated Feb. 4, 2008 (3 pages).
Canadian Patent Office Action for Application No. 2,420,328 dated Dec. 7, 2009 (3 pages).
Canadian Patent Office Action for Application No. 2,525,582 dated Jan. 2, 2008 (5 pages).
Canadian Patent Office Action for Application No. 2,525,582 dated Dec. 30, 2009 (3 pages).
Chinese Patent Office Action for Application No. 200580039282.5 dated Aug. 7, 2009 (10 pages) with English translation.
European Patent Office Examination Report for Application No. 01964425.1 dated Jun. 27, 2005 (12 pages).
European Patent Office Examination Report for Application No. 01964425.1 dated Nov. 23, 2006 (13 pages).
European Patent Office Summons to Attend Oral Proceedings for Application No. 01964425.1 dated Feb. 8, 2008 (11 pages).
European Patent Office Action for Application No. 01964425.1 dated Jun. 9, 2008 (9 pages).
European Patent Office Action for Application No. 03819255.5 dated Mar. 17, 2009 (4 pages).
European Patent Office Action for Application No. 03819255 5 mailed May 18, 2007 (5 pages).
European Patent Office Action for Application No. 05797929.6 dated Apr. 2, 2009 (4 pages).
European Patent Office Action for Application No. 05797929.6 dated Mar. 8, 2010 (4 pages).
International Search Report for Application No. PCT/US01/26566 dated Feb. 28, 2003 (7 pages).
International Search Report for Application No. PCT/US03/37117 dated Oct. 31, 2005 (5 pages).
International Preliminary Examination Report for Application No. PCT/US03/37117 dated Feb. 1, 2007 (9 pages).
International Preliminary Report on Patentability for Application No. PCT/US2005/033218 dated Mar. 20, 2007 (9 pages).
International Search Report for Application No. PCT/US2005/033218 dated Mar. 31, 2006 (7 pages).
Written Opinion for Application No. PCT/US2005/033218 dated Mar. 31, 2006 (8 pages).
Partial International Search Report for Application No. PCT/US2005/033218 dated Jan. 12, 2006 (7 pages).
Japanese Patent Office Action for Application No. 2002-521985 mailed Jun. 7, 2006 (6 pages) English translation.
Japanese Patent Office Action for Application No. 2002-521985 mailed Jan. 5, 2010 (8 pages).
Japanese Patent Office Action and Dential of Entry of Amendment for Application No. 2002-521985 mailed Aug. 3, 2010 (65 pages) with English translation.
Japanese Patent Office Action for Application No. 2006-288147 mailed Dec. 3, 2008 (7 pages) with English translation.
Japanese Patent Office Action for Application No. 2005-513754 mailed May 13, 2008 (3 pages).
Japanese Patent Office Action for Application No. 2005-513754 mailed Nov. 13, 2007 (3 pages) with English translation.
United States Patent Office Action for U.S. Appl. No. 09/645,706 dated Feb. 14, 2003 (16 pages).
United States Patent Office Action for U.S. Appl. No. 09/645,706 dated Jan. 6, 2004 (12 pages).
United States Patent Office Action for U.S. Appl. No. 09/645,706 dated Apr. 29, 2004 (6 pages).
United States Patent Office Action for U.S. Appl. No. 09/645,706 dated Sep. 13, 2004 (19 pages).
United States Patent Office Action for U.S. Appl. No. 09/645,706 dated Mar. 22, 2005 (15 pages).
United States Patent Office Action for U.S. Appl. No. 09/645,706 dated Dec. 19, 2005 (29 pages).

United States Patent Office Action for U.S. Appl. No. 09/645,706 dated Sep. 13, 2006 (21 pages).
United States Patent Office Advisory Action for U.S. Appl. No. 09/645,706 dated Mar. 1, 2007 (16 pages).
United States Patent Office Examiner's Answer to Appeal Brief for U.S. Appl. No. 09/645,706 dated Dec. 12, 2007 (67 pages).
United States Patent Office Decision on Appeal for U.S. Appl. No. 09/645,706 dated Sep. 3, 2008 (25 pages).
United States Patent Office Action for U.S. Appl. No. 09/645,706 dated Feb. 3, 2009 (24 pages).
United States Patent Office Action for U.S. Appl. No. 09/645,706 dated Sep. 3, 2009 (13 pages).
United States Patent Office Notice of Allowance for U.S. Appl. No. 09/645,706 dated Jun. 4, 2010 (4 pages).
United States Patent Office Action for U.S. Appl. No. 11/316,042 dated Jun. 11, 2008 (12 pages).
United States Patent Office Action for U.S. Appl. No. 11/316,042 dated Apr. 2, 2009 (8 pages).
United States Patent Office Action for U.S. Appl. No. 11/316,042 dated Sep. 4, 2009 (15 pages).
United States Patent Office Action for U.S. Appl. No. 10/943,508 dated Aug. 6, 2007 (25 pages).
United States Patent Office Action for U.S. Appl. No. 10/943,508 dated Feb. 27, 2007 (17 pages).
United States Patent Office Action for U.S. Appl. No. 10/943,508 dated Jan. 24, 2008 (25 pages).
United States Patent Office Notice of Allowance/Office Action for U.S. Appl. No. 10/943,508 dated Sep. 29, 2008 (7 pages).
United States Patent Office Notice of Allowance for U.S. Appl. No. 10/943,508 dated Dec. 23, 2009 (4 pages).
United States Patent Office Action for U.S. Appl. No. 11/825,304 dated Oct. 30, 2009 (16 pages).
United States Patent Office Action for U.S. Appl. No. 11/825,304 dated Jul. 21, 2010 (7 pages).
United States Patent Office Decision on Appeal for U.S. Appl. No. 10/314,827 dated Jul. 22, 2008 (23 pages).
United States Patent Office Action for U.S. Appl. No. 10/314,827 dated Jul. 2, 2007 (45 pages).
United States Patent Office Action for U.S. Appl. No. 10/314,827 dated Oct. 16, 2006 (8 pages).
United States Patent Office Action for U.S. Appl. No. 10/314,827 dated May 8, 2006 (23 pages).
United States Patent Office Action for U.S. Appl. No. 10/314,827 dated Sep. 12, 2005 (23 pages).

* cited by examiner

| First Position (5' end) | Second position | | | | Third position (3' end) |
|---|---|---|---|---|---|
| | U | C | A | G | |
| U | Phe | Ser | Tyr | Cys | U |
| | Phe | Ser | Tyr | Cys | C |
| | Leu | Ser | Stop | Stop | A |
| | Leu | Ser | Stop | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

```
GRVER51.SEQ   G C T G A G A A T A A C A C T C G C T T C T T T A T T C C T G T A A T C G C T G 280
GR6.SEQ       G C T G A G A A T A A C A C T C G C T T C T T T A T T C C T G T A A T C G C T G 280
GRVER5.SEQ    G C T G A G A A T A A C A C T C G C T T C T T T A T T C C T G T A A T C G C T G 280
GRVER4.SEQ    G C T G A G A A T A A C A C T C G C T T C T T T A T C C C T G T T A T C G C T G 280
GRVER3.SEQ    G C T G A G A A T A A C A C T C G C T T T T T T A T C C C T G T G A T C G C T G 280
GRVER2.SEQ    G C T G A G A A T A A C A C C C G C T T T T T C A T C C C A G T G A T T G C C G 280
GRVER1.SEQ    G C T G A G A A T A A C A C C C G C T T T T T C A T C C C A G T G A T T G C C G 280
YG81-6G1.SEQ  G C C G A G A A T A A T A C A A G A T T T T T A T T C C C G T T A T T G C A G 280
RDVER1.SEQ    G C C G A A A C A A T A C T C G T T T C T T T A T T C C T G T C A T C G C T G 280
RDVER2.SEQ    G C C G A A A C A A T A C T C G T T T C T T T A T T C C T G T C A T C G C T G 280
RDVER3.SEQ    G C C G A A A C A A T A C C C G T T T C T T C A T T C C A G T C A T C G C C G 280
RDVER4.SEQ    G C A G A A A C A A T A C C C G T T T C T T C A T T C C A G T C A T C G C C G 280
RDVER5.SEQ    G C T G A A A A C A A T A C C C G T T T C T T C A T T C C A G T C A T C G C C G 280
RD7.SEQ       G C T G A A A A C A A T A C C C G T T T C T T C A T T C C A G T C A T C G C C G 280
RDVER51.SEQ   G C T G A A A A C A A T A C C C G T T T C T T C A T T C C A G T C A T C G C C G 280
RDVER52.SEQ   G C T G A A A A C A A T A C C C G T T T C T T C A T T C C A G T C A T C G C C G 280
RD1561H9.SEQ  G C T G A A A A C A A T A C C C G T T T C T T C A T T C C A G T C A T C G C C G 280

GRVER51.SEQ   C T T G G T A C A T C G G C A T G A T T G T C G C C C C T G T G A A T G A A T C 320
GR6.SEQ       C T T G G T A C A T C G G C A T G A T T G T C G C C C C T G T G A A T G A A T C 320
GRVER5.SEQ    C T T G G T A C A T C G G C A T G A T T G T C G C C C C T G T G A A T G A A T C 320
GRVER4.SEQ    C T T G G T A C A T C G G C A T G A T T G T C G C C C C T G T G A A T G A A T C 320
GRVER3.SEQ    C T T G G T A C A T C G G C A T G A T T G T C G C C C C T G T G A A T G A A T C 320
GRVER2.SEQ    C T T G G T A C A T C G G C A T G A T T G T C G C C C C T G T G A A T G A A T C 320
GRVER1.SEQ    C T T G G T A C A T C G G C A T G A T T G T C G C C C C T G T G A A T G A A T C 320
YG81-6G1.SEQ  C T T G G T A T A T T G G T A T G A T T G T A G C A C C T G T T A A T G A A A G 320
RDVER1.SEQ    C C T G G T A T A T T G G T A T G A T C G T G G C T C C A G T C A A C G A G A G 320
RDVER2.SEQ    C C T G G T A T A T T G G T A T G A T C G T G G C T C C A G T C A A C G A G A G 320
RDVER3.SEQ    C C T G G T A T A T C G G T A T G A T C G T G G C T C C A G T C A A C G A G A G 320
RDVER4.SEQ    C A T G G T A T A T C G G T A T G A T C G T G G C T C C A G T C A A C G A G A G 320
RDVER5.SEQ    C A T G G T A T A T C G G T A T G A T C G T G G C T C C A G T C A A C G A G A G 320
RD7.SEQ       C A T G G T A T A T C G G T A T G A T C G T G G C T C C A G T C A A C G A G A G 320
RDVER51.SEQ   C A T G G T A T A T C G G T A T G A T C G T G G C T C C A G T C A A C G A G A G 320
RDVER52.SEQ   C A T G G T A T A T C G G T A T G A T C G T G G C T C C A G T C A A C G A G A G 320
RD1561H9.SEQ  C A T G G T A T A T C G G T A T G A T C G T G G C T C C A G T C A A C G A G A G 320

GRVER51.SEQ   T T A C A T C C C A G A T G A G C T G T G T A A G G T T A T G G G T A T T A G C 360
GR6.SEQ       T T A C A T C C C A G A T G A G C T G T G T A A G G T T A T G G G T A T T A G C 360
GRVER5.SEQ    T T A C A T C C C A G A T G A G C T G T G T A A G G T T A T G G G T A T T A G C 360
GRVER4.SEQ    T T A C A T C C C A G A T G A G C T G T G T A A G G T T A T G G G T A T T A G C 360
GRVER3.SEQ    T T A C A T C C C A G A T G A G T T G T G T A A G G T G A T G G G T A T T A G C 360
GRVER2.SEQ    T T A T A T C C C A G A C G A G T T G T G C A A G G T C A T G G G T A T T A G C 360
GRVER1.SEQ    T T A T A T C C C A G A C G A G T T G T G C A A G G T C A T G G G T A T T A G C 360
YG81-6G1.SEQ  T T A C A T C C C A G A T G A A C T C T G T A A G G T G A T G G G T A T A T C G 360
RDVER1.SEQ    C T A C A T T C C T G A T G A A C T G T G T A A A G T G A T G G G C A T C T C T 360
RDVER2.SEQ    C T A C A T T C C T G A T G A A C T G T G T A A A G T G A T G G G C A T C T C T 360
RDVER3.SEQ    C T A C A T T C C T G A C G A A C T G T G T A A A G T C A T G G G T A T C T C T 360
RDVER4.SEQ    C T A C A T T C C C G A C G A A C T G T G T A A A G T C A T G G G T A T C T C T 360
RDVER5.SEQ    C T A C A T T C C C G A C G A A C T G T G T A A A G T C A T G G G T A T C T C T 360
RD7.SEQ       C T A C A T T C C C G A C G A A C T G T G T A A A G T C A T G G G T A T C T C T 360
RDVER51.SEQ   C T A C A T T C C C G A C G A A C T G T G T A A A G T C A T G G G T A T C T C T 360
RDVER52.SEQ   C T A C A T T C C C G A C G A A C T G T G T A A A G T C A T G G G T A T C T C T 360
RD1561H9.SEQ  C T A C A T T C C C G A C G A A C T G T G T A A A G T C A T G G G T A T C T C T 360
```

*FIG. 2C*

```
GRVER51.SEQ  A A A C C T C A A A T C G T C T T T A C T A C C A A A A A C A T C T T G A A T A  400
GR6.SEQ      A A A C C T C A A A T C G T C T T T A C T A C C A A A A A C A T C T T G A A T A  400
GRVER5.SEQ   A A A C C T C A A A T C G T C T T T A C T A C C A A A A A A T A T C C T G A A T A  400
GRVER4.SEQ   A A A C C T C A A A T C G T C T T T A C T A C C A A A A A C A T C C T G A A T A  400
GRVER3.SEQ   A A A C C T C A A A T C G T C T T T A C T A C C A A A A A C A T C C T G A A T A  400
GRVER2.SEQ   A A A C C T C A A A T C G T G T T T A C T A C C A A G A A C A T T C T G A A T A  400
GRVER1.SEQ   A A A C C T C A A A T C G T G T T T A C T A C C A A G A A C A T T C T G A A T A  400
YG81-6G1.SEQ A A A C C A C A A A T A G T T T T T A C G A C A A A G A A C A T T T T A A A T A  400
RDVER1.SEQ   A A G C C A C A G A T T G T C T T C A C C A C T A A A A A T A T C T T G A A C A  400
RDVER2.SEQ   A A G C C A C A G A T T G T C T T C A C C A C T A A A A A T A T C T T G A A C A  400
RDVER3.SEQ   A A G C C A C A G A T T G T G T T C A C C A C T A A G A A T A T T T T G A A C A  400
RDVER4.SEQ   A A G C C A C A G A T T G T C T T C A C C A C T A A G A A T A T T C T G A A C A  400
RDVER5.SEQ   A A G C C A C A G A T T G T C T T C A C C A C T A A G A A T A T T C T G A A C A  400
RD7.SEQ      A A G C C A C A G A T T G T C T T C A C C A C T A A G A A T A T T C T G A A C A  400
RDVER51.SEQ  A A G C C A C A G A T T G T C T T C A C C A C T A A G A A T A T T C T G A A C A  400
RDVER52.SEQ  A A G C C A C A G A T T G T C T T C A C C A C T A A G A A T A T T C T G A A C A  400
RD1561H9.SEQ A A G C C A C A G A T T G T C T T C A C C A C T A A G A A T A T T C T G A A C A  400

GRVER51.SEQ  A G G T C T T G G A A G T C C A G T C T C G T A C T A A C T T C A T C A A A C G  440
GR6.SEQ      A G G T C T T G G A A G T C C A G T C T C G T A C T A A C T T C A T C A A A C G  440
GRVER5.SEQ   A G G T C T T G G A A G T C C A G T C T C G T A C T A A C T T C A T C A A A C G  440
GRVER4.SEQ   A G G T C T T G G A A G T C C A G T C T C G T A C T A A C T T C A T C A A A C G  440
GRVER3.SEQ   A G G T C T T G G A A G T C C A G T C T C G T A C T A A T T T C A T C A A A C G  440
GRVER2.SEQ   A G G T C T T G G A A G T G C A G T C T C G T A C T A A C T T C A T C A A G C G  440
GRVER1.SEQ   A A G T C T T G G A A G T G C A G T C T C G T A C T A A C T T C A T C A A G C G  440
YG81-6G1.SEQ A G G T A T T G G A G G T A C A G A G C A G A A C T A A T T T C A T A A A A G  440
RDVER1.SEQ   A G G T G C T G G A G G T C C A A A G C C G C A C C A A T T T T A T T A A A C G  440
RDVER2.SEQ   A A G T G C T G G A G G T C C A A A G C C G C A C C A A T T T T A T T A A A C G  440
RDVER3.SEQ   A A G T G C T G G A A G T C C A A A G C C G C A C C A A C T T T A T T A A G C G  440
RDVER4.SEQ   A A G T C C T G G A A G T C C A A A G C C G C A C C A A C T T T A T T A A G C G  440
RDVER5.SEQ   A A G T C C T G G A A G T C C A A A G C C G C A C C A A C T T T A T T A A G C G  440
RD7.SEQ      A A G T C C T G G A A G T C C A A A G C C G C A C C A A C T T T A T T A A G C G  440
RDVER51.SEQ  A A G T C C T G G A A G T C C A A A G C C G C A C C A A C T T T A T T A A G C G  440
RDVER52.SEQ  A A G T C C T G G A A G T C C A A A G C C G C A C C A A C T T T A T T A A G C G  440
RD1561H9.SEQ A A G T C C T G G A A G T C C A A A G C C G C A C C A A C T T T A T T A A G C G  440

GRVER51.SEQ  C A T C A T T A T T C T G G A T A C C G T C G A A A A C A T C C A C G G C T G T  480
GR6.SEQ      C A T C A T T A T T C T G G A T A C C G T C G A A A A C A T C C A C G G C T G T  480
GRVER5.SEQ   C A T C A T T A T T C T G G A T A C C G T C G A A A A C A T C C A C G G C T G T  480
GRVER4.SEQ   C A T C A T T A T T C T G G A T A C C G T C G A A A A C A T C C A T G G C T G T  480
GRVER3.SEQ   C A T T A T T A T T C T G G A T A C C G T C G A A A A C A T C C A C G G C T G T  480
GRVER2.SEQ   C A T T A T C A T T C T G G A T A C C G T C G A G A A T A T C C A C G G C T G T  480
GRVER1.SEQ   C A T T A T C A T T C T G G A T A C C G T C G A G A A T A T C C A C G G C T G T  480
YG81-6G1.SEQ G A T C A T C A T A C T T G A T A C T G T A G A A A A C A T A C A C G G T T G T  480
RDVER1.SEQ   T A T C A T T A T C T T G G A C A C T G T G G A A A A C A T T C A T G G T T G C  480
RDVER2.SEQ   T A T C A T T A T C T T G G A C A C T G T G G A A A A C A T T C A T G G T T G C  480
RDVER3.SEQ   T A T C A T C A T C T T G G A C A C T G T G G A G A A T A T T C A T G G T T G C  480
RDVER4.SEQ   T A T C A T C A T C T T G G A C A C T G T G G A G A A T A T C A C G G T T G C  480
RDVER5.SEQ   T A T C A T C A T C T T G G A C A C T G T G G A G A A T A T T C A C G G T T G C  480
RD7.SEQ      T A T C A T C A T C T T G G A C A C T G T G G A G A A T A T T C A C G G T T G C  480
RDVER51.SEQ  T A T C A T C A T C T T G G A C A C T G T G G A G A A T A T T C A C G G T T G C  480
RDVER52.SEQ  T A T C A T C A T C T T G G A C A C T G T G G A G A A T A T T C A C G G T T G C  480
RD1561H9.SEQ T A T C A T C A T C T T G G A C A C T G T G G A G A A T A T T C A C G G T T G C  480
```

*FIG. 2D*

```
GRVER51.SEQ   G A G A G C C T C C C T A A C T T C A T C T C T C G T T A C A G C G A T G G T A  520
GR6.SEQ       G A G A G C C T C C C T A A C T T C A T C T C T C G T T A C A G C G A T G G T A  520
GRVER5.SEQ    G A G A G C C T C C C T A A C T T C A T C T C T C G T T A C A G C G A T G G T A  520
GRVER4.SEQ    G A G A G C C T G C C T A A C T T C A T C T C T C G T T A C A G C G A T G G T A  520
GRVER3.SEQ    G A G A G C T T G C C T A A C T T T A T C T C T C G T T A C A G C G A T G G T A  520
GRVER2.SEQ    G A G A G C T T G C C A A A C T T T A T T T C T C G T T A T A G C G A C G G T A  520
GRVER1.SEQ    G A A A G C T T G C C A A A C T T T A T T T C T C G T T A T A G C G A C G G T A  520
YG81-6G1.SEQ  G A A A G T C T T C C C A A T T T T A T T T C T C G T T A T T C G G A T G G A A  520
RDVER1.SEQ    G A G T C T C T G C C T A A T T T C A T C A G C C G C T A C T C T G A T G G C A  520
RDVER2.SEQ    G A A T C T C T G C C T A A T T T C A T C A G C C G C T A C T C T G A T G G C A  520
RDVER3.SEQ    G A A T C T C T G C C T A A T T T C A T T A G C C G C T A T T C T G A C G G C A  520
RDVER4.SEQ    G A A T C T T T G C C T A A T T T T A T T A G C C G C T A T T C A G A C G G A A  520
RDVER5.SEQ    G A A T C T T T G C C T A A T T T C A T C T C T C G C T A T T C A G A C G G C A  520
RD7.SEQ       G A A T C T T T G C C T A A T T T C A T C T C T C G C T A T T C A G A C G G C A  520
RDVER51.SEQ   G A A T C T T T G C C T A A T T T C A T C T C T C G C T A T T C A G A C G G C A  520
RDVER52.SEQ   G A A T C T T T G C C T A A T T T C A T C T C T C G C T A T T C A G A C G G C A  520
RD1561H9.SEQ  G A A T C T T T G C C T A A T T T C A T C T C T C G C T A T T C A G A C G G C A  520

GRVER51.SEQ   A T A T C G C T A A T T T C A A G C C C T T G C A T T T T G A T C C A G T C G A  560
GR6.SEQ       A T A T C G C T A A T T T C A A G C C C T T G C A T T T T G A T C C A G T C G A  560
GRVER5.SEQ    A T A T C G C T A A T T T C A A G C C C T T G C A T T T T G A T C C A G T C G A  560
GRVER4.SEQ    A T A T C G C T A A T T T C A A A C C A C T G C A T T T T G A T C C A G T C G A  560
GRVER3.SEQ    A T A T C G C T A A T T T C A A G C C A C T G C A T T T T G A T C C A G T C G A  560
GRVER2.SEQ    A T A T C G C T A A C T T C A A G C C T C T G C A T T T T G A T C C A G T G G A  560
GRVER1.SEQ    A T A T C G C T A A C T T C A A G C C T C T G C A T T T T G A T C C A G T G G A  560
YG81-6G1.SEQ  A T A T T G C C A A C T T C A A A C C T T T A C A T T T C G A T C C T G T T G A  560
RDVER1.SEQ    A C A T T G C C A A T T T T A A A C C A T T G C A C T T C G A C C C T G T C G A  560
RDVER2.SEQ    A C A T T G C C A A T T T T A A A C C A T T G C A C T T C G A C C C T G T C G A  560
RDVER3.SEQ    A C A T C G C C A A C T T T A A A C C T T T G C A T T T C G A C C C T G T G G A  560
RDVER4.SEQ    A C A T C G C C A A C T T T A A G C C T C T C C A T T T C G A C C C T G T G G A  560
RDVER5.SEQ    A C A T C G C A A A C T T T A A A C C A C T C C A C T T C G A C C C T G T G G A  560
RD7.SEQ       A C A T C G C A A A C T T T A A A C C A C T C C A C T T C G A C C C T G T G G A  560
RDVER51.SEQ   A C A T C G C A A A C T T T A A A C C A C T C C A C T T C G A C C C T G T G G A  560
RDVER52.SEQ   A C A T C G C A A A C T T T A A A C C A C T C C A C T T C G A C C C T G T G G A  560
RD1561H9.SEQ  A C A T C G C A A A C T T T A A A C C A C T C C A C T T C G A C C C T G T G G A  560

GRVER51.SEQ   G C A A G T G G C C G C T A T T T T G T G C T C C T C C G G C A C C A C T G G T  600
GR6.SEQ       G C A A G T G G C C G C T A T T T T G T G C T C C T C C G G C A C C A C T G G T  600
GRVER5.SEQ    G C A A G T G G C C G C T A T T T T G T G C T C C T C C G G C A C C A C T G G T  600
GRVER4.SEQ    G C A A G T G G C C G C T A T T T T G T G C T C T T C C G G C A C C A C T G G T  600
GRVER3.SEQ    G C A G G T C G C C G C C A T T T T G T G C T C T T C T G G C A C C A C T G G T  600
GRVER2.SEQ    G C A A G T C G C C G C T A T T T T G T G C T C T A G C G G C A C C A C C G G T  600
GRVER1.SEQ    G C A A G T C G C C G C T A T T T T G T G C T C T A G C G G C A C T A C C G G T  600
YG81-6G1.SEQ  G C A A G T G G C A G C T A T C T T A T G T T C G T C A G G C A C T A C T G G A  600
RDVER1.SEQ    A C A G G T G G C T G C C A T C C T G T G T A G C T C T G G T A C C A C T G G C  600
RDVER2.SEQ    A C A G G T G G C T G C C A T C C T G T G T A G C T C T G G T A C T A C T G G C  600
RDVER3.SEQ    A C A A G T G G C T G C T A T C C T G T G T A G C A G C G G T A C T A C T G G C  600
RDVER4.SEQ    A C A A G T T G C T G C A A T C C T G T G T A G C A G C G G T A C T A C T G G A  600
RDVER5.SEQ    A C A A G T T G C A G C C A T T C T G T G T A G C A G C G G T A C T A C T G G A  600
RD7.SEQ       A C A A G T T G C A G C C A T T C T G T G T A G C A G C G G T A C T A C T G G A  600
RDVER51.SEQ   A C A A G T T G C A G C C A T T C T G T G T A G C A G C G G T A C T A C T G G A  600
RDVER52.SEQ   A C A A G T T G C A G C C A T T C T G T G T A G C A G C G G T A C T A C T G G A  600
RD1561H9.SEQ  A C A A G T T G C A G C C A T T C T G T G T A G C A G C G G T A C T A C T G G A  600
```

```
GRVER51.SEQ  T T T C A C G C C T T T G G T T T C T C T A T T A C C C T G G G C T A T T T C A  760
GR6.SEQ      T T T C A C G C C T T T G G T T T C T C T A T T A C C C T G G G C T A T T T C A  760
GRVER5.SEQ   T T T C A C G C C T T T G G T T T C T C T A T T A C C C T G G G C T A T T T C A  760
GRVER4.SEQ   T T T C A C G C C T T T G G T T T T T C T A T T A C C C T G G G C T A T T T C A  760
GRVER3.SEQ   T T T C A C G C C T T T G G T T T T T C T A T C A C C C T G G G C T A T T T C A  760
GRVER2.SEQ   T T T C A C G C C T T C G G T T T T T C T A T T A C C C T G G G C T A T T T C A  760
GRVER1.SEQ   T T T C A C G C C T T C G G T T T T T C T A T T A C C C T G G G C T A T T T C A  760
YG81-6G1.SEQ T T C C A T G C T T T T G G G T T C T C T A T A A C C T T G G G A T A C T T C A  760
RDVER1.SEQ   T T C C A T G C T T T T G G C T T C C A C A T C A C T T T G G G T T A C T T T A  760
RDVER2.SEQ   T T C C A T G C T T T T G G C T T C C A C A T C A C T T T G G G T T A C T T T A  760
RDVER3.SEQ   T T C C A T G C T T T C G G C T T C C A C A T T A C T T T G G G T T A C T T T A  760
RDVER4.SEQ   T T C C A T G C T T T C G G C T T C C A T A T T A C T T T G G G T T A C T T T A  760
RDVER5.SEQ   T T C C A T G C T T T C G G C T T T C A T A T T A C T T T G G G T T A C T T T A  760
RD7.SEQ      T T C C A T G C T T T C G G C T T T C A T A T T A C T T T G G G T T A C T T T A  760
RDVER51.SEQ  T T C C A T G C T T T C G G C T T T C A T A T T A C T T T G G G T T A C T T T A  760
RDVER52.SEQ  T T C C A T G C T T T C G G C T T T C A T A T T A C T T T G G G T T A C T T T A  760
RD1561H9.SEQ T T C C A T G C T T T C G G C T T T C A T A T T A C T T T G G G T T A C T T T A  760

GRVER51.SEQ  T G G T C G G C T T G C G T G T C A T C A T G T T T C G T C G C T T C G A C C A  800
GR6.SEQ      T G G T C G G C T T G C G T G T C A T C A T G T T T C G T C G C T T C G A C C A  800
GRVER5.SEQ   T G G T C G G C T T G C G T G T C A T C A T G T T T C G T C G C T T C G A C C A  800
GRVER4.SEQ   T G G T C G G C T T G C G T G T C A T C A T G T T T C G T C G C T T C G A C C A  800
GRVER3.SEQ   T G G T C G G C T T G C G T G T G A T C A T G T T T C G T C G C T T C G A C C A  800
GRVER2.SEQ   T G G T C G G T T T G C C G T G A T C A T G T T T C G T C G C T T C G A T C A  800
GRVER1.SEQ   T G G T C G G T T T G C G C G T G A T C A T G T T T C G T C G C T T C G A T C A  800
YG81-6G1.SEQ T G G T G G G T C T T C G T G T T A T C A T G T T C A G A C G A T T T G A T C A  800
RDVER1.SEQ   T G G T G G G C C T G C G T G T C A T T A T G T T C C G C C G T T T T G A C C A  800
RDVER2.SEQ   T G G T G G G C C T G C G T G T C A T T A T G T T C C G C C G T T T T G A C C A  800
RDVER3.SEQ   T G G T C G G T C T G C G T G T C A T T A T G T T C C G C C G T T T T G A T C A  800
RDVER4.SEQ   T G G T C G G T C T G C G T G T G A T T A T G T T C C G C C G T T T T G A T C A  800
RDVER5.SEQ   T G G T C G G T C T C C G C G T G A T T A T G T T C C G C C G T T T T G A T C A  800
RD7.SEQ      T G G T C G G T C T C C G C G T G A T T A T G T T C C G C C G T T T T G A T C A  800
RDVER51.SEQ  T G G T C G G T C T C C G C G T G A T T A T G T T C C G C C G T T T T G A T C A  800
RDVER52.SEQ  T G G T C G G T C T C C G C G T G A T T A T G T T C C G C C G T T T T G A T C A  800
RD1561H9.SEQ T G G T C G G T C T C C G C G T G A T T A T G T T C C G C C G T T T T G A T C A  800

GRVER51.SEQ  A G A A G C C T T C T T G A A G G C T A T T C A A G A C T A C G A G G T G C G T  840
GR6.SEQ      A G A A G C C T T C T T G A A G G C T A T T C A A G A C T A C G A G G T G C G T  840
GRVER5.SEQ   A G A A G C C T T C T T G A A G G C T A T T C A A G A C T A C G A G G T G C G T  840
GRVER4.SEQ   A G A A G C C T T C T T G A A G G C T A T T C A A G A C T A C G A G G T G C G T  840
GRVER3.SEQ   A G A A G C C T T C C T G A A G G C T A T T C A A G A C T A C G A G G T G C G T  840
GRVER2.SEQ   A G A A G C C T T T C T G A A G G C C A T T C A A G A C T A C G A G G T C C G T  840
GRVER1.SEQ   A G A A G C T T T T C T G A A G G C C A T T C A G G A C T A C G A G G T C C G T  840
YG81-6G1.SEQ A G A A G C A T T T C T A A A A G C T A T T C A G G A T T A T G A A G T T C G A  840
RDVER1.SEQ   G G A G G C C T T C T T G A A A G C T A T C C A A G A T T A T G A A G T G C G C  840
RDVER2.SEQ   G G A G G C T T T C T T G A A A G C T A T C C A A G A T T A T G A A G T G C G C  840
RDVER3.SEQ   G G A G G C T T T T T T G A A A G C C A T C C A A G A T T A T G A A G T C C G C  840
RDVER4.SEQ   G G A G G C T T T C T T G A A A G C C A T C C A A G A T T A T G A A G T C C G C  840
RDVER5.SEQ   G G A G G C T T T C T T G A A A G C C A T C C A A G A T T A T G A A G T C C G C  840
RD7.SEQ      G G A G G C T T T C T T G A A A G C C A T C C A A G A T T A T G A A G T C C G C  840
RDVER51.SEQ  G G A G G C T T T C T T G A A A G C C A T C C A A G A T T A T G A A G T C C G C  840
RDVER52.SEQ  G G A G G C T T T C T T G A A A G C C A T C C A A G A T T A T G A A G T C C G C  840
RD1561H9.SEQ G G A G G C T T T C T T G A A A G C C A T C C A A G A T T A T G A A G T C C G C  840
```

```
GRVER51.SEQ  A A T G T G G A G G C C A C T A A A G A A G C C A T T G A T G A T G A T G G C T 1240
GR6.SEQ      A A T G T G G A G G C C A C T A A A G A A G C C A T T G A T G A T G A T G G C T 1240
GRVER5.SEQ   A A T G T G G A G G C C A C T A A A G A A G C C A T T G A T G A T G A T G G C T 1240
GRVER4.SEQ   A A T G T G G A G G C C A C T A A A G A A G C C A T T G A T G A T G A T G G C T 1240
GRVER3.SEQ   A A T G T G G A G G C C A C T A A A G A A G C T A T T G A T G A T G A T G G T T 1240
GRVER2.SEQ   A A T G T G G A G G C C A C T A A G G A A G C T A T T G A T G A C G A T G G T T 1240
GRVER1.SEQ   A A T G T G G A G G C C A C T A A G G A A G C T A T C G A T G A C G A T G G T T 1240
YG81-6G1.SEQ A A T G T A G A A G C T A C C A A A G A A G C T A T T G A T G A T G A T G G T T 1240
RDVER1.SEQ   A A C G T C G A A G C T A C C A A A G A G G C C A T T G A C G A T G A C G G C T 1240
RDVER2.SEQ   A A C G T C G A A G C T A C C A A A G A G G C C A T C G A C G A T G A C G G C T 1240
RDVER3.SEQ   A A C G T C G A A G C T A C C A A G G A G G C C A T C G A C G A C G A C G G C T 1240
RDVER4.SEQ   A A C G T C G A A G C T A C C A A G G A G G C T A T C G A C G A C G A C G G C T 1240
RDVER5.SEQ   A A C G T C G A A G C T A C C A A G G A G G C C A T C G A C G A C G A C G G C T 1240
RD7.SEQ      A A C G T T G A A G C T A C C A A G G A G G C C A T C G A C G A C G A C G G C T 1240
RDVER51.SEQ  A A C G T T G A A G C T A C C A A G G A G G C C A T C G A C G A C G A C G G C T 1240
RDVER52.SEQ  A A C G T T G A A G C T A C C A A G G A G G C C A T C G A C G A C G A C G G C T 1240
RD1561H9.SEQ A A C G T T G A A G C T A C C A A G G A G G C C A T C G A C G A C G A C G G C T 1240

GRVER51.SEQ  G G C T C C A T A G C G G C G A C T T C G G T T A C T A T G A T G A G G A C G A 1280
GR6.SEQ      G G C T C C A T A G C G G C G A C T T C G G T T A C T A T G A T G A G G A C G A 1280
GRVER5.SEQ   G G C T C C A T A G C G G C G A C T T C G G T T A C T A T G A T G A G G A C G A 1280
GRVER4.SEQ   G G C T C C A T A G C G G C G A C T T C G G T T A C T A T G A T G A G G A C G A 1280
GRVER3.SEQ   G G T T G C A T A G C G G C G A C T T C G G T T A T T A T G A T G A G G A C G A 1280
GRVER2.SEQ   G G C T G C A C A G C G G C G A C T T T G G T T A T T A C G A T G A G G A C G A 1280
GRVER1.SEQ   G G C T G C A C A G C G G C G A C T T T G G T T A T T A C G A T G A G G A C G A 1280
YG81-6G1.SEQ G G C T T C A C T C T G G A G A C T T T G G A T A C T A T G A T G A G G A T G A 1280
RDVER1.SEQ   G G T T G C A T T C T G G T G A T T T C G G C T A C T A T G A C G A A G A T G A 1280
RDVER2.SEQ   G G T T G C A T T C T G G T G A T T T C G G C T A C T A T G A C G A A G A T G A 1280
RDVER3.SEQ   G G C T G C A T T C T G G T G A T T T T G G C T A C T A C G A C G A A G A T G A 1280
RDVER4.SEQ   G G T T G C A T T C T G G T G A T T T T G G A T A T T A C G A C G A A G A T G A 1280
RDVER5.SEQ   G G T T G C A T T C T G G T G A T T T T G G A T A T T A C G A C G A A G A T G A 1280
RD7.SEQ      G G T T G C A T T C T G G T G A T T T T G G A T A T T A C G A C G A A G A T G A 1280
RDVER51.SEQ  G G T T G C A T T C T G G T G A T T T T G G A T A T T A C G A C G A A G A T G A 1280
RDVER52.SEQ  G G T T G C A T T C T G G T G A T T T T G G A T A T T A C G A C G A A G A T G A 1280
RD1561H9.SEQ G T T T G C A T T C T G G T G A T T T T G G A T A T T A C G A C G A A G A T G A 1280

GRVER51.SEQ  A C A C T T C T A T G T G G T C G A T C G C T A C A A A G A A T T G A T T A A G 1320
GR6.SEQ      A C A C T T C T A T G T G G T C G A T C G C T A C A A A G A A T T G A T T A A G 1320
GRVER5.SEQ   A C A C T T C T A T G T G G T C G A T C G C T A C A A A G A A T T G A T T A A G 1320
GRVER4.SEQ   A C A C T T C T A T G T G G T C G A T C G C T A C A A A G A A T T G A T T A A G 1320
GRVER3.SEQ   A C A C T T C T A T G T G G T C G A T C G C T A T A A A G A A T T G A T T A A G 1320
GRVER2.SEQ   A C A T T T C T A T G T C G T C G A T C G C T A C A A A G A G T T G A T T A A G 1320
GRVER1.SEQ   A C A T T T C T A T G T C G T G G A T C G C T A C A A A G A G T T G A T T A A G 1320
YG81-6G1.SEQ G C A T T T C T A T G T G G T G G A C C G T T A C A A G G A A T T G A T T A A A 1320
RDVER1.SEQ   G C A C T T T T A C G T G G T C G A C C G T T A T A A G G A A C T G A T C A A A 1320
RDVER2.SEQ   G C A C T T T T A C G T G G T G G A C C G T T A T A A G G A A C T G A T C A A A 1320
RDVER3.SEQ   G C A T T T T T A C G T C G T G G A T C G T T A C A A G G A G C T G A T C A A A 1320
RDVER4.SEQ   G C A T T T T T A C G T C G T G G A T C G T T A C A A G G A G C T G A T C A A A 1320
RDVER5.SEQ   G C A T T T T T A C G T C G T G G A T C G T T A C A A G G A G C T G A T C A A A 1320
RD7.SEQ      G C A T T T T T A C G T C G T G G A T C G T T A C A A G G A G C T G A T C A A A 1320
RDVER51.SEQ  G C A T T T T T A C G T C G T G G A T C G T T A C A A G G A G C T G A T C A A A 1320
RDVER52.SEQ  G C A T T T T T A C G T C G T G G A T C G T T A C A A G G A G C T G A T C A A A 1320
RD1561H9.SEQ G C A T T T T T A C G T C G T G G A T C G T T A C A A G G A G C T G A T C A A A 1320
```

*FIG. 2K*

```
GRVER51.SEQ  T A C A A A G G C T C T C A A G T C G C A C C A G C C G A A C T G G A A G A A A  1360
GR6.SEQ      T A C A A A G G C T C T C A A G T C G C A C C A G C C G A A C T G G A A G A A A  1360
GRVER5.SEQ   T A C A A A G G C T C T C A A G T C G C A C C A G C C G A A C T G G A A G A A A  1360
GRVER4.SEQ   T A C A A A G G C T C T C A A G T C G C C C C A G C C G A A C T G G A A G A A A  1360
GRVER3.SEQ   T A C A A A G G C T C T C A A G T C G C C C C A G C T G A A C T G G A A G A A A  1360
GRVER2.SEQ   T A T A A A G G C T C T C A A G T C G C C C C A G C T G A G C T G G A A G A A A  1360
GRVER1.SEQ   T A T A A A G G C T C T C A G G T C G C C C C A G C T G A G C T G G A A G A G A  1360
YG81-6G1.SEQ T A T A A G G G C T C T C A G G T A G C A C C T G C A G A A C T A G A A G A G A  1360
RDVER1.SEQ   T A C A A G G G T A G C C A A G T G G C T C C T G C C G A A T T G G A G G A A A  1360
RDVER2.SEQ   T A C A A G G G T A G C C A A G T G G C T C C T G C C G A A T T G G A G G A G A  1360
RDVER3.SEQ   T A C A A G G G T A G C C A G G T G G C T C C A C C G A G T T G G A G G A G A  1360
RDVER4.SEQ   T A C A A G G G T A G C C A G G T T G C T C C A G C T G A G T T G G A G G A G A  1360
RDVER5.SEQ   T A C A A G G G T A G C C A G G T T G C T C C A G C T G A G T T G G A G G A G A  1360
RD7.SEQ      T A C A A G G G T A G C C A G G T T G C T C C A G C T G A G T T G G A G G A G A  1360
RDVER51.SEQ  T A C A A G G G T A G C C A G G T T G C T C C A G C T G A G T T G G A G G A G A  1360
RDVER52.SEQ  T A C A A G G G T A G C C A G G T T G C T C C A G C T G A G T T G G A G G A G A  1360
RD1561H9.SEQ T A C A A G G G T A G C C A G G T T G C T C C A G C T G A G T T G G A G G A G A  1360

GRVER51.SEQ  T T T T G C T G A A G A A C C C T T G T A T C C G C G A C G T G C C G T C G T  1400
GR6.SEQ      T T T T G C T G A A G A A C C C T T G T A T C C G C G A C G T G C C G T C G T  1400
GRVER5.SEQ   T T T T G C T G A A G A A C C C T T G T A T C C G C G A C G T G C C G T C G T  1400
GRVER4.SEQ   T T T T G C T G A A G A A C C C T T G T A T C C G C G A C G T G C C G T C G T  1400
GRVER3.SEQ   T T T T G C T G A A G A A C C C T T G T A T T C G C G A C G T G C C G T C G T  1400
GRVER2.SEQ   T C T T G C T G A A G A A C C C T T G C A T T C G T G A C G T G C C G T C G T  1400
GRVER1.SEQ   T C T T G C T G A A G A A C C C T T G C A T T C G T G A C G T G C C G T C G T  1400
YG81-6G1.SEQ T T T T A T T G A A A A A T C C A T G T A T C A G A G A T G T T G C T G T G G T  1400
RDVER1.SEQ   T T C T G T T G A A A A A T C C A T G T A T C C G C G A T G T C G C T G T G G T  1400
RDVER2.SEQ   T T C T G T T G A A A A A T C C A T G T A T C C G C G A T G T C G C T G T G G T  1400
RDVER3.SEQ   T T C T G T T G A A A A A T C C A T G C A T C C G T G A T G T C G C T G T G G T  1400
RDVER4.SEQ   T T C T G T T G A A A A A T C C A T G C A T T C G C G A T G T C G C T G T G G T  1400
RDVER5.SEQ   T T C T G T T G A A A A A T C C A T G C A T T C G C G A T G T C G C T G T G G T  1400
RD7.SEQ      T T C T G T T G A A A A A T C C A T G C A T T C G C G A T G T C G C T G T G G T  1400
RDVER51.SEQ  T T C T G T T G A A A A A T C C A T G C A T T C G C G A T G T C G C T G T G G T  1400
RDVER52.SEQ  T T C T G T T G A A A A A T C C A T G C A T T C G C G A T G T C G C T G T G G T  1400
RD1561H9.SEQ T T C T G T T G A A A A A T C C A T G C A T T C G C G A T G T C G C T G T G G T  1400

GRVER51.SEQ  G G G T A T C C C A G A C T T G G A A G C T G G C G A G T T G C C T A G C G C C  1440
GR6.SEQ      G G G T A T C C C A G A C T T G G A A G C T G G C G A G T T G C C T A G C G C C  1440
GRVER5.SEQ   G G G T A T C C C A G A C T T G G A A G C T G G C G A G T T G C C T A G C G C C  1440
GRVER4.SEQ   G G G T A T C C C A G A C T T G G A A G C T G G T G A G T T G C C T A G C G C C  1440
GRVER3.SEQ   G G G T A T C C C A G A C T T G G A A G C T G G C G A G T T G C C T A G C G C C  1440
GRVER2.SEQ   G G G T A T C C C A G A T T T G G A A G C T G G C G A G C T G C C T A G C G C C  1440
GRVER1.SEQ   G G G T A T C C C A G A T T T G G A A G C T G G C G A G C T G C C T A G C G C C  1440
YG81-6G1.SEQ G G T A T T C C T G A T C T A G A A G C T G G A G A A C T G C C A T C T G C G    1440
RDVER1.SEQ   C G G C A T T C C T G A C C T G G A G G C C G G T G A A T T G C C A T C T G C T  1440
RDVER2.SEQ   C G G C A T T C C T G A C C T G G A G G C C G G T G A A T T G C C A T C T G C T  1440
RDVER3.SEQ   C G G C A T T C C T G A T C T G G A G G C C G G T G A A C T G C C T T C T G C T  1440
RDVER4.SEQ   C G G C A T T C C T G A T C T G G A G G C C G G C G A A C T G C C T T C T G C T  1440
RDVER5.SEQ   C G G C A T T C C T G A T C T G G A G G C C G G C G A A C T G C C T T C T G C T  1440
RD7.SEQ      C G G C A T T C C T G A T C T G G A G G C C G G C G A A C T G C C T T C T G C T  1440
RDVER51.SEQ  C G G C A T T C C T G A T C T G G A G G C C G G C G A A C T G C C T T C T G C T  1440
RDVER52.SEQ  C G G C A T T C C T G A T C T G G A G G C C G G C G A A C T G C C T T C T G C T  1440
RD1561H9.SEQ C G G C A T T C C T G A T C T G G A G G C C G G C G A A C T G C C T T C T G C T  1440
```

```
GRVER51.SEQ   M M K R E K N V I Y G P E P L H P L E D L T A G E M L F R A L R K H S H L P Q A  118
GR6.SEQ       M M K R E K N V I Y G P E P L H P L E D L T A G E M L F R A L R K H S H L P Q A  118
GRVER5.SEQ    M M K R E K N V I Y G P E P L H P L E D L T A G E M L F R A L R K H S H L P Q A  118
GRVER4.SEQ    M M K R E K N V I Y G P E P L H P L E D L T A G E M L F R A L R K H S H L P Q A  118
GRVER3.SEQ    M M K R E K N V I Y G P E P L H P L E D L T A G E M L F R A L R K H S H L P Q A  118
GRVER2.SEQ    M M K R E K N V I Y G P E P L H P L E D L T A G E M L F R A L R K H S H L P Q A  118
GRVER1.SEQ    M M K R E K N V I Y G P E P L H P L E D L T A G E M L F R A L R K H S H L P Q A  118
YG81-6G1.SEQ  M M K R E K N V I Y G P E P L H P L E D L T A G E M L F R A L R K H S H L P Q A  118
RDVER1.SEQ    M M K R E K N V I Y G P E P L H P L E D L T A G E M L F R A L R K H S H L P Q A  118
RDVER2.SEQ    M M K R E K N V I Y G P E P L H P L E D L T A G E M L F R A L R K H S H L P Q A  118
RDVER3.SEQ    M M K R E K N V I Y G P E P L H P L E D L T A G E M L F R A L R K H S H L P Q A  118
RDVER4.SEQ    M M K R E K N V I Y G P E P L H P L E D L T A G E M L F R A L R K H S H L P Q A  118
RDVER5.SEQ    M M K R E K N V I Y G P E P L H P L E D L T A G E M L F R A L R K H S H L P Q A  118
RD7.SEQ       M M K R E K N V I Y G P E P L H P L E D L T A G E M L F R A L R K H S [Y] L P Q A  118
RDVER51.SEQ   M M K R E K N V I Y G P E P L H P L E D L T A G E M L F R A L R K H S H L P Q A  118
RDVER52.SEQ   M M K R E K N V I Y G P E P L H P L E D L T A G E M L F R A L R K H S H L P Q A  118
RD1561H9.SEQ  M [I] K R E K N V I Y G P E P L H P L E D L T A G E M L F R A L R K H S H L P Q A  118

GRVER51.SEQ   L V D V V G D E S L S Y K E F F E A T V L L A Q S L H N C G Y.K M N D V V S I C  238
GR6.SEQ       L V D V V G D E [N] L S Y K E F F E A T V L L A Q S L H N C G Y K M N D V V S I C  238
GRVER5.SEQ    L V D V V G D E S L S Y K E F F E A T V L L A Q S L H N C G Y K M N D V V S I C  238
GRVER4.SEQ    L V D V V G D E S L S Y K E F F E A T V L L A Q S L H N C G Y K M N D V V S I C  238
GRVER3.SEQ    L V D V V G D E S L S Y K E F F E A T V L L A Q S L H N C G Y K M N D V V S I C  238
GRVER2.SEQ    L V D V V G D E S L S Y K E F F E A T V L L A Q S L H N C G Y K M N D V V S I C  238
GRVER1.SEQ    L V D V V G D E S L S Y K E F F E A T V L L A Q S L H N C G Y K M N D V V S I C  238
YG81-6G1.SEQ  L V D V V G D E S L S Y K E F F E A T V L L A Q S L H N C G Y K M N D V V S I C  238
RDVER1.SEQ    L V D V V G D E S L S Y K E F F E A T V L L A Q S L H N C G Y K M N D V V S I C  238
RDVER2.SEQ    L V D V V G D E S L S Y K E F F E A T V L L A Q S L H N C G Y K M N D V V S I C  238
RDVER3.SEQ    L V D V V G D E S L S Y K E F F E A T V L L A Q S L H N C G Y K M N D V V S I C  238
RDVER4.SEQ    L V D V V G D E S L S Y K E F F E A T V L L A Q S L H N C G Y K M N D V V S I C  238
RDVER5.SEQ    L V D V V G·D E S L S Y K E F F E A T V L L A Q S L H N C G Y K M N D V V S I C  238
RD7.SEQ       L V D V V G D E S L S Y K E F F E A T V L L A Q S L H N C G Y K M N D V V S I C  238
RDVER51.SEQ   L V D V V G D E S L S Y K E F F E A T V L L A Q S L H N C G Y K M N D V V S I C  238
RDVER52.SEQ   L V D V V G D E S L S Y K E F F E A T V L L A Q S L H N C G Y K M N D V V S I C  238
RD1561H9.SEQ  L V D V V G D E S L S Y K E F F E A T V L L A Q S L H N C G Y K M N D V V S I C  238

GRVER51.SEQ   A E N N T R F F I P V I A A W Y I G M I V A P V N E S Y I P D E L C K V M G I S  358
GR6.SEQ       A E N N T R F F I P V I A A W Y I G M I V A P V N E S Y I P D E L C K V M G I S  358
GRVER5.SEQ    A E N N T R F F I P V I A A W Y I G M I V A P V N E S Y I P D E L C K V M G I S  358
GRVER4.SEQ    A E N N T R F F I P V I A A W Y I G M I V A P V N E S Y I P D E L C K V M G I S  358
GRVER3.SEQ    A E N N T R F F I P V I A A W Y I G M I V A P V N E S Y I P D E L C K V M G I S  358
GRVER2.SEQ    A E N N T R F F I P V I A A W Y I G M I V A P V N E S Y I P D E L C K V M G I S  358
GRVER1.SEQ    A E N N T R F F I P V I A A W Y I G M I V A P V N E S Y I P D E L C K V M G I S  358
YG81-6G1.SEQ  A E N N T R F F I P V I A A W Y I G M I V A P V N E S Y I P D E L C K V M G I S  358
RDVER1.SEQ    A E N N T R F F I P V I A A W Y I G M I V A P V N E S Y I P D E L C K V M G I S  358
RDVER2.SEQ    A E N N T R F F I P V I A A W Y I G M I V A P V N E S Y I P D E L C K V M G I S  358
RDVER3.SEQ    A E N N T R F F I P V I A A W Y I G M I V A P V N E S Y I P D E L C K V M G I S  358
RDVER4.SEQ    A E N N T R F F I P V I A A W Y I G M I V A P V N E S Y I P D E L C K V M G I S  358
RDVER5.SEQ    A E N N T R F F I P V I A A W Y I G M I V A P V N E S Y I P D E L C K V M G I S  358
RD7.SEQ       A E N N T R F·F I P V I A A W Y I G M I V A P V N E S Y I P D E L C K V M G I S  358
RDVER51.SEQ   A E N N T R F F I P V I A A W Y I G M I V A P V N E S Y I P D E L C K V M G I S  358
RDVER52.SEQ   A E N N T R F F I P V I A A W Y I G M I V A P V N E S Y I P D E L C K V M G I S  358
RD1561H9.SEQ  A E N N T R F F I P V I A A W Y I G M I V A P V N E S Y I P D E L C K V M G I S  358
```

*FIG. 3A*

```
GRVER51.SEQ  K P Q I V F T T K N I L N K V L E V Q S R T N F I K R I I I L D T V E N I H G C  478
GR6.SEQ      K P Q I V F T T K N I L N K V L E V Q S R T N F I K R I I I L D T V E N I H G C  478
GRVER5.SEQ   K P Q I V F T T K N I L N K V L E V Q S R T N F I K R I I I L D T V E N I H G C  478
GRVER4.SEQ   K P Q I V F T T K N I L N K V L E V Q S R T N F I K R I I I L D T V E N I H G C  478
GRVER3.SEQ   K P Q I V F T T K N I L N K V L E V Q S R T N F I K R I I I L D T V E N I H G C  478
GRVER2.SEQ   K P Q I V F T T K N I L N K V L E V Q S R T N F I K R I I I L D T V E N I H G C  478
GRVER1.SEQ   K P Q I V F T T K N I L N K V L E V Q S R T N F I K R I I I L D T V E N I H G C  478
YG81-6G1.SEQ K P Q I V F T T K N I L N K V L E V Q S R T N F I K R I I I L D T V E N I H G C  478
RDVER1.SEQ   K P Q I V F T T K N I L N K V L E V Q S R T N F I K R I I I L D T V E N I H G C  478
RDVER2.SEQ   K P Q I V F T T K N I L N K V L E V Q S R T N F I K R I I I L D T V E N I H G C  478
RDVER3.SEQ   K P Q I V F T T K N I L N K V L E V Q S R T N F I K R I I I L D T V E N I H G C  478
RDVER4.SEQ   K P Q I V F T T K N I L N K V L E V Q S R T N F I K R I I I L D T V E N I H G C  478
RDVER5.SEQ   K P Q I V F T T K N I L N K V L E V Q S R T N F I K R I I I L D T V E N I H G C  478
RD7.SEQ      K P Q I V F T T K N I L N K V L E V Q S R T N F I K R I I I L D T V E N I H G C  478
RDVER51.SEQ  K P Q I V F T T K N I L N K V L E V Q S R T N F I K R I I I L D T V E N I H G C  478
RDVER52.SEQ  K P Q I V F T T K N I L N K V L E V Q S R T N F I K R I I I L D T V E N I H G C  478
RD1561H9.SEQ K P Q I V F T T K N I L N K V L E V Q S R T N F I K R I I I L D T V E N I H G C  478

GRVER51.SEQ  E S L P N F I S R Y S D G N I A N F K P L H F D P V E Q V A A I L C S S G T T G  598
GR6.SEQ      E S L P N F I S R Y S D G N I A N F K P L H F D P V E Q V A A I L C S S G T T G  598
GRVER5.SEQ   E S L P N F I S R Y S D G N I A N F K P L H F D P V E Q V A A I L C S S G T T G  598
GRVER4.SEQ   E S L P N F I S R Y S D G N I A N F K P L H F D P V E Q V A A I L C S S G T T G  598
GRVER3.SEQ   E S L P N F I S R Y S D G N I A N F K P L H F D P V E Q V A A I L C S S G T T G  598
GRVER2.SEQ   E S L P N F I S R Y S D G N I A N F K P L H F D P V E Q V A A I L C S S G T T G  598
GRVER1.SEQ   E S L P N F I S R Y S D G N I A N F K P L H F D P V E Q V A A I L C S S G T T G  598
YG81-6G1.SEQ E S L P N F I S R Y S D G N I A N F K P L H F D P V E Q V A A I L C S S G T T G  598
RDVER1.SEQ   E S L P N F I S R Y S D G N I A N F K P L H F D P V E Q V A A I L C S S G T T G  598
RDVER2.SEQ   E S L P N F I S R Y S D G N I A N F K P L H F D P V E Q V A A I L C S S G T T G  598
RDVER3.SEQ   E S L P N F I S R Y S D G N I A N F K P L H F D P V E Q V A A I L C S S G T T G  598
RDVER4.SEQ   E S L P N F I S R Y S D G N I A N F K P L H F D P V E Q V A A I L C S S G T T G  598
RDVER5.SEQ   E S L P N F I S R Y S D G N I A N F K P L H F D P V E Q V A A I L C S S G T T G  598
RD7.SEQ      E S L P N F I S R Y S D G N I A N F K P L H F D P V E Q V A A I L C S S G T T G  598
RDVER51.SEQ  E S L P N F I S R Y S D G N I A N F K P L H F D P V E Q V A A I L C S S G T T G  598
RDVER52.SEQ  E S L P N F I S R Y S D G N I A N F K P L H F D P V E Q V A A I L C S S G T T G  598
RD1561H9.SEQ E S L P N F I S R Y S D G N I A N F K P L H F D P V E Q V A A I L C S S G T T G  598

GRVER51.SEQ  L P K G V M Q T H Q N I C V R L I H A L D P R V G T Q L I P G V T V L V Y L P F  718
GR6.SEQ      L P K G V M Q T H Q N I C V R L I H A L D P R V G T Q L I S G V T V L V Y L P F  718
GRVER5.SEQ   L P K G V M Q T H Q N I C V R L I H A L D P R V G T Q L I P G V T V L V Y L P F  718
GRVER4.SEQ   L P K G V M Q T H Q N I C V R L I H A L D P R V G T Q L I P G V T V L V Y L P F  718
GRVER3.SEQ   L P K G V M Q T H Q N I C V R L I H A L D P R V G T Q L I P G V T V L V Y L P F  718
GRVER2.SEQ   L P K G V M Q T H Q N I C V R L I H A L D P R V G T Q L I P G V T V L V Y L P F  718
GRVER1.SEQ   L P K G V M Q T H Q N I C V R L I H A L D P R V G T Q L I P G V T V L V Y L P F  718
YG81-6G1.SEQ L P K G V M Q T H Q N I C V R L I H A L D P R A G T Q L I P G V T V L V Y L P F  718
RDVER1.SEQ   L P K G V M Q T H Q N I C V R L I H A L D P R Y G T Q L I P G V T V L V Y L P F  718
RDVER2.SEQ   L P K G V M Q T H Q N I C V R L I H A L D P R Y G T Q L I P G V T V L V Y L P F  718
RDVER3.SEQ   L P K G V M Q T H Q N I C V R L I H A L D P R Y G T Q L I P G V T V L V Y L P F  718
RDVER4.SEQ   L P K G V M Q T H Q N I C V R L I H A L D P R Y G T Q L I P G V T V L V Y L P F  718
RDVER5.SEQ   L P K G V M Q T H Q N I C V R L I H A L D P R Y G T Q L I P G V T V L V Y L P F  718
RD7.SEQ      L P K G V M Q T H Q N I C V R L I H A L D P R Y G T Q L I P G V T V L V Y L P F  718
RDVER51.SEQ  L P K G V M Q T H Q N I C V R L I H A L D P R Y G T Q L I P G V T V L V Y L P F  718
RDVER52.SEQ  L P K G V M Q T H Q N I C V R L I H A L D P R Y G T Q L I P G V T V L V Y L P F  718
RD1561H9.SEQ L P K G V M Q T H Q N I C V R L I H A L D P R Y G T Q L I P G V T V L V Y L P F  718
```

*FIG. 3B*

```
GRVER51.SEQ  F H A F G F S I T L G Y F M V G L R V I M F R R F D Q E A F L K A I Q D Y E V R  838
GR6.SEQ      F H A F G F S I T L G Y F M V G L R V I M F R R F D Q E A F L K A I Q D Y E V R  838
GRVER5.SEQ   F H A F G F S I T L G Y F M V G L R V I M F R R F D Q E A F L K A I Q D Y E V R  838
GRVER4.SEQ   F H A F G F S I T L G Y F M V G L R V I M F R R F D Q E A F L K A I Q D Y E V R  838
GRVER3.SEQ   F H A F G F S I T L G Y F M V G L R V I M F R R F D Q E A F L K A I Q D Y E V R  838
GRVER2.SEQ   F H A F G F S I T L G Y F M V G L R V I M F R R F D Q E A F L K A I Q D Y E V R  838
GRVER1.SEQ   F H A F G F S I T L G Y F M V G L R V I M F R R F D Q E A F L K A I Q D Y E V R  838
YG81-6G1.SEQ F H A F G F S I T L G Y F M V G L R V I M F R R F D Q E A F L K A I Q D Y E V R  838
RDVER1.SEQ   F H A F G F H I T L G Y F M V G L R V I M F R R F D Q E A F L K A I Q D Y E V R  838
RDVER2.SEQ   F H A F G F H I T L G Y F M V G L R V I M F R R F D Q E A F L K A I Q D Y E V R  838
RDVER3.SEQ   F H A F G F H I T L G Y F M V G L R V I M F R R F D Q E A F L K A I Q D Y E V R  838
RDVER4.SEQ   F H A F G F H I T L G Y F M V G L R V I M F R R F D Q E A F L K A I Q D Y E V R  838
RDVER5.SEQ   F H A F G F H I T L G Y F M V G L R V I M F R R F D Q E A F L K A I Q D Y E V R  838
RD7.SEQ      F H A F G F H I T L G Y F M V G L R V I M F R R F D Q E A F L K A I Q D Y E V R  838
RDVER51.SEQ  F H A F G F H I T L G Y F M V G L R V I M F R R F D Q E A F L K A I Q D Y E V R  838
RDVER52.SEQ  F H A F G F H I T L G Y F M V G L R V I M F R R F D Q E A F L K A I Q D Y E V R  838
RD1561H9.SEQ F H A F G F H I T L G Y F M V G L R V I M F R R F D Q E A F L K A I Q D Y E V R  838

GRVER51.SEQ  S V I N V P S V I L F L S K S P L V D K Y D L S S L R E L C C G A A P L A K E V  958
GR6.SEQ      S V I N V P S V I L F L S K S P L V D K Y D L S S L R E L C C G A A P L A K E V  958
GRVER5.SEQ   S V I N V P S V I L F L S K S P L V D K Y D L S S L R E L C C G A A P L A K E V  958
GRVER4.SEQ   S V I N V P S V I L F L S K S P L V D K Y D L S S L R E L C C G A A P L A K E V  958
GRVER3.SEQ   S V I N V P S V I L F L S K S P L V D K Y D L S S L R E L C C G A A P L A K E V  958
GRVER2.SEQ   S V I N V P S V I L F L S K S P L V D K Y D L S S L R E L C C G A A P L A K E V  958
GRVER1.SEQ   S V I N V P S V I L F L S K S P L V D K Y D L S S L R E L C C G A A P L A K E V  958
YG81-6G1.SEQ S V I N V P S V I L F L S K S P L V D K Y D L S S L R E L C C G A A P L A K E V  958
RDVER1.SEQ   S V I N V P S V I L F L S K S P L V D K Y D L S S L R E L C C G A A P L A K E V  958
RDVER2.SEQ   S V I N V P S V I L F L S K S P L V D K Y D L S S L R E L C C G A A P L A K E V  958
RDVER3.SEQ   S V I N V P S V I L F L S K S P L V D K Y D L S S L R E L C C G A A P L A K E V  958
RDVER4.SEQ   S V I N V P S V I L F L S K S P L V D K Y D L S S L R E L C C G A A P L A K E V  958
RDVER5.SEQ   S V I N V P S V I L F L S K S P L V D K Y D L S S L R E L C C G A A P L A K E V  958
RD7.SEQ      S V I N V P S V I L F L S K S P L V D K Y D L S S L R E L C C G A A P L A K E V  958
RDVER51.SEQ  S V I N V P S V I L F L S K S P L V D K Y D L S S L R E L C C G A A P L A K E V  958
RDVER52.SEQ  S V I N V P S V I L F L S K S P L V D K Y D L S S L R E L C C G A A P L A K E V  958
RD1561H9.SEQ S V I N V P S V I L F L S K S P L V D K Y D L S S L R E L C C G A A P L A K E V  958

GRVER51.SEQ  A E V A A K R L N L P G I R C G F G L T E S T S A N I H S L R D E F K S G S L G  1078
GR6.SEQ      A E V A A K R L N L P G I R C G F G L T E S T S A N I H S L R D E F K S G S L G  1078
GRVER5.SEQ   A E V A A K R L N L P G I R C G F G L T E S T S A N I H S L R D E F K S G S L G  1078
GRVER4.SEQ   A E V A A K R L N L P G I R C G F G L T E S T S A N I H S L R D E F K S G S L G  1078
GRVER3.SEQ   A E V A A K R L N L P G I R C G F G L T E S T S A N I H S L R D E F K S G S L G  1078
GRVER2.SEQ   A E V A A K R L N L P G I R C G F G L T E S T S A N I H S L R D E F K S G S L G  1078
GRVER1.SEQ   A E V A A K R L N L P G I R C G F G L T E S T S A N I H S L R D E F K S G S L G  1078
YG81-6G1.SEQ A E V A A K R L N L P G I R C G F G L T E S T S A N I H S L R D E F K S G S L G  1078
RDVER1.SEQ   A E V A A K R L N L P G I R C G F G L T E S T S A I I Q S L R D E F K S G S L G  1078
RDVER2.SEQ   A E V A A K R L N L P G I R C G F G L T E S T S A I I Q S L R D E F K S G S L G  1078
RDVER3.SEQ   A E V A A K R L N L P G I R C G F G L T E S T S A I I Q S L R D E F K S G S L G  1078
RDVER4.SEQ   A E V A A K R L N L P G I R C G F G L T E S T S A I I Q S L R D E F K S G S L G  1078
RDVER5.SEQ   A E V A A K R L N L P G I R C G F G L T E S T S A I I Q S L R D E F K S G S L G  1078
RD7.SEQ      A E V A A K R L N L P G I R C G F G L T E S T S A I I Q S L R D E F K S G S L G  1078
RDVER51.SEQ  A E V A A K R L N L P G I R C G F G L T E S T S A I I Q S L R D E F K S G S L G  1078
RDVER52.SEQ  A E V A A K R L N L P G I R C G F G L T E S T S A I I Q S L G D E F K S G S L G  1078
RD1561H9.SEQ A E V A A K R L N L P G I R C G F G L T E S T S A I I Q T L G D E F K S G S L G  1078
```

*FIG. 3C*

```
GRVER51.SEQ  R V T P L M A A K I A D R E T G K A L G P N Q V G E L C I K G P M V S K G Y V N  1198
GR6.SEQ      R V T P L M A A K I A D R E T G K A L G P N Q V G E L C I K G P M V S K G Y V N  1198
GRVER5.SEQ   R V T P L M A A K I A D R E T G K A L G P N Q V G E L C I K G P M V S K G Y V N  1198
GRVER4.SEQ   R V T P L M A A K I A D R E T G K A L G P N Q V G E L C I K G P M V S K G Y V N  1198
GRVER3.SEQ   R V T P L M A A K I A D R E T G K A L G P N Q V G E L C I K G P M V S K G Y V N  1198
GRVER2.SEQ   R V T P L M A A K I A D R E T G K A L G P N Q V G E L C I K G P M V S K G Y V N  1198
GRVER1.SEQ   R V T P L M A A K I A D R E T G K A L G P N Q V G E L C I K G P M V S K G Y V N  1198
YG81-6G1.SEQ R V T P L M A A K I A D R E T G K A L G P N Q V G E L C I K G P M V S K G Y V N  1198
RDVER1.SEQ   R V T P L M A A K I A D R E T G K A L G P N Q V G E L C I K G P M V S K G Y V N  1198
RDVER2.SEQ   R V T P L M A A K I A D R E T G K A L G P N Q V G E L C I K G P M V S K G Y V N  1198
RDVER3.SEQ   R V T P L M A A K I A D R E T G K A L G P N Q V G E L C I K G P M V S K G Y V N  1198
RDVER4.SEQ   R V T P L M A A K I A D R E T G K A L G P N Q V G E L C I K G P M V S K G Y V N  1198
RDVER5.SEQ   R V T P L M A A K I A D R E T G K A L G P N Q V G E L C I K G P M V S K G Y V N  1198
RD7.SEQ      R V T P L M A A K I A D R E T G K A L G P N Q V G E L C I K G P M V S K G Y V N  1198
RDVER51.SEQ  R V T P L M A A K I A D R E T G K A L G P N Q V G E L C I K G P M V S K G Y V N  1198
RDVER52.SEQ  R V T P L M A A K I A D R E T G K A L G P N Q V G E L C I K G P M V S K G Y V N  1198
RD1561H9.SEQ R V T P L M A A K I A D R E T G K A L G P N Q V G E L C I K G P M V S K G Y V N  1198

GRVER51.SEQ  N V E A T K E A I D D D G W L H S G D F G Y Y D E D E H F Y V.V D R Y K E L I K  1318
GR6.SEQ      N V E A T K E A I D D D G W L H S G D F G Y Y D E D E H F Y V V D R Y K E L I K  1318
GRVER5.SEQ   N V E A T K E A I D D D G W L H S G D F G Y Y D E D E H F Y V V D R Y K E L I K  1318
GRVER4.SEQ   N V E A T K E A I D D D G W L H S G D F G Y Y D E D E H F Y V V D R Y K E L I K  1318
GRVER3.SEQ   N V E A T K E A I D D D G W L H S G D F G Y Y D E D E H F Y V V D R Y K E L I K  1318
GRVER2.SEQ   N V E A T K E A I D D D G W L H S G D F G Y Y D E D E H F Y V V D R Y K E L I K  1318
GRVER1.SEQ   N V E A T K E A I D D D G W L H S G D F G Y Y D E D E H F Y V V D R Y K E L I K  1318
YG81-6G1.SEQ N V E A T K E A I D D D G W L H S G D F G Y Y D E D E H F Y V V D R Y K E L I K  1318
RDVER1.SEQ   N V E A T K E A I D D D G W L H S G D F G Y Y D E D E H F Y V V D R Y K E L I K  1318
RDVER2.SEQ   N V E A T K E A I D D D G W L H S G D F G Y Y D E D E H F Y V V D R Y K E L I K  1318
RDVER3.SEQ   N V E A T K E A I D D D G W L H S G D F G Y Y D E D E H F Y V V D R Y K E L I K  1318
RDVER4.SEQ   N V E A T K E A I D D D G W L H S G D F G Y Y D E D E H F Y V V D R Y K E L I K  1318
RDVER5.SEQ   N V E A T K E A I D D D G W L H S G D F G Y Y D E D E H F Y V V D R Y K E L I K  1318
RD7.SEQ      N V E A T K E A I D D D G W L H S G D F G Y Y D E D E H F Y V V D R Y K E L I K  1318
RDVER51.SEQ  N V E A T K E A I D D D G W L H S G D F G Y Y D E D E H F Y V V D R Y K E L I K  1318
RDVER52.SEQ  N V E A T K E A I D D D G W L H S G D F G Y Y D E D E H F Y V V D R Y K E L I K  1318
RD1561H9.SEQ N V E A T K E A I D D D G W L H S G D F G Y Y D E D E H F Y V V D R Y K E L I K  1318

GRVER51.SEQ  Y K G S Q V A P A E L E E I L L K N P C I R D V A V V G I P D L E A G E L P S A  1438
GR6.SEQ      Y K G S Q V A P A E L E E I L L K N P C I R D V A V V G I P D L E A G E L P S A  1438
GRVER5.SEQ   Y K G S Q V A P A E L E E I L L K N P C I R D V A V V G I P D L E A G E L P S A  1438
GRVER4.SEQ   Y K G S Q V A P A E L E E I L L K N P C I R D V A V V G I P D L E A G E L P S A  1438
GRVER3.SEQ   Y K G S Q V A P A E L E E I L L K N P C I R D V A V V G I P D L E A G E L P S A  1438
GRVER2.SEQ   Y K G S Q V A P A E L E E I L L K N P C I R D V A V V G I P D L E A G E L P S A  1438
GRVER1.SEQ   Y K G S Q V A P A E L E E I L L K N P C I R D V A V V G I P D L E A G E L P S A  1438
YG81-6G1.SEQ Y K G S Q V A P A E L E E I L L K N P C I R D V A V V G I P D L E A G E L P S A  1438
RDVER1.SEQ   Y K G S Q V A P A E L E E I L L K N P C I R D V A V V G I P D L E A G E L P S A  1438
RDVER2.SEQ   Y K G S Q V A P A E L E E I L L K N P C I R D V A V V G I P D L E A G E L P S A  1438
RDVER3.SEQ   Y K G S Q V A P A E L E E I L L K N P C I R D V A V V G I P D L E A G E L P S A  1438
RDVER4.SEQ   Y K G S Q V A P A E L E E I L L K N P C I R D V A V V G I P D L E A G E L P S A  1438
RDVER5.SEQ   Y K G S Q V A P A E L E E I L L K N P C I R D V A V V G I P D L E A G E L P S A  1438
RD7.SEQ      Y K G S Q V A P A E L E E I L L K N P C I R D V A V V G I P D L E A G E L P S A  1438
RDVER51.SEQ  Y K G S Q V A P A E L E E I L L K N P C I R D V A V V G I P D L E A G E L P S A  1438
RDVER52.SEQ  Y K G S Q V A P A E L E E I L L K N P C I R D V A V V G I P D L E A G E L P S A  1438
RD1561H9.SEQ Y K G S Q V A P A E L E E I L L K N P C I R D V A V V G I P D L E A G E L P S A  1438
```

*FIG. 3D*

```
GRVER51.SEQ    F V V K Q P G K E I T A K E V Y D Y L A E R V S H T K Y L R G G V R F V D S I P  1558
GR6.SEQ        F V V K Q P G K E I T A K E V Y D Y L A E R V S H T K Y L R G G V R F V D S I P  1558
GRVER5.SEQ     F V V K Q P G K E I T A K E V Y D Y L A E R V S H T K Y L R G G V R F V D S I P  1558
GRVER4.SEQ     F V V K Q P G K E I T A K E V Y D Y L A E R V S H T K Y L R G G V R F V D S I P  1558
GRVER3.SEQ     F V V K Q P G K E I T A K E V Y D Y L A E R V S H T K Y L R G G V R F V D S I P  1558
GRVER2.SEQ     F V V K Q P G K E I T A K E V Y D Y L A E R V S H T K Y L R G G V R F V D S I P  1558
GRVER1.SEQ     F V V K Q P G K E I T A K E V Y D Y L A E R V S H T K Y L R G G V R F V D S I P  1558
YG81-6G1.SEQ   F V V K Q P G K E I T A K E V Y D Y L A E R V S H T K Y L R G G V R F V D S I P  1558
RDVER1.SEQ     F V V K Q P G K E I T A K E V Y D Y L A E R V S H T K Y L R G G V R F V D S I P  1558
RDVER2.SEQ     F V V K Q P G K E I T A K E V Y D Y L A E R V S H T K Y L R G G V R F V D S I P  1558
RDVER3.SEQ     F V V K Q P G K E I T A K E V Y D Y L A E R V S H T K Y L R G G V R F V D S I P  1558
RDVER4.SEQ     F V V K Q P G K E I T A K E V Y D Y L A E R V S H T K Y L R G G V R F V D S I P  1558
RDVER5.SEQ     F V V K Q P G K E I T A K E V Y D Y L A E R V S H T K Y L R G G V R F V D S I P  1558
RD7.SEQ        F V V K Q P G K E I T A K E V Y D Y L A E R V S H T K Y L R G G V R F V D S I P  1558
RDVER51.SEQ    F V V K Q P G K E I T A K E V Y D Y L A E R V S H T K Y L R G G V R F V D S I P  1558
RDVER52.SEQ    F V V K Q P G K E I T A K E V Y D Y L A E R V S H T K Y L R G G V R F V D S I P  1558
RD1561H9.SEQ   F V V K Q P G [T] E I T A K E V Y D Y L A E R V S H T K Y L R G G V R F V D S I P  1558

GRVER51.SEQ    R N V T G K I T R K E L L K Q L L E K A G G  1624
GR6.SEQ        R N V T G K I T R K E L L K Q L L E K A G G  1624
GRVER5.SEQ     R N V T G K I T R K E L L K Q L L E K A G G  1624
GRVER4.SEQ     R N V T G K I T R K E L L K Q L L E K A G G  1624
GRVER3.SEQ     R N V T G K I T R K E L L K Q L L E K A G G  1624
GRVER2.SEQ     R N V T G K I T R K E L L K Q L L E K A G G  1624
GRVER1.SEQ     R N V T G K I T R K E L L K Q L L E K A G G  1624
YG81-6G1.SEQ   R N V T G K I T R K E L L K Q L L E K A G G  1624
RDVER1.SEQ     R N V T G K I T R K E L L K Q L L E K A G G  1624
RDVER2.SEQ     R N V T G K I T R K E L L K Q L L E K A G G  1624
RDVER3.SEQ     R N V T G K I T R K E L L K Q L L E K A G G  1624
RDVER4.SEQ     R N V T G K I T R K E L L K Q L L E K A G G  1624
RDVER5.SEQ     R N V T G K I T R K E L L K Q L L E K A G G  1624
RD7.SEQ        R N V T G K I T R K E L L K Q L L E K A G G  1624
RDVER51.SEQ    R N V T G K I T R K E L L K Q L L E K A G G  1624
RDVER52.SEQ    R N V T G K I T R K E L L K Q L L E K A G G  1624
RD1561H9.SEQ   R N V T G K I T R K E L L K Q L L [V] K A G G  1624
```

*FIG. 3E* per SdT total codons

| | YG881-6O | ver1 GR | ver1 RD | ver5 GR | ver5 RD | HUM |
|---|---|---|---|---|---|---|
| CGA | 7 | 0 | 0 | 2 | 0 | 3 |
| CGC | 1 | 13 | 13 | 11 | 12 | 6 |
| CGG | 0 | 0 | 0 | 0 | 0 | 6 |
| CGT | 5 | 13 | 13 | 13 | 14 | 3 |
| AGA | 6 | 0 | 0 | 0 | 0 | 5 |
| Arg AGG | 7 | 0 | 0 | 0 | 0 | 6 |
| CTA | 5 | 0 | 0 | 0 | 0 | 3 |
| CTC | 4 | 0 | 1 | 12 | 11 | 11 |
| CTG | 4 | 28 | 27 | 19 | 18 | 23 |
| CTT | 12 | 0 | 0 | 1 | 1 | 6 |
| TTA | 17 | 0 | 0 | 0 | 0 | 3 |
| Leu TTG | 13 | 27 | 27 | 23 | 25 | 6 |
| TCA | 6 | 0 | 0 | 1 | 2 | 5 |
| TCC | 2 | 0 | 0 | 4 | 2 | 10 |
| TCG | 7 | 0 | 0 | 0 | 0 | 2 |
| TCT | 7 | 16 | 15 | 11 | 12 | 7 |
| AGC | 2 | 15 | 15 | 14 | 12 | 10 |
| Ser AGT | 7 | 0 | 0 | 1 | 2 | 5 |
| ACA | 10 | 0 | 0 | 0 | 1 | 8 |
| ACC | 2 | 11 | 11 | 8 | 11 | 12 |
| ACG | 2 | 0 | 0 | 0 | 0 | 4 |
| Thr ACT | 8 | 11 | 11 | 14 | 10 | 7 |
| CCA | 9 | 14 | 14 | 9 | 12 | 8 |
| CCC | 8 | 0 | 0 | 2 | 1 | 11 |
| CCG | 2 | 0 | 0 | 0 | 0 | 4 |
| Pro CCT | 9 | 14 | 14 | 17 | 15 | 8 |
| GCA | 14 | 0 | 0 | 5 | 4 | 8 |
| GCC | 4 | 19 | 18 | 14 | 12 | 16 |
| GCG | 5 | 0 | 0 | 0 | 0 | 4 |
| Ala GCT | 15 | 18 | 19 | 18 | 21 | 11 |
| GGA | 18 | 0 | 0 | 1 | 3 | 9 |
| GGC | 3 | 20 | 19 | 21 | 21 | 14 |
| GGG | 2 | 0 | 0 | 1 | 1 | 9 |
| Gly GGT | 16 | 19 | 20 | 16 | 14 | 6 |
| GTA | 13 | 0 | 0 | 1 | 1 | 3 |
| GTC | 4 | 25 | 24 | 21 | 26 | 9 |
| GTG | 12 | 25 | 25 | 25 | 17 | 17 |
| Val GTT | 20 | 0 | 0 | 3 | 5 | 6 |
| AAA | 23 | 17 | 18 | 19 | 13 | 12 |
| Lys AAG | 12 | 18 | 17 | 16 | 22 | 19 |
| AAC | 6 | 11 | 11 | 13 | 12 | 12 |
| Asn AAT | 16 | 11 | 10 | 9 | 9 | 9 |
| CAA | 8 | 7 | 8 | 11 | 7 | 6 |
| Gln CAG | 6 | 7 | 7 | 3 | 8 | 18 |
| CAC | 6 | 7 | 6 | 7 | 4 | 8 |
| His CAT | 7 | 6 | 7 | 6 | 9 | 5 |
| GAA | 26 | 19 | 19 | 19 | 18 | 15 |
| Glu GAG | 12 | 19 | 19 | 19 | 20 | 22 |
| GAC | 6 | 13 | 13 | 14 | 12 | 16 |
| Asp GAT | 20 | 13 | 13 | 12 | 14 | 12 |
| TAC | 8 | 10 | 10 | 12 | 13 | 10 |
| Tyr TAT | 11 | 9 | 10 | 7 | 7 | 7 |
| TGC | 3 | 6 | 5 | 3 | 4 | 8 |
| Cys TGT | 8 | 5 | 6 | 4 | 7 | 5 |
| TTC | 11 | 13 | 12 | 15 | 12 | 12 |
| Phe TTT | 14 | 12 | 13 | 10 | 13 | 9 |
| ATA | 12 | 0 | 0 | 0 | 0 | 3 |
| ATC | 7 | 19 | 19 | 23 | 20 | 13 |
| Ile ATT | 19 | 19 | 20 | 15 | 19 | 8 |
| Met ATG | 11 | 11 | 11 | 11 | 11 | 12 |
| Trp TGG | 2 | 2 | 2 | 2 | 2 | 7 | relative codon usage for each aa (*100)

| | YG881-6O | ver5 GR | ver5 RD | HUM |
|---|---|---|---|---|
| CGA | 27 | 8 | 0 | 10 |
| CGC | 4 | 42 | 46 | 21 |
| CGG | 0 | 0 | 0 | 19 |
| CGT | 19 | 50 | 54 | 9 |
| AGA | 23 | 0 | 0 | 19 |
| Arg AGG | 27 | 0 | 0 | 21 |
| CTA | 9 | 0 | 0 | 6 |
| CTC | 7 | 22 | 20 | 21 |
| CTG | 7 | 35 | 33 | 44 |
| CTT | 22 | 2 | 2 | 11 |
| TTA | 31 | 0 | 0 | 6 |
| Leu TTG | 24 | 42 | 45 | 11 |
| TCA | 19 | 3 | 7 | 13 |
| TCC | 6 | 13 | 7 | 25 |
| TCG | 23 | 0 | 0 | 6 |
| TCT | 23 | 35 | 40 | 18 |
| AGC | 6 | 45 | 40 | 26 |
| Ser AGT | 23 | 3 | 7 | 13 |
| ACA | 45 | 0 | 5 | 25 |
| ACC | 9 | 36 | 50 | 40 |
| ACG | 9 | 0 | 0 | 12 |
| Thr ACT | 36 | 64 | 45 | 22 |
| CCA | 32 | 32 | 43 | 26 |
| CCC | 29 | 7 | 4 | 35 |
| CCG | 7 | 0 | 0 | 12 |
| Pro CCT | 32 | 61 | 54 | 27 |
| GCA | 37 | 13 | 11 | 19 |
| GCC | 11 | 37 | 32 | 40 |
| GCG | 13 | 0 | 0 | 10 |
| Ala GCT | 39 | 47 | 55 | 27 |
| GGA | 46 | 3 | 8 | 24 |
| GGC | 8 | 54 | 54 | 36 |
| GGG | 5 | 3 | 3 | 25 |
| Gly GGT | 41 | 41 | 36 | 16 |
| GTA | 27 | 2 | 2 | 9 |
| GTC | 8 | 42 | 53 | 25 |
| GTG | 24 | 50 | 35 | 48 |
| Val GTT | 41 | 6 | 10 | 16 |
| AAA | 66 | 54 | 37 | 39 |
| Lys AAG | 34 | 46 | 63 | 61 |
| AAC | 27 | 59 | 57 | 58 |
| Asn AAT | 73 | 41 | 43 | 43 |
| CAA | 57 | 79 | 47 | 25 |
| Gln CAG | 43 | 21 | 53 | 76 |
| CAC | 46 | 54 | 31 | 59 |
| His CAT | 54 | 46 | 69 | 39 |
| GAA | 68 | 50 | 47 | 39 |
| Glu GAG | 32 | 50 | 53 | 61 |
| GAC | 23 | 54 | 46 | 56 |
| Asp GAT | 77 | 46 | 54 | 42 |
| TAC | 42 | 63 | 65 | 60 |
| Tyr TAT | 58 | 37 | 35 | 40 |
| TGC | 27 | 27 | 36 | 60 |
| Cys TGT | 73 | 73 | 64 | 41 |
| TTC | 44 | 60 | 48 | 58 |
| Phe TTT | 56 | 40 | 52 | 41 |
| ATA | 32 | 0 | 0 | 13 |
| ATC | 18 | 61 | 51 | 55 |
| Ile ATT | 50 | 39 | 49 | 34 |
| Met ATG | 100 | 100 | 100 | 100 |
| Trp TGG | 100 | 100 | 100 | 100 |

*FIG. 4*

Codon Usage  YG#81-6G01  (yellow-green)

| | | | | | | | |
|---|---|---|---|---|---|---|---|
| TTT Phe | 14 | TCT Ser | 7 | TAT Tyr | 11 | TGT Cys | 8 |
| TTC Phe | 11 | TCC Ser | 2 | TAC Tyr | 8 | TGC Cys | 3 |
| TTA Leu | 17 | TCA Ser | 6 | TAA *** | 0 | TGA *** | 0 |
| TTG Leu | 13 | TCG Ser | 7 | TAG *** | 0 | TGG Trp | 2 |
| CTT Leu | 12 | CCT Pro | 9 | CAT His | 7 | CGT Arg | 5 |
| CTC Leu | 4 | CCC Pro | 8 | CAC His | 6 | CGC Arg | 1 |
| CTA Leu | 5 | CCA Pro | 9 | CAA Gln | 8 | CGA Arg | 7 |
| CTG Leu | 4 | CCG Pro | 2 | CAG Gln | 6 | CGG Arg | 0 |
| ATT Ile | 19 | ACT Thr | 8 | AAT Asn | 16 | AGT Ser | 7 |
| ATC Ile | 7 | ACC Thr | 2 | AAC Asn | 6 | AGC Ser | 2 |
| ATA Ile | 12 | ACA Thr | 10 | AAA Lys | 23 | AGA Arg | 6 |
| ATG Met | 11 | ACG Thr | 2 | AAG Lys | 12 | AGG Arg | 7 |
| GTT Val | 20 | GCT Ala | 15 | GAT Asp | 20 | GGT Gly | 16 |
| GTC Val | 4 | GCC Ala | 4 | GAC Asp | 6 | GGC Gly | 3 |
| GTA Val | 13 | GCA Ala | 14 | GAA Glu | 26 | GGA Gly | 18 |
| GTG Val | 12 | GCG Ala | 5 | GAG Glu | 12 | GGG Gly | 2 |

*FIG. 5A*

Codon Usage: GRver1

| | | | | | | | | |
|---|---|---|---|---|---|---|---|---|
| TTT Phe | 12 | TCT Ser | 16 | TAT Tyr | 9 | TGT Cys | 5 |
| TTC Phe | 13 | TCC Ser | 0 | TAC Tyr | 10 | TGC Cys | 6 |
| TTA Leu | 0 | TCA Ser | 0 | TAA *** | 0 | TGA *** | 0 |
| TTG Leu | 27 | TCG Ser | 0 | TAG *** | 0 | TGG Trp | 2 |
| CTT Leu | 0 | CCT Pro | 14 | CAT His | 6 | CGT Arg | 13 |
| CTC Leu | 0 | CCC Pro | 0 | CAC His | 7 | CGC Arg | 13 |
| CTA Leu | 0 | CCA Pro | 14 | CAA Gln | 7 | CGA Arg | 0 |
| CTG Leu | 28 | CCG Pro | 0 | CAG Gln | 7 | CGG Arg | 0 |
| ATT Ile | 19 | ACT Thr | 11 | AAT Asn | 11 | AGT Ser | 0 |
| ATC Ile | 19 | ACC Thr | 11 | AAC Asn | 11 | AGC Ser | 15 |
| ATA Ile | 0 | ACA Thr | 0 | AAA Lys | 17 | AGA Arg | 0 |
| ATG Met | 11 | ACG Thr | 0 | AAG Lys | 18 | AGG Arg | 0 |
| GTT Val | 0 | GCT Ala | 18 | GAT Asp | 13 | GGT Gly | 19 |
| GTC Val | 25 | GCC Ala | 19 | GAC Asp | 13 | GGC Gly | 20 |
| GTA Val | 0 | GCA Ala | 0 | GAA Glu | 19 | GGA Gly | 0 |
| GTG Val | 25 | GCG Ala | 0 | GAG Glu | 19 | GGG Gly | 0 |

*FIG. 5B*

Codon Usage: RDver1

| | | | | | | | | | | |
|---|---|---|---|---|---|---|---|---|---|---|
| TTT | Phe | 13 | TCT | Ser | 15 | TAT | Tyr | 10 | TGT | Cys | 6 |
| TTC | Phe | 12 | TCC | Ser | 0 | TAC | Tyr | 10 | TGC | Cys | 5 |
| TTA | Leu | 0 | TCA | Ser | 0 | TAA | *** | 0 | TGA | *** | 0 |
| TTG | Leu | 27 | TCG | Ser | 0 | TAG | *** | 0 | TGG | Trp | 2 |
| CTT | Leu | 0 | CCT | Pro | 14 | CAT | His | 7 | CGT | Arg | 13 |
| CTC | Leu | 1 | CCC | Pro | 0 | CAC | His | 6 | CGC | Arg | 13 |
| CTA | Leu | 0 | CCA | Pro | 14 | CAA | Gln | 8 | CGA | Arg | 0 |
| CTG | Leu | 27 | CCG | Pro | 0 | CAG | Gln | 7 | CGG | Arg | 0 |
| ATT | Ile | 20 | ACT | Thr | 11 | AAT | Asn | 10 | AGT | Ser | 0 |
| ATC | Ile | 19 | ACC | Thr | 11 | AAC | Asn | 11 | AGC | Ser | 15 |
| ATA | Ile | 0 | ACA | Thr | 0 | AAA | Lys | 18 | AGA | Arg | 0 |
| ATG | Met | 11 | ACG | Thr | 0 | AAG | Lys | 17 | AGG | Arg | 0 |
| GTT | Val | 0 | GCT | Ala | 19 | GAT | Asp | 13 | GGT | Gly | 20 |
| GTC | Val | 24 | GCC | Ala | 18 | GAC | Asp | 13 | GGC | Gly | 19 |
| GTA | Val | 0 | GCA | Ala | 0 | GAA | Glu | 19 | GGA | Gly | 0 |
| GTG | Val | 25 | GCG | Ala | 0 | GAG | Glu | 19 | GGG | Gly | 0 |

*FIG. 5C*

Codon Usage: Grver2

| | | | | | | | |
|---|---|---|---|---|---|---|---|
| TTT Phe | 12 | TCT Ser | 15 | TAT Tyr | 9 | TGT Cys | 5 |
| TTC Phe | 13 | TCC Ser | 0 | TAC Tyr | 10 | TGC Cys | 6 |
| TTA Leu | 0 | TCA Ser | 0 | TAA *** | 0 | TGA *** | 0 |
| TTG Leu | 27 | TCG Ser | 0 | TAG *** | 0 | TGG Trp | 2 |
| CTT Leu | 0 | CCT Pro | 14 | CAT His | 6 | CGT Arg | 13 |
| CTC Leu | 0 | CCC Pro | 0 | CAC His | 7 | CGC Arg | 13 |
| CTA Leu | 0 | CCA Pro | 14 | CAA Gln | 10 | CGA Arg | 0 |
| CTG Leu | 28 | CCG Pro | 0 | CAG Gln | 4 | CGG Arg | 0 |
| ATT Ile | 20 | ACT Thr | 11 | AAT Asn | 11 | AGT Ser | 0 |
| ATC Ile | 18 | ACC Thr | 11 | AAC Asn | 11 | AGC Ser | 16 |
| ATA Ile | 0 | ACA Thr | 0 | AAA Lys | 16 | AGA Arg | 0 |
| ATG Met | 11 | ACG Thr | 0 | AAG Lys | 19 | AGG Arg | 0 |
| GTT Val | 0 | GCT Ala | 18 | GAT Asp | 13 | GGT Gly | 18 |
| GTC Val | 28 | GCC Ala | 19 | GAC Asp | 13 | GGC Gly | 21 |
| GTA Val | 0 | GCA Ala | 0 | GAA Glu | 17 | GGA Gly | 0 |
| GTG Val | 22 | GCG Ala | 0 | GAG Glu | 21 | GGG Gly | 0 |

*FIG. 5D*

Codon usage: Rdver2

| | | | | | | | | | | |
|---|---|---|---|---|---|---|---|---|---|---|
| TTT | Phe | 13 | TCT | Ser | 16 | TAT | Tyr | 10 | TGT Cys | 6 |
| TTC | Phe | 12 | TCC | Ser | 0 | TAC | Tyr | 10 | TGC Cys | 5 |
| TTA | Leu | 0 | TCA | Ser | 0 | TAA | *** | 0 | TGA *** | 0 |
| TTG | Leu | 27 | TCG | Ser | 0 | TAG | *** | 0 | TGG Trp | 2 |
| | | | | | | | | | | |
| CTT | Leu | 0 | CCT | Pro | 15 | CAT | His | 7 | CGT Arg | 13 |
| CTC | Leu | 1 | CCC | Pro | 0 | CAC | His | 6 | CGC Arg | 13 |
| CTA | Leu | 0 | CCA | Pro | 13 | CAA | Gln | 8 | CGA Arg | 0 |
| CTG | Leu | 27 | CCG | Pro | 0 | CAG | Gln | 7 | CGG Arg | 0 |
| | | | | | | | | | | |
| ATT | Ile | 19 | ACT | Thr | 11 | AAT | Asn | 10 | AGT Ser | 0 |
| ATC | Ile | 20 | ACC | Thr | 11 | AAC | Asn | 11 | AGC Ser | 14 |
| ATA | Ile | 0 | ACA | Thr | 0 | AAA | Lys | 19 | AGA Arg | 0 |
| ATG | Met | 11 | ACG | Thr | 0 | AAG | Lys | 16 | AGG Arg | 0 |
| | | | | | | | | | | |
| GTT | Val | 0 | GCT | Ala | 19 | GAT | Asp | 13 | GGT Gly | 21 |
| GTC | Val | 21 | GCC | Ala | 17 | GAC | Asp | 13 | GGC Gly | 18 |
| GTA | Val | 0 | GCA | Ala | 1 | GAA | Glu | 21 | GGA Gly | 0 |
| GTG | Val | 28 | GCG | Ala | 0 | GAG | Glu | 17 | GGG Gly | 0 |

FIG. 5E

Codon Usage: GRver3

| | | | | | | | |
|---|---|---|---|---|---|---|---|
| TTT Phe | 13 | TCT Ser | 16 | TAT Tyr | 9 | TGT Cys | 7 |
| TTC Phe | 12 | TCC Ser | 0 | TAC Tyr | 10 | TGC Cys | 4 |
| TTA Leu | 0 | TCA Ser | 0 | TAA *** | 0 | TGA *** | 0 |
| TTG Leu | 26 | TCG Ser | 0 | TAG *** | 0 | TGG Trp | 2 |
| | | | | | | | |
| CTT Leu | 0 | CCT Pro | 18 | CAT His | 6 | CGT Arg | 14 |
| CTC Leu | 5 | CCC Pro | 0 | CAC His | 7 | CGC Arg | 12 |
| CTA Leu | 0 | CCA Pro | 10 | CAA Gln | 9 | CGA Arg | 0 |
| CTG Leu | 24 | CCG Pro | 0 | CAG Gln | 5 | CGG Arg | 0 |
| | | | | | | | |
| ATT Ile | 14 | ACT Thr | 14 | AAT Asn | 11 | AGT Ser | 0 |
| ATC Ile | 24 | ACC Thr | 8 | AAC Asn | 11 | AGC Ser | 15 |
| ATA Ile | 0 | ACA Thr | 0 | AAA Lys | 21 | AGA Arg | 0 |
| ATG Met | 11 | ACG Thr | 0 | AAG Lys | 14 | AGG Arg | 0 |
| | | | | | | | |
| GTT Val | 1 | GCT Ala | 18 | GAT Asp | 12 | GGT Gly | 18 |
| GTC Val | 22 | GCC Ala | 18 | GAC Asp | 14 | GGC Gly | 21 |
| GTA Val | 0 | GCA Ala | 1 | GAA Glu | 20 | GGA Gly | 0 |
| GTG Val | 27 | GCG Ala | 0 | GAG Glu | 18 | GGG Gly | 0 |

*FIG. 5F*

Codon Usage: RDver3

| | | | | | | | |
|---|---|---|---|---|---|---|---|
| TTT Phe | 13 | TCT Ser | 14 | TAT Tyr | 7 | TGT Cys | 6 |
| TTC Phe | 12 | TCC Ser | 1 | TAC Tyr | 13 | TGC Cys | 5 |
| TTA Leu | 0 | TCA Ser | 0 | TAA *** | 0 | TGA *** | 0 |
| TTG Leu | 27 | TCG Ser | 0 | TAG *** | 0 | TGG Trp | 2 |
| CTT Leu | 0 | CCT Pro | 16 | CAT His | 10 | CGT Arg | 16 |
| CTC Leu | 6 | CCC Pro | 0 | CAC His | 3 | CGC Arg | 10 |
| CTA Leu | 0 | CCA Pro | 12 | CAA Gln | 8 | CGA Arg | 0 |
| CTG Leu | 22 | CCG Pro | 0 | CAG Gln | 7 | CGG Arg | 0 |
| ATT Ile | 20 | ACT Thr | 10 | AAT Asn | 10 | AGT Ser | 0 |
| ATC Ile | 19 | ACC Thr | 12 | AAC Asn | 11 | AGC Ser | 15 |
| ATA Ile | 0 | ACA Thr | 0 | AAA Lys | 13 | AGA Arg | 0 |
| ATG Met | 11 | ACG Thr | 0 | AAG Lys | 22 | AGG Arg | 0 |
| GTT Val | 0 | GCT Ala | 20 | GAT Asp | 14 | GGT Gly | 16 |
| GTC Val | 27 | GCC Ala | 16 | GAC Asp | 12 | GGC Gly | 23 |
| GTA Val | 0 | GCA Ala | 1 | GAA Glu | 18 | GGA Gly | 0 |
| GTG Val | 22 | GCG Ala | 0 | GAG Glu | 20 | GGG Gly | 0 |

*FIG. 5G*

Codon Usage: GRver4

| | | | | | | | |
|---|---|---|---|---|---|---|---|
| TTT Phe | 11 | TCT Ser | 13 | TAT Tyr | 7 | TGT Cys | 8 |
| TTC Phe | 14 | TCC Ser | 2 | TAC Tyr | 12 | TGC Cys | 3 |
| TTA Leu | 0 | TCA Ser | 1 | TAA *** | 0 | TGA *** | 0 |
| TTG Leu | 21 | TCG Ser | 0 | TAG *** | 0 | TGG Trp | 2 |
| | | | | | | | |
| CTT Leu | 1 | CCT Pro | 18 | CAT His | 7 | CGT Arg | 14 |
| CTC Leu | 11 | CCC Pro | 0 | CAC His | 6 | CGC Arg | 11 |
| CTA Leu | 0 | CCA Pro | 10 | CAA Gln | 11 | CGA Arg | 1 |
| CTG Leu | 22 | CCG Pro | 0 | CAG Gln | 3 | CGG Arg | 0 |
| | | | | | | | |
| ATT Ile | 13 | ACT Thr | 14 | AAT Asn | 11 | AGT Ser | 1 |
| ATC Ile | 25 | ACC Thr | 8 | AAC Asn | 11 | AGC Ser | 14 |
| ATA Ile | 0 | ACA Thr | 0 | AAA Lys | 20 | AGA Arg | 0 |
| ATG Met | 11 | ACG Thr | 0 | AAG Lys | 15 | AGG Arg | 0 |
| | | | | | | | |
| GTT Val | 3 | GCT Ala | 19 | GAT Asp | 12 | GGT Gly | 17 |
| GTC Val | 22 | GCC Ala | 15 | GAC Asp | 14 | GGC Gly | 19 |
| GTA Val | 0 | GCA Ala | 3 | GAA Glu | 20 | GGA Gly | 3 |
| GTG Val | 25 | GCG Ala | 0 | GAG Glu | 18 | GGG Gly | 0 |

*FIG. 5H*

Codon Usage: RDver4

| | | | | | | | |
|---|---|---|---|---|---|---|---|
| TTT Phe | 13 | TCT Ser | 11 | TAT Tyr | 7 | TGT Cys | 7 |
| TTC Phe | 12 | TCC Ser | 2 | TAC Tyr | 13 | TGC Cys | 4 |
| TTA Leu | 0 | TCA Ser | 2 | TAA *** | 0 | TGA *** | 0 |
| TTG Leu | 28 | TCG Ser | 0 | TAG *** | 0 | TGG Trp | 2 |
| CTT Leu | 0 | CCT Pro | 16 | CAT His | 11 | CGT Arg | 15 |
| CTC Leu | 7 | CCC Pro | 2 | CAC His | 2 | CGC Arg | 11 |
| CTA Leu | 0 | CCA Pro | 10 | CAA Gln | 7 | CGA Arg | 0 |
| CTG Leu | 20 | CCG Pro | 0 | CAG Gln | 8 | CGG Arg | 0 |
| ATT Ile | 21 | ACT Thr | 11 | AAT Asn | 10 | AGT Ser | 1 |
| ATC Ile | 18 | ACC Thr | 11 | AAC Asn | 11 | AGC Ser | 14 |
| ATA Ile | 0 | ACA Thr | 0 | AAA Lys | 13 | AGA Arg | 0 |
| ATG Met | 11 | ACG Thr | 0 | AAG Lys | 22 | AGG Arg | 0 |
| GTT Val | 3 | GCT Ala | 22 | GAT Asp | 15 | GGT Gly | 14 |
| GTC Val | 27 | GCC Ala | 11 | GAC Asp | 11 | GGC Gly | 21 |
| GTA Val | 0 | GCA Ala | 4 | GAA Glu | 18 | GGA Gly | 4 |
| GTG Val | 19 | GCG Ala | 0 | GAG Glu | 20 | GGG Gly | 0 |

*FIG. 51*

Codon Usage: GRver5 ver5: GR hum.cod+color+del.RE+Splice+TF#3+final

| | | | | | | | |
|---|---|---|---|---|---|---|---|
| TTT Phe | 10 | TCT Ser | 11 | TAT Tyr | 7 | TGT Cys | 8 |
| TTC Phe | 15 | TCC Ser | 4 | TAC Tyr | 12 | TGC Cys | 3 |
| TTA Leu | 0 | TCA Ser | 1 | TAA *** | 0 | TGA *** | 0 |
| TTG Leu | 23 | TCG Ser | 0 | TAG *** | 0 | TGG Trp | 2 |
| | | | | | | | |
| CTT Leu | 1 | CCT Pro | 17 | CAT His | 6 | CGT Arg | 13 |
| CTC Leu | 12 | CCC Pro | 2 | CAC His | 7 | CGC Arg | 11 |
| CTA Leu | 0 | CCA Pro | 9 | CAA Gln | 11 | CGA Arg | 2 |
| CTG Leu | 19 | CCG Pro | 0 | CAG Gln | 3 | CGG Arg | 0 |
| | | | | | | | |
| ATT Ile | 15 | ACT Thr | 14 | AAT Asn | 9 | AGT Ser | 1 |
| ATC Ile | 23 | ACC Thr | 8 | AAC Asn | 13 | AGC Ser | 14 |
| ATA Ile | 0 | ACA Thr | 0 | AAA Lys | 19 | AGA Arg | 0 |
| ATG Met | 11 | ACG Thr | 0 | AAG Lys | 16 | AGG Arg | 0 |
| | | | | | | | |
| GTT Val | 3 | GCT Ala | 18 | GAT Asp | 12 | GGT Gly | 16 |
| GTC Val | 21 | GCC Ala | 14 | GAC Asp | 14 | GGC Gly | 21 |
| GTA Val | 1 | GCA Ala | 5 | GAA Glu | 19 | GGA Gly | 1 |
| GTG Val | 25 | GCG Ala | 0 | GAG Glu | 19 | GGG Gly | 1 |

*FIG. 5J*

Codon Usage: RDver5

| | | | | | | | |
|---|---|---|---|---|---|---|---|
| TTT Phe | 13 | TCT Ser | 12 | TAT Tyr | 7 | TGT Cys | 7 |
| TTC Phe | 12 | TCC Ser | 2 | TAC Tyr | 13 | TGC Cys | 4 |
| TTA Leu | 0 | TCA Ser | 2 | TAA *** | 0 | TGA *** | 0 |
| TTG Leu | 25 | TCG Ser | 0 | TAG *** | 0 | TGG Trp | 2 |
| CTT Leu | 1 | CCT Pro | 15 | CAT His | 9 | CGT Arg | 14 |
| CTC Leu | 11 | CCC Pro | 1 | CAC His | 4 | CGC Arg | 12 |
| CTA Leu | 0 | CCA Pro | 12 | CAA Gln | 7 | CGA Arg | 0 |
| CTG Leu | 18 | CCG Pro | 0 | CAG Gln | 8 | CGG Arg | 0 |
| ATT Ile | 19 | ACT Thr | 10 | AAT Asn | 9 | AGT Ser | 2 |
| ATC Ile | 20 | ACC Thr | 11 | AAC Asn | 12 | AGC Ser | 12 |
| ATA Ile | 0 | ACA Thr | 1 | AAA Lys | 13 | AGA Arg | 0 |
| ATG Met | 11 | ACG Thr | 0 | AAG Lys | 22 | AGG Arg | 0 |
| GTT Val | 5 | GCT Ala | 21 | GAT Asp | 14 | GGT Gly | 14 |
| GTC Val | 26 | GCC Ala | 12 | GAC Asp | 12 | GGC Gly | 21 |
| GTA Val | 1 | GCA Ala | 4 | GAA Glu | 18 | GGA Gly | 3 |
| GTG Val | 17 | GCG Ala | 0 | GAG Glu | 20 | GGG Gly | 1 |

*FIG. 5K*

Synthetic oligos for engineered GR/RD genes
(All oligos listed 5' to 3')

Coding strand:      5'_____ _____(_____)n_____ _____3'
Non-coding strand:  3'_____ _____(_____)n_____ _____5'

Oligos with pRAM flanking sequence identical for GR/RD
1) coding strand upstream flanking
RAM-C1: ACGCCAGCCCAAGCTTAGGCCTGAGTGGC           (SEQ ID NO:35)
RAM-C2: CTTAATTCTCCCCATCCCCTGTTGACAATTAATCATCGGCTCG  (SEQ ID NO:36)
RAM-C3: TATAATGTGAGGAATTGCGAGCGGATAACAATTTCACACA  (SEQ ID NO:37)

2) coding strand downstream flanking
RAM-C4: ATGGGATGTTACCTAGACCAATATGAAATATTTGGTAAAT  (SEQ ID NO:38)
RAM-C5: AAATGCTTAATGAATTTCAAAAAAAAAAAAAAAGGAATTC  (SEQ ID NO:39)
RAM-C6: GATATCAAGCTTATCGATACCGTCGACCTCGAGGATTATA  (SEQ ID NO:40)
RAM-C7: TAGAAAAAGGCCTCGGCGGCCGCTAGTTCAGTCAGTT     (SEQ ID NO:41)

3) non-coding strand downstream flanking
RAM-N1: AACTGACTGAACTAGCG                        (SEQ ID NO:42)
RAM-N2: GCCGCCGAGGCCTTTTTCTATATAATCCTCGAGGTCGACG (SEQ ID NO:43)
RAM-N3: GTATCGATAAGCTTGATATCGAATTCCTTTTTTTTTTTT  (SEQ ID NO:44)
RAM-N3b:AGCTTGATATCGAATTCCTTTTTTTTTTTTTTGAAATTC  (SEQ ID NO:45)
RAM-N4: TTGAAATTCATTAAGCATTTATTTACCAAATATTTCATAT (SEQ ID NO:46)
RAM-N5: TGGTCTAGGTAACATCCCATCACTAGCTTTTTTTTCTATA (SEQ ID NO:47)

4) non-coding strand upstream flanking
RAM-N6: TCGCAATTCCTCACATTATACGAGCCGATGATTAATTGTC (SEQ ID NO:48)
RAM-N7: AACAGGGGGATGGGGAGAATTAAGGCCACTCAGGCCTAAGCTTGGGCTGGCGT
                                                 (SEQ ID NO:49)

GRver5 with flanking seq. of pRAM to end of Sfi I primers
1) Coding strand (Start and stop codons are underlined)
GR-C1:  GGAAACAGGATCCCATGATGAAACGCGAAAAGAACGTGAT (SEQ ID NO:50)
GR-C2:  CTACGGCCCAGAACCACTGCATCCACTGGAAGACCTCACC (SEQ ID NO:51)
GR-C3:  GCTGGTGAGATGCTCTTCCGAGCACTGCGTAAACATAGTC (SEQ ID NO:52)
GR-C4:  ACCTCCCTCAAGCACTCGTGGACGTCGTGGGAGACGAGAG (SEQ ID NO:53)
GR-C5:  CCTCTCCTACAAAGAATTTTTCGAAGCTACTGTGCTGTTG (SEQ ID NO:54)
GR-C6:  GCCCAAAGCCTCCATAATTGTGGGTACAAAATGAACGATG (SEQ ID NO:55)
GR-C7:  TGGTGAGCATTTGTGCTGAGAATAACACTCGCTTCTTTAT (SEQ ID NO:56)
GR-C8:  TCCTGTAATCGCTGCTTGGTACATCGGCATGATTGTCGCC (SEQ ID NO:57)
GR-C9:  CCTGTGAATGAATCTTACATCCCAGATGAGCTGTGTAAGG (SEQ ID NO:58)
GR-C10: TTATGGGTATTAGCAAACCTCAAATCGTCTTTACTACCAA (SEQ ID NO:59)
GR-C11: AAACATCTTGAATAAGGTCTTGGAAGTCCAGTCTCGTACT (SEQ ID NO:60)
GR-C12: AACTTCATCAAACGCATCATTATTCTGGATACCGTCGAAA (SEQ ID NO:61)
GR-C13: ACATCCACGGCTGTGAGAGCCTCCCTAACTTCATCTCTCG (SEQ ID NO:62)
GR-C14: TTACAGCGATGGTAATATCGCTAATTTCAAGCCCTTGCAT (SEQ ID NO:63)
GR-C15: TTTGATCCAGTCGAGCAAGTGGCCGCTATTTTGTGCTCCT (SEQ ID NO:64)
GR-C16: CCGGCACCACTGGTTTGCCTAAAGGTGTCATGCAGACTCA (SEQ ID NO:65)
GR-C17: CCAGAATATCTGTGTGCGTTTGATCCACGCTCTCGACCCT (SEQ ID NO:66)
GR-C18: CGTGTGGGTACTCAATTGATCCCTGGCGTGACTGTGCTGG (SEQ ID NO:67)
GR-C19: TGTATCTGCCTTTCTTTCACGCCTTTGGTTTCTCTATTAC (SEQ ID NO:68)
GR-C20: CCTGGGCTATTTCATGGTCGGCTTGCGTGTCATCATGTTT (SEQ ID NO:69)

FIG. 6A

GR-C21: CGTCGCTTCGACCAAGAAGCCTTCTTGAAGGCTATTCAAG (SEQ ID NO:70)
GR-C22: ACTACGAGGTGCGTTCCGTGATCAACGTCCCTTCAGTCAT (SEQ ID NO:71)
GR-C23: TTTGTTCCTGAGCAAATCTCCTTTGGTTGACAAGTATGATCTG (SEQ ID NO:72)
GR-C24: AGCAGCTTGCGTGAGCTGTGCTGTGGCGCTGCTCCTT (SEQ ID NO:73)
GR-C25: TGGCCAAAGAAGTGGCCGAGGTCGCTGCTAAGCGTCTGAA (SEQ ID NO:74)
GR-C26: CCTCCCTGGTATCCGCTGCGGTTTTGGTTTGACTGAGAGC (SEQ ID NO:75)
GR-C27: ACTTCTGCTAACATCCATAGCTTGCGAGACGAGTTTAAGT (SEQ ID NO:76)
GR-C28: CTGGTAGCCTGGGTCGCGTGACTCCTCTTATGGCTGCAAA (SEQ ID NO:77)
GR-C29: GATCGCCGACCGTGAGACCGGCAAAGCACTGGGCCCAAAT (SEQ ID NO:78)
GR-C30: CAAGTCGGTGAATTGTGTATTAAGGGCCCTATGGTCTCTA (SEQ ID NO:79)
GR-C31: AAGGCTACGTGAACAATGTGGAGGCCACTAAAGAAGCCAT (SEQ ID NO:80)
GR-C32: TGATGATGATGGCTGGCTCCATAGCGGCGACTTCGGTTAC (SEQ ID NO:81)
GR-C33: TATGATGAGGACGAACACTTCTATGTGGTCGATCGCTACA (SEQ ID NO:82)
GR-C34: AAGAATTGATTAAGTACAAAGGCTCTCAAGTCGCACCAGC (SEQ ID NO:83)
GR-C35: CGAACTGGAAGAAATTTTGCTGAAGAACCCTTGTATCCGC (SEQ ID NO:84)
GR-C36: GACGTGGCCGTCGTGGGTATCCCAGACTTGGAAGCTGGCG (SEQ ID NO:85)
GR-C37: AGTTGCCTAGCGCCTTTGTGGTGAAACAACCCGGCAAGGA (SEQ ID NO:86)
GR-C38: GATCACTGCTAAGGAGGTCTACGACTATTTGGCCGAGCGC (SEQ ID NO:87)
GR-C39: GTGTCTCACACCAAATATCTGCGTGGCGGCGTCCGCTTCG (SEQ ID NO:88)
GR-C40: TCGATTCTATTCCACGCAACGTTACCGGTAAGATCACTCG (SEQ ID NO:89)
GR-C41: TAAAGAGTTGCTGAAGCAACTCCTCGAAAAAGCTGGCGGC (SEQ ID NO:90)
GR-C42: TAGTAAAGTCTTCATGATTATATAGAAAAAAAGCTAGTG (SEQ ID NO:91)

2) non-coding strand
GR-N1:  TAATCATGAAGACTTTACTAGCCGCCAGCTTTTTCGAGGA (SEQ ID NO:92)
GR-N2:  GTTGCTTCAGCAACTCTTTACGAGTGATCTTACCGGTAAC (SEQ ID NO:93)
GR-N3:  GTTGCGTGGAATAGAATCGACGAAGCGGACGCCGCCACG (SEQ ID NO:94)
GR-N4:  CAGATATTTGGTGTGAGACACGCGCTCGGCCAAATAGTCGT (SEQ ID NO:95)
GR-N5:  AGACCTCCTTAGCAGTGATCTCCTTGCCGGGTTGTTTCAC (SEQ ID NO:96)
GR-N6:  CACAAAGGCGCTAGGCAACTCGCCAGCTTCCAAGTCTGGG (SEQ ID NO:97)
GR-N7:  ATACCCACGACGGCCACGTCGCGGATACAAGGGTTCTTCA (SEQ ID NO:98)
GR-N8:  GCAAAATTTCTTCCAGTTCGGCTGGTGCGACTTGAGAGCC (SEQ ID NO:99)
GR-N9:  TTTGTACTTAATCAATTCTTTGTAGCGATCGACCACATAG (SEQ ID NO:100)
GR-N10: AAGTGTTCGTCCTCATCATAGTAACCGAAGTCGCCGCTAT (SEQ ID NO:101)
GR-N11: GGAGCCAGCCATCATCATCAATGGCTTCTTTAGTGGCCTC (SEQ ID NO:102)
GR-N12: CACATTGTTCACGTAGCCTTTAGAGACCATAGGGCCCTTA (SEQ ID NO:103)
GR-N13: ATACACAATTCACCGACTTGATTTGGGCCCAGTGCTTTGC (SEQ ID NO:104)
GR-N14: CGGTCTCACGGTCGGCGATCTTTGCAGCCATAAGAGGAGT (SEQ ID NO:105)
GR-N15: CACGCGACCCAGGCTACCAGACTTAAACTCGTCTCGCAAG (SEQ ID NO:106)
GR-N16: CTATGGATGTTAGCAGAAGTGCTCTCAGTCAAACCAAAAC (SEQ ID NO:107)
GR-N17: CGCAGCGGATACCAGGGAGGTTCAGACGCTTAGCAGCGAC (SEQ ID NO:108)
GR-N18: CTCGGCCACTTCTTTGGCCAAAGGAGCAGCGCCACAGCAC (SEQ ID NO:109)
GR-N19: AGCTCACGCAAGCTGCTCAGATCATACTTGTCAACCAAAG (SEQ ID NO:110)
GR-N20: GAGATTTGCTCAGGAACAAAATGACTGAAGGGACGTTGAT (SEQ ID NO:111)
GR-N21: CACGGAACGCACCTCGTAGTCTTGAATAGCCTTCAA (SEQ ID NO:112)
GR-N22: GAAGGCTTCTTGGTCGAAGCGACGAAACATGATGACACGCAAGC (SEQ ID NO:113)
GR-N23: CGACCATGAAATAGCCCAGGGTAATAGAGAAACCAAAGGC (SEQ ID NO:114)
GR-N24: GTGAAAGAAAGGCAGATACACCAGCACAGTCACGCCAGGG (SEQ ID NO:115)
GR-N25: ATCAATTGAGTACCCACACGAGGGTCGAGAGCGTGGATCA (SEQ ID NO:116)
GR-N26: AACGCACACAGATATTCTGGTGAGTCTGCATGACACCTTT (SEQ ID NO:117)
GR-N27: AGGCAAACCAGTGGTGCCGGAGGAGCACAAAATAGCGGCC (SEQ ID NO:118)

*FIG. 6B*

```
GR-N28: ACTTGCTCGACTGGATCAAAATGCAAGGGCTTGAAATTAG      (SEQ ID NO:119)
GR-N29: CGATATTACCATCGCTGTAACGAGAGATGAAGTTAGGGAG      (SEQ ID NO:120)
GR-N30: GCTCTCACAGCCGTGGATGTTTTCGACGGTATCCAGAATA      (SEQ ID NO:121)
GR-N31: ATGATGCGTTTGATGAAGTTAGTACGAGACTGGACTTCCA      (SEQ ID NO:122)
GR-N32: AGACCTTATTCAAGATGTTTTTGGTAGTAAAGACGATTTG      (SEQ ID NO:123)
GR-N33: AGGTTTGCTAATACCCATAACCTTACACAGCTCATCTGGG      (SEQ ID NO:124)
GR-N34: ATGTAAGATTCATTCACAGGGGCGACAATCATGCCGATGT      (SEQ ID NO:125)
GR-N35: ACCAAGCAGCGATTACAGGAATAAAGAAGCGAGTGTTATT      (SEQ ID NO:126)
GR-N36: CTCAGCACAAATGCTCACCACATCGTTCATTTTGTACCCA      (SEQ ID NO:127)
GR-N37: CAATTATGGAGGCTTTGGGCCAACAGCACAGTAGCTTCGA      (SEQ ID NO:128)
GR-N38: AAAATTCTTTGTAGGAGAGGCTCTCGTCTCCCACGACGTC      (SEQ ID NO:129)
GR-N39: CACGAGTGCTTGAGGGAGGTGACTATGTTTACGCAGTGCT      (SEQ ID NO:130)
GR-N40: CGGAAGAGCATCTCACCAGCGGTGAGGTCTTCCAGTGGAT      (SEQ ID NO:131)
GR-N41: GCAGTGGTTCTGGGCCGTAGATCACGTTCTTTTCGCGTTT      (SEQ ID NO:132)
GR-N42: CATCATGGATCCTGTTTCCTGTGTGAAATTGTTATCCGC       (SEQ ID NO:133)

RDver5 with flanking sequence of pRAM to end of Sfi I primers
1) coding strand
RD-C1:  GGAAACAGGATCCCATGATGAAGCGTGAGAAAAATGTCAT      (SEQ ID NO:134)
RD-C2:  CTATGGCCCTGAGCCTCTCCATCCTTTGGAGGATTTGACT      (SEQ ID NO:135)
RD-C3:  GCCGGCGAAATGCTGTTTCGTGCTCTCCGCAAGCACTCTC      (SEQ ID NO:136)
RD-C4:  ATTTGCCTCAAGCCTTGGTCGATGTGGTCGGCGATGAATC      (SEQ ID NO:137)
RD-C5:  TTTGAGCTACAAGGAGTTTTTTGAGGCAACCGTCTTGCTG      (SEQ ID NO:138)
RD-C6:  GCTCAGTCCCTCCACAATTGTGGCTACAAGATGAACGACG      (SEQ ID NO:139)
RD-C7:  TCGTTAGTATCTGTGCTGAAAACAATACCCGTTTCTTCAT      (SEQ ID NO:140)
RD-C8:  TCCAGTCATCGCCGCATGGTATATCGGTATGATCGTGGCT      (SEQ ID NO:141)
RD-C9:  CCAGTCAACGAGAGCTACATTCCCGACGAACTGTGTAAAG      (SEQ ID NO:142)
RD-C10: TCATGGGTATCTCTAAGCCACAGATTGTCTTCACCACTAA      (SEQ ID NO:143)
RD-C11: GAATATTCTGAACAAAGTCCTGGAAGTCCAAAGCCGCACC      (SEQ ID NO:144)
RD-C12: AACTTTATTAAGCGTATCATCATCTTGGACACTGTGGAGA      (SEQ ID NO:145)
RD-C13: ATATTCACGGTTGCGAATCTTTGCCTAATTTCATCTCTCG      (SEQ ID NO:146)
RD-C14: CTATTCAGACGGCAACATCGCAAACTTTAAACCACTCCAC      (SEQ ID NO:147)
RD-C15: TTCGACCCTGTGGAACAAGTTGCAGCCATTCTGTGTAGCA      (SEQ ID NO:148)
RD-C16: GCGGTACTACTGGACTCCCAAAGGGAGTCATGCAGACCCA      (SEQ ID NO:149)
RD-C17: TCAAAACATTTGCGTGCGTCTGATCCATGCTCTCGATCCA      (SEQ ID NO:150)
RD-C18: CGCTACGGCACTCAGCTGATTCCTGGTGTCACCGTCTTGG      (SEQ ID NO:151)
RD-C19: TCTACTTGCCTTTCTTCCATGCTTTCGGCTTTCATATTAC      (SEQ ID NO:152)
RD-C20: TTTGGGTTACTTTATGGTCGGTCTCCGCGTGATTATGTTC      (SEQ ID NO:153)
RD-C21: CGCCGTTTTGATCAGGAGGCTTTCTTGAAAGCCATCCAAG      (SEQ ID NO:154)
RD-C22: ATTATGAAGTCCGCAGTGTCATCAACGTGCCTAGCGTGAT      (SEQ ID NO:155)
RD-C23: CCTGTTTTTGTCTAAGAGCCCACTCGTGGACAAGTACGAC      (SEQ ID NO:156)
RD-C24: TTGTCTTCACTGCGTGAATTGTGTTGCGGTGCCGCTCCAC      (SEQ ID NO:157)
RD-C25: TGGCTAAGGAGGTCGCTGAAGTGGCCGCCAAACGCTTGAA      (SEQ ID NO:158)
RD-C26: TCTTCCAGGGATTCGTTGTGGCTTCGGCCTCACCGAATCT      (SEQ ID NO:159)
RD-C27: ACCAGCGCTATTATTCAGTCTCTCCGCGATGAGTTTAAGA      (SEQ ID NO:160)
RD-C28: GCGGCTCTTTGGGCCGTGTCACTCCACTCATGGCTGCTAA      (SEQ ID NO:161)
RD-C29: GATCGCTGATCGCGAAACTGGTAAGGCTTTGGGCCCTAAC      (SEQ ID NO:162)
RD-C30: CAAGTGGGCGAGCTGTGTATCAAAGGCCCTATGGTGAGCA      (SEQ ID NO:163)
RD-C31: AGGGTTATGTCAATAACGTCGAAGCTACCAAGGAGGCCAT      (SEQ ID NO:164)
RD-C32: CGACGACGACGGCTGGTTGCATTCTGGTGATTTTGGATAT      (SEQ ID NO:165)
RD-C33: TACGACGAAGATGAGCATTTTTACGTCGTGGATCGTTACA      (SEQ ID NO:166)
RD-C34: AGGAGCTGATCAAATACAAGGGTAGCCAGGTTGCTCCAGC      (SEQ ID NO:167)
RD-C35: TGAGTTGGAGGAGATTCTGTTGAAAAATCCATGCATTCGC      (SEQ ID NO:168)
```

*FIG. 6C*

```
RD-C36:GATGTCGCTGTGGTCGGCATTCCTGATCTGGAGGCCGGCG          (SEQ ID NO:169)
RD-C37:AACTGCCTTCTGCTTTCGTTGTCAAGCAGCCTGGTAAAGA          (SEQ ID NO:170)
RD-C38:AATTACCGCCAAAGAAGTGTATGATTACCTGGCTGAACGT          (SEQ ID NO:171)
RD-C39:GTGAGCCATACTAAGTACTTGCGTGGCGGCGTGCGTTTTG          (SEQ ID NO:172)
RD-C40:TTGACTCCATCCCTCGTAACGTAACAGGCAAAATTACCCG          (SEQ ID NO:173)
RD-C41:CAAGGAGCTGTTGAAACAATTGTTGGAGAAGGCCGGCGGT          (SEQ ID NO:174)
RD-C42:TAGTAAAGTCTTCATGATTATATAGAAAAAAAGCTAGTG           (SEQ ID NO:175)

2) non-coding strand
RD-N1:  TAATCATGAAGACTTTACTAACCGCCGGCCTTCTCCAACA         (SEQ ID NO:176)
RD-N2:  ATTGTTTCAACAGCTCCTTGCGGGTAATTTTGCCTGTTAC         (SEQ ID NO:177)
RD-N3:  GTTACGAGGGATGGAGTCAACAAAACGCACGCCGCCACGC         (SEQ ID NO:178)
RD-N4:  AAGTACTTAGTATGGCTCACACGTTCAGCCAGGTAATCAT         (SEQ ID NO:179)
RD-N5:  ACACTTCTTTGGCGGTAATTTCTTTACCAGGCTGCTTGAC         (SEQ ID NO:180)
RD-N6:  AACGAAAGCAGAAGGCAGTTCGCCGGCCTCCAGATCAGGA         (SEQ ID NO:181)
RD-N7:  ATGCCGACCACAGCGACATCGCGAATGCATGGATTTTTCA         (SEQ ID NO:182)
RD-N8:  ACAGAATCTCCTCCAACTCAGCTGGAGCAACCTGGCTACC         (SEQ ID NO:183)
RD-N9:  CTTGTATTTGATCAGCTCCTTGTAACGATCCACGACGTAA         (SEQ ID NO:184)
RD-N10: AAATGCTCATCTTCGTCGTAATATCCAAAATCACCAGAAT         (SEQ ID NO:185)
RD-N11: GCAACCAGCCGTCGTCGTCGATGGCCTCCTTGGTAGCTTC         (SEQ ID NO:186)
RD-N12: GACGTTATTGACATAACCCTTGCTCACCATAGGGCCTTTG         (SEQ ID NO:187)
RD-N13: ATACACAGCTCGCCCACTTGGTTAGGGCCCAAAGCCTTAC         (SEQ ID NO:188)
RD-N14: CAGTTTCGCGATCAGCGATCTTAGCAGCCATGAGTGGAGT         (SEQ ID NO:189)
RD-N15: GACACGGCCCAAAGAGCCGCTCTTAAACTCATCGCGGAGA         (SEQ ID NO:190)
RD-N16: GACTGAATAATAGCGCTGGTAGATTCGGTGAGGCCGA            (SEQ ID NO:191)
RD-N17: AGCCACAACGAATCCCTGGAAGATTCAAGCGTTTGGCGGCCAC      (SEQ ID NO:192)
RD-N18: TTCAGCGACCTCCTTAGCCAGTGGAGCGGCACCGCAACAC         (SEQ ID NO:193)
RD-N19: AATTCACGCAGTGAAGACAAGTCGTACTTGTCCACGAGTG         (SEQ ID NO:194)
RD-N20: GGCTCTTAGACAAAAACAGGATCACGCTAGGCACGTTGAT         (SEQ ID NO:195)
RD-N21: GACACTGCGGACTTCATAATCTTGGATGGCTTTCAAGAAA         (SEQ ID NO:196)
RD-N22: GCCTCCTGATCAAAACGGCGGAACATAATCACGCGGAGAC         (SEQ ID NO:197)
RD-N23: CGACCATAAAGTAACCCAAAGTAATATGAAAGCCGAAAGC         (SEQ ID NO:198)
RD-N24: ATGGAAGAAAGGCAAGTAGACCAAGACGGTGACACCAGGA         (SEQ ID NO:199)
RD-N25: ATCAGCTGAGTGCCGTAGCGTGGATCGAGAGCATGGATCA         (SEQ ID NO:200)
RD-N26: GACGCACGCAAATGTTTTGATGGGTCTGCATGACTCCCTT         (SEQ ID NO:201)
RD-N27: TGGGAGTCCAGTAGTACCGCTGCTACACAGAATGGCTGCA         (SEQ ID NO:202)
RD-N28: ACTTGTTCCACAGGGTCGAAGTGGAGTGGTTTAAAGTTTG         (SEQ ID NO:203)
RD-N29: CGATGTTGCCGTCTGAATAGCGAGAGATGAAATTAGGCAA         (SEQ ID NO:204)
RD-N30: AGATTCGCAACCGTGAATATTCTCCACAGTGTCCAAGATG         (SEQ ID NO:205)
RD-N31: ATGATACGCTTAATAAAGTTGGTGCGGCTTTGGACTTCCA         (SEQ ID NO:206)
RD-N32: GGACTTTGTTCAGAATATTCTTAGTGGTGAAGACAATCTG         (SEQ ID NO:207)
RD-N33: TGGCTTAGAGATACCCATGACTTTACACAGTTCGTCGGGA         (SEQ ID NO:208)
RD-N34: ATGTAGCTCTCGTTGACTGGAGCCACGATCATACCGATAT         (SEQ ID NO:209)
RD-N35: ACCATGCGGCGATGACTGGAATGAAGAAACGGGTATTGTT         (SEQ ID NO:210)
RD-N36: TTCAGCACAGATACTAACGACGTCGTTCATCTTGTAGCCA         (SEQ ID NO:211)
RD-N37: CAATTGTGGAGGGACTGAGCCAGCAAGACGGTTGCCTCAA         (SEQ ID NO:212)
RD-N38: AAAACTCCTTGTAGCTCAAAGATTCATCGCCGACCACATC         (SEQ ID NO:213)
RD-N39: GACCAAGGCTTGAGGCAAATGAGAGTGCTTGCGGAGAGCA         (SEQ ID NO:214)
RD-N40: CGAAACAGCATTTCGCCGGCAGTCAAATCCTCCAAAGGAT         (SEQ ID NO:215)
RD-N41: GGAGAGGCTCAGGGCCATAGATGACATTTTTCTCACGCTT         (SEQ ID NO:216)
RD-N42: CATCATGGGATCCTGTTTCCTGTGTGAAATTGTTATCCGC         (SEQ ID NO:217)
```

*FIG. 6D*

```
RELLUC.SEQ   A T G A C T T C G A A A G T T T A T G A T C C A G A A C A A A G G A A A C G G A  40
RLUCVER1.SEQ A T G C T T C C A A G G T G T A C G A C C C C G A G C A G C G C A A G C G C A  40
RLUCVER2.SEQ A T G C T T C C A A G G T G T A C G A C C C C G A G C A A C G C A A A C G C A  40
RLUCFINL.SEQ A T G C T T C C A A G G T G T A C G A C C C G A G C A A C G C A A A C G C A  40

RELLUC.SEQ   T G A T A A C T G G T C C G C A G T G G T G G G C C A G A T G T A A A C A A A T  80
RLUCVER1.SEQ T G A T C A C C G G C C C T C A G T G G T G G G C C C G C T G C A A G C A G A T  80
RLUCVER2.SEQ T G A T C A C T G G G C C T C A G T G G T G G G C T C G C T G C A A G C A A A T  80
RLUCFINL.SEQ T G A T C A C T G G G C C T C A G T G G T G G G C T C G C T G C A A G C A A A T  80

RELLUC.SEQ   G A A T G T T C T T G A T T C A T T T A T T A A T T A T T A T G A T T C A G A A  120
RLUCVER1.SEQ G A A C G T G C T G G A C T C C T T C A T C A A C T A C T A C G A C A G C G A G  120
RLUCVER2.SEQ G A A C G T G C T G G A C T C C T T C A T C A A C T A C T A T G A T T C C G A G  120
RLUCFINL.SEQ G A A C G T G C T G G A C T C C T T C A T C A A C T A C T A T G A T T C C G A G  120

RELLUC.SEQ   A A A C A T G C A G A A A A T G C T G T T A T T T T T T A C A T G G T A A C G  160
RLUCVER1.SEQ A A G C A C G C C C G A G A A C G C C G T G A T C T T C C T G C A C G G C A A C G  160
RLUCVER2.SEQ A A G C A C G C C C G A G A A C G C C G T G A T T T T T C T G C A T G G T A A C G  160
RLUCFINL.SEQ A A G C A C G C C C G A G A A C G C C G T G A T T T T T C T G C A T G G T A A C G  160

RELLUC.SEQ   C G G C C T C T T C T T A T T T A T G G C G A C A T G T T G T G C C A C A T A T  200
RLUCVER1.SEQ C C G C C T C C A G C T A C C T G T G G A G G C A C G T G G T G C C T C A C A T  200
RLUCVER2.SEQ C T G C C T C C A G C T A C C T G T G G A G G C A C G T C G T G C C T C A C A T  200
RLUCFINL.SEQ C T G C C T C C A G C T A C C T G T G G A G G C A C G T C G T G C C T C A C A T  200

RELLUC.SEQ   T G A G C C A G T A G C G C G G T G T A T T A T A C C A G A T C T T A T T G G T  240
RLUCVER1.SEQ C G A G C C C G T G G C C C G C T G C A T C A T C C C T G A C T G A T C G G C  240
RLUCVER2.SEQ C G A G C C C G T G G C T C G C T G C A T C A T C C C T G A T C T G A T C G G A  240
RLUCFINL.SEQ C G A G C C C G T G G C T A G A T G C A T C A T C C C T G A T C T G A T C G G A  240

RELLUC.SEQ   A T G G G C A A A T C A G G C A A A T C T G G T A A T G G T T C T T A T A G G T  280
RLUCVER1.SEQ A T G G G C A A G T C C G G C A A G A G C G G C A A C G G C T C C T A C C G C C  280
RLUCVER2.SEQ A T G G G T A A G T C C G G C A A G A G C G G G A A T G G C T C A T A T C G C C  280
RLUCFINL.SEQ A T G G G T A A G T C C G G C A A G A G C G G G A A T G G C T C A T A T C G C C  280

RELLUC.SEQ   T A C T T G A T C A T T A C A A A T A T C T T A C T G C A T G G T T T G A A C T  320
RLUCVER1.SEQ T G C T G G A C A C T A C A A G T A C C T G A C C G C C T G G T T C G A G C T  320
RLUCVER2.SEQ T C C T G G A T C A C T A C A A G T A C C T C A C C G C T T G G T T C G A G C T  320
RLUCFINL.SEQ T C C T G G A T C A C T A C A A G T A C C T C A C C G C T T G G T T C G A G C T  320

RELLUC.SEQ   T C T T A A T T T A C C A A A G A A G A T C A T T T T T G T C G G C C A T G A T  360
RLUCVER1.SEQ G C T G A A C C T G C C C A A G A A G A T C A T C T T C G T G G G C C A C G A C  360
RLUCVER2.SEQ G C T G A A C C T T C C A A A G A A A A T C A T C T T T G T G G G C C A C G A C  360
RLUCFINL.SEQ G C T G A A C C T T C C A A A G A A A A T C A T C T T T G T G G G C C A C G A C  360

RELLUC.SEQ   T G G G G T G C T T G T T T G G C A T T T C A T T A T A G C T A T G A G C A T C  400
RLUCVER1.SEQ T G G G G A G C C T G C C T G G C C T T C C A C T A C T C C T A C G A G C A C C  400
RLUCVER2.SEQ T G G G G G G C T T G T C T G G C C T T T C A C T A C T C C T A C G A G C A C C  400
RLUCFINL.SEQ T G G G G G G C T T G T C T G G C C T T T C A C T A C T C C T A C G A G C A C C  400

RELLUC.SEQ   A A G A T A A G A T C A A A G C A A T A G T T C A C G C T G A A A G T G T A G T  440
RLUCVER1.SEQ A G G A C A A G A T C A A G G C C A T C G T G C A C G C C G A G A G C G T G G T  440
RLUCVER2.SEQ A A G A C A A G A T C A A G G C C A T C G T C C A T G C T G A G A G T G T C G T  440
RLUCFINL.SEQ A A G A C A A G A T C A A G G C C A T C G T C C A T G C T G A G A G T G T C G T  440
```

*FIG. 7A*

```
RELLUC.SEQ    A G A T G T G A T T G A A T C A T G G G A T G A A T G G C C T G A T A T T G A A 480
RLUCVER1.SEQ  G G A C G T G A T C G A G T C C T G G G A C G A G T G G C C T G A C A T C G A G 480
RLUCVER2.SEQ  G G A C G T G A T C G A G T C C T G G G A C G A G T G G C C T G A C A T C G A G 480
RLUCFINL.SEQ  G G A C G T G A T C G A G T C C T G G G A C G A G T G G C C T G A C A T C G A G 480

RELLUC.SEQ    G A A G A T A T T G C G T T G A T C A A A T C T G A A G A A G G A G A A A A A 520
RLUCVER1.SEQ  G A G G A C A T C G C C C T G A T C A A G A G C G A G G A G G G C G A G A A G A 520
RLUCVER2.SEQ  G A G G A T A T C G C C C T G A T C A A G A G C G A A G A G G G C G A G A A A A 520
RLUCFINL.SEQ  G A G G A T A T C G C C C T G A T C A A G A G C G A A G A G G G C G A G A A A A 520

RELLUC.SEQ    T G G T T T T G G A G A A T A A C T T C T T C G T G G A A A C C A T G T T G C C 560
RLUCVER1.SEQ  T G G T G C T G G A G A A C A A C T T C T T C G T G G A G A C C A T G C T G C C 560
RLUCVER2.SEQ  T G G T G C T T G A G A A T A A C T T C T T C G T C G A G A C C A T G C T C C C 560
RLUCFINL.SEQ  T G G T G C T T G A G A A T A A C T T C T T C G T C G A G A C C A T G C T C C C 560

RELLUC.SEQ    A T C A A A A A T C A T G A G A A A G T T A G A A C C A G A A G A A T T T G C A 600
RLUCVER1.SEQ  C A G C A A G A T C A T G C G C A A G C T G G A G C C T G A G G A G T T C G C C 600
RLUCVER2.SEQ  A A G C A A G A T C A T G C G G A A A C T G G A G C C T G A G G A G T T C G C T 600
RLUCFINL.SEQ  A A G C A A G A T C A T G C G G A A A C T G G A G C C T G A G G A G T T C G C T 600

RELLUC.SEQ    G C A T A T C T T G A A C C A T T C A A A G A G A A A G G T G A A G T T C G T C 640
RLUCVER1.SEQ  G C C T A C C T G G A G C C C T T C A A G G A G A A G G G C G A G G T G C G C C 640
RLUCVER2.SEQ  G C C T A C C T G G A G C C C T T C A A G G A G A A G G G C G A G G T T A G A C 640
RLUCFINL.SEQ  G C C T A C C T G G A G C C A T T C A A G G A G A A G G G C G A G G T T A G A C 640

RELLUC.SEQ    G T C C A A C A T T A T C A T G G C C T C G T G A A A T C C C G T T A G T A A A 680
RLUCVER1.SEQ  G C C C T A C C C T G T C C T G G C C C C G C G A G A T C C C T C T G G T G A A 680
RLUCVER2.SEQ  G G C C T A C C C T C T C C T G G C C T C G C G A G A T C C C T C T C G T T A A 680
RLUCFINL.SEQ  G G C C T A C C C T C T C C T G G C C T C G C G A G A T C C C T C T C G T T A A 680

RELLUC.SEQ    A G G T G G T A A A C C T G A C G T T G T A C A A A T T G T T A G G A A T T A T 720
RLUCVER1.SEQ  G G G C G G C A A G C C C G A C G T G G T G C A G A T C G T G C G C A A C T A C 720
RLUCVER2.SEQ  G G G A G G C A A G C C C G A C G T C G T C C A G A T T G T C C G C A A C T A C 720
RLUCFINL.SEQ  G G G A G G C A A G C C C G A C G T C G T C C A G A T T G T C C G C A A C T A C 720

RELLUC.SEQ    A A T G C T T A T C T A C G T G C A A G T G A T G A T T T A C C A A A A A T G T 760
RLUCVER1.SEQ  A A C G C C T A C C T G C G G C C A G C G A C C T G C C T A A G A T G T 760
RLUCVER2.SEQ  A A C G C C T A C C T T C G G G C C A G C G A T C T G C C T A A G A T G T 760
RLUCFINL.SEQ  A A C G C C T A C C T T C G G G C C A G C G A T C T G C C T A A G A T G T 760

RELLUC.SEQ    T T A T T G A A T C G G A T C C A G G A T T C T T T T C C A A T G C T A T T G T 800
RLUCVER1.SEQ  T C A T C G A G T C C G A C C C T G G C T T C T T C T C C A A C G C C A T C G T 800
RLUCVER2.SEQ  T C A T C G A G T C C G A C C C T G G G T T C T T T T C C A A C G C T A T T G T 800
RLUCFINL.SEQ  T C A T C G A G T C C G A C C C T G G G T T C T T T T C C A A C G C T A T T G T 800

RELLUC.SEQ    T G A A G G C G C C A A G A A G T T T C C T A A T A C T G A A T T T G T C A A A 840
RLUCVER1.SEQ  C G A G G G A G C C A A G A A G T T C C C C A A C A C C G A G T T C G T G A A G 840
RLUCVER2.SEQ  C G A G G G A G C T A A G A A G T T C C C T A A C A C C G A G T T C G T G A A G 840
RLUCFINL.SEQ  C G A G G G A G C T A A G A A G T T C C C T A A C A C C G A G T T C G T G A A G 840

RELLUC.SEQ    G T A A A A G G T C T T C A T T T T T C G C A A G A A G A T G C A C C T G A T G 880
RLUCVER1.SEQ  G T G A A G G G C C T G C A C T T C T C C C A G G A G G A C G C C C C T G A C G 880
RLUCVER2.SEQ  G T G A A G G G C C T C C A C T T C A G C C A G G A G G A C G C T C C A G A T G 880
RLUCFINL.SEQ  G T G A A G G G C C T C C A C T T C A G C C A G G A G G A C G C T C C A G A T G 880
```

*FIG. 7B*

```
RELLUC.SEQ    A A A T G G G A A A A T A T A T C A A A T C G T T C G T T G A G C G A G T T C T  920
RLUCVER1.SEQ A G A T G G G C A A G T A C A T C A A G A G C T T C G T G G A G C G C G T G C T  920
RLUCVER2.SEQ A A A T G G G T A A G T A C A T C A A G A G C T T C G T G G A G C G C G T G C T  920
RLUCFINL.SEQ A A A T G G G T A A G T A C A T C A A G A G C T T C G T G G A G C G C G T G C T  920

RELLUC.SEQ    C A A A A A T G A A C A A                                                      933
RLUCVER1.SEQ G A A G A A C G A G C A G                                                      933
RLUCVER2.SEQ G A A G A A C G A G C A G                                                      933
RLUCFINL.SEQ G A A G A A C G A G C A G                                                      933
```

*FIG. 7C*

```
RELLUC.SEQ    M T S K V Y D P E Q R K R M I T G P Q W W A R C K Q M N V L D S F I N Y Y D S E  118
RLUCVER1.SEQ  M A S K V Y D P E Q R K R M I T G P Q W W A R C K Q M N V L D S F I N Y Y D S E  118
RLUCVER2.SEQ  M A S K V Y D P E Q R K R M I T G P Q W W A R C K Q M N V L D S F I N Y Y D S E  118
RLUCFINL.SEQ  M A S K V Y D P E Q R K R M I T G P Q W W A R C K Q M N V L D S F I N Y Y D S E  118

RELLUC.SEQ    K H A E N A V I F L H G N A A S S Y L W R H V V P H I E P V A R C I I P D L I G  238
RLUCVER1.SEQ  K H A E N A V I F L H G N A A S S Y L W R H V V P H I E P V A R C I I P D L I G  238
RLUCVER2.SEQ  K H A E N A V I F L H G N A A S S Y L W R H V V P H I E P V A R C I I P D L I G  238
RLUCFINL.SEQ  K H A E N A V I F L H G N A A S S Y L W R H V V P H I E P V A R C I I P D L I G  238

RELLUC.SEQ    M G K S G K S G N G S Y R L L D H Y K Y L T A W F E L L N L P K K I I F V G H D  358
RLUCVER1.SEQ  M G K S G K S G N G S Y R L L D H Y K Y L T A W F E L L N L P K K I I F V G H D  358
RLUCVER2.SEQ  M G K S G K S G N G S Y R L L D H Y K Y L T A W F E L L N L P K K I I F V G H D  358
RLUCFINL.SEQ  M G K S G K S G N G S Y R L L D H Y K Y L T A W F E L L N L P K K I I F V G H D  358

RELLUC.SEQ    W G A C L A F H Y S Y E H Q D K I K A I V H A E S V V D V I E S W D E W P D I E  478
RLUCVER1.SEQ  W G A C L A F H Y S Y E H Q D K I K A I V H A E S V V D V I E S W D E W P D I E  478
RLUCVER2.SEQ  W G A C L A F H Y S Y E H Q D K I K A I V H A E S V V D V I E S W D E W P D I E  478
RLUCFINL.SEQ  W G A C L A F H Y S Y E H Q D K I K A I V H A E S V V D V I E S W D E W P D I E  478

RELLUC.SEQ    E D I A L I K S E E G E K M V L E N N F F V E T M L P S K I M R K L E P E E F A  598
RLUCVER1.SEQ  E D I A L I K S E E G E K M V L E N N F F V E T M L P S K I M R K L E P E E F A  598
RLUCVER2.SEQ  E D I A L I K S E E G E K M V L E N N F F V E T M L P S K I M R K L E P E E F A  598
RLUCFINL.SEQ  E D I A L I K S E E G E K M V L E N N F F V E T M L P S K I M R K L E P E E F A  598

RELLUC.SEQ    A Y L E P F K E K G E V R R P T L S W P R E I P L V K G G K P D V V Q I V R N Y  718
RLUCVER1.SEQ  A Y L E P F K E K G E V R R P T L S W P R E I P L V K G G K P D V V Q I V R N Y  718
RLUCVER2.SEQ  A Y L E P F K E K G E V R R P T L S W P R E I P L V K G G K P D V V Q I V R N Y  718
RLUCFINL.SEQ  A Y L E P F K E K G E V R R P T L S W P R E I P L V K G G K P D V V Q I V R N Y  718

RELLUC.SEQ    N A Y L R A S D D L P K M F I E S D P G F F S N A I V E G A K K F P N T E F V K  838
RLUCVER1.SEQ  N A Y L R A S D D L P K M F I E S D P G F F S N A I V E G A K K F P N T E F V K  838
RLUCVER2.SEQ  N A Y L R A S D D L P K M F I E S D P G F F S N A I V E G A K K F P N T E F V K  838
RLUCFINL.SEQ  N A Y L R A S D D L P K M F I E S D P G F F S N A I V E G A K K F P N T E F V K  838

RELLUC.SEQ    V K G L H F S Q E D A P D E M G K Y I K S F V E R V L K N E Q                    931
RLUCVER1.SEQ  V K G L H F S Q E D A P D E M G K Y I K S F V E R V L K N E Q                    931
RLUCVER2.SEQ  V K G L H F S Q E D A P D E M G K Y I K S F V E R V L K N E Q                    931
RLUCFINL.SEQ  V K G L H F S Q E D A P D E M G K Y I K S F V E R V L K N E Q                    931
```

FIG. 8

Codon usage in RELLUC
(*Renilla* Reniformis; Genbank ACCESSION:M63501; Medline:91239583)

| | | | | | | | | | | | |
|---|---|---|---|---|---|---|---|---|---|---|---|
| TTT | Phe | 11 | TCT | Ser | 5 | TAT | Tyr | 12 | TGT | Cys | 3 |
| TTC | Phe | 5 | TCC | Ser | 1 | TAC | Tyr | 1 | TGC | Cys | 0 |
| TTA | Leu | 8 | TCA | Ser | 6 | TAA | *** | 0 | TGA | *** | 0 |
| TTG | Leu | 4 | TCG | Ser | 4 | TAG | *** | 0 | TGG | Trp | 8 |
| CTT | Leu | 8 | CCT | Pro | 5 | CAT | His | 9 | CGT | Arg | 4 |
| CTC | Leu | 1 | CCC | Pro | 0 | CAC | His | 1 | CGC | Arg | 0 |
| CTA | Leu | 1 | CCA | Pro | 11 | CAA | Gln | 6 | CGA | Arg | 2 |
| CTG | Leu | 0 | CCG | Pro | 2 | CAG | Gln | 1 | CGG | Arg | 2 |
| ATT | Ile | 12 | ACT | Thr | 4 | AAT | Asn | 11 | AGT | Ser | 2 |
| ATC | Ile | 6 | ACC | Thr | 1 | AAC | Asn | 2 | AGC | Ser | 1 |
| ATA | Ile | 3 | ACA | Thr | 1 | AAA | Lys | 21 | AGA | Arg | 2 |
| ATG | Met | 9 | ACG | Thr | 0 | AAG | Lys | 6 | AGG | Arg | 3 |
| GTT | Val | 12 | GCT | Ala | 5 | GAT | Asp | 16 | GGT | Gly | 10 |
| GTC | Val | 2 | GCC | Ala | 3 | GAC | Asp | 1 | GGC | Gly | 4 |
| GTA | Val | 6 | GCA | Ala | 8 | GAA | Glu | 25 | GGA | Gly | 3 |
| GTG | Val | 3 | GCG | Ala | 3 | GAG | Glu | 5 | GGG | Gly | 0 |

*FIG. 9A*

Codon Usage in Rluc-final

| | | | | | | | | | | | |
|---|---|---|---|---|---|---|---|---|---|---|---|
| TTT | Phe | 4 | TCT | Ser | 0 | TAT | Tyr | 2 | TGT | Cys | 1 |
| TTC | Phe | 12 | TCC | Ser | 10 | TAC | Tyr | 11 | TGC | Cys | 2 |
| TTA | Leu | 0 | TCA | Ser | 1 | TAA | *** | 0 | TGA | *** | 0 |
| TTG | Leu | 0 | TCG | Ser | 0 | TAG | *** | 0 | TGG | Trp | 8 |
| CTT | Leu | 3 | CCT | Pro | 11 | CAT | His | 2 | CGT | Arg | 0 |
| CTC | Leu | 6 | CCC | Pro | 3 | CAC | His | 8 | CGC | Arg | 7 |
| CTA | Leu | 0 | CCA | Pro | 4 | CAA | Gln | 3 | CGA | Arg | 0 |
| CTG | Leu | 13 | CCG | Pro | 0 | CAG | Gln | 4 | CGG | Arg | 3 |
| ATT | Ile | 3 | ACT | Thr | 1 | AAT | Asn | 2 | AGT | Ser | 1 |
| ATC | Ile | 18 | ACC | Thr | 4 | AAC | Asn | 11 | AGC | Ser | 7 |
| ATA | Ile | 0 | ACA | Thr | 0 | AAA | Lys | 4 | AGA | Arg | 2 |
| ATG | Met | 9 | ACG | Thr | 0 | AAG | Lys | 23 | AGG | Arg | 1 |
| GTT | Val | 2 | GCT | Ala | 11 | GAT | Asp | 6 | GGT | Gly | 3 |
| GTC | Val | 8 | GCC | Ala | 9 | GAC | Asp | 11 | GGC | Gly | 7 |
| GTA | Val | 0 | GCA | Ala | 0 | GAA | Glu | 2 | GGA | Gly | 3 |
| GTG | Val | 13 | GCG | Ala | 0 | GAG | Glu | 28 | GGG | Gly | 4 |

*FIG. 9B*

Oligonucleotides used for the assembly of synthetic *Renilla* luciferase gene

Sense Strand

| Oligo name | Oligo sequence from 5' to 3' | |
|---|---|---|
| RLS1 (1-40) | AACCATGGCTTCCAAGGTGTACGACCCCGAGCAACGCAAA | (SEQ ID NO:246) |
| RLS2 (41-80) | CGCATGATCACTGGGCCTCAGTGGTGGGCTCGCTGCAAGC | (SEQ ID NO:247) |
| RLS3 (81-120) | AAATGAACGTGCTGGACTCCTTCATCAACTACTATGATTC | (SEQ ID NO:248 |
| RLS4 (121-170) | CGAGAAGCACGCCGAGAACGCCGTGATTTTTCTGCATGGTAACGCTGCCT | |
| | | (SEQ ID NO: 249) |
| RLS5 (171-210) | CCAGCTACCTGTGGAGGCACGTCGTGCCTCACATCGAGCC | (SEQ ID NO:250) |
| RLS6 (211-250) | CGTGGCTAGATGCATCATCCCTGATCTGATCGGAATGGGT | (SEQ ID NO:251) |
| RLS7 (251-290) | AAGTCCGGCAAGAGCGGGAATGGCTCATATCGCCTCCTGG | (SEQ ID NO:252) |
| RLS8 (291-330) | ATCACTACAAGTACCTCACCGCTTGGTTCGAGCTGCTGAA | (SEQ ID NO:253) |
| RLS9 (331-370) | CCTTCCAAAGAAAATCATCTTTGTGGGCCACGACTGGGGG | (SEQ ID NO:254) |
| RLS10 (371-410) | GCTTGTCTGGCCTTTCACTACTCCTACGAGCACCAAGACA | (SEQ ID NO:255) |
| RLS11 (411-450) | AGATCAAGGCCATCGTCCATGCTGAGAGTGTCGTGGACGT | (SEQ ID NO:256) |
| RLS12 (451-495) | GATCGAGTCCTGGGACGAGTGGCCTGACATCGAGGAGGATATCGC | (SEQ ID NO:257) |
| RLS13 (496-535) | CCTGATCAAGAGCGAAGAGGGCGAGAAAATGGTGCTTGAG | (SEQ ID NO:258) |
| RLS14 (536-575) | AATAACTTCTTCGTCGAGACCATGCTCCCAAGCAAGATCA | (SEQ ID NO:259) |
| RLS15 (576-620) | TGCGGAAACTGGAGCCTGAGGAGTTCGCTGCCTACCTGGAGCCAT | (SEQ ID NO:260) |
| RLS16 (621-660) | TCAAGGAGAAGGGCGAGGTTAGACGGCCTACCCTCTCCTG | (SEQ ID NO:261) |
| RLS17 (661-700) | GCCTCGCGAGATCCCTCTCGTTAAGGGAGGCAAGCCCGAC | (SEQ ID NO:262) |
| RLS18 (701-740) | GTCGTCCAGATTGTCCGCAACTACAACGCCTACCTTCGGG | (SEQ ID NO:263) |
| RLS19 (741-780) | CCAGCGACGATCTGCCTAAGATGTTCATCGAGTCCGACCC | (SEQ ID NO:264) |
| RLS20 (781-820) | TGGGTTCTTTTCCAACGCTATTGTCGAGGGAGCTAAGAAG | (SEQ ID NO:265) |
| RLS21 (821-860) | TTCCCTAACACCGAGTTCGTGAAGGTGAAGGGCCTCCACT | (SEQ ID NO:266) |
| RLS22 (861-900) | TCAGCCAGGAGGACGCTCCAGATGAAATGGGTAAGTACAT | (SEQ ID NO:267) |
| RLS23 (901-949) | CAAGAGCTTCGTGGAGCGCGTGCTGAAGAACGAGCAGTAATTCTAGAGC | |
| | | (SEQ ID NO:268) |

Anti-sense Strand

| Oligo name | Oligo Sequence from 5' to 3' | |
|---|---|---|
| RLAS1 (1-29) | GCTCTAGAATTACTGCTCGTTCTTCAGCA | (SEQ ID NO:269) |
| RLAS2 (30-69) | CGCGCTCCACGAAGCTCTTGATGTACTTACCCATTTCATC | (SEQ ID NO:270) |
| RLAS3 (70-109) | TGGAGCGTCCTCCTGGCTGAAGTGGAGGCCCTTCACCTTC | (SEQ ID NO:271) |
| RLAS4 (110-149) | ACGAACTCGGTGTTAGGGAACTTCTTAGCTCCCTCGACAA | (SEQ ID NO:272) |
| RLAS5 (150-189) | TAGCGTTGGAAAAGAACCCAGGGTCGGACTCGATGAACAT | (SEQ ID NO:273) |
| RLAS6 (190-229) | CTTAGGCAGATCGTCGCTGGCCCGAAGGTAGGCGTTGTAG | (SEQ ID NO:274) |
| RLAS7 (230-269) | TTGCGGACAATCTGGACGACGTCGGGCTTGCCTCCCTTAA | (SEQ ID NO:275) |
| RLAS8 (270-309) | CGAGAGGGATCTCGCGAGGCCAGGAGAGGGTAGGCCGTCT | (SEQ ID NO:276) |
| RLAS9 (310-349) | AACCTCGCCCTTCTCCTTGAATGGCTCCAGGTAGGCAGCG | (SEQ ID NO:277) |
| RLAS10 (350-394) | AACTCCTCAGGCTCCAGTTTCCGCATGATCTTGCTTGGGAGCATG | (SEQ ID NO:278) |
| RLAS11 (395-434) | GTCTCGACGAAGAAGTTATTCTCAAGCACCATTTTCTCGC | (SEQ ID NO:279) |
| RLAS12 (435-474) | CCTCTTCGCTCTTGATCAGGGCGATATCCTCCTCGATGTC | (SEQ ID NO:280) |
| RLAS13 (475-517) | AGGCCACTCGTCCCAGGACTCGATCACGTCCACGACACTCTCA | (SEQ ID NO:281) |
| RLAS14 (518-559) | GCATGGACGATGGCCTTGATCTTGTCTTGGTGCTCGTAGGAG | (SEQ ID NO:282) |
| RLAS15 (560-599) | TAGTGAAAGGCCAGACAAGCCCCCAGTCGTGGCCCACAA | (SEQ ID NO:283) |
| RLAS16 (600-639) | AGATGATTTTCTTTGGAAGGTTCAGCAGCTCGAACCAAGC | (SEQ ID NO:284) |
| RLAS17 (640-679) | GGTGAGGTACTTGTAGTGATCCAGGAGGCGATATGAGCCA | (SEQ ID NO:285) |
| RLAS18 (680-719) | TTCCCGCTCTTGCCGGACTTACCCATTCCGATCAGATCAG | (SEQ ID NO:286) |
| RLAS19 (720-764) | GGATGATGCATCTAGCCACGGGCTCGATGTGAGGCACGACGTGCC | (SEQ ID NO:287) |
| RLAS20 (765-804) | TCCACAGGTAGCTGGAGGCAGCGTTACCATGCAGAAAAAT | (SEQ ID NO:288) |
| RLAS21 (805-849) | CACGGCGTTCTCGGCGTGCTTCTCGGAATCATAGTAGTTGATGAA | (SEQ ID NO:289) |
| RLAS22 (850-889) | GGAGTCCAGCACGTTCATTTGCTTGCAGCGAGCCCACCAC | (SEQ ID NO:290) |
| RLAS23 (890-929) | TGAGGCCCAGTGATCATGCGTTTGCGTTGCTCGGGGTCGT | (SEQ ID NO:291) |
| RLAS24 (930-949) | ACACCTTGGAAGCCATGGTT | (SEQ ID NO:292) |

*FIG. 10*

```
GRVER51.SEQ  A T G A T G A A[A C]G[C]G A[A]A A[G]A A[C]G T[G]A T[C]T A[C]G G[C]C C[A]G A A C  40
LUCPPLYG.SEQ A T G A T G A A G A G A G A G A A A A A T G T T A T A T A T G G A C C C G A A C  40
RD1561H9.SEQ A T G A T[A]A A G[C]G[T]G A G A A A A A T G T[C]A T[C]T A T G G[C]C C[T]G A[G]C  40

GRVER51.SEQ  C[A]C T[G]C A[T]C C[A C]T G G A A G A C[T]C A C[C]G C[T]G G[T]G A[G]A T G C T  80
LUCPPLYG.SEQ C C C T A C A C C C C T T G G A A G A C T T A A C A G C A G G A G A A A T G C T  80
RD1561H9.SEQ C[T]C T[C]C A[T]C C[T]T T G G A[G]G A[T]T T[G]A C[T]G C[C]G G[C]G A A A T G C T  80

GRVER51.SEQ  C T T C[C]G[A]G C[A]C T[G]C G[T]A A A C A T[A G]T C A[C C]T[C]C C[T]C A[A]G C[A]  120
LUCPPLYG.SEQ C T T C A G G G C C C T T C G A A A A C A T T C T C A T T T A C C G C A G G C T  120
RD1561H9.SEQ[G]T T[T C]G[T]G C[T]C T[C]C G[C]A A[G]C A[C]T C T C A T T T[G]C C[T]C A[A]G C[C]  120

GRVER51.SEQ [C]T[C]G T[G]G A[C]G T[C]G T[G]G G[A]G A C G A[G A G C]T[C]T C C T A[C]A A A G  160
LUCPPLYG.SEQ T T A G T A G A T G T G T T T G G T G A C G A A T C G C T T T C C T A T A A A G  160
RD1561H9.SEQ T T[G]C T[C]G A T G T G[G]T[C]G G[C]G A[T]G A A T C[T T]T[G A G]C T A[C]A A[G]G  160

GRVER51.SEQ  A[A]T T T T T[C]G A A G C T A C[T G T G]C T[G T]T[G]G C[C]A A A G[C]T C C A  200
LUCPPLYG.SEQ A G T T T T T T G A A G C T A C A T G C C T C C T A G C G C A A A G T C T C C A  200
RD1561H9.SEQ A G T T T T T T G A[G]G C[A]A C[C G T]C[T]T[G]C T[G]G C[T]C A[G T C C]T C C A  200

GRVER51.SEQ [T]A A T T G T G G[G]T A C A A[A]A T G A A[C]G A T G T[G]G T G[A G C]A T[T]T G[T]  240
LUCPPLYG.SEQ C A A T T G T G G A T A C A A G A T G A A T G A T G T A G T G T C G A T C T G C  240
RD1561H9.SEQ C A A T T G T G G[C]T A C A A G A T G A A[C]G A[C]G T[C]G T[T A G T]A T C T G[T]  240

GRVER51.SEQ  G C[T]G A G A A T A A[C]A[C T C]G[C]T T[C]T T T A T T C C[T]G[T]A A T[C]G C[T]G  280
LUCPPLYG.SEQ G C C G A G A A T A A T A A A A G A T T T T T T A T T C C C A T T A T T G C A G  280
RD1561H9.SEQ G C[T]G A[A]A[C]A A T A[C C C]G[T]T T[C]T T[C]A T T C C[A G]T[C]A T[C]G C[C]G  280

GRVER51.SEQ  C T T G G T A[C]A T[C]G G[C]A T G A T T G T[C]G C[C]C C T G T[G]A A T G A A[T C]  320
LUCPPLYG.SEQ C T T G G T A T A T T G G T A T G A T T G T A G C A C C T G T T A A T G A A A A  320
RD1561H9.SEQ C[A]T G G T A T A T[C]G G T A T G A T[C]G T[G]G C[T]C C[A]G T[C]A A[C]G A[G]A G  320

GRVER51.SEQ  T T A C A T C C C A G A T G A[G]C T[G]T G T A A G G T[T]A T G G G T A T[T A G C]  360
LUCPPLYG.SEQ T T A C A T C C C A G A T G A A C T C T G T A A G G T C A T G G G T A T A T C G  360
RD1561H9.SEQ[C]T A C A T[T]C C[C]G A[C]G A A C T[G]T G T A A[A]G T C A T G G G T A T[C]T C[T]  360

GRVER51.SEQ  A A A C C[T]C A A A T[C]G T[C]T T T A[C]T A C[C]A A[A]A A C A T[C]T T[G]A A T A  400
LUCPPLYG.SEQ A A A C C A C A A A T A G T T T T T T G T A C A A A G A A C A T T T T A A A T A  400
RD1561H9.SEQ A A[G]C C A C A[G]A T[T]G T[C]T T[C A C C]A C[T]A A G A A[T]A T T[C]T[G]A A[C]A  400

GRVER51.SEQ  A G G T[C]T T G G A[A]G T[C]C A G[T C T C]G[T]A C T A A[C]T T C A T[C]A A A[C]G  440
LUCPPLYG.SEQ A G G T A T T G G A G G T A C A G A G C A G A A C T A A T T T C A T A A A A A G  440
RD1561H9.SEQ A[A]G T[C C]T G G A[A]G T[C]C A[A]A G C[C]G[C]A C[C]A A[C]T T[A]T T[A]A[G C]G  440

GRVER51.SEQ [C]A T C A T[T]A T[T]C T[G]G A T A C[C]G T[C]G A A A A C A T[C]C A C G G[C]T G T  480
LUCPPLYG.SEQ G A T C A T C A T A C T T G A T A C T G T A G A A A A C A T A C A C G G T T G T  480
RD1561H9.SEQ[T]A T C A T C A T[C T]T[G]G A[C]A C T G T[G]G A[G]A A[T]A T[T]C A C G G T T G[C]  480

GRVER51.SEQ  G A[G]A G[C]C T[C]C C[T]A A[C]T T[C]A T[C]T C T C G T T A[C A G C]G A T G G[T]A  520
LUCPPLYG.SEQ G A A A G T C T T C C C A A T T T T A T T T C T C G T T A T T C G G A T G G A A  520
RD1561H9.SEQ G A A[T C]T[T]T[G]C C[T]A A T T T[C]A T[C]T C T C G[C]T A T T C[A]G A[C]G G[C]A  520

GRVER51.SEQ  A T A T[C]G C[T]A A[T]T T C A A[G]C C[C]T T[G]C A T T[T T]G A T C C[A]G T[C]G A  560
LUCPPLYG.SEQ A T A T T G C C A A C T T C A A A C C T T T A C A T T A C G A T C C T G T T G A  560
RD1561H9.SEQ A[C]A T[C]G C[A]A A C T T[T]A A A C C[A C]T[C]C A[C]T[T]C G A[C]C C T G T[G]G A  560
```

*FIG. 11A*

```
GRVER51.SEQ  G C A A G T G G C[C]G C T A T[T]T T[G]T G[C]T C[C]T C[C]G G C A C[C]A C T G G[T] 600
LUCPPLYG.SEQ G C A A G T G G C A G C T A T C T T A T G T T C G T C A G G C A C T A C T G G A 600
RD1561H9.SEQ[A]C A A G T[T]G C A G C[C]A T[T C]T[G]T G T[A G C A G C]G G[T]A C T A C T G G A 600

GRVER51.SEQ  T T[G]C C[T]A A A G G T G T[C]A T G C A[G]A C T C A C C A[G]A A T A T[C]T G T G 640
LUCPPLYG.SEQ T T A C C G A A A G G T G T A A T G C A A A C T C A C C A A A A T A T T T G T G 640
RD1561H9.SEQ[C]T[C]C C[A]A A[G]G[A]G T[C]A T G C A[G]A C[C]A[T]C A A A A[C]A T T T G[C]G 640

GRVER51.SEQ  T[G]C G[T T]T[G]A T[C]A[C]G C T[C]T[C]G A C C C[T C]G[T]G[T]G G G[T]A C[T]C A 680
LUCPPLYG.SEQ T C C G A C T T A T A C A T G C T T T A G A C C C C A G G G C A G G A A C G C A 680
RD1561H9.SEQ T[G]C G[T]C T[G]A T[C]A T G C T C[C]T[C]G A[T]C C[A C]G[C T A C]G G[C]A C[T]C A 680

GRVER51.SEQ  A[T]T[G]A T[C]C C T G G[C]G T G A C[T]G T[G C]T[G]G T[G]T A T C T G C C T T T[C] 720
LUCPPLYG.SEQ A C T T A T T C C T G G T G T G A C A G T C T T A G T A T A T C T G C C T T T T 720
RD1561H9.SEQ[G]C T[G]A T T C C T G G T G T[C]A C[C]G T C T T[G]G T[C]T A[C T]T G C C T T T[C] 720

GRVER51.SEQ  T T[T]C A[C]G C[C]T T T G G[T]T T C T C T A T[T]A[C]C[C]T G G G[C]T A[T]T C A 760
LUCPPLYG.SEQ T T C C A T G C T T T T G G G T T C T C T A T A A A C T T G G G A T A C T T C A 760
RD1561H9.SEQ T T C C A T G C T T T[C]G G[C]T T[T C A]T A T[T]A[C T]T T G G G[T]A C T T[T]A 760

GRVER51.SEQ  T G G T[C]G G[C T]T[G]C G T G T[C]A T C A T G T T[T C]G[T]C G[C]T T[C]G A[C]C A 800
LUCPPLYG.SEQ T G G T G G G T C T T C G T G T T A T C A T G T T A A G A C G A T T T G A T C A 800
RD1561H9.SEQ T G G T[C]G G T C T[C]C G[C]G T[G]A T[T]A T G T T[C C]G[C]C G[T]T T T G A T C A 800

GRVER51.SEQ  A G A A G C[C]T T[C T]T[G]A A[G]G C T A T T C A[A]G A[C]T A[C]G A[G]G T[G]C G[T] 840
LUCPPLYG.SEQ A G A A G C A T T T C T A A A A G C T A T T C A G G A T T A T G A A G T T C G A 840
RD1561H9.SEQ[G]G A[G]G C[T]T T[C T]T[G]A A A G C[C]A T[C]C A[A]G A T T A T G A A G T[C]C G[C] 840

GRVER51.SEQ [T C C]G T[G]A T[C]A A C G T[C]C C[T T]C A G T[C]A T[T]T T G T T C[C]T[G A G C]A 880
LUCPPLYG.SEQ A G T G T A A T T A A C G T T C C A G C A A T A A T A T T G T T C T T A T C G A 880
RD1561H9.SEQ A G T G T[C]A T[C]A A C G T[G]C C[T A G C]T[G]A T[C C]T G T T[T]T T[G]T C[T]A 880

GRVER51.SEQ  A A[T C]T C C T T T G G T T G A C A A[G]T A[T]G A T[C]T[G A G C]A G[C]T T[G C]G 920
LUCPPLYG.SEQ A A A G T C C T T T G G T T G A C A A A T A C G A T T T A T C A A G T T T A A G 920
RD1561H9.SEQ A[G]A G[C]C C[A C]T[C]G T[G]A C A A[G]T A C G A[C]T T[G]T C[T T C A C]T[G C]G 920

GRVER51.SEQ [T]G A[G C]T G T G[C]T G[T]G G[C]G C[T]G C[T]C C[T]T[G]C[C]A A A G A A G T[G] 960
LUCPPLYG.SEQ G G A A T T G T G T T G C G G T G C G G C A C C A T T A G C A A A A G A A G T T 960
RD1561H9.SEQ[T]G A A T T G T G T T G C G G T G C[C]G C[T]C C A[C]T[G]C[T]A A[G]G A[G]G T[C] 960

GRVER51.SEQ  G C[C]G A G G T[C]G C[T]G[C T]A A[G]C G[T C]T[G]A A C[C]T[C]C C[T]G G[T]A T[C]C 1000
LUCPPLYG.SEQ G C T G A G G T T G C A G T A A A A C G A T T A A A C T T G C C A G G A A T T C 1000
RD1561H9.SEQ G C T G A[A]G T[G]G C[C]G[C C]A A A C G[C]T T[G]A A[T C]T[T T]C C A G G[G]A T T C 1000

GRVER51.SEQ  G C T G[C]G G[T]T T T G G T T T G A C[T]G A[G A G C]A C T T C[T]G C T A A[C]A T 1040
LUCPPLYG.SEQ G C T G T G G A T T T G G T T T G A C A G A A T C T A C T T C A G C T A A T A T 1040
RD1561H9.SEQ G C T G[T]T G T G G[C]T T[C]G G[C C]T[C]A C[C]G A A T C T A C[C A G T]G C[G]A[T]A T 1040

GRVER51.SEQ [C]C A[T]A G[C T]T[G C]G[A]G A[C]G A[G]T T T A A[G]T C[T]G G[T A G C]T[G]G G[T] 1080
LUCPPLYG.SEQ A C A C A G T C T T G G G G A T G A A T T T A A A T C A G G A T C A C T T G G A 1080
RD1561H9.SEQ[C]C A[G]A[C]T C T[C]G G G G A T G A[G]T T T A A[G A G C]G G[C]T C[T T]T[G]G G[C] 1080

GRVER51.SEQ [C]G[C]G T[G]A C T C C T[C]T[T]A T G G C[T]G C[A]A A[G]A T[C]G C[C]G A[C C]G[T]G 1120
LUCPPLYG.SEQ A G A G T T A C T C C T T T T A A T G G C A G C T A A A A T A G C A G A T A G G G 1120
RD1561H9.SEQ[C]G[T]G T[C]A C T C C[A C]T[C]A T G G C[T]G C T A A[G]A T[C]G C[T]G A T[C]G[C]G 1120
```

```
GRVER51.SEQ    M M K R E K N V I Y G P E P L H P L E D L T A G E M L F R A L R K H S H L P Q A  118
LUCPPLYG.SEQ   M M K R E K N V I Y G P E P L H P L E D L T A G E M L F R A L R K H S H L P Q A  118
RD1561H9.SEQ   M [I] K R E K N V I Y G P E P L H P L E D L T A G E M L F R A L R K H S H L P Q A  118

GRVER51.SEQ    L V D V [V] G D E S L S Y K E F F E A T [V] L L A Q S L H N C G Y K M N D V V S I C  238
LUCPPLYG.SEQ   L V D V F G D E S L S Y K E F F E A T C L L A Q S L H N C G Y K M N D V V S I C  238
RD1561H9.SEQ   L V D V [V] G D E S L S Y K E F F E A T [V] L L A Q S L H N C G Y K M N D V V S I C  238

GRVER51.SEQ    A E N N [T] R F F I P [V] I A A W Y I G M I V A P V N E S Y I P D E L C K V M G I S  358
LUCPPLYG.SEQ   A E N N K R F F I P I I A A W Y I G M I V A P V N E S Y I P D E L C K V M G I S  358
RD1561H9.SEQ   A E N N [T] R F F I P [V] I A A W Y I G M I V A P V N E S Y I P D E L C K V M G I S  358

GRVER51.SEQ    K P Q I V F [T] T K N I L N K V L E V Q S R T N F I K R I I I L D T V E N I H G C  478
LUCPPLYG.SEQ   K P Q I V F C T K N I L N K V L E V Q S R T N F I K R I I I L D T V E N I H G C  478
RD1561H9.SEQ   K P Q I V F [T] T K N I L N K V L E V Q S R T N F I K R I I I L D T V E N I H G C  478

GRVER51.SEQ    E S L P N F I S R Y S D G N I A N F K P L H [F] D P V E Q V A A I L C S S G T T G  598
LUCPPLYG.SEQ   E S L P N F I S R Y S D G N I A N F K P L H Y D P V E Q V A A I L C S S G T T G  598
RD1561H9.SEQ   E S L P N F I S R Y S D G N I A N F K P L H [F] D P V E Q V A A I L C S S G T T G  598

GRVER51.SEQ    L P K G V M Q T H Q N I C V R L I H A L D P R [V] G T Q L I P G V T V L V Y L P F  718
LUCPPLYG.SEQ   L P K G V M Q T H Q N I C V R L I H A L D P R A G T Q L I P G V T V L V Y L P F  718
RD1561H9.SEQ   L P K G V M Q T H Q N I C V R L I H A L D P R [Y] G T Q L I P G V T V L V Y L P F  718

GRVER51.SEQ    F H A F G F S I [T] L G Y F M V G L R V I M [F] R R F D Q E A F L K A I Q D Y E V R  838
LUCPPLYG.SEQ   F H A F G F S I N L G Y F M V G L R V I M L R R F D Q E A F L K A I Q D Y E V R  838
RD1561H9.SEQ   F H A F G F [H] I [T] L G Y F M V G L R V I M [F] R R F D Q E A F L K A I Q D Y E V R  838

GRVER51.SEQ    S V I N V P [S V] I L F L S K S P L V D K Y D L S S L R E L C C G A A P L A K E V  958
LUCPPLYG.SEQ   S V I N V P A I I L F L S K S P L V D K Y D L S S L R E L C C G A A P L A K E V  958
RD1561H9.SEQ   S V I N V P [S V] I L F L S K S P L V D K Y D L S S L R E L C C G A A P L A K E V  958

GRVER51.SEQ    A E V A [A] K R L N L P G I R C G F G L T E S T S A N I H S L [R] D E F K S G S L G  1078
LUCPPLYG.SEQ   A E V A V K R L N L P G I R C G F G L T E S T S A N I H S L G D E F K S G S L G  1078
RD1561H9.SEQ   A E V A [A] K R L N L P G I R C G F G L T E S T S A [I] I [Q T] L G D E F K S G S L G  1078

GRVER51.SEQ    R V T P L M A A K I A D R E T G K A L G P N Q V G E L C [I] K G P M V S K G Y V N  1198
LUCPPLYG.SEQ   R V T P L M A A K I A D R E T G K A L G P N Q V G E L C V K G P M V S K G Y V N  1198
RD1561H9.SEQ   R V T P L M A A K I A D R E T G K A L G P N Q V G E L C [I] K G P M V S K G Y V N  1198

GRVER51.SEQ    N V E A T K E A I D D D G W L H S G D F G Y Y D E D E H F Y V V D R Y K E L I K  1318
LUCPPLYG.SEQ   N V E A T K E A I D D D G W L H S G D F G Y Y D E D E H F Y V V D R Y K E L I K  1318
RD1561H9.SEQ   N V E A T K E A I D D D G W L H S G D F G Y Y D E D E H F Y V V D R Y K E L I K  1318

GRVER51.SEQ    Y K G S Q V A P A E L E E I L L K N P C I R D V A V V G I P D L E A G E L P S A  1438
LUCPPLYG.SEQ   Y K G S Q V A P A E L E E I L L K N P C I R D V A V V G I P D L E A G E L P S A  1438
RD1561H9.SEQ   Y K G S Q V A P A E L E E I L L K N P C I R D V A V V G I P D L E A G E L P S A  1438

GRVER51.SEQ    F V V K Q P G K E I T A K E V Y D Y L A E R V S H T K Y L R G G V R F V D S I P  1558
LUCPPLYG.SEQ   F V V K Q P G K E I T A K E V Y D Y L A E R V S H T K Y L R G G V R F V D S I P  1558
RD1561H9.SEQ   F V V K Q P G [T] E I T A K E V Y D Y L A E R V S H T K Y L R G G V R F V D S I P  1558

GRVER51.SEQ    R N V T G K I T R K E L L K Q L L E K [A G G]                                    1624
LUCPPLYG.SEQ   R N V T G K I T R K E L L K Q L L E K S S K L                                    1627
RD1561H9.SEQ   R N V T G K I T R K E L L K Q L L [V] K [A G G]                                  1624
```

*FIG. 12*

GRver5.1 DNA sequence of pGL3 vectors

```
ATGGTGAAACGCGAAAAGAACGTGATCTACGGCCCAGAACCACTGCATCC    50
ACTGGAAGACCTCACCGCTGGTGAGATGCTCTTCCGAGCACTGCGTAAAC   100
ATAGTCACCTCCCTCAAGCACTCGTGGACGTCGTGGGAGACGAGAgCCTC   150
TCCTACAAAGAATTTTCGAAGCTACTGTGCTGTTGGCCCAAAGCCTCCA    200
TAATTGTGGGTACAAAATGAACGATGTGGTGAGCATTTGTGCTGAGAATA   250
ACACTCGCTTCTTTATTCCTGTAATCGCTGCTTGGTACATCGGCATGATT   300
GTCGCCCTGTGAATGAATCTTACATCCCAGATGAGCTGTGTAAGGTTAT    350
GGGTATTAGCAAACCTCAAATCGTCTTTACTACCAAAACATCTTGAATA    400
AGGTCTTGGAAGTCCAGTCTCGTACTAACTTCATCAAACGCATCATTATT   450
CTGGATACCGTCGAAAACATCCACGGCTGTGAGAGCCTCCCTAACTTCAT   500
CTCTCGTTACAGCGATGGTAATATCGCTAATTTCAAGCCCTTGCATTTTG   550
ATCCAGTCGAGCAAGTGGCCGCTATTTTGTGCTCCTCCGGCACCACTGGT   600
TTGCCTAAAGGTGTCATGCAGACTCACCAGAATATCTGTGTGCGTTTGAT   650
CCACGCTCTCGACCCTCGTGTGGGTACTCAATTGATCcCTGGCGTGACTG   700
TGCTGGTGTATCTGCCTTTCTTTCACGCCTTTGGTTTCTCTATTACCCTG   750
GGCTATTTCATGGTCGGCTTGCGTGTCATCATGTTTCGTCGCTTCGACCA   800
AGAAGCCTTCTTGAAGGCTATTCAAGACTACGAGGTGCGTTCCGTGATCA   850
ACGTCCCTTCAGTCATTTTGTTCCTGAGCAAATCTCCTTTGGTTGACAAG   900
TATGATCTGAGCAGCTTGCGTGAGCTGTGCTGTGGCGCTGCTCCTTTGGC   950
CAAAGAAGTGGCCGAGGTCGCTGCTAAGCGTCTGAACCTCCCTGGTATCC  1000
GCTGCGGTTTTGGTTTGACTGAGAGCACTTCTGCTAACATCCATAGCTTG  1050
CGAGACGAGTTTAAGTCTGGTAGCCTGGGTCGCGTGACTCCTCTTATGGC  1100
TGCAAAGATCGCCGACCGTGAGACCGGCAAAGCACTGGGCCCAAATCAAG  1150
TCGGTGAATTGTGTATTAAGGGCCCTATGGTCTCTAAAGGCTACGTGAAC  1200
AATGTGGAGGCCACTAAAGAAGCCATTGATGATGATGGCTGGCTCCATAG  1250
CGGCGACTTCGGTTACTATGATGAGGACGAACACTTCTATGTGGTCGATC  1300
GCTACAAAGAATTGATTAAGTACAAAGGCTCTCAAGTCGCACCAGCCGAA  1350
CTGGAAGAAATTTTGCTGAAGAACCCTTGTATCCGCGACGTGGCCGTCGT  1400
GGGTATCCCAGACTTGGAAGCTGGCGAGTTGCCTAGCGCCTTTGTGGTGA  1450
AACAACCCGGCAAGGAGATCACTGCTAAGGAGGTCTACGACTATTTGGCC  1500
GAGCGCGTGTCTCACACCAAATATCTGCGTGGCGGCGTCCGCTTCGTCGA  1550
TTCTATTCCACGCAACGTTACCGGTAAGATCACTCGTAAAGAGTTGCTGA  1600
AGCAACTCCTCGAAAAAGCTGGCGGC                          1626
```

FIG. 18A

RDver5.1 DNA sequence of pGL3 vectors

```
ATGGTGAAGCGTGAGAAAAATGTCATCTATGGCCCTGAGCCTCTCCATCC    50
TTTGGAGGATTTGACTGCCGGCGAAATGCTGTTTCGTGCTCTCCGCAAGC   100
ACTCTcATTTGCCTCAAGCCTTGGTCGATGTGGTCGGCGATGAATCTTTG   150
AGCTACAAGGAGTTTTTTGAGGCAACCGTCTTGCTGGCTCAGTCCCTCCA   200
CAATTGTGGCTACAAGATGAACGACGTCGTTAGTATCTGTGCTGAAAACA   250
ATACCCGTTTCTTCATTCCAGTCATCGCCGCATGGTATATCGGTATGATC   300
GTGGCTCCAGTCAACGAGAGCTACATTCCCGACGAACTGTGTAAAGTCAT   350
GGGTATCTCTAAGCCACAGATTGTCTTCACCACTAAGAATATTCTGAACA   400
AAGTCCTGGAAGTCCAAAGCCGCACCAACTTTATTAAGCGTATCATCATC   450
TTGGACACTGTGGAGAATATTCACGGTTGCGAATCTTTGCCTAATTTCAT   500
CTCTCGCTATTCAGACGGCAACATCGCAAACTTTAAACCACTCCACTTCG   550
ACCCTGTGGAACAAGTTGCAGCCATTCTGTGTAGCAGCGGTACTACTGGA   600
CTCCCAAAGGGAGTCATGCAGACCCATCAAAACATTTGCGTGCGTCTGAT   650
CCATGCTCTCGATCCACGCTACGGCACTCAGCTGATTCCTGGTGTCACCG   700
TCTTGGTCTACTTGCCTTTCTTCCATGCTTTCGGCTTTCATATTACTTTG   750
GGTTACTTTATGGTCGGTCTCCGCGTGATTATGTTCCGCCGTTTTGATCA   800
GGAGGCTTTCTTGAAAGCCATCCAAGATTATGAAGTCCGCAGTGTCATCA   850
ACGTGCCTAGCGTGATCCTGTTTTGTCTAAGAGCCCACTCGTGGACAAG   900
TACGACTTGTCTTCACTGCGTGAATTGTGTTGCGGTGCCGCTCCACTGGC   950
TAAGGAGGTCGCTGAAGTGGCCGCCAAACGCTTGAATCTTCCAGGGATTC  1000
GTTGTGGCTTCGGCCTCACCGAATCTACCAGCGCTATTATTCAGTCTCTC  1050
CGCGATGAGTTTAAGAGCGGCTCTTTGGGCCGTGTCACTCCACTCATGGC  1100
TGCTAAGATCGCTGATCGCGAAACTGGTAAGGCTTTGGGCCCGAACCAAG  1150
TGGGCGAGCTGTGTATCAAAGGCCCTATGGTGAGCAAGGGTTATGTCAAT  1200
AACGTTGAAGCTACCAAGGAGGCCATCGACGACGACGGCTGGTTGCATTC  1250
TGGTGATTTTGGATATTACGACGAAGATGAGCATTTTTACGTCGTGGATC  1300
GTTACAAGGAGCTGATCAAATACAAGGGTAGCCAGGTTGCTCCAGCTGAG  1350
TTGGAGGAGATTCTGTTGAAAAATCCATGCATTCGCGATGTCGCTGTGGT  1400
CGGCATTCCTGATCTGGAGGCCGGCGAACTGCCTTCTGCTTTCGTTGTCA  1450
AGCAGCCTGGTAAAGAAATTACCGCCAAAGAAGTGTATGATTACCTGGCT  1500
GAACGTGTGAGCCATACTAAGTACTTGCGTGGCGGCGTGCGTTTTGTTGA  1550
CTCCATCCCTCGTAACGTAACAGGCAAAATTACCCGCAAGGAGCTGTTGA  1600
AACAATTGTTGGAGAAGGCCGGCGGT                          1626
```

*FIG. 18B*

RD1561H9 DNA sequence of pGL3 vectors

| Sequence | Position |
|---|---|
| ATGGTAAAGCGTGAGAAAAATGTCATCTATGGCCCTGAGCCTCTCCATCC | 50 |
| TTTGGAGGATTTGACTGCCGGCGAAATGCTGTTTCGTGCTCTCCGCAAGC | 100 |
| ACTCTCATTTGCCTCAAGCCTTGGTCGATGTGGTCGGCGATGAATCTTTG | 150 |
| AGCTACAAGGAGTTTTTTGAGGCAACCGTCTTGCTGGCTCAGTCCCTCCA | 200 |
| CAATTGTGGCTACAAGATGAACGACGTCGTTAGTATCTGTGCTGAAAACA | 250 |
| ATACCCGTTTCTTCATTCCAGTCATCGCCGCATGGTATATCGGTATGATC | 300 |
| GTGGCTCCAGTCAACGAGAGCTACATTCCCGACGAACTGTGTAAAGTCAT | 350 |
| GGGTATCTCTAAGCCACAGATTGTCTTCACCACTAAGAATATTCTGAACA | 400 |
| AAGTCCTGGAAGTCCAAAGCCGCACCAACTTTATTAAGCGTATCATCATC | 450 |
| TTGGACACTGTGGAGAATATTCACGGTTGCGAATCTTTGCCTAATTTCAT | 500 |
| CTCTCGCTATTCAGACGGCAACATCGCAAACTTTAAACCACTCCACTTCG | 550 |
| ACCCTGTGGAACAAGTTGCAGCCATTCTGTGTAGCAGCGGTACTACTGGA | 600 |
| CTCCCAAAGGGAGTCATGCAGACCCATCAAAACATTTGCGTGCGTCTGAT | 650 |
| CCATGCTCTCGATCCACGCTACGGCACTCAGCTGATTCCTGGTGTCACCG | 700 |
| TCTTGGTCTACTTGCCTTTCTTCCATGCTTTCGGCTTTCATATTACTTTG | 750 |
| GGTTACTTTATGGTCGGTCTCCGCGTGATTATGTTCCGCCGTTTTGATCA | 800 |
| GGAGGCTTTCTTGAAAGCCATCCAAGATTATGAAGTCCGCAGTGTCATCA | 850 |
| ACGTGCCTAGCGTGATCCTGTTTTTGTCTAAGAGCCCACTCGTGGACAAG | 900 |
| TACGACTTGTCTTCACTGCGTGAATTGTGTTGCGGTGCCGCTCCACTGGC | 950 |
| TAAGGAGGTCGCTGAAGTGGCCGCCAAACGCTTGAATCTTCCAGGGATTC | 1000 |
| GTTGTGGCTTCGGCCTCACCGAATCTACCAGTGCGATTATCCAGACTCTC | 1050 |
| GGGGATGAGTTTAAGAGCGGCTCTTTGGGCCGTGTCACTCCACTCATGGC | 1100 |
| TGCTAAGATCGCTGATCGCGAAACTGGTAAGGCTTTGGGCCCGAACCAAG | 1150 |
| TGGGCGAGCTGTGTATCAAAGGCCCTATGGTGAGCAAGGGTTATGTCAAT | 1200 |
| AACGTTGAAGCTACCAAGGAGGCCATCGACGACGACGGCTGGTTGCATTC | 1250 |
| TGGTGATTTTGGATATTACGACGAAGATGAGCATTTTTACGTCGTGGATC | 1300 |
| GTTACAAGGAGCTGATCAAATACAAGGGTAGCCAGGTTGCTCCAGCTGAG | 1350 |
| TTGGAGGAGATTCTGTTGAAAAATCCATGCATTCGCGATGTCGCTGTGGT | 1400 |
| CGGCATTCCTGATCTGGAGGCCGGCGAACTGCCTTCTGCTTTCGTTGTCA | 1450 |
| AGCAGCCTGGTACAGAAATTACCGCCAAAGAAGTGTATGATTACCTGGCT | 1500 |
| GAACGTGTGAGCCATACTAAGTACTTGCGTGGCGGCGTGCGTTTTGTTGA | 1550 |
| CTCCATCCCTCGTAACGTAACAGGCAAAATTACCCGCAAGGAGCTGTTGA | 1600 |
| AACAATTGTTGGTGAAGGCCGGCGGT | 1626 |

FIG. 18C

GRver5.1 protein sequence of pGL3 vectors

```
MVKREKNVIYGPEPLHPLEDLTAGEMLFRALRKHSHLPQALVDVVGDESL  50
SYKEFFEATVLLAQSLHNCGYKMNDVVSICAENNTRFFIPVIAAWYIGMI  100
VAPVNESYIPDELCKVMGISKPQIVFTTKNILNKVLEVQSRTNFIKRIII  150
LDTVENIHGCESLPNFISRYSDGNIANFKPLHFDPVEQVAAILCSSGTTG  200
LPKGVMQTHQNICVRLIHALDPRVGTQLIPGVTVLVYLPFFHAFGFSITL  250
GYFMVGLRVIMFRRFDQEAFLKAIQDYEVRSVINVPSVILFLSKSPLVDK  300
YDLSSLRELCCGAAPLAKEVAEVAAKRLNLPGIRCGFGLTESTSANIHSL  350
RDEFKSGSLGRVTPLMAAKIADRETGKALGPNQVGELCIKGPMVSKGYVN  400
NVEATKEAIDDDGWLHSGDFGYYDEDEHFYVVDRYKELIKYKGSQVAPAE  450
LEEILLKNPCIRDVAVVGIPDLEAGELPSAFVVKQPGKEITAKEVYDYLA  500
ERVSHTKYLRGGVRFVDSIPRNVTGKITRKELLKQLLEKAGG          542
```

RDver5.1 protein sequence of pGL3 vectors

```
MVKREKNVIYGPEPLHPLEDLTAGEMLFRALRKHSHLPQALVDVVGDESL  50
SYKEFFEATVLLAQSLHNCGYKMNDVVSICAENNTRFFIPVIAAWYIGMI  100
VAPVNESYIPDELCKVMGISKPQIVFTTKNILNKVLEVQSRTNFIKRIII  150
LDTVENIHGCESLPNFISRYSDGNIANFKPLHFDPVEQVAAILCSSGTTG  200
LPKGVMQTHQNICVRLIHALDPRYGTQLIPGVTVLVYLPFFHAFGFHITL  250
GYFMVGLRVIMFRRFDQEAFLKAIQDYEVRSVINVPSVILFLSKSPLVDK  300
YDLSSLRELCCGAAPLAKEVAEVAAKRLNLPGIRCGFGLTESTSAIIQSL  350
RDEFKSGSLGRVTPLMAAKIADRETGKALGPNQVGELCIKGPMVSKGYVN  400
NVEATKEAIDDDGWLHSGDFGYYDEDEHFYVVDRYKELIKYKGSQVAPAE  450
LEEILLKNPCIRDVAVVGIPDLEAGELPSAFVVKQPGKEITAKEVYDYLA  500
ERVSHTKYLRGGVRFVDSIPRNVTGKITRKELLKQLLEKAGG          542
```

RD1561H9 protein sequence of pGL3 vectors

```
MVKREKNVIYGPEPLHPLEDLTAGEMLFRALRKHSHLPQALVDVVGDESL  50
SYKEFFEATVLLAQSLHNCGYKMNDVVSICAENNTRFFIPVIAAWYIGMI  100
VAPVNESYIPDELCKVMGISKPQIVFTTKNILNKVLEVQSRTNFIKRIII  150
LDTVENIHGCESLPNFISRYSDGNIANFKPLHFDPVEQVAAILCSSGTTG  200
LPKGVMQTHQNICVRLIHALDPRYGTQLIPGVTVLVYLPFFHAFGFHITL  250
GYFMVGLRVIMFRRFDQEAFLKAIQDYEVRSVINVPSVILFLSKSPLVDK  300
YDLSSLRELCCGAAPLAKEVAEVAAKRLNLPGIRCGFGLTESTSAIIQTL  350
GDEFKSGSLGRVTPLMAAKIADRETGKALGPNQVGELCIKGPMVSKGYVN  400
NVEATKEAIDDDGWLHSGDFGYYDEDEHFYVVDRYKELIKYKGSQVAPAE  450
LEEILLKNPCIRDVAVVGIPDLEAGELPSAFVVKQPGTEITAKEVYDYLA  500
ERVSHTKYLRGGVRFVDSIPRNVTGKITRKELLKQLLVKAGG          542
```

*FIG. 18D*

SEQUENCE LISTING

<160> NUMBER OF SEQ ID NOS: 302

<210> SEQ ID NO 1
<211> LENGTH: 1629
<212> TYPE: DNA
<213> ORGANISM: Pyrophorus plagiophthalamus

<400> SEQUENCE: 1

```
atgatgaaga gagagaaaaa tgttatatat ggacccgaac ccctacaccc cttggaagac      60
ttaacagcag gagaaatgct cttcagggcc cttcgaaaac attctcattt accgcaggct     120
ttagtagatg tgtttggtga cgaatcgctt tcctataaag agttttttga agctacatgc     180
ctcctagcgc aaagtctcca caattgtgga tacaagatga atgatgtagt gtcgatctgc     240
gccgagaata ataaaagatt tttttattccc attattgcag cttggtatat tggtatgatt     300
gtagcacctg ttaatgaaag ttacatccca gatgaactct gtaaggtcat gggtatatcg     360
aaaccacaaa tagttttttg tacaaagaac attttaaata aggtattgga ggtacagagc     420
agaactaatt tcataaaaag gatcatcata cttgatactg tagaaaacat acacggttgt     480
gaaagtcttc ccaattttat ttctcgttat tcggatggaa atattgccaa cttcaaacct     540
ttacattacg atcctgttga gcaagtggca gctatcttat gttcgtcagg cactactgga     600
ttaccgaaag gtgtaatgca aactcaccaa atatttgtg tccgacttat acatgcttta     660
gaccccaggg caggaacgca acttattcct ggtgtgacag tcttagtata tctgcctttt     720
ttccatgctt ttgggttctc tataaaacttg ggatacttca tggtgggtct tcgtgttatc     780
atgttaagac gatttgatca agaagcattt ctaaaagcta ttcaggatta tgaagttcga     840
agtgtaatta acgttccagc aataatattg ttcttatcga aaagtccttt ggttgacaaa     900
tacgatttat caagtttaag ggaattgtgt tgcggtgcgg caccattagc aaaagaagtt     960
gctgaggttg cagtaaaacg attaaacttg ccaggaattc gctgtggatt tggtttgaca    1020
gaatctactt cagctaatat acacagtctt ggggatgaat ttaaatcagg atcacttgga    1080
agagttactc ctttaatggc agctaaaata gcagataggg aaactggtaa agcattggga    1140
ccaaatcaag ttggtgaatt atgcgttaaa ggtcccatgg tatcgaaagg ttacgtgaac    1200
aatgtagaag ctaccaaaga agctattgat gatgatggtt ggcttcactc tggagacttt    1260
ggatactatg atgaggatga gcatttctat gtggtggacc gttacaagga attgattaaa    1320
tataagggct ctcaggtagc acctgcagaa ctagaagaga ttttattgaa aaatccatgt    1380
atcagagatg ttgctgtggt tggtattcct gatctagaag ctggagaact gccatctgcg    1440
tttgtggtta aacagcccgg aaaggagatt acagctaaag aagtgtacga ttatcttgcc    1500
gagagggtct cccatacaaa gtatttgcgt ggagggggttc gattcgttga tagcataccca   1560
aggaatgtta caggtaaaat tacaagaaag gaacttctga agcagttgct ggagaagagt    1620
tctaaactt                                                             1629
```

<210> SEQ ID NO 2
<211> LENGTH: 1626
<212> TYPE: DNA
<213> ORGANISM: Artificial Sequence
<220> FEATURE:
<223> OTHER INFORMATION: Sequence of clone YG#81-6G01

<400> SEQUENCE: 2

```
atgatgaagc gagagaaaaa tgttatatat ggacccgaac ccctacaccc cttggaagac      60
```

```
ttaacagctg gagaaatgct cttccgtgcc cttcgaaaac attctcattt accgcaggct    120
ttagtagatg tggttggcga cgaatcgctt tcctataaag agtttttga agcgacagtc    180 ctcctagcgc aaagtctcca caattgtgga tacaagatga atgatgtagt gtcgatctgc    240
gccgagaata atacaagatt ttttattccc gttattgcag cttggtatat tggtatgatt    300
gtagcacctg ttaatgaaag ttacatccca gatgaactct gtaaggtgat gggtatatcg    360
aaaccacaaa tagttttac gacaaagaac attttaaata aggtattgga ggtacagagc    420
agaactaatt tcataaaaag gatcatcata cttgatactg tagaaaacat acacggttgt    480
gaaagtcttc ccaattttat ttctcgttat tcggatggaa atattgccaa cttcaaacct    540
ttacatttcg atcctgttga gcaagtggca gctatcttat gttcgtcagg cactactgga    600
ttaccgaaag gtgtaatgca aactcaccaa atatttgtg tccgacttat acatgcttta    660
gaccccaggg caggaacgca acttattcct ggtgtgacag tcttagtata tctgccttt    720 ttccatgctt ttgggttctc tataaccttg gatacttca tggtgggtct tcgtgttatc    780
atgttcagac gatttgatca agaagcattt ctaaaagcta ttcaggatta tgaagttcga    840
agtgtaatta cgttccatc agtaatattg ttcttatcga aaagtccttt ggttgacaaa    900
tacgatttat caagtttaag ggaattgtgt tgcggtgcgg caccattagc aaaagaagtt    960
gctgaggttg cagcaaaacg attaaacttg ccaggaattc gctgtggatt tggtttgaca   1020
gaatctactt cagctaatat acacagtctt agggatgaat ttaaatcagg atcacttgga   1080
agagttactc ctttaatggc agctaaaata gcagataggg aaactggtaa agcattggga   1140
ccaaatcaag ttggtgaatt atgcattaaa ggtcccatgg tatcgaaagg ttacgtgaac   1200
aatgtagaag ctaccaaaga agctattgat gatgatggtt ggcttcactc tggagacttt   1260
ggatactatg atgaggatga gcatttctat gtggtggacc gttacaagga attgattaaa   1320
tataagggct ctcaggtagc acctgcagaa ctagaagaga ttttattgaa aaatccatgt   1380
atcagagatg ttgctgtggt tggtattcct gatctagaag ctggagaact gccatctgcg   1440
tttgtggtta acagcccgg aaaggagatt acagctaaag aagtgtacga ttatcttgcc   1500
gagagggtct cccatacaaa gtatttgcgt ggagggttc gattcgttga tagcatacca   1560
aggaatgtta caggtaaaat tacaagaaag gaacttctga agcagttgct ggagaaggcg   1620
ggaggt                                                                1626
```

<210> SEQ ID NO 3
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 3

```
atgatgaaac gcgaaaagaa cgtcatctac ggcccagagc ctctgcaccc attggaagac     60
ctgaccgccg gtgagatgtt gttccgtgct ctgcgtaaac attctcactt gcctcaagcc    120
ctggtggatg tcgtgggcga cgaaagcttg tcttataagg agtttttcga agctactgtc    180
ctgttggccc agtctctgca taattgcggt tacaaaatga acgatgtggt cagcatttgt    240
gctgagaata caccgcttt tcatccca gtgattgccg cttggtacat cggcatgatt    300
gtcgcccctg tgaatgaatc ttatatccca gacgagttgt gcaaggtcat gggtattagc    360
aaacctcaaa tcgtgtttac taccaagaac attctgaata agtcttgga agtgcagtct    420 cgtactaact tcatcaagcg cattatcatt ctggataccg tcgagaatat ccacggctgt    480
```

| | |
|---|---|
| gaaagcttgc caaactttat ttctcgttat agcgacggta atatcgctaa cttcaagcct | 540 |
| ctgcattttg atccagtgga gcaagtcgcc gctattttgt gctctagcgg cactaccggt | 600 |
| ctgcctaaag gcgtgatgca gactcaccaa aatatctgtg tccgcttgat tcatgccctg | 660 |
| gacccacgtg tgggtaccca gttgatccct ggcgtgactg tcctggtgta cttgccattc | 720 |
| tttcacgcct tcggtttttc tattaccctg gctatttca tggtcggttt gcgcgtgatc | 780 |
| atgtttcgtc gcttcgatca agaagctttt ctgaaggcca ttcaggacta cgaggtccgt | 840 |
| agcgtgatca acgtcccttc tgtgattttg ttcctgagca aatctccatt ggtcgataag | 900 |
| tatgacctga gctctttgcg cgaactgtgc tgtggcgctg ccccttttggc taaagaggtg | 960 |
| gccgaagtcg ctgccaagcg tctgaatttg ccaggtatcc gctgcggctt tggtctgact | 1020 |
| gagagcacct ctgctaacat tcatagcttg cgtgatgaat tcaaatctgg cagcctgggt | 1080 |
| cgcgtgactc cttttgatggc cgctaagatc gccgaccgtg agaccggcaa agctctgggt | 1140 |
| ccaaatcaag tcggcgaatt gtgtattaag ggtcctatgg tgtctaaagg ctacgtcaac | 1200 |
| aatgtggagg ccactaagga agctatcgat gacgatggtt ggctgcacag cggcgacttt | 1260 |
| ggttattacg atgaggacga acatttctat gtcgtggatc gctacaaaga gttgattaag | 1320 |
| tataaaggct ctcaggtcgc cccagctgag ctggaagaga tcttgctgaa gaacccttgc | 1380 |
| attcgtgacg tggccgtcgt gggtatccca gatttggaag ctggcgagct gcctagcgcc | 1440 |
| tttgtcgtga acaaccagg taaggaaatt accgctaaag aggtctacga ctatttggcc | 1500 |
| gaacgcgtgt ctcacactaa gtacctgcgt ggcggtgtcc gcttcgtgga tagcatccct | 1560 |
| cgcaatgtca ccggcaaaat tactcgtaag gagttgctga acagttgct ggaaaaggct | 1620 |
| ggtggc | 1626 |

```
<210> SEQ ID NO 4
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 4
```

| | |
|---|---|
| atgatgaaac gcgaaaagaa cgtcatctac ggcccagagc ctctgcaccc attggaagac | 60 |
| ctgaccgctg gtgagatgtt gttccgtgct ctgcgtaaac attctcactt gcctcaagcc | 120 |
| ctggtcgatg tcgtgggcga cgagagcttg tcttataagg aatttttcga agctactgtc | 180 |
| ctgttggccc aatctctgca taattgcggt tacaaaatga cgatgtggt cagcatttgt | 240 |
| gctgagaata cacccgcctt tttcatccca gtgattgccg cttggtacat cggcatgatt | 300 |
| gtcgcccctg tgaatgaatc ttatatccca gacgagttgt gcaaggtcat gggtattagc | 360 |
| aaacctcaaa tcgtgtttac taccaagaac attctgaata aggtcttgga agtgcagtct | 420 |
| cgtactaact tcatcaagcg cattatcatt ctggataccg tcgagaatat ccacggctgt | 480 |
| gagagcttgc caaactttat ttctcgttat agcgacggta atatcgctaa cttcaagcct | 540 |
| ctgcattttg atccagtgga gcaagtcgcc gctattttgt gctctagcgg caccaccggt | 600 |
| ctgcctaaag gcgtgatgca gactcaccaa aatatctgtg tccgcttgat tcatgccctg | 660 |
| gacccacgtg tgggtactca gttgatccct ggcgtgactg tcctggtgta cttgccattc | 720 |
| tttcacgcct tcggtttttc tattaccctg gctatttca tggtcggttt gcgcgtgatc | 780 |
| atgtttcgtc gcttcgatca agaagctttt ctgaaggcca ttcaggacta cgaggtccgt | 840 |
| agcgtgatca acgtcccttc tgtgattttg ttcctgagca aatctccatt ggtcgataag | 900 |

| | |
|---|---|
| tatgacctga gcagcttgcg cgaactgtgc tgtggcgctg cccctttggc taaagaggtg | 960 |
| gccgaagtcg ctgccaagcg tctgaatttg ccaggtatcc gctgcggctt tggtctgact | 1020 |
| gagagcacct ctgctaacat tcatagcttg cgtgatgagt tcaaatctgg cagcctgggt | 1080 |
| cgcgtgactc ctttgatggc cgctaagatc gccgaccgtg agaccggcaa agctctgggt | 1140 |
| ccaaatcaag tcggcgaatt gtgtattaag ggtcctatgg tgtctaaagg ctacgtcaac | 1200 |
| aatgtggagg ccactaagga agctattgat gacgatggtt ggctgcacag cggcgacttt | 1260 |
| ggttattacg atgaggacga acatttctat gtcgtcgatc gctacaaaga gttgattaag | 1320 |
| tataaaggct ctcaagtcgc cccagctgag ctggaagaaa tcttgctgaa gaacccttgc | 1380 |
| attcgtgacg tggccgtcgt gggtatccca gatttggaag ctggcgagct gcctagcgcc | 1440 |
| tttgtcgtga acaaccagg caaggaaatt accgctaaag aggtctacga ctatttggcc | 1500 |
| gagcgcgtgt ctcacactaa gtacctgcgt ggcggtgtcc gcttcgtcga tagcatccct | 1560 |
| cgcaatgtca ccggcaaaat tactcgtaag gagttgctga acagttgct ggaaaaggct | 1620 |
| ggtggc | 1626 |

<210> SEQ ID NO 5
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 5

| | |
|---|---|
| atgatgaaac gcgaaaagaa cgtgatctac ggcccagaac cactgcatcc actggaagac | 60 |
| ctcaccgctg gtgagatgct gttccgtgcc ctgcgtaaac atagccacct gcctcaagct | 120 |
| ctcgtggacg tcgtgggtga cgagagcctg tcttacaaag aattttttcga agctactgtg | 180 |
| ctgttggccc aaagcctgca taattgtggt tacaaaatga cgatgtggt gagcatctgt | 240 |
| gctgagaata acactcgctt ttttatccct gtgatcgctg cttggtacat cggcatgatt | 300 |
| gtcgccctg tgaatgaatc ttacatccca gatgagttgt gtaaggtgat gggtattagc | 360 |
| aaacctcaaa tcgtctttac taccaaaaac atcctgaata aggtcttgga agtccagtct | 420 |
| cgtactaatt tcatcaaacg cattattatt ctggataccg tcgaaaacat ccacggctgt | 480 |
| gagagcttgc ctaactttat ctctcgttac agcgatggta atatcgctaa tttcaagcca | 540 |
| ctgcattttg atccagtcga gcaggtcgcc gccattttgt gctcttctgg caccactggt | 600 |
| ttgcctaaag tgtcatgca gactcaccag aatatctgtg tgcgcttgat ccacgccctc | 660 |
| gaccctcgtg tgggtactca attgatccct ggcgtgactg tgctggtgta tttgcctttc | 720 |
| tttcacgcct ttggttttc tatcaccctg ggctatttca tggtcggctt gcgtgtgatc | 780 |
| atgtttcgtc gcttcgacca agaagccttc ctgaaggcta ttcaagacta cgaggtgcgt | 840 |
| tctgtgatca atgtcccatc tgtcattttg ttcctgagca atctcccttt ggttgacaag | 900 |
| tatgatctga gcagcttgcg tgaactgtgc tgtggcgctg ctccctttggc caagaagtg | 960 |
| gccgaggtcg ctgctaagcg tctgaaccte cctggtatcc gctgcggttt tggttttgact | 1020 |
| gagagcactt ctgccaacat ccatagcttg cgtgacgagt ttaaatctgg tagcctgggt | 1080 |
| cgcgtgaccc ctttgatggc tgcaaagatc gccgaccgtg agaccggcaa agccctgggc | 1140 |
| ccaaatcagg tcggtgaatt gtgcattaag ggccctatgg tctctaaagg ctacgtgaac | 1200 |
| aatgtggagg ccactaaaga agctattgat gatgatggtt ggttgcatag cggcgacttc | 1260 |
| ggttattatg atgaggacga acacttctat gtggtcgatc gctataaaga attgattaag | 1320 |

```
tacaaaggct ctcaagtcgc cccagctgaa ctggaagaaa ttttgctgaa gaacccttgt    1380
attcgcgacg tggccgtcgt gggtatccca gacttggaag ctggcgagtt gcctagcgcc    1440
tttgtggtga acaacctgg caaggagatt actgctaagg aggtctacga ctatttggcc    1500
gagcgcgtgt ctcacactaa atatctgcgt ggcggcgtcc gcttcgtcga ttctatccct    1560
cgcaacgtca ccggcaagat cactcgtaaa gagttgctga acaattgct cgaaaaagct    1620 ggcggc                                                                1626

<210> SEQ ID NO 6
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 6
atgatgaaac gcgaaaagaa cgtgatctac ggcccagaac cactgcatcc actggaagac      60
ctcaccgctg gtgagatgct cttccgtgca ctgcgtaaac atagtcacct ccctcaagct     120
ctcgtggacg tcgtgggaga cgagagcctc tcttacaaag aattttttcga agctactgtg    180 ctgttggccc aaagcctcca taattgtgga tacaaaatga cgatgtggt gagcatttgt     240 gctgagaata acactcgctt ctttatccct gttatcgctg cttggtacat cggcatgatt    300
gtcgcccctg tgaatgaatc ttacatccca gatgagctgt gtaaggttat gggtattagc    360
aaacctcaaa tcgtctttac taccaaaaat atcctgaata aggtcttgga agtccagtct    420
cgtactaact tcatcaaacg catcattatt ctggataccg tcgaaaacat ccatggctgt    480
gagagcctgc taacttcat ctctcgttac agcgatggta atatcgctaa tttcaaacca     540
ctgcattttg atccagtcga gcaagtggcc gctattttgt gctcttccgg caccactggt    600
ttgcctaaag gtgtcatgca gactcaccag aatatctgtg tgcgtttgat ccacgctctc    660
gaccctcgtg tgggtactca attgatccct ggcgtgactg tgctggtgta tctgcctttc    720
tttcacgcct ttggtttttc tattaccctg gctatttca tggtcggctt gcgtgtcatc    780
atgtttcgtc gcttcgacca agaagccttc ttgaaggcta ttcaagacta cgaggtgcgt    840
tctgtcatca atgtcccttc agtcattttg ttcctgagca atctccttt ggttgacaag    900 tatgatctga gcagcttgcg tgagctgtgc tgtggcgctg ctcctttggc caagaagtg     960 gccgaggtcg ctgctaagcg tctgaacctc ctggtatcc gctgcggttt tggtttgact    1020
gagagcactt ctgctaacat ccatagcttg cgagacgagt ttaagtctgg tagcctgggt    1080
cgcgtgactc ctcttatggc tgcaaagatc gccgaccgtg agaccggcaa agcactgggc    1140
ccaaatcaag tcggtgaatt gtgtattaag ggccctatgg tctctaaagg ctacgtgaac    1200
aatgtggagg ccactaaaga agccattgat gatgatggct ggctccatag cggcgacttc    1260
ggttactatg atgaggacga acacttctat gtggtcgatc gctacaaaga attgattaag    1320
tacaaaggct ctcaagtcgc cccagccgaa ctggaagaaa ttttgctgaa gaacccttgt    1380
atccgcgacg tggccgtcgt gggtatccca gacttggaag ctggtgagtt gcctagcgcc    1440
tttgtggtga acaacctgg aaaggagatc actgctaagg aggtctacga ctatttggcc    1500
gagcgcgtgt ctcacaccaa atatctgcgt ggcggcgtcc gcttcgtcga ttccatccca    1560
cgcaacgtga ccggtaagat cactcgtaaa gaattgctga agcaactcct cgaaaaagct    1620
ggcggc                                                               1626

<210> SEQ ID NO 7
```

```
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 7
atgatgaaac gcgaaaagaa cgtgatctac ggcccagaac cactgcatcc actggaagac      60
ctcaccgctg gtgagatgct cttccgagca ctgcgtaaac atagtcacct ccctcaagca     120
ctcgtggacg tcgtgggaga cgagagcctc tcctacaaag aattttttcga agctactgtg    180
ctgttggccc aaagcctcca taattgtggg tacaaaatga cgatgtggt gagcatttgt      240
gctgagaata cactcgctt ctttattcct gtaatcgctg cttggtacat cggcatgatt     300
gtcgccctg tgaatgaatc ttacatccca gatgagctgt gtaaggttat gggtattagc      360
aaacctcaaa tcgtctttac taccaaaaac atcttgaata aggtcttgga agtccagtct    420
cgtactaact tcatcaaacg catcattatt ctggataccg tcgaaaacat ccacggctgt     480
gagagcctcc ctaacttcat ctctcgttac agcgatggta atatcgctaa tttcaagccc    540
ttgcattttg atccagtcga gcaagtggcc gctattttgt gctcctccgg caccactggt     600
ttgcctaaag gtgtcatgca gactcaccag aatatctgtg tgcgtttgat ccacgctctc      660
gaccctcgtg tgggtactca attgatccct ggcgtgactg tgctggtgta tctgcctttc    720
tttcacgcct ttggtttctc tattaccctg gctatttca tggtcggctt gcgtgtcatc      780
atgtttcgtc gcttcgacca agaagccttc ttgaaggcta ttcaagacta cgaggtgcgt     840
tccgtgatca acgtcccttc agtcattttg ttcctgagca aatctccttt ggttgacaag     900
tatgatctga gcagcttgcg tgagctgtgc tgtggcgctg ctcctttggc caaagaagtg     960
gccgaggtcg ctgctaagcg tctgaacctc cctggtatcc gctgcggttt tggtttgact    1020
gagagcactt ctgctaacat ccatagcttg cgagacgagt ttaagtctgg tagcctgggt    1080
cgcgtgactc ctcttatggc tgcaaagatc gccgaccgtg agaccggcaa agcactgggc    1140
ccaaatcaag tcggtgaatt gtgtattaag ggccctatgg tctctaaagg ctacgtgaac    1200
aatgtggagg ccactaaaga agccattgat gatgatggct ggctccatag cggcgacttc    1260
ggttactatg atgaggacga acacttctat gtggtcgatc gctacaaaga attgattaag    1320
tacaaaggct ctcaagtcgc accagccgaa ctggaagaaa ttttgctgaa gaaccccttgt   1380
atccgcgacg tggccgtcgt gggtatccca gacttggaag ctggcgagtt gcctagcgcc   1440
tttgtggtga acaacccggg caaggagatc actgctaagg aggtctacga ctatttggcc   1500
gagcgcgtgt ctcacaccaa atatctgcgt ggcggcgtcc gcttcgtcga ttctattcca    1560
cgcaacgtta ccggtaagat cactcgtaaa gagttgctga agcaactcct cgaaaaagct   1620
ggcggc                                                               1626

<210> SEQ ID NO 8
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 8
atgatgaaac gcgaaaagaa cgtgatctac ggcccagaac cactgcatcc actggaagac      60
ctcaccgctg gtgagatgct cttccgagca ctgcgtaaac atagtcacct ccctcaagca    120
ctcgtggacg tcgtgggaga cgagaaccctc tcctacaaag aattttttcga agctactgtg   180
```

```
ctgttggccc aaagcctcca taattgtggg tacaaaatga acgatgtggt gagcatttgt      240
gctgagaata acactcgctt ctttattcct gtaatcgctg cttggtacat cggcatgatt      300 gtcgccctg tgaatgaatc ttacatccca gatgagctgt gtaaggttat gggtattagc       360
aaacctcaaa tcgtctttac taccaaaaac atcttgaata aggtcttgga agtccagtct      420
cgtactaact tcatcaaacg catcattatt ctggataccg tcgaaaacat ccacggctgt      480
gagagcctcc ctaacttcat ctctcgttac agcgatggta atatcgctaa tttcaagccc      540
ttgcattttg atccagtcga gcaagtggcc gctattttgt gctcctccgg caccactggt      600
ttgcctaaag gtgtcatgca gactcaccag aatatctgtg tgcgtttgat ccacgctctc      660
gaccctcgtg tgggtactca attgatctct ggcgtgactg tgctggtgta tctgcctttc      720
tttcacgcct ttggtttctc tattaccctg ggctatttca tggtcggctt gcgtgtcatc      780
atgtttcgtc gcttcgacca agaagccttc ttgaaggcta ttcaagacta cgaggtgcgt      840
tccgtgatca acgtcccttc agtcattttg ttcctgagca atctcccttt ggttgacaag      900
tatgatctga gcagcttgcg tgagctgtgc tgtggcgctg ctcctttggc caaagaagtg      960
gccgaggtcg ctgctaagcg tctgaacctc cctggtatcc gctgcggttt tggtttgact     1020
gagagcactt ctgctaacat ccatagcttg cgagacgagt ttaagtctgg tagcctgggt     1080
cgcgtgactc ctcttatggc tgcaaagatc gccgaccgtg agaccggcaa agcactgggc     1140
ccaaatcaag tcggtgaatt gtgtattaag ggccctatgg tctctaaagg ctacgtgaac     1200
aatgtggagg ccactaaaga agccattgat gatgatggct ggctccatag cggcgacttc     1260
ggttactatg atgaggacga acacttctat gtggtcgatc gctacaaaga attgattaag     1320
tacaaaggct ctcaagtcgc accagccgaa ctggaagaaa ttttgctgaa gaacccttgt     1380
atccgcgacg tggccgtcgt gggtatccca gacttggaag ctggcgagtt gcctagcgcc     1440
tttgtggtga acaacccgg caaggagatc actgctaagg aggtctacga ctatttggcc      1500
gagcgcgtgt ctcacaccaa atatctgcgt ggcggcgtcc gcttcgtcga ttctattcca     1560
cgcaacgtta ccggtaagat cactcgtaaa gagttgctga agcaactcct cgaaaaagct     1620
ggcggc                                                                1626
```

<210> SEQ ID NO 9
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 9

```
atgatgaaac gcgaaaagaa cgtgatctac ggcccagaac cactgcatcc actggaagac       60
ctcaccgctg gtgagatgct cttccgagca ctgcgtaaac atagtcacct ccctcaagca      120
ctcgtggacg tcgtgggaga cgagagcctc tcctacaaag aattttttcga agctactgtg      180 ctgttggccc aaagcctcca taattgtggg tacaaaatga acgatgtggt gagcatttgt      240
gctgagaata acactcgctt ctttattcct gtaatcgctg cttggtacat cggcatgatt      300 gtcgccctg tgaatgaatc ttacatccca gatgagctgt gtaaggttat gggtattagc       360
aaacctcaaa tcgtctttac taccaaaaac atcttgaata aggtcttgga agtccagtct      420
cgtactaact tcatcaaacg catcattatt ctggataccg tcgaaaacat ccacggctgt      480
gagagcctcc ctaacttcat ctctcgttac agcgatggta atatcgctaa tttcaagccc      540
ttgcattttg atccagtcga gcaagtggcc gctattttgt gctcctccgg caccactggt      600
```

```
ttgcctaaag gtgtcatgca gactcaccag aatatctgtg tgcgtttgat ccacgctctc      660
gaccctcgtg tgggtactca attgatccct ggcgtgactg tgctggtgta tctgcctttc      720
tttcacgcct ttggtttctc tattaccctg ggctatttca tggtcggctt gcgtgtcatc      780
atgtttcgtc gcttcgacca agaagccttc ttgaaggcta ttcaagacta cgaggtgcgt      840
tccgtgatca acgtcccttc agtcattttg ttcctgagca aatctccttt ggttgacaag      900
tatgatctga gcagcttgcg tgagctgtgc tgtggcgctg ctcctttggc caaagaagtg      960
gccgaggtcg ctgctaagcg tctgaacctc cctggtatcc gctgcggttt tggtttgact     1020
gagagcactt ctgctaacat ccatagcttg cgagacgagt ttaagtctgg tagcctgggt     1080
cgcgtgactc ctcttatggc tgcaaagatc gccgaccgtg agaccggcaa agcactgggc     1140
ccaaatcaag tcggtgaatt gtgtattaag ggccctatgg tctctaaagg ctacgtgaac     1200
aatgtggagg ccactaaaga agccattgat gatgatggct ggctccatag cggcgacttc     1260
ggttactatg atgaggacga acacttctat gtggtcgatc gctacaaaga attgattaag     1320
tacaaaggct ctcaagtcgc accagccgaa ctggaagaaa ttttgctgaa gaacccttgt     1380
atccgcgacg tggccgtcgt gggtatccca gacttggaag ctggcgagtt gcctagcgcc     1440
tttgtggtga acaacccgg caaggagatc actgctaagg aggtctacga ctatttggcc     1500
gagcgcgtgt ctcacaccaa atatctgcgt ggcggcgtcc gcttcgtcga ttctattcca     1560
cgcaacgtta ccggtaagat cactcgtaaa gagttgctga agcaactcct cgaaaaagct     1620
ggcggc                                                                1626

<210> SEQ ID NO 10
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 10
atgatgaagc gtgagaaaaa tgtgatttat ggtcctgaac cattgcatcc tctggaggat       60
ttgactgctg gcgaaatgct gtttcgcgcc ttgcgcaagc acagccatct gccacaggct      120
ttggtcgacg tggtcggtga tgagtctctg agctacaaag aattctttga ggccaccgtg      180
ttgctggctc aaagcttgca caactgtggc tataagatga atgacgtcgt gtctatctgc      240
gccgaaaaca atactcgttt ctttattcct gtcatcgctg cctggtatat tggtatgatc      300
gtggctccag tcaacgagag ctacattcct gatgaactgt gtaaagtgat gggcatctct      360
aagccacaga ttgtcttcac cactaaaaat atcttgaaca aggtgctgga ggtccaaagc      420
cgcaccaatt ttattaaacg tatcattatc ttggacactg tggaaaacat tcatggttgc      480
gagtctctgc ctaatttcat cagccgctac tctgatggca acattgccaa ttttaaacca      540
ttgcacttcg accctgtcga acaggtggct gccatcctgt gtagctctgg taccactggc      600
ttgccaaagg gtgtcatgca aacccatcag aacatttgcg tgcgtctgat ccacgctctc      660
gatcctcgct acggcactca actgattcca ggtgtcaccg tgttggtcta tctgcctttt      720
ttccatgctt ttggcttcca catcactttg ggttacttta tggtgggcct gcgtgtcatt      780
atgttccgcc gttttgacca ggaggccttc ttgaaagcta tccaagatta tgaagtgcgc      840
tctgtcatta atgtgccaag cgtcatcctg tttttgtcta gagccctct ggtggacaaa      900 tacgatttgt ctagcctgcg tgagttgtgt tgcggtgccg ctccactggc caaggaagtc      960
gctgaggtgg ccgctaaacg cttgaacctg cctggcattc gttgtggttt cggcttgacc     1020
```

```
gaatctacta gcgccattat ccaatctctg cgcgacgagt ttaagagcgg ttctttgggc    1080
cgtgtcaccc cactgatggc tgccaaaatt gctgatcgcg aaactggtaa ggccttgggc    1140
cctaaccagg tgggtgagct gtgcatcaaa ggcccaatgg tcagcaaggg ttatgtgaat    1200
aacgtcgaag ctaccaaaga ggccattgac gatgacggcg ggttgcattc tggtgatttc    1260
ggctactatg acgaagatga gcactttttac gtggtcgacc gttataagga actgatcaaa    1320
tacaagggta gccaagtggc tcctgccgaa ttggaggaaa ttctgttgaa aaatccatgt    1380
atccgcgatg tcgctgtggt cggcattcct gacctggagg ccggtgaatt gccatctgct    1440
ttcgtggtca gcagcctgg caaagagatc actgccaagg aagtgtatga ttacctggct    1500
gagcgtgtca gccataccaa atatttgcgc ggtggcgtgc gttttgtcga ctctattcca    1560
cgtaacgtga ctggtaagat cacccgcaaa gaactgttga agcaactgtt ggagaaagcc    1620
ggcggt                                                              1626

<210> SEQ ID NO 11
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 11
atgatgaagc gtgagaaaaa tgtgatttat ggtcctgaac cattgcatcc tctggaggat      60
ttgactgccg cgaaatgct gtttcgcgcc ttgcgcaagc acagccatct gccacaagct     120
ttggtggacg tggtcggtga tgaatctctg agctacaaag agttctttga ggcaaccgtg     180
ttgctggctc agagcttgca caactgtggc tataagatga tgacgtcgt gtctatctgc     240 gccgaaaaca atactcgttt ctttattcct gtcatcgctg cctggtatat tggtatgatc     300
gtggctccag tcaacgagag ctacattcct gatgaactgt gtaaagtgat gggcatctct     360
aagccacaga ttgtcttcac cactaaaaat atcttgaaca aagtgctgga ggtccaaagc     420
cgcaccaatt ttattaaacg tatcattatc ttggacactg tggaaaacat tcatggttgc     480
gaatctctgc ctaatttcat cagccgctac tctgatggca acattgccaa ttttaaacca     540
ttgcacttcg accctgtcga acaggtggct gccatcctgt gtagctctgg tactactggc     600
ttgccaaagg gtgtcatgca aacccatcag aacatttgcg tgcgtctgat ccacgctctc     660
gatcctcgct acggcaccca actgattcct ggtgtcaccg tgttggtcta tctgccttt     720 ttccatgctt ttggcttcca catcactttg ggttacttta tggtgggcct gcgtgtcatt     780
atgttccgcc gttttgacca ggaggctttc ttgaaagcta tccaagatta tgaagtgcgc     840
tctgtcatta tgtgtccaag cgtcatcctg ttttttgtcta agagccctct ggtggacaaa     900
tacgatttgt cttctctgcg tgagttgtgt tgcggtgccg ctccactggc caaggaagtc     960
gctgaggtgg ccgctaaacg cttgaacctg cctggcattc gttgtggttt cggcttgacc    1020
gaatctacta gcgccattat ccaatctctg cgcgacgaat ttaagagcgg ttctttgggc    1080
cgtgtcaccc cactgatggc tgccaaaatt gctgatcgcg aaactggtaa ggccttgggc    1140
cctaaccagg tgggtgagct gtgcatcaaa ggcccaatgg tcagcaaggg ttatgtgaat    1200
aacgtcgaag ctaccaaaga ggccatcgac gatgacggcg ggttgcattc tggtgatttc    1260
ggctactatg acgaagatga gcactttttac gtggtggacc gttataagga actgatcaaa    1320
tacaagggta gccaagtggc tcctgccgaa ttggaggaga ttctgttgaa aaatccatgt    1380
atccgcgatg tcgctgtggt cggcattcct gacctggagg ccggtgaatt gccatctgct    1440
```

-continued

| | |
|---|---|
| ttcgtggtca agcagcctgg taaagagatc actgccaagg aagtgtatga ttacctggct | 1500 |
| gaacgtgtca gccataccaa atatttgcgc ggtggcgtgc gttttgtgga ctctattcca | 1560 |
| cgtaacgtga ctggtaagat cacccgcaaa gaactgttga agcaactgtt ggagaaagcc | 1620 |
| ggcggt | 1626 |

<210> SEQ ID NO 12
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 12

| | |
|---|---|
| atgatgaagc gtgagaaaaa tgtcatctat ggccctgagc ctttgcaccc tttggaggat | 60 |
| ttgactgccg gcgaaatgct gtttcgcgct ttgcgtaagc actctcattt gcctcaagcc | 120 |
| ttggtcgatg tggtcggcga tgaatctttg agctataagg agttttttga ggcaaccgtc | 180 |
| ttgctggctc agtctttgca taattgcggc tacaagatga cgacgtcgt ctctatttgt | 240 |
| gccgaaaaca taccgtttt cttcattcca gtcatcgccg cctggtatat cggtatgatc | 300 |
| gtggctccag tcaacgagag ctacattcct gacgaactgt gtaaagtcat gggtatctct | 360 |
| aagccacaga ttgtgttcac cactaagaat attttgaaca agtgctgga agtccaaagc | 420 |
| cgcaccaact ttattaagcg tatcatcatc ttggacactg tggagaatat tcatggttgc | 480 |
| gaatctctgc taatttcat tagccgctat tctgacggca acatcgccaa ctttaaacct | 540 |
| ttgcatttcg accctgtgga acaagtggct gctatcctgt gtagcagcgg tactactggc | 600 |
| ctcccaaagg gcgtcatgca gacccatcaa aacatttgcg tgcgtctgat ccatgctctc | 660 |
| gatccacgct acggcactca gctgattcct ggtgtcaccg tcttggtcta cctgcctttc | 720 |
| ttccatgctt tcggcttcca cattactttg ggttacttta tggtcggtct gcgtgtcatt | 780 |
| atgttccgcc gttttgatca ggaggctttt ttgaaagcca tccaagatta tgaagtccgc | 840 |
| agcgtcatta acgtgcctag cgtgatcctg tttttgtcta agagcccact cgtggacaag | 900 |
| tacgacttgt cttccctgcg tgagttgtgt tgcggtgccg ccccactggc taaggaggtc | 960 |
| gctgaagtgg ccgccaaacg cttgaatctg ccaggcattc gttgtggctt cggcctcacc | 1020 |
| gaatctacca cgctattat tcaatctctc cgcgatgagt ttaagagcgg ctcttttgggc | 1080 |
| cgtgtcactc cactcatggc tgctaaaatc gctgatcgcg aaactggtaa ggctttgggc | 1140 |
| cctaaccaag tgggcgagct gtgtatcaaa ggccctatgg tgagcaaggg ttatgtcaat | 1200 |
| aacgtcgaag ctaccaagga ggccatcgac gacgacggct ggctgcattc tggtgatttt | 1260 |
| ggctactacg acgaagatga gcattttttac gtcgtggatc gttacaagga gctgatcaaa | 1320 |
| tacaagggta gccaggtggc tccagccgag ttggaggaga ttctgttgaa aaatccatgc | 1380 |
| atccgtgatg tcgctgtggt cggcattcct gatctggagg ccggtgaact gccttctgct | 1440 |
| ttcgtcgtca gcagcctgg taaagaaatc accgccaaag aagtgtatga ttacctggct | 1500 |
| gaacgtgtga gccataccaa gtacttgcgt ggcggcgtgc gttttgtgga cagcattcca | 1560 |
| cgtaatgtga ctggtaaaat tacccgcaag gaactgttga agcaattgtt ggagaaggcc | 1620 |
| ggcggt | 1626 |

<210> SEQ ID NO 13
<211> LENGTH: 1626
<212> TYPE: DNA
<213> ORGANISM: Artificial Sequence
<220> FEATURE:

<223> OTHER INFORMATION: Sequence of a synthetic luciferase

<400> SEQUENCE: 13

```
atgatgaagc gtgagaaaaa tgtcatctat ggccctgagc ctttgcatcc tttggaggat      60
ttgactgccg gcgaaatgct gtttcgtgct ttgcgtaaac actctcattt gcctcaagcc     120
ttggtcgatg tggtcggcga tgaatctttg agctacaagg agttttttga ggcaaccgtc     180
ttgctggctc agtccttgca taattgtggc tacaagatga cgacgtcgt ctccatttgt      240
gcagaaaaca atacccgttt cttcattcca gtcatcgccg catggtatat cggtatgatc     300
gtggctccag tcaacgagag ctacattccc gacgaactgt gtaaagtcat gggtatctct     360
aagccacaga ttgtcttcac cactaagaat attctgaaca agtcctgga agtccaaagc      420
cgcaccaact ttattaagcg tatcatcatc ttggacactg tggagaatat tcacggttgc     480
gaatctttgc ctaattttat tagccgctat tcagacggaa acatcgccaa ctttaagcct     540
ctccatttcg accctgtgga acaagttgct gcaatcctgt gtagcagcgg tactactgga     600
ctcccaaagg gagtcatgca gacccatcaa aacatttgcg tgcgtctgat ccatgctctc     660
gatccacgct acggcactca gctgattcct ggtgtcaccg tcttggtcta cttgcctttc     720
ttccatgctt tcggcttcca tattactttg ggttacttta tggtcggtct gcgtgtgatt     780
atgttccgcc gttttgatca ggaggctttc ttgaaagcca tccaagatta tgaagtccgc     840
agtgtcatca acgtgcctag cgtgatcctg tttttgtcta agagcccact cgtggacaag     900
tacgacttgt cttcactgcg tgaattgtgt tgcggtgccg ctccactggc taaggaggtc     960
gctgaagtgg ccgccaaacg cttgaatctg cccggcattc gttgtggctt cggcctcacc    1020
gaatctacca gcgctattat tcagtctctc cgcgatgagt ttaagagcgg ctctttgggc    1080
cgtgtcactc cactcatggc tgctaagatc gctgatcgcg aaactggtaa ggctttgggc    1140
cctaaccaag tgggcgagct gtgtatcaaa ggccctatgg tgagcaaggg ttatgtcaat    1200
aacgtcgaag ctaccaagga ggctatcgac gacgacggct ggttgcattc tggtgatttt    1260
ggatattacg acgaagatga gcattttta gtcgtggatc gttacaagga gctgatcaaa    1320
tacaagggta gccaggttgc tccagctgag ttggaggaga ttctgttgaa aaatccatgc    1380
attcgcgatg tcgctgtggt cggcattcct gatctggagg ccggcgaact gccttctgct    1440
ttcgttgtca gcagcctgg taaagaaatt accgccaaag aagtgtatga ttacctggct    1500
gaacgtgtga gccatactaa gtacttgcgt ggcggcgtgc gttttgtgga tagcattcct    1560
cgcaatgtga ctggcaaaat tacccgcaag gagctgttga acaattgtt ggagaaggcc    1620
ggcggt                                                              1626
```

<210> SEQ ID NO 14
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 14

```
atgatgaagc gtgagaaaaa tgtcatctat ggccctgagc tctccatcc tttggaggat       60
ttgactgccg gcgaaatgct gtttcgtgct ctccgcaagc actctcattt gcctcaagcc     120
ttggtcgatg tggtcggcga tgaatctttg agctacaagg agttttttga ggcaaccgtc     180
ttgctggctc agtccctcca caattgtggc tacaagatga cgacgtcgt tagtatctgt     240
gctgaaaaca atacccgttt cttcattcca gtcatcgccg catggtatat cggtatgatc     300
```

```
gtggctccag tcaacgagag ctacattccc gacgaactgt gtaaagtcat gggtatctct    360
aagccacaga ttgtcttcac cactaagaat attctgaaca aagtcctgga agtccaaagc    420
cgcaccaact ttattaagcg tatcatcatc ttggacactg tggagaatat tcacggttgc    480
gaatctttgc ctaatttcat ctctcgctat tcagacggca catcgcaaa ctttaaacca    540 ctccacttcg accctgtgga acaagttgca gccattctgt gtagcagcgg tactactgga    600
ctcccaaagg gagtcatgca gacccatcaa aacatttgcg tgcgtctgat ccatgctctc    660
gatccacgct acggcactca gctgattcct ggtgtcaccg tcttggtcta cttgcctttc    720
ttccatgctt tcggctttca tattactttg ggttacttta tggtcggtct ccgcgtgatt    780
atgttccgcc gttttgatca ggaggctttc ttgaaagcca tccaagatta tgaagtccgc    840
agtgtcatca acgtgcctag cgtgatcctg tttttgtcta agagcccact cgtggacaag    900
tacgacttgt cttcactgcg tgaattgtgt tgcggtgccg ctccactggc taaggaggtc    960
gctgaagtgg ccgccaaacg cttgaatctt ccagggattc gttgtggctt cggcctcacc    1020
gaatctacca gcgctattat tcagtctctc cgcgatgagt ttaagagcgg ctctttgggc    1080
cgtgtcactc cactcatggc tgctaagatc gctgatcgcg aaactggtaa ggctttgggc    1140
cctaaccaag tgggcgagct gtgtatcaaa ggccctatgg tgagcaaggg ttatgtcaat    1200
aacgtcgaag ctaccaagga ggccatcgac gacgacggcg ggttgcattc tggtgatttt    1260
ggatattacg acgaagatga gcatttttac gtcgtggatc gttacaagga gctgatcaaa    1320
tacaagggta gccaggttgc tccagctgag ttggaggaga ttctgttgaa aaatccatgc    1380
attcgcgatg tcgctgtggt cggcattcct gatctggagg ccggcgaact gccttctgct    1440
ttcgttgtca gcagcctgg taaagaaatt accgccaaag aagtgtatga ttacctggct    1500
gaacgtgtga gccatactaa gtacttgcgt ggcggcgtgc gttttgttga ctccatccct    1560
cgtaacgtaa caggcaaaat tacccgcaag gagctgttga acaattgtt ggagaaggcc    1620 ggcggt                                                              1626

<210> SEQ ID NO 15
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 15
atgatgaagc gtgagaaaaa tgtcatctat ggccctgagc ctctccatcc tttggaggat     60
ttgactgccg gcgaaatgct gtttcgtgct ctccgcaagc actcttattt gcctcaagcc    120
ttggtcgatg tggtcggcga tgaatctttg agctacaagg agttttttga ggcaaccgtc    180
ttgctggctc agtccctcca caattgtggc tacaagatga cgacgtcgt tagtatctgt    240 gctgaaaaca ataccccgttt cttcattcca gtcatcgccg catggtatat cggtatgatc    300
gtggctccag tcaacgagag ctacattccc gacgaactgt gtaaagtcat gggtatctct    360
aagccacaga ttgtcttcac cactaagaat attctgaaca aagtcctgga agtccaaagc    420
cgcaccaact ttattaagcg tatcatcatc ttggacactg tggagaatat tcacggttgc    480
gaatctttgc ctaatttcat ctctcgctat tcagacggca catcgcaaa ctttaaacca    540 ctccacttcg accctgtgga acaagttgca gccattctgt gtagcagcgg tactactgga    600
ctcccaaagg gagtcatgca gacccatcaa aacatttgcg tgcgtctgat ccatgctctc    660
gatccacgct acggcactca gctgattcct ggtgtcaccg tcttggtcta cttgcctttc    720
```

-continued

```
ttccatgctt tcggctttca tattactttg ggttacttta tggtcggtct ccgcgtgatt   780
atgttccgcc gttttgatca ggaggctttc ttgaaagcca tccaagatta tgaagtccgc   840
agtgtcatca acgtgcctag cgtgatcctg tttttgtcta agagcccact cgtggacaag   900
tacgacttgt cttcactgcg tgaattgtgt tgcggtgccg ctccactggc taaggaggtc   960
gctgaagtgg ccgccaaacg cttgaatctt ccagggattc gttgtggctt cggcctcacc  1020
gaatctacca gcgctattat tcagtctctc cgcgatgagt taagagcgg ctctttgggc   1080
cgtgtcactc cactcatggc tgctaagatc gctgatcgcg aaactggtaa ggctttgggc  1140
ccgaaccaag tgggcgagct gtgtatcaaa ggccctatgg tgagcaaggg ttatgtcaat  1200
aacgttgaag ctaccaagga ggccatcgac gacgacggct ggttgcattc tggtgatttt  1260
ggatattacg acgaagatga gcatttttac gtcgtggatc gttacaagga gctgatcaaa  1320
tacaagggta gccaggttgc tccagctgag ttggaggaga ttctgttgaa aaatccatgc  1380
attcgcgatg tcgctgtggt cggcattcct gatctggagg ccggcgaact gccttctgct  1440
ttcgttgtca agcagcctgg taaagaaatt accgccaaag aagtgtatga ttacctggct  1500
gaacgtgtga gccatactaa gtacttgcgt ggcggcgtgc gttttgttga ctccatccct  1560
cgtaacgtaa caggcaaaat tacccgcaag gagctgttga acaattgtt ggagaaggcc  1620
ggcggt                                                            1626
```

<210> SEQ ID NO 16
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 16

```
atgatgaagc gtgagaaaaa tgtcatctat ggccctgagc ctctccatcc tttggaggat     60
ttgactgccg gcgaaatgct gtttcgtgct ctccgcaagc actctcattt gcctcaagcc   120
ttggtcgatg tggtcggcga tgaatctttg agctacaagg agttttttga ggcaaccgtc   180
ttgctggctc agtccctcca caattgtggc tacaagatga cgacgtcgt tagtatctgt   240
gctgaaaaca tacccgtttc cttcattcca gtcatcgccg catggtatat cggtatgatc   300
gtggctccag tcaacgagag ctacattccc gacgaactgt gtaaagtcat gggtatctct  360
aagccacaga ttgtcttcac cactaagaat attctgaaca agtcctgga agtccaaagc   420
cgcaccaact ttattaagcg tatcatcatc ttggacactg tggagaatat tcacggttgc   480
gaatctttgc ctaatttcat ctctcgctat tcagacggca acatcgcaaa ctttaaacca   540
ctccacttcg accctgtgga acaagttgca gccattctgt gtagcagcgg tactactgga   600
ctcccaaagg gagtcatgca gacccatcaa acatttgcg tgcgtctgat ccatgctctc   660
gatccacgct acggcactca gctgattcct ggtgtcaccg tcttggtcta cttgcctttc   720
ttccatgctt tcggctttca tattactttg ggttacttta tggtcggtct ccgcgtgatt   780
atgttccgcc gttttgatca ggaggctttc ttgaaagcca tccaagatta tgaagtccgc   840
agtgtcatca acgtgcctag cgtgatcctg tttttgtcta agagcccact cgtggacaag   900
tacgacttgt cttcactgcg tgaattgtgt tgcggtgccg ctccactggc taaggaggtc   960
gctgaagtgg ccgccaaacg cttgaatctt ccagggattc gttgtggctt cggcctcacc  1020
gaatctacca gcgctattat tcagtctctc cgcgatgagt taagagcgg ctctttgggc  1080
cgtgtcactc cactcatggc tgctaagatc gctgatcgcg aaactggtaa ggctttgggc  1140
```

```
ccgaaccaag tgggcgagct gtgtatcaaa ggccctatgg tgagcaaggg ttatgtcaat    1200
aacgttgaag ctaccaagga ggccatcgac gacgacggct ggttgcattc tggtgatttt    1260
ggatattacg acgaagatga gcattttac gtcgtggatc gttacaagga gctgatcaaa     1320
tacaagggta gccaggttgc tccagctgag ttggaggaga ttctgttgaa aaatccatgc    1380
attcgcgatg tcgctgtggt cggcattcct gatctggagg ccggcgaact gccttctgct    1440
ttcgttgtca agcagcctgg taaagaaatt accgccaaag aagtgtatga ttacctggct    1500
gaacgtgtga gccatactaa gtacttgcgt ggcggcgtgc gttttgttga ctccatccct    1560
cgtaacgtaa caggcaaaat tacccgcaag gagctgttga aacaattgtt ggagaaggcc    1620
ggcggt                                                              1626

<210> SEQ ID NO 17
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 17
atgatgaagc gtgagaaaaa tgtcatctat ggccctgagc ctctccatcc tttggaggat      60
ttgactgccg cgaaatgct gtttcgtgct ctccgcaagc actctcattt gcctcaagcc     120
ttggtcgatg tggtcggcga tgaatctttg agctacaagg agttttttga ggcaaccgtc     180
ttgctggctc agtccctcca caattgtggc tacaagatga cgacgtcgt tagtatctgt      240 gctgaaaaca tacccgtttt cttcattcca gtcatcgccg catggtatat cggtatgatc     300
gtggctccag tcaacgagag ctacattccc gacgaactgt gtaaagtcat gggtatctct     360
aagccacaga ttgtcttcac cactaagaat attctgaaca aagtcctgga agtccaaagc     420
cgcaccaact ttattaagcg tatcatcatc ttggacactg tggagaatat tcacggttgc     480
gaatctttgc ctaatttcat ctctcgctat tcagacggca catcgcaaa ctttaaacca      540 ctccacttcg accctgtgga acaagttgca gccattctgt gtagcagcgg tactactgga     600
ctcccaaagg gagtcatgca gacccatcaa aacatttgcg tgcgtctgat ccatgctctc     660
gatccacgct acggcactca gctgattcct ggtgtcaccg tcttggtcta cttgcctttc     720
ttccatgctt tcggctttca tattactttg ggttacttta tggtcggtct ccgcgtgatt     780
atgttccgcc gttttgatca ggaggctttc ttgaaagcca tccaagatta tgaagtccgc     840
agtgtcatca acgtgcctag cgtgatcctg tttttgtcta agagcccact cgtggacaag     900
tacgacttgt cttcactgcg tgaattgtgt tgcggtgccg ctccactggc taaggaggtc     960
gctgaagtgg ccgccaaacg cttgaatctt ccagggattc gttgtggctt cggcctcacc    1020
gaatctacca gcgctattat tcagtctctc ggggatgagt ttaagagcgg ctcttttggc     1080
cgtgtcactc cactcatggc tgctaagatc gctgatcgcg aaactggtaa ggctttgggc    1140
ccgaaccaag tgggcgagct gtgtatcaaa ggccctatgg tgagcaaggg ttatgtcaat    1200
aacgttgaag ctaccaagga ggccatcgac gacgacggct ggttgcattc tggtgatttt    1260
ggatattacg acgaagatga gcattttac gtcgtggatc gttacaagga gctgatcaaa     1320
tacaagggta gccaggttgc tccagctgag ttggaggaga ttctgttgaa aaatccatgc    1380
attcgcgatg tcgctgtggt cggcattcct gatctggagg ccggcgaact gccttctgct    1440
ttcgttgtca agcagcctgg taaagaaatt accgccaaag aagtgtatga ttacctggct    1500
gaacgtgtga gccatactaa gtacttgcgt ggcggcgtgc gttttgttga ctccatccct    1560
```

```
cgtaacgtaa caggcaaaat tacccgcaag gagctgttga aacaattgtt ggagaaggcc    1620
ggcggt                                                              1626

<210> SEQ ID NO 18
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 18
atgataaagc gtgagaaaaa tgtcatctat ggccctgagc ctctccatcc tttggaggat     60
ttgactgccg gcgaaatgct gtttcgtgct ctccgcaagc actctcattt gcctcaagcc    120
ttggtcgatg tggtcggcga tgaatctttg agctacaagg agttttttga ggcaaccgtc    180
ttgctggctc agtccctcca caattgtggc tacaagatga cgacgtcgt tagtatctgt     240 gctgaaaaca tacccgtttt cttcattcca gtcatcgccg catggtatat cggtatgatc    300
gtggctccag tcaacgagag ctacattccc gacgaactgt gtaaagtcat gggtatctct    360
aagccacaga ttgtcttcac cactaagaat attctgaaca agtcctgga agtccaaagc     420 cgcaccaact ttattaagcg tatcatcatc ttggacactg tggagaatat tcacggttgc    480
gaatctttgc ctaatttcat ctctcgctat tcagacggca acatcgcaaa ctttaaacca    540
ctccacttcg accctgtgga acaagttgca gccattctgt gtagcagcgg tactactgga    600
ctcccaaagg gagtcatgca gacccatcaa aacatttgcg tgcgtctgat ccatgctctc    660
gatccacgct acggcactca gctgattcct ggtgtcaccg tcttggtcta cttgcctttc    720
ttccatgctt tcggctttca tattactttg ggttacttta tggtcggtct ccgcgtgatt    780
atgttccgcc gttttgatca ggaggctttc ttgaaagcca tccaagatta tgaagtccgc    840
agtgtcatca acgtgcctag cgtgatcctg tttttgtcta agagcccact cgtggacaag    900
tacgacttgt cttcactgcg tgaattgtgt tgcggtgccg ctccactggc taaggaggtc    960
gctgaagtgg ccgccaaacg cttgaatctt ccagggattc gttgtggctt cggcctcacc   1020
gaatctacca gtcgcgattat ccagactctc ggggatgagt taagagcgg ctctttgggc   1080 cgtgtcactc cactcatggc tgctaagatc gctgatcgcg aaactggtaa ggctttgggc   1140
ccgaaccaag tgggcgagct gtgtatcaaa ggccctatgg tgagcaaggg ttatgtcaat   1200
aacgttgaag ctaccaagga ggccatcgac gacgacggct ggttgcattc tggtgatttt   1260
ggatattacg acgaagatga gcatttttac gtcgtggatc gttacaagga gctgatcaaa   1320
tacaagggta gccaggttgc tccagctgag ttggaggaga ttctgttgaa aaatccatgc   1380
attcgcgatg tcgctgtggt cggcattcct gatctgaggg ccggcgaact gccttctgct   1440
ttcgttgtca gcagcctgg tacagaaatt accgccaaag aagtgtatga ttacctggct   1500
gaacgtgtga gccatactaa gtacttgcgt ggcggcgtgc gttttgttga ctccatccct   1560
cgtaacgtaa caggcaaaat tacccgcaag gagctgttga aacaattgtt ggtgaaggcc   1620
ggcggt                                                              1626

<210> SEQ ID NO 19
<211> LENGTH: 933
<212> TYPE: DNA
<213> ORGANISM: Renilla reniformis

<400> SEQUENCE: 19
atgacttcga aagtttatga tccagaacaa aggaaacgga tgataactgg tccgcagtgg     60
```

```
tgggccagat gtaaacaaat gaatgttctt gattcattta ttaattatta tgattcagaa     120
aaacatgcag aaaatgctgt tattttttta catggtaacg cggcctcttc ttatttatgg     180
cgacatgttg tgccacatat tgagccagta gcgcggtgta ttataccaga tcttattggt     240
atgggcaaat caggcaaatc tggtaatggt tcttataggt tacttgatca ttacaaatat     300
cttactgcat ggtttgaact tcttaattta ccaagaagat catttttgtc ggccatgatt     360
tggggtgctt gtttggcatt tcattatagc tatgagcatc aagataagat caaagcaata     420
gttcacgctg aaagtgtagt agatgtgatt gaatcatggg atgaatggcc tgatattgaa     480
gaagatattg cgttgatcaa atctgaagaa ggagaaaaaa tggttttgga gaataacttc     540
ttcgtggaaa ccatgttgcc atcaaaaatc atgagaaagt tagaaccaga agaatttgca     600
gcatatcttg aaccattcaa agagaaaggt gaagttcgtc gtccaacatt atcatggcct     660
cgtgaaatcc cgttagtaaa aggtggtaaa cctgacgttg tacaaattgt taggaattat     720
aatgcttatc tacgtgcaag tgatgattta ccaaaaatgt ttattgaatc ggatccagga     780 ttctttttcca atgctattgt tgaaggcgcc aagaagtttc taatactga atttgtcaaa     840 gtaaaaggtc ttcattttc gcaagaagat gcacctgatg aaatgggaaa atatatcaaa     900
tcgttcgttg agcgagttct caaaaatgaa caa                                  933

<210> SEQ ID NO 20
<211> LENGTH: 933
<212> TYPE: DNA
<213> ORGANISM: Artificial Sequence
<220> FEATURE:
<223> OTHER INFORMATION: Sequence of a synthetic luciferase

<400> SEQUENCE: 20
atggcttcca aggtgtacga ccccgagcag cgcaagcgca tgatcaccgg ccctcagtgg      60
tgggcccgct gcaagcagat gaacgtgctg gactccttca tcaactacta cgacagcgag     120
aagcacgccg agaacgccgt gatcttcctg cacggcaacg ccgcctccag ctacctgtgg     180
aggcacgtgg tgcctcacat cgagcccgtg gcccgctgca tcatccctga cctgatcggc     240
atgggcaagt ccggcaagag cggcaacggc tcctaccgcc tgctggacca ctacaagtac     300
ctgaccgcct ggttcgagct gctgaacctg cccaagaaga tcatcttcgt gggccacgac     360
tggggagcct gcctggcctt ccactactcc tacgagcacc aggacaagat caaggccatc     420
gtgcacgccg agagcgtggt ggacgtgatc gagtcctggg acgagtggcc tgacatcgag     480
gaggacatcg ccctgatcaa gagcgaggag ggcgagaaga tggtgctgga gaacaacttc     540
ttcgtggaga ccatgctgcc cagcaagatc atgcgcaagc tggagcctga ggagttcgcc     600
gcctacctgg agcccttcaa ggagaagggc gaggtgcgcc gccctaccct gtcctggccc     660
cgcgagatcc ctctggtgaa gggcggcaag cccgacgtgg tgcagatcgt gcgcaactac     720
aacgcctacc tgcgcgccag cgacgacctg cctaagatgt catcgagtc cgaccctggc     780 ttcttctcca acgccatcgt cgagggagcc aagaagttcc ccaacaccga gttcgtgaag     840
gtgaagggcc tgcacttctc ccaggaggac gcccctgacg agatgggcaa gtacatcaag     900
agcttcgtgg agcgcgtgct gaagaacgag cag                                   933

<210> SEQ ID NO 21
<211> LENGTH: 933
<212> TYPE: DNA
<213> ORGANISM: Artificial Sequence
<220> FEATURE:
<223> OTHER INFORMATION: Sequence of a synthetic luciferase
```

<400> SEQUENCE: 21

```
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gattttttctg catggtaacg ctgcctccag ctacctgtgg    180
aggcacgtcg tgcctcacat cgagcccgtg gctcgctgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tgggggcctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agcccttcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca acgctattgt cgagggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cag                                 933
```

<210> SEQ ID NO 22
<211> LENGTH: 933
<212> TYPE: DNA
<213> ORGANISM: Artificial Sequence
<220> FEATURE:
<223> OTHER INFORMATION: Sequence of a synthetic luciferase

<400> SEQUENCE: 22

```
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gattttttctg catggtaacg ctgcctccag ctacctgtgg    180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tgggggcctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca acgctattgt cgagggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cag                                 933
```

<210> SEQ ID NO 23
<211> LENGTH: 543
<212> TYPE: PRT

<213> ORGANISM: Pyrophorus plagiophthalamus

<400> SEQUENCE: 23

```
Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Phe Gly Asp Glu
        35                  40                  45

Ser Leu Ser Tyr Lys Glu Phe Phe Glu Ala Thr Cys Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Lys Arg Phe Phe Ile Pro Ile Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Cys Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Tyr Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Ala
    210                 215                 220

Gly Thr Gln Leu Ile Pro Gly Val Thr Val Leu Val Tyr Leu Pro Phe
225                 230                 235                 240

Phe His Ala Phe Gly Phe Ser Ile Asn Leu Gly Tyr Phe Met Val Gly
                245                 250                 255

Leu Arg Val Ile Met Leu Arg Arg Phe Asp Gln Glu Ala Phe Leu Lys
            260                 265                 270

Ala Ile Gln Asp Tyr Glu Val Arg Ser Val Ile Asn Val Pro Ala Ile
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Val Lys Arg Leu Asn Leu Pro Gly Ile Arg Cys Gly
                325                 330                 335

Phe Gly Leu Thr Glu Ser Thr Ser Ala Asn Ile His Ser Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Val Lys Gly Pro Met Val Ser Lys Gly Tyr Val Asn
385                 390                 395                 400

Asn Val Glu Ala Thr Lys Glu Ala Ile Asp Asp Asp Gly Trp Leu His
```

```
                        405                 410                 415
Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ser Ser Lys Leu
530                 535                 540

<210> SEQ ID NO 24
<211> LENGTH: 542
<212> TYPE: PRT
<213> ORGANISM: Artificial Sequence
<220> FEATURE:
<223> OTHER INFORMATION: Sequence of clone YG#81-6G01

<400> SEQUENCE: 24

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Gly Asp Glu
        35                  40                  45

Ser Leu Ser Tyr Lys Glu Phe Phe Glu Ala Thr Val Leu Leu Ala Gln
50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Ala
210                 215                 220

Gly Thr Gln Leu Ile Pro Gly Val Thr Val Leu Val Tyr Leu Pro Phe
225                 230                 235                 240
```

```
Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540
```

<210> SEQ ID NO 25
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 25

```
Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60
```

```
Ser Leu His Asn Cys Gly Tyr Lys Met Asn Asp Val Val Ser Ile Cys
 65                  70                  75                  80

Ala Glu Asn Asn Thr Arg Phe Phe Ile Pro Val Ile Ala Ala Trp Tyr
                 85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
210                 215                 220

Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495
```

```
Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
            515                 520                 525

Arg Lys Glu Leu Lys Gln Leu Leu Glu Lys Ala Gly Gly
            530                 535                 540

<210> SEQ ID NO 26
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 26

Met Met Lys Arg Glu Lys Asn Val Ile Tyr Gly Pro Glu Pro Leu His
  1               5                  10                  15

Pro Leu Glu Asp Leu Thr Ala Gly Glu Met Leu Phe Arg Ala Leu Arg
             20                  25                  30

Lys His Ser His Leu Pro Gln Ala Leu Val Asp Val Val Gly Asp Glu
         35                  40                  45

Ser Leu Ser Tyr Lys Glu Phe Phe Glu Ala Thr Val Leu Leu Ala Gln
     50                  55                  60

Ser Leu His Asn Cys Gly Tyr Lys Met Asn Asp Val Val Ser Ile Cys
 65                  70                  75                  80

Ala Glu Asn Asn Thr Arg Phe Phe Ile Pro Val Ile Ala Ala Trp Tyr
                 85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
    210                 215                 220

Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320
```

```
Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
        370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
            450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
        530                 535                 540

<210> SEQ ID NO 27
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 27

Met Met Lys Arg Glu Lys Asn Val Ile Tyr Gly Pro Glu Pro Leu His
1               5                  10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
```

```
            145                 150                 155                 160
Glu Ser Leu Pro Asn Phe Ile Ser Arg Tyr Ser Asp Gly Asn Ile Ala
                    165                 170                 175
Asn Phe Lys Pro Leu His Phe Asp Pro Val Glu Gln Val Ala Ala Ile
                    180                 185                 190
Leu Cys Ser Ser Gly Thr Thr Gly Leu Pro Lys Gly Val Met Gln Thr
                    195                 200                 205
His Gln Asn Ile Cys Val Arg Leu Ile His Ala Leu Asp Pro Arg Val
        210                 215                 220
Gly Thr Gln Leu Ile Pro Gly Val Thr Val Leu Val Tyr Leu Pro Phe
225                 230                 235                 240
Phe His Ala Phe Gly Phe Ser Ile Thr Leu Gly Tyr Phe Met Val Gly
                    245                 250                 255
Leu Arg Val Ile Met Phe Arg Arg Phe Asp Gln Glu Ala Phe Leu Lys
                    260                 265                 270
Ala Ile Gln Asp Tyr Glu Val Arg Ser Val Ile Asn Val Pro Ser Val
                    275                 280                 285
Ile Leu Phe Leu Ser Lys Ser Pro Leu Val Asp Lys Tyr Asp Leu Ser
        290                 295                 300
Ser Leu Arg Glu Leu Cys Cys Gly Ala Ala Pro Leu Ala Lys Glu Val
305                 310                 315                 320
Ala Glu Val Ala Ala Lys Arg Leu Asn Leu Pro Gly Ile Arg Cys Gly
                    325                 330                 335
Phe Gly Leu Thr Glu Ser Thr Ser Ala Asn Ile His Ser Leu Arg Asp
                    340                 345                 350
Glu Phe Lys Ser Gly Ser Leu Gly Arg Val Thr Pro Leu Met Ala Ala
                    355                 360                 365
Lys Ile Ala Asp Arg Glu Thr Gly Lys Ala Leu Gly Pro Asn Gln Val
        370                 375                 380
Gly Glu Leu Cys Ile Lys Gly Pro Met Val Ser Lys Gly Tyr Val Asn
385                 390                 395                 400
Asn Val Glu Ala Thr Lys Glu Ala Ile Asp Asp Gly Trp Leu His
                    405                 410                 415
Ser Gly Asp Phe Gly Tyr Tyr Asp Glu Asp Glu His Phe Tyr Val Val
                    420                 425                 430
Asp Arg Tyr Lys Glu Leu Ile Lys Tyr Lys Gly Ser Gln Val Ala Pro
                    435                 440                 445
Ala Glu Leu Glu Glu Ile Leu Leu Lys Asn Pro Cys Ile Arg Asp Val
        450                 455                 460
Ala Val Val Gly Ile Pro Asp Leu Glu Ala Gly Glu Leu Pro Ser Ala
465                 470                 475                 480
Phe Val Val Lys Gln Pro Gly Lys Glu Ile Thr Ala Lys Glu Val Tyr
                    485                 490                 495
Asp Tyr Leu Ala Glu Arg Val Ser His Thr Lys Tyr Leu Arg Gly Gly
                    500                 505                 510
Val Arg Phe Val Asp Ser Ile Pro Arg Asn Val Thr Gly Lys Ile Thr
                    515                 520                 525
Arg Lys Glu Leu Leu Lys Gln Leu Leu Glu Lys Ala Gly Gly
        530                 535                 540

<210> SEQ ID NO 28
<211> LENGTH: 542
<212> TYPE: PRT
<213> ORGANISM: Artificial Sequence
<220> FEATURE:
```

<223> OTHER INFORMATION: Sequence of a synthetic luciferase

<400> SEQUENCE: 28

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
210                 215                 220

Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Asp Gly Trp Leu His

```
                    405                 410                 415
Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
530                 535                 540

<210> SEQ ID NO 29
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 29

Met Met Lys Arg Glu Lys Asn Val Ile Tyr Gly Pro Glu Pro Leu His
 1               5                  10                  15

Pro Leu Glu Asp Leu Thr Ala Gly Glu Met Leu Phe Arg Ala Leu Arg
                20                  25                  30

Lys His Ser His Leu Pro Gln Ala Leu Val Asp Val Val Gly Asp Glu
            35                  40                  45

Ser Leu Ser Tyr Lys Glu Phe Phe Glu Ala Thr Val Leu Leu Ala Gln
        50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
210                 215                 220

Gly Thr Gln Leu Ile Pro Gly Val Thr Val Leu Val Tyr Leu Pro Phe
225                 230                 235                 240
```

```
Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540

<210> SEQ ID NO 30
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 30

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Asn Leu Ser Tyr Lys Glu Phe Phe Glu Ala Thr Val Leu Leu Ala Gln
    50                  55                  60
```

```
Ser Leu His Asn Cys Gly Tyr Lys Met Asn Asp Val Val Ser Ile Cys
 65                  70                  75                  80

Ala Glu Asn Asn Thr Arg Phe Phe Ile Pro Val Ile Ala Ala Trp Tyr
                 85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
210                 215                 220

Gly Thr Gln Leu Ile Ser Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495
```

```
Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
            515                 520                 525

Arg Lys Glu Leu Leu Lys Gln Leu Leu Glu Lys Ala Gly Gly
            530                 535                 540

<210> SEQ ID NO 31
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 31

Met Met Lys Arg Glu Lys Asn Val Ile Tyr Gly Pro Glu Pro Leu His
  1               5                  10                  15

Pro Leu Glu Asp Leu Thr Ala Gly Glu Met Leu Phe Arg Ala Leu Arg
             20                  25                  30

Lys His Ser His Leu Pro Gln Ala Leu Val Asp Val Val Gly Asp Glu
         35                  40                  45

Ser Leu Ser Tyr Lys Glu Phe Phe Glu Ala Thr Val Leu Leu Ala Gln
 50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                 85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
    210                 215                 220

Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320
```

```
Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
        370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
            450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
                515                 520                 525

Arg Lys Glu Leu Leu Lys Gln Leu Leu Glu Lys Ala Gly Gly
        530                 535                 540

<210> SEQ ID NO 32
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 32

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
```

```
                145                 150                 155                 160
        Glu Ser Leu Pro Asn Phe Ile Ser Arg Tyr Ser Asp Gly Asn Ile Ala
                        165                 170                 175

Asn Phe Lys Pro Leu His Phe Asp Pro Val Glu Gln Val Ala Ala Ile
                        180                 185                 190

Leu Cys Ser Ser Gly Thr Thr Gly Leu Pro Lys Gly Val Met Gln Thr
                        195                 200                 205

His Gln Asn Ile Cys Val Arg Leu Ile His Ala Leu Asp Pro Arg Tyr
                        210                 215                 220

Gly Thr Gln Leu Ile Pro Gly Val Thr Val Leu Val Tyr Leu Pro Phe
        225                 230                 235                 240

Phe His Ala Phe Gly Phe His Ile Thr Leu Gly Tyr Phe Met Val Gly
                        245                 250                 255

Leu Arg Val Ile Met Phe Arg Arg Phe Asp Gln Glu Ala Phe Leu Lys
                        260                 265                 270

Ala Ile Gln Asp Tyr Glu Val Arg Ser Val Ile Asn Val Pro Ser Val
                        275                 280                 285

Ile Leu Phe Leu Ser Lys Ser Pro Leu Val Asp Lys Tyr Asp Leu Ser
                        290                 295                 300

Ser Leu Arg Glu Leu Cys Cys Gly Ala Ala Pro Leu Ala Lys Glu Val
        305                 310                 315                 320

Ala Glu Val Ala Ala Lys Arg Leu Asn Leu Pro Gly Ile Arg Cys Gly
                        325                 330                 335

Phe Gly Leu Thr Glu Ser Thr Ser Ala Ile Ile Gln Ser Leu Arg Asp
                        340                 345                 350

Glu Phe Lys Ser Gly Ser Leu Gly Arg Val Thr Pro Leu Met Ala Ala
                        355                 360                 365

Lys Ile Ala Asp Arg Glu Thr Gly Lys Ala Leu Gly Pro Asn Gln Val
                        370                 375                 380

Gly Glu Leu Cys Ile Lys Gly Pro Met Val Ser Lys Gly Tyr Val Asn
        385                 390                 395                 400

Asn Val Glu Ala Thr Lys Glu Ala Ile Asp Asp Asp Gly Trp Leu His
                        405                 410                 415

Ser Gly Asp Phe Gly Tyr Tyr Asp Glu Asp Glu His Phe Tyr Val Val
                        420                 425                 430

Asp Arg Tyr Lys Glu Leu Ile Lys Tyr Lys Gly Ser Gln Val Ala Pro
                        435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
        465                 470                 475                 480

Phe Val Val Lys Gln Pro Gly Lys Glu Ile Thr Ala Lys Glu Val Tyr
                        485                 490                 495

Asp Tyr Leu Ala Glu Arg Val Ser His Thr Lys Tyr Leu Arg Gly Gly
                        500                 505                 510

Val Arg Phe Val Asp Ser Ile Pro Arg Asn Val Thr Gly Lys Ile Thr
                        515                 520                 525

Arg Lys Glu Leu Leu Lys Gln Leu Leu Glu Lys Ala Gly Gly
        530                 535                 540

<210> SEQ ID NO 33
<211> LENGTH: 542
<212> TYPE: PRT
<213> ORGANISM: Artificial Sequence
<220> FEATURE:
```

<223> OTHER INFORMATION: Sequence of a synthetic luciferase

<400> SEQUENCE: 33

```
Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Asp Gly Trp Leu His
```

```
                    405                 410                 415
Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
530                 535                 540

<210> SEQ ID NO 34
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 34

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240
```

```
Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
            325                 330                 335

Phe Gly Leu Thr Glu Ser Thr Ser Ala Ile Ile Gln Ser Leu Arg Asp
        340                 345                 350

Glu Phe Lys Ser Gly Ser Leu Gly Arg Val Thr Pro Leu Met Ala Ala
    355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
            405                 410                 415

Ser Gly Asp Phe Gly Tyr Tyr Asp Glu Asp Glu His Phe Tyr Val Val
        420                 425                 430

Asp Arg Tyr Lys Glu Leu Ile Lys Tyr Lys Gly Ser Gln Val Ala Pro
    435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
            485                 490                 495

Asp Tyr Leu Ala Glu Arg Val Ser His Thr Lys Tyr Leu Arg Gly Gly
        500                 505                 510

Val Arg Phe Val Asp Ser Ile Pro Arg Asn Val Thr Gly Lys Ile Thr
    515                 520                 525

Arg Lys Glu Leu Leu Lys Gln Leu Leu Glu Lys Ala Gly Gly
530                 535                 540

<210> SEQ ID NO 35
<211> LENGTH: 29
<212> TYPE: DNA
<213> ORGANISM: Artificial Sequence
<220> FEATURE:
<223> OTHER INFORMATION: An oligonucleotide

<400> SEQUENCE: 35
acgccagccc aagcttaggc ctgagtggc                                    29

<210> SEQ ID NO 36
<211> LENGTH: 44
<212> TYPE: DNA
<213> ORGANISM: Artificial Sequence
<220> FEATURE:
<223> OTHER INFORMATION: An oligonucleotide

<400> SEQUENCE: 36
```
cttaattctc cccatccccc tgttgacaat taatcatcgg ctcg          44

<210> SEQ ID NO 37
<211> LENGTH: 40
<212> TYPE: DNA
<213> ORGANISM: Artificial Sequence
<220> FEATURE:
<223> OTHER INFORMATION: An oligonucleotide

<400> SEQUENCE: 37
tataatgtga ggaattgcga gcggataaca atttcacaca               40

<210> SEQ ID NO 38
<211> LENGTH: 40
<212> TYPE: DNA
<213> ORGANISM: Artificial Sequence
<220> FEATURE:
<223> OTHER INFORMATION: An oligonucleotide

<400> SEQUENCE: 38
atgggatgtt acctagacca atatgaaata tttggtaaat               40

<210> SEQ ID NO 39
<211> LENGTH: 40
<212> TYPE: DNA
<213> ORGANISM: Artificial Sequence
<220> FEATURE:
<223> OTHER INFORMATION: An oligonucleotide

<400> SEQUENCE: 39
aaatgcttaa tgaatttcaa aaaaaaaaaa aaaggaattc                40

<210> SEQ ID NO 40
<211> LENGTH: 40
<212> TYPE: DNA
<213> ORGANISM: Artificial Sequence
<220> FEATURE:
<223> OTHER INFORMATION: An oligonucleotide

<400> SEQUENCE: 40
gatatcaagc ttatcgatac cgtcgacctc gaggattata              40

<210> SEQ ID NO 41
<211> LENGTH: 37
<212> TYPE: DNA
<213> ORGANISM: Artificial Sequence
<220> FEATURE:
<223> OTHER INFORMATION: An oligonucleotide

<400> SEQUENCE: 41
tagaaaaagg cctcggcggc cgctagttca gtcagtt                 37

<210> SEQ ID NO 42
<211> LENGTH: 17
<212> TYPE: DNA
<213> ORGANISM: Artificial Sequence
<220> FEATURE:
<223> OTHER INFORMATION: An oligonucleotide

<400> SEQUENCE: 42
aactgactga actagcg                                        17

<210> SEQ ID NO 43
<211> LENGTH: 40
<212> TYPE: DNA
<213> ORGANISM: Artificial Sequence
<220> FEATURE:

<223> OTHER INFORMATION: An oligonucleotide

<400> SEQUENCE: 43
gccgccgagg ccttttttcta tataatcctc gaggtcgacg                40

<210> SEQ ID NO 44
<211> LENGTH: 40
<212> TYPE: DNA
<213> ORGANISM: Artificial Sequence
<220> FEATURE:
<223> OTHER INFORMATION: An oligonucleotide

<400> SEQUENCE: 44
gtatcgataa gcttgatatc gaattccttt ttttttttt                 40

<210> SEQ ID NO 45
<211> LENGTH: 40
<212> TYPE: DNA
<213> ORGANISM: Artificial Sequence
<220> FEATURE:
<223> OTHER INFORMATION: An oligonucleotide

<400> SEQUENCE: 45
agcttgatat cgaattcctt tttttttttt tttgaaattc                40

<210> SEQ ID NO 46
<211> LENGTH: 40
<212> TYPE: DNA
<213> ORGANISM: Artificial Sequence
<220> FEATURE:
<223> OTHER INFORMATION: An oligonucleotide

<400> SEQUENCE: 46
ttgaaattca ttaagcattt atttaccaaa tatttcatat                40

<210> SEQ ID NO 47
<211> LENGTH: 40
<212> TYPE: DNA
<213> ORGANISM: Artificial Sequence
<220> FEATURE:
<223> OTHER INFORMATION: An oligonucleotide

<400> SEQUENCE: 47
tggtctaggt aacatcccat cactagcttt ttttctata                 40

<210> SEQ ID NO 48
<211> LENGTH: 40
<212> TYPE: DNA
<213> ORGANISM: Artificial Sequence
<220> FEATURE:
<223> OTHER INFORMATION: An oligonucleotide

<400> SEQUENCE: 48
tcgcaattcc tcacattata cgagccgatg attaattgtc                40

<210> SEQ ID NO 49
<211> LENGTH: 53
<212> TYPE: DNA
<213> ORGANISM: Artificial Sequence
<220> FEATURE:
<223> OTHER INFORMATION: An oligonucleotide

<400> SEQUENCE: 49
aacaggggga tggggagaat taaggccact caggcctaag cttgggctgg cgt      53

<210> SEQ ID NO 50

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 50
ggaaacagga tcccatgatg aaacgcgaaa agaacgtgat                    40

<210> SEQ ID NO 51
<211> LENGTH: 40
<212> TYPE: DNA
<213> ORGANISM: Artificial Sequence
<220> FEATURE:
<223> OTHER INFORMATION: An oligonucleotide

<400> SEQUENCE: 51
ctacggccca gaaccactgc atccactgga agacctcacc                    40

<210> SEQ ID NO 52
<211> LENGTH: 40
<212> TYPE: DNA
<213> ORGANISM: Artificial Sequence
<220> FEATURE:
<223> OTHER INFORMATION: An oligonucleotide

<400> SEQUENCE: 52
gctggtgaga tgctcttccg agcactgcgt aaacatagtc                    40

<210> SEQ ID NO 53
<211> LENGTH: 40
<212> TYPE: DNA
<213> ORGANISM: Artificial Sequence
<220> FEATURE:
<223> OTHER INFORMATION: An oligonucleotide

<400> SEQUENCE: 53
acctccctca agcactcgtg gacgtcgtgg gagacgagag                    40

<210> SEQ ID NO 54
<211> LENGTH: 40
<212> TYPE: DNA
<213> ORGANISM: Artificial Sequence
<220> FEATURE:
<223> OTHER INFORMATION: An oligonucleotide

<400> SEQUENCE: 54
cctctcctac aaagaatttt tcgaagctac tgtgctgttg                    40

<210> SEQ ID NO 55
<211> LENGTH: 40
<212> TYPE: DNA
<213> ORGANISM: Artificial Sequence
<220> FEATURE:
<223> OTHER INFORMATION: An oligonucleotide

<400> SEQUENCE: 55
gcccaaagcc tccataattg tgggtacaaa atgaacgatg                    40

<210> SEQ ID NO 56
<211> LENGTH: 40
<212> TYPE: DNA
<213> ORGANISM: Artificial Sequence
<220> FEATURE:
<223> OTHER INFORMATION: An oligonucleotide

<400> SEQUENCE: 56
```

```
tggtgagcat ttgtgctgag aataacactc gcttctttat                              40

<210> SEQ ID NO 57
<211> LENGTH: 40
<212> TYPE: DNA
<213> ORGANISM: Artificial Sequence
<220> FEATURE:
<223> OTHER INFORMATION: An oligonucleotide

<400> SEQUENCE: 57
tcctgtaatc gctgcttggt acatcggcat gattgtcgcc                              40

<210> SEQ ID NO 58
<211> LENGTH: 40
<212> TYPE: DNA
<213> ORGANISM: Artificial Sequence
<220> FEATURE:
<223> OTHER INFORMATION: An oligonucleotide

<400> SEQUENCE: 58
cctgtgaatg aatcttacat cccagatgag ctgtgtaagg                              40

<210> SEQ ID NO 59
<211> LENGTH: 40
<212> TYPE: DNA
<213> ORGANISM: Artificial Sequence
<220> FEATURE:
<223> OTHER INFORMATION: An oligonucleotide

<400> SEQUENCE: 59
ttatgggtat tagcaaacct caaatcgtct ttactaccaa                              40

<210> SEQ ID NO 60
<211> LENGTH: 40
<212> TYPE: DNA
<213> ORGANISM: Artificial Sequence
<220> FEATURE:
<223> OTHER INFORMATION: An oligonucleotide

<400> SEQUENCE: 60
aaacatcttg aataaggtct tggaagtcca gtctcgtact                              40

<210> SEQ ID NO 61
<211> LENGTH: 40
<212> TYPE: DNA
<213> ORGANISM: Artificial Sequence
<220> FEATURE:
<223> OTHER INFORMATION: An oligonucleotide

<400> SEQUENCE: 61
aacttcatca aacgcatcat tattctggat accgtcgaaa                              40

<210> SEQ ID NO 62
<211> LENGTH: 40
<212> TYPE: DNA
<213> ORGANISM: Artificial Sequence
<220> FEATURE:
<223> OTHER INFORMATION: An oligonucleotide

<400> SEQUENCE: 62
acatccacgg ctgtgagagc ctccctaact tcatctctcg                              40

<210> SEQ ID NO 63
<211> LENGTH: 40
<212> TYPE: DNA
<213> ORGANISM: Artificial Sequence
<220> FEATURE:
```

<223> OTHER INFORMATION: An oligonucleotide

<400> SEQUENCE: 63
ttacagcgat ggtaatatcg ctaatttcaa gcccttgcat                    40

<210> SEQ ID NO 64
<211> LENGTH: 40
<212> TYPE: DNA
<213> ORGANISM: Artificial Sequence
<220> FEATURE:
<223> OTHER INFORMATION: An oligonucleotide

<400> SEQUENCE: 64
tttgatccag tcgagcaagt ggccgctatt ttgtgctcct                    40

<210> SEQ ID NO 65
<211> LENGTH: 40
<212> TYPE: DNA
<213> ORGANISM: Artificial Sequence
<220> FEATURE:
<223> OTHER INFORMATION: An oligonucleotide

<400> SEQUENCE: 65
ccggcaccac tggtttgcct aaaggtgtca tgcagactca                    40

<210> SEQ ID NO 66
<211> LENGTH: 40
<212> TYPE: DNA
<213> ORGANISM: Artificial Sequence
<220> FEATURE:
<223> OTHER INFORMATION: An oligonucleotide

<400> SEQUENCE: 66
ccagaatatc tgtgtgcgtt tgatccacgc tctcgaccct                    40

<210> SEQ ID NO 67
<211> LENGTH: 40
<212> TYPE: DNA
<213> ORGANISM: Artificial Sequence
<220> FEATURE:
<223> OTHER INFORMATION: An oligonucleotide

<400> SEQUENCE: 67
cgtgtgggta ctcaattgat ccctggcgtg actgtgctgg                    40

<210> SEQ ID NO 68
<211> LENGTH: 40
<212> TYPE: DNA
<213> ORGANISM: Artificial Sequence
<220> FEATURE:
<223> OTHER INFORMATION: An oligonucleotide

<400> SEQUENCE: 68
tgtatctgcc tttctttcac gcctttggtt tctctattac                    40

<210> SEQ ID NO 69
<211> LENGTH: 40
<212> TYPE: DNA
<213> ORGANISM: Artificial Sequence
<220> FEATURE:
<223> OTHER INFORMATION: An oligonucleotide

<400> SEQUENCE: 69
cctgggctat ttcatggtcg gcttgcgtgt catcatgttt                    40

<210> SEQ ID NO 70

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 70
cgtcgcttcg accaagaagc cttcttgaag gctattcaag                              40

<210> SEQ ID NO 71
<211> LENGTH: 40
<212> TYPE: DNA
<213> ORGANISM: Artificial Sequence
<220> FEATURE:
<223> OTHER INFORMATION: An oligonucleotide

<400> SEQUENCE: 71
actacgaggt gcgttccgtg atcaacgtcc cttcagtcat                              40

<210> SEQ ID NO 72
<211> LENGTH: 43
<212> TYPE: DNA
<213> ORGANISM: Artificial Sequence
<220> FEATURE:
<223> OTHER INFORMATION: An oligonucleotide

<400> SEQUENCE: 72
tttgttcctg agcaaatctc ctttggttga caagtatgat ctg                          43

<210> SEQ ID NO 73
<211> LENGTH: 37
<212> TYPE: DNA
<213> ORGANISM: Artificial Sequence
<220> FEATURE:
<223> OTHER INFORMATION: An oligonucleotide

<400> SEQUENCE: 73
agcagcttgc gtgagctgtg ctgtggcgct gctcctt                                 37

<210> SEQ ID NO 74
<211> LENGTH: 40
<212> TYPE: DNA
<213> ORGANISM: Artificial Sequence
<220> FEATURE:
<223> OTHER INFORMATION: An oligonucleotide

<400> SEQUENCE: 74
tggccaaaga agtggccgag gtcgctgcta agcgtctgaa                              40

<210> SEQ ID NO 75
<211> LENGTH: 40
<212> TYPE: DNA
<213> ORGANISM: Artificial Sequence
<220> FEATURE:
<223> OTHER INFORMATION: An oligonucleotide

<400> SEQUENCE: 75
cctccctggt atccgctgcg gttttggttt gactgagagc                              40

<210> SEQ ID NO 76
<211> LENGTH: 40
<212> TYPE: DNA
<213> ORGANISM: Artificial Sequence
<220> FEATURE:
<223> OTHER INFORMATION: An oligonucleotide

<400> SEQUENCE: 76
```
acttctgcta acatccatag cttgcgagac gagtttaagt                        40

<210> SEQ ID NO 77
<211> LENGTH: 40
<212> TYPE: DNA
<213> ORGANISM: Artificial Sequence
<220> FEATURE:
<223> OTHER INFORMATION: An oligonucleotide

<400> SEQUENCE: 77
ctggtagcct gggtcgcgtg actcctctta tggctgcaaa                        40

<210> SEQ ID NO 78
<211> LENGTH: 40
<212> TYPE: DNA
<213> ORGANISM: Artificial Sequence
<220> FEATURE:
<223> OTHER INFORMATION: An oligonucleotide

<400> SEQUENCE: 78
gatcgccgac cgtgagaccg gcaaagcact gggcccaaat                        40

<210> SEQ ID NO 79
<211> LENGTH: 40
<212> TYPE: DNA
<213> ORGANISM: Artificial Sequence
<220> FEATURE:
<223> OTHER INFORMATION: An oligonucleotide

<400> SEQUENCE: 79
caagtcggtg aattgtgtat taagggccct atggtctcta                        40

<210> SEQ ID NO 80
<211> LENGTH: 40
<212> TYPE: DNA
<213> ORGANISM: Artificial Sequence
<220> FEATURE:
<223> OTHER INFORMATION: An oligonucleotide

<400> SEQUENCE: 80
aaggctacgt gaacaatgtg gaggccacta aagaagccat                        40

<210> SEQ ID NO 81
<211> LENGTH: 40
<212> TYPE: DNA
<213> ORGANISM: Artificial Sequence
<220> FEATURE:
<223> OTHER INFORMATION: An oligonucleotide

<400> SEQUENCE: 81
tgatgatgat ggctggctcc atagcggcga cttcggttac                        40

<210> SEQ ID NO 82
<211> LENGTH: 40
<212> TYPE: DNA
<213> ORGANISM: Artificial Sequence
<220> FEATURE:
<223> OTHER INFORMATION: An oligonucleotide

<400> SEQUENCE: 82
tatgatgagg acgaacactt ctatgtggtc gatcgctaca                        40

<210> SEQ ID NO 83
<211> LENGTH: 40
<212> TYPE: DNA
<213> ORGANISM: Artificial Sequence
<220> FEATURE:

<223> OTHER INFORMATION: An oligonucleotide

<400> SEQUENCE: 83
aagaattgat taagtacaaa ggctctcaag tcgcaccagc                              40

<210> SEQ ID NO 84
<211> LENGTH: 40
<212> TYPE: DNA
<213> ORGANISM: Artificial Sequence
<220> FEATURE:
<223> OTHER INFORMATION: An oligonucleotide

<400> SEQUENCE: 84
cgaactggaa gaaattttgc tgaagaaccc ttgtatccgc                              40

<210> SEQ ID NO 85
<211> LENGTH: 40
<212> TYPE: DNA
<213> ORGANISM: Artificial Sequence
<220> FEATURE:
<223> OTHER INFORMATION: An oligonucleotide

<400> SEQUENCE: 85
gacgtggccg tcgtgggtat cccagacttg gaagctggcg                              40

<210> SEQ ID NO 86
<211> LENGTH: 40
<212> TYPE: DNA
<213> ORGANISM: Artificial Sequence
<220> FEATURE:
<223> OTHER INFORMATION: An oligonucleotide

<400> SEQUENCE: 86
agttgcctag cgcctttgtg gtgaaacaac ccggcaagga                              40

<210> SEQ ID NO 87
<211> LENGTH: 40
<212> TYPE: DNA
<213> ORGANISM: Artificial Sequence
<220> FEATURE:
<223> OTHER INFORMATION: An oligonucleotide

<400> SEQUENCE: 87
gatcactgct aaggaggtct acgactattt ggccgagcgc                              40

<210> SEQ ID NO 88
<211> LENGTH: 40
<212> TYPE: DNA
<213> ORGANISM: Artificial Sequence
<220> FEATURE:
<223> OTHER INFORMATION: An oligonucleotide

<400> SEQUENCE: 88
gtgtctcaca ccaaatatct gcgtggcggc gtccgcttcg                              40

<210> SEQ ID NO 89
<211> LENGTH: 40
<212> TYPE: DNA
<213> ORGANISM: Artificial Sequence
<220> FEATURE:
<223> OTHER INFORMATION: An oligonucleotide

<400> SEQUENCE: 89
tcgattctat tccacgcaac gttaccggta agatcactcg                              40

<210> SEQ ID NO 90

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 90
taaagagttg ctgaagcaac tcctcgaaaa agctggcggc                              40

<210> SEQ ID NO 91
<211> LENGTH: 40
<212> TYPE: DNA
<213> ORGANISM: Artificial Sequence
<220> FEATURE:
<223> OTHER INFORMATION: An oligonucleotide

<400> SEQUENCE: 91
tagtaaagtc ttcatgatta tatagaaaaa aaagctagtg                              40

<210> SEQ ID NO 92
<211> LENGTH: 40
<212> TYPE: DNA
<213> ORGANISM: Artificial Sequence
<220> FEATURE:
<223> OTHER INFORMATION: An oligonucleotide

<400> SEQUENCE: 92
taatcatgaa gactttacta gccgccagct ttttcgagga                              40

<210> SEQ ID NO 93
<211> LENGTH: 40
<212> TYPE: DNA
<213> ORGANISM: Artificial Sequence
<220> FEATURE:
<223> OTHER INFORMATION: An oligonucleotide

<400> SEQUENCE: 93
gttgcttcag caactcttta cgagtgatct taccggtaac                              40

<210> SEQ ID NO 94
<211> LENGTH: 39
<212> TYPE: DNA
<213> ORGANISM: Artificial Sequence
<220> FEATURE:
<223> OTHER INFORMATION: An oligonucleotide

<400> SEQUENCE: 94
gttgcgtgga atagaatcga cgaagcggac gccgccacg                               39

<210> SEQ ID NO 95
<211> LENGTH: 41
<212> TYPE: DNA
<213> ORGANISM: Artificial Sequence
<220> FEATURE:
<223> OTHER INFORMATION: An oligonucleotide

<400> SEQUENCE: 95
cagatatttg gtgtgagaca cgcgctcggc caaatagtcg t                            41

<210> SEQ ID NO 96
<211> LENGTH: 40
<212> TYPE: DNA
<213> ORGANISM: Artificial Sequence
<220> FEATURE:
<223> OTHER INFORMATION: An oligonucleotide

<400> SEQUENCE: 96
```
agacctcctt agcagtgatc tccttgccgg gttgtttcac                40

```
<210> SEQ ID NO 97
<211> LENGTH: 40
<212> TYPE: DNA
<213> ORGANISM: Artificial Sequence
<220> FEATURE:
<223> OTHER INFORMATION: An oligonucleotide

<400> SEQUENCE: 97
```
cacaaaggcg ctaggcaact cgccagcttc caagtctggg                40

```
<210> SEQ ID NO 98
<211> LENGTH: 40
<212> TYPE: DNA
<213> ORGANISM: Artificial Sequence
<220> FEATURE:
<223> OTHER INFORMATION: An oligonucleotide

<400> SEQUENCE: 98
```
atacccacga cggccacgtc gcggatacaa gggttcttca                40

```
<210> SEQ ID NO 99
<211> LENGTH: 40
<212> TYPE: DNA
<213> ORGANISM: Artificial Sequence
<220> FEATURE:
<223> OTHER INFORMATION: An oligonucleotide

<400> SEQUENCE: 99
```
gcaaaatttc ttccagttcg gctggtgcga cttgagagcc                40

```
<210> SEQ ID NO 100
<211> LENGTH: 40
<212> TYPE: DNA
<213> ORGANISM: Artificial Sequence
<220> FEATURE:
<223> OTHER INFORMATION: An oligonucleotide

<400> SEQUENCE: 100
```
tttgtactta atcaattctt tgtagcgatc gaccacatag                40

```
<210> SEQ ID NO 101
<211> LENGTH: 40
<212> TYPE: DNA
<213> ORGANISM: Artificial Sequence
<220> FEATURE:
<223> OTHER INFORMATION: An oligonucleotide

<400> SEQUENCE: 101
```
aagtgttcgt cctcatcata gtaaccgaag tcgccgctat                40

```
<210> SEQ ID NO 102
<211> LENGTH: 40
<212> TYPE: DNA
<213> ORGANISM: Artificial Sequence
<220> FEATURE:
<223> OTHER INFORMATION: An oligonucleotide

<400> SEQUENCE: 102
```
ggagccagcc atcatcatca atggcttctt tagtggcctc                40

```
<210> SEQ ID NO 103
<211> LENGTH: 40
<212> TYPE: DNA
<213> ORGANISM: Artificial Sequence
<220> FEATURE:
```

<223> OTHER INFORMATION: An oligonucleotide

<400> SEQUENCE: 103
cacattgttc acgtagcctt tagagaccat agggcccttA                              40

<210> SEQ ID NO 104
<211> LENGTH: 40
<212> TYPE: DNA
<213> ORGANISM: Artificial Sequence
<220> FEATURE:
<223> OTHER INFORMATION: An oligonucleotide

<400> SEQUENCE: 104
atacacaatt caccgacttg atttgggccc agtgctttgc                              40

<210> SEQ ID NO 105
<211> LENGTH: 40
<212> TYPE: DNA
<213> ORGANISM: Artificial Sequence
<220> FEATURE:
<223> OTHER INFORMATION: An oligonucleotide

<400> SEQUENCE: 105
cggtctcacg gtcggcgatc tttgcagcca taagaggagt                              40

<210> SEQ ID NO 106
<211> LENGTH: 40
<212> TYPE: DNA
<213> ORGANISM: Artificial Sequence
<220> FEATURE:
<223> OTHER INFORMATION: An oligonucleotide

<400> SEQUENCE: 106
cacgcgaccc aggctaccag acttaaactc gtctcgcaag                              40

<210> SEQ ID NO 107
<211> LENGTH: 40
<212> TYPE: DNA
<213> ORGANISM: Artificial Sequence
<220> FEATURE:
<223> OTHER INFORMATION: An oligonucleotide

<400> SEQUENCE: 107
ctatggatgt tagcagaagt gctctcagtc aaaccaaaac                              40

<210> SEQ ID NO 108
<211> LENGTH: 40
<212> TYPE: DNA
<213> ORGANISM: Artificial Sequence
<220> FEATURE:
<223> OTHER INFORMATION: An oligonucleotide

<400> SEQUENCE: 108
cgcagcggat accagggagg ttcagacgct tagcagcgac                              40

<210> SEQ ID NO 109
<211> LENGTH: 40
<212> TYPE: DNA
<213> ORGANISM: Artificial Sequence
<220> FEATURE:
<223> OTHER INFORMATION: An oligonucleotide

<400> SEQUENCE: 109
ctcggccact tctttggcca aaggagcagc gccacagcac                              40

<210> SEQ ID NO 110

<211> LENGTH: 40
<212> TYPE: DNA
<213> ORGANISM: Artificial Sequence
<220> FEATURE:
<223> OTHER INFORMATION: An oligonucleotide

<400> SEQUENCE: 110
agctcacgca agctgctcag atcatacttg tcaaccaaag         40

<210> SEQ ID NO 111
<211> LENGTH: 40
<212> TYPE: DNA
<213> ORGANISM: Artificial Sequence
<220> FEATURE:
<223> OTHER INFORMATION: An oligonucleotide

<400> SEQUENCE: 111
gagatttgct caggaacaaa atgactgaag ggacgttgat         40

<210> SEQ ID NO 112
<211> LENGTH: 36
<212> TYPE: DNA
<213> ORGANISM: Artificial Sequence
<220> FEATURE:
<223> OTHER INFORMATION: An oligonucleotide

<400> SEQUENCE: 112
cacggaacgc acctcgtagt cttgaatagc cttcaa            36

<210> SEQ ID NO 113
<211> LENGTH: 44
<212> TYPE: DNA
<213> ORGANISM: Artificial Sequence
<220> FEATURE:
<223> OTHER INFORMATION: An oligonucleotide

<400> SEQUENCE: 113
gaaggcttct tggtcgaagc gacgaaacat gatgacacgc aagc    44

<210> SEQ ID NO 114
<211> LENGTH: 40
<212> TYPE: DNA
<213> ORGANISM: Artificial Sequence
<220> FEATURE:
<223> OTHER INFORMATION: An oligonucleotide

<400> SEQUENCE: 114
cgaccatgaa atagcccagg gtaatagaga aaccaaaggc         40

<210> SEQ ID NO 115
<211> LENGTH: 40
<212> TYPE: DNA
<213> ORGANISM: Artificial Sequence
<220> FEATURE:
<223> OTHER INFORMATION: An oligonucleotide

<400> SEQUENCE: 115
gtgaaagaaa ggcagataca ccagcacagt cacgccaggg         40

<210> SEQ ID NO 116
<211> LENGTH: 40
<212> TYPE: DNA
<213> ORGANISM: Artificial Sequence
<220> FEATURE:
<223> OTHER INFORMATION: An oligonucleotide

<400> SEQUENCE: 116

```
atcaattgag tacccacacg agggtcgaga gcgtggatca                    40
```

<210> SEQ ID NO 117
<211> LENGTH: 40
<212> TYPE: DNA
<213> ORGANISM: Artificial Sequence
<220> FEATURE:
<223> OTHER INFORMATION: An oligonucleotide

<400> SEQUENCE: 117

```
aacgcacaca gatattctgg tgagtctgca tgacaccttt                    40
```

<210> SEQ ID NO 118
<211> LENGTH: 40
<212> TYPE: DNA
<213> ORGANISM: Artificial Sequence
<220> FEATURE:
<223> OTHER INFORMATION: An oligonucleotide

<400> SEQUENCE: 118

```
aggcaaacca gtggtgccgg aggagcacaa aatagcggcc                    40
```

<210> SEQ ID NO 119
<211> LENGTH: 40
<212> TYPE: DNA
<213> ORGANISM: Artificial Sequence
<220> FEATURE:
<223> OTHER INFORMATION: An oligonucleotide

<400> SEQUENCE: 119

```
acttgctcga ctggatcaaa atgcaagggc ttgaaattag                    40
```

<210> SEQ ID NO 120
<211> LENGTH: 40
<212> TYPE: DNA
<213> ORGANISM: Artificial Sequence
<220> FEATURE:
<223> OTHER INFORMATION: An oligonucleotide

<400> SEQUENCE: 120

```
cgatattacc atcgctgtaa cgagagatga agttagggag                    40
```

<210> SEQ ID NO 121
<211> LENGTH: 40
<212> TYPE: DNA
<213> ORGANISM: Artificial Sequence
<220> FEATURE:
<223> OTHER INFORMATION: An oligonucleotide

<400> SEQUENCE: 121

```
gctctcacag ccgtggatgt tttcgacggt atccagaata                    40
```

<210> SEQ ID NO 122
<211> LENGTH: 40
<212> TYPE: DNA
<213> ORGANISM: Artificial Sequence
<220> FEATURE:
<223> OTHER INFORMATION: An oligonucleotide

<400> SEQUENCE: 122

```
atgatgcgtt tgatgaagtt agtacgagac tggacttcca                    40
```

<210> SEQ ID NO 123
<211> LENGTH: 40
<212> TYPE: DNA
<213> ORGANISM: Artificial Sequence
<220> FEATURE:

<223> OTHER INFORMATION: An oligonucleotide

<400> SEQUENCE: 123
agaccttatt caagatgttt ttggtagtaa agacgatttg                    40

<210> SEQ ID NO 124
<211> LENGTH: 40
<212> TYPE: DNA
<213> ORGANISM: Artificial Sequence
<220> FEATURE:
<223> OTHER INFORMATION: An oligonucleotide

<400> SEQUENCE: 124
aggtttgcta atacccataa ccttacacag ctcatctggg                    40

<210> SEQ ID NO 125
<211> LENGTH: 40
<212> TYPE: DNA
<213> ORGANISM: Artificial Sequence
<220> FEATURE:
<223> OTHER INFORMATION: An oligonucleotide

<400> SEQUENCE: 125
atgtaagatt cattcacagg ggcgacaatc atgccgatgt                    40

<210> SEQ ID NO 126
<211> LENGTH: 40
<212> TYPE: DNA
<213> ORGANISM: Artificial Sequence
<220> FEATURE:
<223> OTHER INFORMATION: An oligonucleotide

<400> SEQUENCE: 126
accaagcagc gattacagga ataaagaagc gagtgttatt                    40

<210> SEQ ID NO 127
<211> LENGTH: 40
<212> TYPE: DNA
<213> ORGANISM: Artificial Sequence
<220> FEATURE:
<223> OTHER INFORMATION: An oligonucleotide

<400> SEQUENCE: 127
ctcagcacaa atgctcacca catcgttcat tttgtaccca                    40

<210> SEQ ID NO 128
<211> LENGTH: 40
<212> TYPE: DNA
<213> ORGANISM: Artificial Sequence
<220> FEATURE:
<223> OTHER INFORMATION: An oligonucleotide

<400> SEQUENCE: 128
caattatgga ggctttgggc caacagcaca gtagcttcga                    40

<210> SEQ ID NO 129
<211> LENGTH: 40
<212> TYPE: DNA
<213> ORGANISM: Artificial Sequence
<220> FEATURE:
<223> OTHER INFORMATION: An oligonucleotide

<400> SEQUENCE: 129
aaaattcttt gtaggagagg ctctcgtctc ccacgacgtc                    40

<210> SEQ ID NO 130

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 130
cacgagtgct tgagggaggt gactatgttt acgcagtgct                    40

<210> SEQ ID NO 131
<211> LENGTH: 40
<212> TYPE: DNA
<213> ORGANISM: Artificial Sequence
<220> FEATURE:
<223> OTHER INFORMATION: An oligonucleotide

<400> SEQUENCE: 131
cggaagagca tctcaccagc ggtgaggtct tccagtggat                    40

<210> SEQ ID NO 132
<211> LENGTH: 40
<212> TYPE: DNA
<213> ORGANISM: Artificial Sequence
<220> FEATURE:
<223> OTHER INFORMATION: An oligonucleotide

<400> SEQUENCE: 132
gcagtggttc tgggccgtag atcacgttct tttcgcgttt                    40

<210> SEQ ID NO 133
<211> LENGTH: 40
<212> TYPE: DNA
<213> ORGANISM: Artificial Sequence
<220> FEATURE:
<223> OTHER INFORMATION: An oligonucleotide

<400> SEQUENCE: 133
catcatggga tcctgtttcc tgtgtgaaat tgttatccgc                    40

<210> SEQ ID NO 134
<211> LENGTH: 40
<212> TYPE: DNA
<213> ORGANISM: Artificial Sequence
<220> FEATURE:
<223> OTHER INFORMATION: An oligonucleotide

<400> SEQUENCE: 134
ggaaacagga tcccatgatg aagcgtgaga aaaatgtcat                    40

<210> SEQ ID NO 135
<211> LENGTH: 40
<212> TYPE: DNA
<213> ORGANISM: Artificial Sequence
<220> FEATURE:
<223> OTHER INFORMATION: An oligonucleotide

<400> SEQUENCE: 135
ctatggccct gagcctctcc atcctttgga ggatttgact                    40

<210> SEQ ID NO 136
<211> LENGTH: 40
<212> TYPE: DNA
<213> ORGANISM: Artificial Sequence
<220> FEATURE:
<223> OTHER INFORMATION: An oligonucleotide

<400> SEQUENCE: 136
```

```
gccggcgaaa tgctgtttcg tgctctccgc aagcactctc                              40
```

<210> SEQ ID NO 137
<211> LENGTH: 40
<212> TYPE: DNA
<213> ORGANISM: Artificial Sequence
<220> FEATURE:
<223> OTHER INFORMATION: An oligonucleotide

<400> SEQUENCE: 137

```
atttgcctca agccttggtc gatgtggtcg gcgatgaatc                              40
```

<210> SEQ ID NO 138
<211> LENGTH: 40
<212> TYPE: DNA
<213> ORGANISM: Artificial Sequence
<220> FEATURE:
<223> OTHER INFORMATION: An oligonucleotide

<400> SEQUENCE: 138

```
tttgagctac aaggagtttt ttgaggcaac cgtcttgctg                              40
```

<210> SEQ ID NO 139
<211> LENGTH: 40
<212> TYPE: DNA
<213> ORGANISM: Artificial Sequence
<220> FEATURE:
<223> OTHER INFORMATION: An oligonucleotide

<400> SEQUENCE: 139

```
gctcagtccc tccacaattg tggctacaag atgaacgacg                              40
```

<210> SEQ ID NO 140
<211> LENGTH: 40
<212> TYPE: DNA
<213> ORGANISM: Artificial Sequence
<220> FEATURE:
<223> OTHER INFORMATION: An oligonucleotide

<400> SEQUENCE: 140

```
tcgttagtat ctgtgctgaa aacaataccc gtttcttcat                              40
```

<210> SEQ ID NO 141
<211> LENGTH: 40
<212> TYPE: DNA
<213> ORGANISM: Artificial Sequence
<220> FEATURE:
<223> OTHER INFORMATION: An oligonucleotide

<400> SEQUENCE: 141

```
tccagtcatc gccgcatggt atatcggtat gatcgtggct                              40
```

<210> SEQ ID NO 142
<211> LENGTH: 40
<212> TYPE: DNA
<213> ORGANISM: Artificial Sequence
<220> FEATURE:
<223> OTHER INFORMATION: An oligonucleotide

<400> SEQUENCE: 142

```
ccagtcaacg agagctacat tcccgacgaa ctgtgtaaag                              40
```

<210> SEQ ID NO 143
<211> LENGTH: 40
<212> TYPE: DNA
<213> ORGANISM: Artificial Sequence
<220> FEATURE:

<223> OTHER INFORMATION: An oligonucleotide

<400> SEQUENCE: 143
tcatgggtat ctctaagcca cagattgtct tcaccactaa          40

<210> SEQ ID NO 144
<211> LENGTH: 40
<212> TYPE: DNA
<213> ORGANISM: Artificial Sequence
<220> FEATURE:
<223> OTHER INFORMATION: An oligonucleotide

<400> SEQUENCE: 144
gaatattctg aacaaagtcc tggaagtcca agccgcacc          40

<210> SEQ ID NO 145
<211> LENGTH: 40
<212> TYPE: DNA
<213> ORGANISM: Artificial Sequence
<220> FEATURE:
<223> OTHER INFORMATION: An oligonucleotide

<400> SEQUENCE: 145
aactttatta agcgtatcat catcttggac actgtggaga          40

<210> SEQ ID NO 146
<211> LENGTH: 40
<212> TYPE: DNA
<213> ORGANISM: Artificial Sequence
<220> FEATURE:
<223> OTHER INFORMATION: An oligonucleotide

<400> SEQUENCE: 146
atattcacgg ttgcgaatct ttgcctaatt tcatctctcg          40

<210> SEQ ID NO 147
<211> LENGTH: 40
<212> TYPE: DNA
<213> ORGANISM: Artificial Sequence
<220> FEATURE:
<223> OTHER INFORMATION: An oligonucleotide

<400> SEQUENCE: 147
ctattcagac ggcaacatcg caaactttaa accactccac          40

<210> SEQ ID NO 148
<211> LENGTH: 40
<212> TYPE: DNA
<213> ORGANISM: Artificial Sequence
<220> FEATURE:
<223> OTHER INFORMATION: An oligonucleotide

<400> SEQUENCE: 148
ttcgaccctg tggaacaagt tgcagccatt ctgtgtagca          40

<210> SEQ ID NO 149
<211> LENGTH: 40
<212> TYPE: DNA
<213> ORGANISM: Artificial Sequence
<220> FEATURE:
<223> OTHER INFORMATION: An oligonucleotide

<400> SEQUENCE: 149
gcggtactac tggactccca aagggagtca tgcagaccca          40

<210> SEQ ID NO 150

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 150
tcaaaacatt tgcgtgcgtc tgatccatgc tctcgatcca                               40

<210> SEQ ID NO 151
<211> LENGTH: 40
<212> TYPE: DNA
<213> ORGANISM: Artificial Sequence
<220> FEATURE:
<223> OTHER INFORMATION: An oligonucleotide

<400> SEQUENCE: 151
cgctacggca ctcagctgat tcctggtgtc accgtcttgg                               40

<210> SEQ ID NO 152
<211> LENGTH: 40
<212> TYPE: DNA
<213> ORGANISM: Artificial Sequence
<220> FEATURE:
<223> OTHER INFORMATION: An oligonucleotide

<400> SEQUENCE: 152
tctacttgcc tttcttccat gctttcggct ttcatattac                               40

<210> SEQ ID NO 153
<211> LENGTH: 40
<212> TYPE: DNA
<213> ORGANISM: Artificial Sequence
<220> FEATURE:
<223> OTHER INFORMATION: An oligonucleotide

<400> SEQUENCE: 153
tttgggttac tttatggtcg gtctccgcgt gattatgttc                               40

<210> SEQ ID NO 154
<211> LENGTH: 40
<212> TYPE: DNA
<213> ORGANISM: Artificial Sequence
<220> FEATURE:
<223> OTHER INFORMATION: An oligonucleotide

<400> SEQUENCE: 154
cgccgttttg atcaggaggc tttcttgaaa gccatccaag                               40

<210> SEQ ID NO 155
<211> LENGTH: 40
<212> TYPE: DNA
<213> ORGANISM: Artificial Sequence
<220> FEATURE:
<223> OTHER INFORMATION: An oligonucleotide

<400> SEQUENCE: 155
attatgaagt ccgcagtgtc atcaacgtgc ctagcgtgat                               40

<210> SEQ ID NO 156
<211> LENGTH: 40
<212> TYPE: DNA
<213> ORGANISM: Artificial Sequence
<220> FEATURE:
<223> OTHER INFORMATION: An oligonucleotide

<400> SEQUENCE: 156
```

```
cctgtttttg tctaagagcc cactcgtgga caagtacgac                              40
```

<210> SEQ ID NO 157
<211> LENGTH: 40
<212> TYPE: DNA
<213> ORGANISM: Artificial Sequence
<220> FEATURE:
<223> OTHER INFORMATION: An oligonucleotide

<400> SEQUENCE: 157

```
ttgtcttcac tgcgtgaatt gtgttgcggt gccgctccac                              40
```

<210> SEQ ID NO 158
<211> LENGTH: 40
<212> TYPE: DNA
<213> ORGANISM: Artificial Sequence
<220> FEATURE:
<223> OTHER INFORMATION: An oligonucleotide

<400> SEQUENCE: 158

```
tggctaagga ggtcgctgaa gtggccgcca aacgcttgaa                              40
```

<210> SEQ ID NO 159
<211> LENGTH: 40
<212> TYPE: DNA
<213> ORGANISM: Artificial Sequence
<220> FEATURE:
<223> OTHER INFORMATION: An oligonucleotide

<400> SEQUENCE: 159

```
tcttccaggg attcgttgtg gcttcggcct caccgaatct                              40
```

<210> SEQ ID NO 160
<211> LENGTH: 40
<212> TYPE: DNA
<213> ORGANISM: Artificial Sequence
<220> FEATURE:
<223> OTHER INFORMATION: An oligonucleotide

<400> SEQUENCE: 160

```
accagcgcta ttattcagtc tctccgcgat gagtttaaga                              40
```

<210> SEQ ID NO 161
<211> LENGTH: 40
<212> TYPE: DNA
<213> ORGANISM: Artificial Sequence
<220> FEATURE:
<223> OTHER INFORMATION: An oligonucleotide

<400> SEQUENCE: 161

```
gcggctcttt gggccgtgtc actccactca tggctgctaa                              40
```

<210> SEQ ID NO 162
<211> LENGTH: 40
<212> TYPE: DNA
<213> ORGANISM: Artificial Sequence
<220> FEATURE:
<223> OTHER INFORMATION: An oligonucleotide

<400> SEQUENCE: 162

```
gatcgctgat cgcgaaactg gtaaggcttt gggccctaac                              40
```

<210> SEQ ID NO 163
<211> LENGTH: 40
<212> TYPE: DNA
<213> ORGANISM: Artificial Sequence
<220> FEATURE:

```
<223> OTHER INFORMATION: An oligonucleotide

<400> SEQUENCE: 163
caagtgggcg agctgtgtat caaaggccct atggtgagca                              40

<210> SEQ ID NO 164
<211> LENGTH: 40
<212> TYPE: DNA
<213> ORGANISM: Artificial Sequence
<220> FEATURE:
<223> OTHER INFORMATION: An oligonucleotide

<400> SEQUENCE: 164
agggttatgt caataacgtc gaagctacca aggaggccat                              40

<210> SEQ ID NO 165
<211> LENGTH: 40
<212> TYPE: DNA
<213> ORGANISM: Artificial Sequence
<220> FEATURE:
<223> OTHER INFORMATION: An oligonucleotide

<400> SEQUENCE: 165
cgacgacgac ggctggttgc attctggtga ttttggatat                              40

<210> SEQ ID NO 166
<211> LENGTH: 40
<212> TYPE: DNA
<213> ORGANISM: Artificial Sequence
<220> FEATURE:
<223> OTHER INFORMATION: An oligonucleotide

<400> SEQUENCE: 166
tacgacgaag atgagcattt ttacgtcgtg gatcgttaca                              40

<210> SEQ ID NO 167
<211> LENGTH: 40
<212> TYPE: DNA
<213> ORGANISM: Artificial Sequence
<220> FEATURE:
<223> OTHER INFORMATION: An oligonucleotide

<400> SEQUENCE: 167
aggagctgat caaatacaag ggtagccagg ttgctccagc                              40

<210> SEQ ID NO 168
<211> LENGTH: 40
<212> TYPE: DNA
<213> ORGANISM: Artificial Sequence
<220> FEATURE:
<223> OTHER INFORMATION: An oligonucleotide

<400> SEQUENCE: 168
tgagttggag gagattctgt tgaaaaatcc atgcattcgc                              40

<210> SEQ ID NO 169
<211> LENGTH: 40
<212> TYPE: DNA
<213> ORGANISM: Artificial Sequence
<220> FEATURE:
<223> OTHER INFORMATION: An oligonucleotide

<400> SEQUENCE: 169
gatgtcgctg tggtcggcat tcctgatctg gaggccggcg                              40

<210> SEQ ID NO 170
```

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 170
aactgccttc tgctttcgtt gtcaagcagc ctggtaaaga        40

<210> SEQ ID NO 171
<211> LENGTH: 40
<212> TYPE: DNA
<213> ORGANISM: Artificial Sequence
<220> FEATURE:
<223> OTHER INFORMATION: An oligonucleotide

<400> SEQUENCE: 171
aattaccgcc aaagaagtgt atgattacct ggctgaacgt        40

<210> SEQ ID NO 172
<211> LENGTH: 40
<212> TYPE: DNA
<213> ORGANISM: Artificial Sequence
<220> FEATURE:
<223> OTHER INFORMATION: An oligonucleotide

<400> SEQUENCE: 172
gtgagccata ctaagtactt gcgtggcggc gtgcgttttg        40

<210> SEQ ID NO 173
<211> LENGTH: 40
<212> TYPE: DNA
<213> ORGANISM: Artificial Sequence
<220> FEATURE:
<223> OTHER INFORMATION: An oligonucleotide

<400> SEQUENCE: 173
ttgactccat ccctcgtaac gtaacaggca aaattacccg        40

<210> SEQ ID NO 174
<211> LENGTH: 40
<212> TYPE: DNA
<213> ORGANISM: Artificial Sequence
<220> FEATURE:
<223> OTHER INFORMATION: An oligonucleotide

<400> SEQUENCE: 174
caaggagctg ttgaaacaat tgttggagaa ggccggcggt        40

<210> SEQ ID NO 175
<211> LENGTH: 40
<212> TYPE: DNA
<213> ORGANISM: Artificial Sequence
<220> FEATURE:
<223> OTHER INFORMATION: An oligonucleotide

<400> SEQUENCE: 175
tagtaaagtc ttcatgatta tatagaaaaa aaagctagtg        40

<210> SEQ ID NO 176
<211> LENGTH: 40
<212> TYPE: DNA
<213> ORGANISM: Artificial Sequence
<220> FEATURE:
<223> OTHER INFORMATION: An oligonucleotide

<400> SEQUENCE: 176
```

```
taatcatgaa gactttacta accgccggcc ttctccaaca                    40

<210> SEQ ID NO 177
<211> LENGTH: 40
<212> TYPE: DNA
<213> ORGANISM: Artificial Sequence
<220> FEATURE:
<223> OTHER INFORMATION: An oligonucleotide

<400> SEQUENCE: 177
attgtttcaa cagctccttg cgggtaattt tgcctgttac                    40

<210> SEQ ID NO 178
<211> LENGTH: 40
<212> TYPE: DNA
<213> ORGANISM: Artificial Sequence
<220> FEATURE:
<223> OTHER INFORMATION: An oligonucleotide

<400> SEQUENCE: 178
gttacgaggg atggagtcaa caaaacgcac gccgccacgc                    40

<210> SEQ ID NO 179
<211> LENGTH: 40
<212> TYPE: DNA
<213> ORGANISM: Artificial Sequence
<220> FEATURE:
<223> OTHER INFORMATION: An oligonucleotide

<400> SEQUENCE: 179
aagtacttag tatggctcac acgttcagcc aggtaatcat                    40

<210> SEQ ID NO 180
<211> LENGTH: 40
<212> TYPE: DNA
<213> ORGANISM: Artificial Sequence
<220> FEATURE:
<223> OTHER INFORMATION: An oligonucleotide

<400> SEQUENCE: 180
acacttcttt ggcggtaatt tctttaccag gctgcttgac                    40

<210> SEQ ID NO 181
<211> LENGTH: 40
<212> TYPE: DNA
<213> ORGANISM: Artificial Sequence
<220> FEATURE:
<223> OTHER INFORMATION: An oligonucleotide

<400> SEQUENCE: 181
aacgaaagca gaaggcagtt cgccggcctc cagatcagga                    40

<210> SEQ ID NO 182
<211> LENGTH: 40
<212> TYPE: DNA
<213> ORGANISM: Artificial Sequence
<220> FEATURE:
<223> OTHER INFORMATION: An oligonucleotide

<400> SEQUENCE: 182
atgccgacca cagcgacatc gcgaatgcat ggattttcca                    40

<210> SEQ ID NO 183
<211> LENGTH: 40
<212> TYPE: DNA
<213> ORGANISM: Artificial Sequence
<220> FEATURE:
```

<223> OTHER INFORMATION: An oligonucleotide

<400> SEQUENCE: 183
acagaatctc ctccaactca gctggagcaa cctggctacc    40

<210> SEQ ID NO 184
<211> LENGTH: 40
<212> TYPE: DNA
<213> ORGANISM: Artificial Sequence
<220> FEATURE:
<223> OTHER INFORMATION: An oligonucleotide

<400> SEQUENCE: 184
cttgtatttg atcagctcct tgtaacgatc cacgacgtaa    40

<210> SEQ ID NO 185
<211> LENGTH: 40
<212> TYPE: DNA
<213> ORGANISM: Artificial Sequence
<220> FEATURE:
<223> OTHER INFORMATION: An oligonucleotide

<400> SEQUENCE: 185
aaatgctcat cttcgtcgta atatccaaaa tcaccagaat    40

<210> SEQ ID NO 186
<211> LENGTH: 40
<212> TYPE: DNA
<213> ORGANISM: Artificial Sequence
<220> FEATURE:
<223> OTHER INFORMATION: An oligonucleotide

<400> SEQUENCE: 186
gcaaccagcc gtcgtcgtcg atggcctcct tggtagcttc    40

<210> SEQ ID NO 187
<211> LENGTH: 40
<212> TYPE: DNA
<213> ORGANISM: Artificial Sequence
<220> FEATURE:
<223> OTHER INFORMATION: An oligonucleotide

<400> SEQUENCE: 187
gacgttattg acataaccct tgctcaccat agggcctttg    40

<210> SEQ ID NO 188
<211> LENGTH: 40
<212> TYPE: DNA
<213> ORGANISM: Artificial Sequence
<220> FEATURE:
<223> OTHER INFORMATION: An oligonucleotide

<400> SEQUENCE: 188
atacacagct cgcccacttg gttagggccc aaagccttac    40

<210> SEQ ID NO 189
<211> LENGTH: 40
<212> TYPE: DNA
<213> ORGANISM: Artificial Sequence
<220> FEATURE:
<223> OTHER INFORMATION: An oligonucleotide

<400> SEQUENCE: 189
cagtttcgcg atcagcgatc ttagcagcca tgagtggagt    40

<210> SEQ ID NO 190

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 190
gacacggccc aaagagccgc tcttaaactc atcgcggaga                              40

<210> SEQ ID NO 191
<211> LENGTH: 37
<212> TYPE: DNA
<213> ORGANISM: Artificial Sequence
<220> FEATURE:
<223> OTHER INFORMATION: An oligonucleotide

<400> SEQUENCE: 191
gactgaataa tagcgctggt agattcggtg aggccga                                 37

<210> SEQ ID NO 192
<211> LENGTH: 43
<212> TYPE: DNA
<213> ORGANISM: Artificial Sequence
<220> FEATURE:
<223> OTHER INFORMATION: An oligonucleotide

<400> SEQUENCE: 192
agccacaacg aatccctgga agattcaagc gtttggcggc cac                          43

<210> SEQ ID NO 193
<211> LENGTH: 40
<212> TYPE: DNA
<213> ORGANISM: Artificial Sequence
<220> FEATURE:
<223> OTHER INFORMATION: An oligonucleotide

<400> SEQUENCE: 193
ttcagcgacc tccttagcca gtggagcggc accgcaacac                              40

<210> SEQ ID NO 194
<211> LENGTH: 40
<212> TYPE: DNA
<213> ORGANISM: Artificial Sequence
<220> FEATURE:
<223> OTHER INFORMATION: An oligonucleotide

<400> SEQUENCE: 194
aattcacgca gtgaagacaa gtcgtacttg tccacgagtg                              40

<210> SEQ ID NO 195
<211> LENGTH: 40
<212> TYPE: DNA
<213> ORGANISM: Artificial Sequence
<220> FEATURE:
<223> OTHER INFORMATION: An oligonucleotide

<400> SEQUENCE: 195
ggctcttaga caaaaacagg atcacgctag gcacgttgat                              40

<210> SEQ ID NO 196
<211> LENGTH: 40
<212> TYPE: DNA
<213> ORGANISM: Artificial Sequence
<220> FEATURE:
<223> OTHER INFORMATION: An oligonucleotide

<400> SEQUENCE: 196
```

| | -continued | |
|---|---|---|
| gacactgcgg acttcataat cttggatggc tttcaagaaa | | 40 |

<210> SEQ ID NO 197
<211> LENGTH: 40
<212> TYPE: DNA
<213> ORGANISM: Artificial Sequence
<220> FEATURE:
<223> OTHER INFORMATION: An oligonucleotide

<400> SEQUENCE: 197
gcctcctgat caaaacggcg aacataatc acgcggagac        40

<210> SEQ ID NO 198
<211> LENGTH: 40
<212> TYPE: DNA
<213> ORGANISM: Artificial Sequence
<220> FEATURE:
<223> OTHER INFORMATION: An oligonucleotide

<400> SEQUENCE: 198
cgaccataaa gtaacccaaa gtaatatgaa agccgaaagc        40

<210> SEQ ID NO 199
<211> LENGTH: 40
<212> TYPE: DNA
<213> ORGANISM: Artificial Sequence
<220> FEATURE:
<223> OTHER INFORMATION: An oligonucleotide

<400> SEQUENCE: 199
atggaagaaa ggcaagtaga ccaagacggt gacaccagga        40

<210> SEQ ID NO 200
<211> LENGTH: 40
<212> TYPE: DNA
<213> ORGANISM: Artificial Sequence
<220> FEATURE:
<223> OTHER INFORMATION: An oligonucleotide

<400> SEQUENCE: 200
atcagctgag tgccgtagcg tggatcgaga gcatggatca        40

<210> SEQ ID NO 201
<211> LENGTH: 40
<212> TYPE: DNA
<213> ORGANISM: Artificial Sequence
<220> FEATURE:
<223> OTHER INFORMATION: An oligonucleotide

<400> SEQUENCE: 201
gacgcacgca aatgttttga tgggtctgca tgactccctt        40

<210> SEQ ID NO 202
<211> LENGTH: 40
<212> TYPE: DNA
<213> ORGANISM: Artificial Sequence
<220> FEATURE:
<223> OTHER INFORMATION: An oligonucleotide

<400> SEQUENCE: 202
tgggagtcca gtagtaccgc tgctacacag aatggctgca        40

<210> SEQ ID NO 203
<211> LENGTH: 40
<212> TYPE: DNA
<213> ORGANISM: Artificial Sequence
<220> FEATURE:

<223> OTHER INFORMATION: An oligonucleotide

<400> SEQUENCE: 203
acttgttcca cagggtcgaa gtggagtggt ttaaagtttg         40

<210> SEQ ID NO 204
<211> LENGTH: 40
<212> TYPE: DNA
<213> ORGANISM: Artificial Sequence
<220> FEATURE:
<223> OTHER INFORMATION: An oligonucleotide

<400> SEQUENCE: 204
cgatgttgcc gtctgaatag cgagagatga aattaggcaa         40

<210> SEQ ID NO 205
<211> LENGTH: 40
<212> TYPE: DNA
<213> ORGANISM: Artificial Sequence
<220> FEATURE:
<223> OTHER INFORMATION: An oligonucleotide

<400> SEQUENCE: 205
agattcgcaa ccgtgaatat tctccacagt gtccaagatg         40

<210> SEQ ID NO 206
<211> LENGTH: 40
<212> TYPE: DNA
<213> ORGANISM: Artificial Sequence
<220> FEATURE:
<223> OTHER INFORMATION: An oligonucleotide

<400> SEQUENCE: 206
atgatacgct taataaagtt ggtgcggctt tggacttcca         40

<210> SEQ ID NO 207
<211> LENGTH: 40
<212> TYPE: DNA
<213> ORGANISM: Artificial Sequence
<220> FEATURE:
<223> OTHER INFORMATION: An oligonucleotide

<400> SEQUENCE: 207
ggactttgtt cagaatattc ttagtggtga agacaatctg         40

<210> SEQ ID NO 208
<211> LENGTH: 40
<212> TYPE: DNA
<213> ORGANISM: Artificial Sequence
<220> FEATURE:
<223> OTHER INFORMATION: An oligonucleotide

<400> SEQUENCE: 208
tggcttagag atacccatga ctttacacag ttcgtcggga         40

<210> SEQ ID NO 209
<211> LENGTH: 40
<212> TYPE: DNA
<213> ORGANISM: Artificial Sequence
<220> FEATURE:
<223> OTHER INFORMATION: An oligonucleotide

<400> SEQUENCE: 209
atgtagctct cgttgactgg agccacgatc ataccgatat         40

<210> SEQ ID NO 210

```
<211> LENGTH: 40
<212> TYPE: DNA
<213> ORGANISM: Artificial Sequence
<220> FEATURE:
<223> OTHER INFORMATION: An oligonucleotide

<400> SEQUENCE: 210
accatgcggc gatgactgga atgaagaaac gggtattgtt                           40

<210> SEQ ID NO 211
<211> LENGTH: 40
<212> TYPE: DNA
<213> ORGANISM: Artificial Sequence
<220> FEATURE:
<223> OTHER INFORMATION: An oligonucleotide

<400> SEQUENCE: 211
ttcagcacag atactaacga cgtcgttcat cttgtagcca                           40

<210> SEQ ID NO 212
<211> LENGTH: 40
<212> TYPE: DNA
<213> ORGANISM: Artificial Sequence
<220> FEATURE:
<223> OTHER INFORMATION: An oligonucleotide

<400> SEQUENCE: 212
caattgtgga gggactgagc cagcaagacg gttgcctcaa                           40

<210> SEQ ID NO 213
<211> LENGTH: 40
<212> TYPE: DNA
<213> ORGANISM: Artificial Sequence
<220> FEATURE:
<223> OTHER INFORMATION: An oligonucleotide

<400> SEQUENCE: 213
aaaactcctt gtagctcaaa gattcatcgc cgaccacatc                           40

<210> SEQ ID NO 214
<211> LENGTH: 40
<212> TYPE: DNA
<213> ORGANISM: Artificial Sequence
<220> FEATURE:
<223> OTHER INFORMATION: An oligonucleotide

<400> SEQUENCE: 214
gaccaaggct tgaggcaaat gagagtgctt gcggagagca                           40

<210> SEQ ID NO 215
<211> LENGTH: 40
<212> TYPE: DNA
<213> ORGANISM: Artificial Sequence
<220> FEATURE:
<223> OTHER INFORMATION: An oligonucleotide

<400> SEQUENCE: 215
cgaaacagca tttcgccggc agtcaaatcc tccaaaggat                           40

<210> SEQ ID NO 216
<211> LENGTH: 40
<212> TYPE: DNA
<213> ORGANISM: Artificial Sequence
<220> FEATURE:
<223> OTHER INFORMATION: An oligonucleotide

<400> SEQUENCE: 216
```

-continued ggagaggctc agggccatag atgacatttt tctcacgctt    40

<210> SEQ ID NO 217
<211> LENGTH: 40
<212> TYPE: DNA
<213> ORGANISM: Artificial Sequence
<220> FEATURE:
<223> OTHER INFORMATION: An oligonucleotide

<400> SEQUENCE: 217
catcatggga tcctgtttcc tgtgtgaaat tgttatccgc    40

<210> SEQ ID NO 218
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 218

Met Met Lys Arg Glu Lys Asn Val Ile Tyr Gly Pro Glu Pro Leu His
 1               5                  10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

```
Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
            325                 330                 335

Phe Gly Leu Thr Glu Ser Thr Ser Ala Ile Ile Gln Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540

<210> SEQ ID NO 219
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 219

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125
```

-continued

```
Lys Asn Ile Leu Asn Lys Val Leu Glu Val Gln Ser Arg Thr Asn Phe
            130                 135                 140

Ile Lys Arg Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
            195                 200                 205

His Gln Asn Ile Cys Val Arg Leu Ile His Ala Leu Asp Pro Arg Tyr
210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
            275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Ser Leu Arg Asp
            340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp His Phe Tyr Val Val
            420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
            515                 520                 525

Arg Lys Glu Leu Leu Lys Gln Leu Leu Glu Lys Ala Gly Gly
530                 535                 540
```

<210> SEQ ID NO 220

```
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 220
```

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser Tyr Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
            405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
            485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
            515                 520                 525

Arg Lys Glu Leu Leu Lys Gln Leu Leu Glu Lys Ala Gly Gly
530                 535                 540

<210> SEQ ID NO 221
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 221

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr

```
               210                 215                 220
Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
            275                 280                 285

Ile Leu Phe Leu Ser Lys Ser Pro Leu Val Asp Lys Tyr Asp Leu Ser
        290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Ser Leu Arg Asp
                340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
        370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540

<210> SEQ ID NO 222
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 222

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45
```

```
Ser Leu Ser Tyr Lys Glu Phe Phe Glu Ala Thr Val Leu Leu Ala Gln
     50                  55                  60

Ser Leu His Asn Cys Gly Tyr Lys Met Asn Asp Val Val Ser Ile Cys
 65                  70                  75                  80

Ala Glu Asn Asn Thr Arg Phe Phe Ile Pro Val Ile Ala Ala Trp Tyr
                 85                  90                  95

Ile Gly Met Ile Val Ala Pro Val Asn Glu Ser Tyr Ile Pro Asp Glu
                100                 105                 110

Leu Cys Lys Val Met Gly Ile Ser Lys Pro Gln Ile Val Phe Thr Thr
                115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
                180                 185                 190

Leu Cys Ser Ser Gly Thr Thr Gly Leu Pro Lys Gly Val Met Gln Thr
                195                 200                 205

His Gln Asn Ile Cys Val Arg Leu Ile His Ala Leu Asp Pro Arg Tyr
210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
                275                 280                 285

Ile Leu Phe Leu Ser Lys Ser Pro Leu Val Asp Lys Tyr Asp Leu Ser
                290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Ser Leu Gly Asp
                340                 345                 350

Glu Phe Lys Ser Gly Ser Leu Gly Arg Val Thr Pro Leu Met Ala Ala
                355                 360                 365

Lys Ile Ala Asp Arg Glu Thr Gly Lys Ala Leu Gly Pro Asn Gln Val
                370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
                435                 440                 445

Ala Glu Leu Glu Glu Ile Leu Leu Lys Asn Pro Cys Ile Arg Asp Val
                450                 455                 460

Ala Val Val Gly Ile Pro Asp Leu Glu Ala Gly Glu Leu Pro Ser Ala
```

```
                    465                 470                 475                 480
Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540

<210> SEQ ID NO 223
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 223

Met Ile Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300
```

```
Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
            325                 330                 335

Phe Gly Leu Thr Glu Ser Thr Ser Ala Ile Ile Gln Thr Leu Gly Asp
        340                 345                 350

Glu Phe Lys Ser Gly Ser Leu Gly Arg Val Thr Pro Leu Met Ala Ala
    355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
            405                 410                 415

Ser Gly Asp Phe Gly Tyr Tyr Asp Glu Asp Glu His Phe Tyr Val Val
        420                 425                 430

Asp Arg Tyr Lys Glu Leu Ile Lys Tyr Lys Gly Ser Gln Val Ala Pro
    435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
            485                 490                 495

Asp Tyr Leu Ala Glu Arg Val Ser His Thr Lys Tyr Leu Arg Gly Gly
        500                 505                 510

Val Arg Phe Val Asp Ser Ile Pro Arg Asn Val Thr Gly Lys Ile Thr
    515                 520                 525

Arg Lys Glu Leu Leu Lys Gln Leu Leu Val Lys Ala Gly Gly
530                 535                 540

<210> SEQ ID NO 224
<211> LENGTH: 311
<212> TYPE: PRT
<213> ORGANISM: Renilla reniformis

<400> SEQUENCE: 224

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
            85                  90                  95

His Tyr Lys Tyr Leu Thr Ala Trp Phe Glu Leu Leu Asn Leu Pro Lys
        100                 105                 110

Lys Ile Ile Phe Val Gly His Asp Trp Gly Ala Cys Leu Ala Phe His
    115                 120                 125

Tyr Ser Tyr Glu His Gln Asp Lys Ile Lys Ala Ile Val His Ala Glu
130                 135                 140
```

```
Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Lys Met Val Leu
            165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
            210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
            245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
            275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 225
<211> LENGTH: 311
<212> TYPE: PRT
<213> ORGANISM: Artificial Sequence
<220> FEATURE:
<223> OTHER INFORMATION: Sequence of a synthetic luciferase

<400> SEQUENCE: 225

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65              70                  75                  80

Met Gly Lys Ser Gly Lys Ser Gly Asn Gly Ser Tyr Arg Leu Leu Asp
            85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Lys Met Val Leu
            165                 170                 175

Glu Asn Asn Phe Phe Val Glu Thr Met Leu Pro Ser Lys Ile Met Arg
            180                 185                 190
```

```
Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 226
<211> LENGTH: 311
<212> TYPE: PRT
<213> ORGANISM: Artificial Sequence
<220> FEATURE:
<223> OTHER INFORMATION: Sequence of a synthetic luciferase

<400> SEQUENCE: 226

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
```

```
                    245                 250                 255
Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 227
<211> LENGTH: 311
<212> TYPE: PRT
<213> ORGANISM: Artificial Sequence
<220> FEATURE:
<223> OTHER INFORMATION: Sequence of a synthetic luciferase

<400> SEQUENCE: 227

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
            85                  90                  95

His Tyr Lys Tyr Leu Thr Ala Trp Phe Glu Leu Leu Asn Leu Pro Lys
        100                 105                 110

Lys Ile Ile Phe Val Gly His Asp Trp Gly Ala Cys Leu Ala Phe His
    115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
            165                 170                 175

Glu Asn Asn Phe Phe Val Glu Thr Met Leu Pro Ser Lys Ile Met Arg
        180                 185                 190

Lys Leu Glu Pro Glu Glu Phe Ala Ala Tyr Leu Glu Pro Phe Lys Glu
    195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Ser Gln
    275                 280                 285

Glu Asp Ala Pro Asp Glu Met Gly Lys Tyr Ile Lys Ser Phe Val Glu
    290                 295                 300
```

Arg Val Leu Lys Asn Glu Gln
305                 310

<210> SEQ ID NO 228
<211> LENGTH: 14
<212> TYPE: DNA
<213> ORGANISM: Artificial Sequence
<220> FEATURE:
<223> OTHER INFORMATION: A consensus sequence
<220> FEATURE:
<221> NAME/KEY: misc_feature
<222> LOCATION: (1)...(14)
<223> OTHER INFORMATION: n = A,T,C or G

<400> SEQUENCE: 228
yggmnnnnng ccaa                                                         14

<210> SEQ ID NO 229
<211> LENGTH: 38
<212> TYPE: DNA
<213> ORGANISM: Artificial Sequence
<220> FEATURE:
<223> OTHER INFORMATION: A primer

<400> SEQUENCE: 229
gtactgagac gacgccagcc caagcttagg cctgagtg                               38

<210> SEQ ID NO 230
<211> LENGTH: 38
<212> TYPE: DNA
<213> ORGANISM: Artificial Sequence
<220> FEATURE:
<223> OTHER INFORMATION: A primer

<400> SEQUENCE: 230
ggcatgagcg tgaactgact gaactagcgg ccgccgag                               38

<210> SEQ ID NO 231
<211> LENGTH: 24
<212> TYPE: DNA
<213> ORGANISM: Artificial Sequence
<220> FEATURE:
<223> OTHER INFORMATION: A primer

<400> SEQUENCE: 231
ggatcccatg gtgaagcgtg agaa                                              24

<210> SEQ ID NO 232
<211> LENGTH: 21
<212> TYPE: DNA
<213> ORGANISM: Artificial Sequence
<220> FEATURE:
<223> OTHER INFORMATION: A primer

<400> SEQUENCE: 232
ggatcccatg gtgaaacgcg a                                                 21

<210> SEQ ID NO 233
<211> LENGTH: 31
<212> TYPE: DNA
<213> ORGANISM: Artificial Sequence
<220> FEATURE:
<223> OTHER INFORMATION: A primer

<400> SEQUENCE: 233
ctagcttttt tttctagata atcatgaaga c                                      31

```
<210> SEQ ID NO 234
<211> LENGTH: 54
<212> TYPE: DNA
<213> ORGANISM: Artificial Sequence
<220> FEATURE:
<223> OTHER INFORMATION: A primer

<400> SEQUENCE: 234
caaaaagctt ggcattccgg tactgttggt aaagccacca tggtgaagcg agag         54

<210> SEQ ID NO 235
<211> LENGTH: 26
<212> TYPE: DNA
<213> ORGANISM: Artificial Sequence
<220> FEATURE:
<223> OTHER INFORMATION: A primer

<400> SEQUENCE: 235
caattgttgt tgttaacttg tttatt                                        26

<210> SEQ ID NO 236
<211> LENGTH: 40
<212> TYPE: DNA
<213> ORGANISM: Artificial Sequence
<220> FEATURE:
<223> OTHER INFORMATION: A primer

<400> SEQUENCE: 236
aaccatggct tccaaggtgt acgaccccga gcaacgcaaa                         40

<210> SEQ ID NO 237
<211> LENGTH: 40
<212> TYPE: DNA
<213> ORGANISM: Artificial Sequence
<220> FEATURE:
<223> OTHER INFORMATION: A primer

<400> SEQUENCE: 237
gctctagaat tactgctcgt tcttcagcac gcgctccacg                         40

<210> SEQ ID NO 238
<211> LENGTH: 31
<212> TYPE: DNA
<213> ORGANISM: Artificial Sequence
<220> FEATURE:
<223> OTHER INFORMATION: A primer

<400> SEQUENCE: 238
cgctagccat ggcttcgaaa gtttatgatc c                                  31

<210> SEQ ID NO 239
<211> LENGTH: 25
<212> TYPE: DNA
<213> ORGANISM: Artificial Sequence
<220> FEATURE:
<223> OTHER INFORMATION: A primer

<400> SEQUENCE: 239
ggccagtaac tctagaatta ttgtt                                         25

<210> SEQ ID NO 240
<211> LENGTH: 5
<212> TYPE: DNA
<213> ORGANISM: Artificial Sequence
<220> FEATURE:
<223> OTHER INFORMATION: An oligonucleotide
```

```
-continued

<400> SEQUENCE: 240 tataa                                                              5

<210> SEQ ID NO 241
<211> LENGTH: 6
<212> TYPE: DNA
<213> ORGANISM: Artificial Sequence
<220> FEATURE:
<223> OTHER INFORMATION: An oligonucleotide

<400> SEQUENCE: 241 stratg                                                             6

<210> SEQ ID NO 242
<211> LENGTH: 9
<212> TYPE: DNA
<213> ORGANISM: Artificial Sequence
<220> FEATURE:
<223> OTHER INFORMATION: An oligonucleotide
<220> FEATURE:
<221> NAME/KEY: misc_feature
<222> LOCATION: (1)...(9)
<223> OTHER INFORMATION: n = A,T,C or G

<400> SEQUENCE: 242 mttncnnma                                                          9

<210> SEQ ID NO 243
<211> LENGTH: 5
<212> TYPE: DNA
<213> ORGANISM: Artificial Sequence
<220> FEATURE:
<223> OTHER INFORMATION: An oligonucleotide

<400> SEQUENCE: 243 tratg                                                              5

<210> SEQ ID NO 244
<211> LENGTH: 7
<212> TYPE: DNA
<213> ORGANISM: Artificial Sequence
<220> FEATURE:
<223> OTHER INFORMATION: A consensus sequence

<400> SEQUENCE: 244 tgastma                                                            7

<210> SEQ ID NO 245
<211> LENGTH: 14
<212> TYPE: DNA
<213> ORGANISM: Artificial Sequence
<220> FEATURE:
<223> OTHER INFORMATION: A consensus sequence
<220> FEATURE:
<221> NAME/KEY: misc_feature
<222> LOCATION: (1)...(14)
<223> OTHER INFORMATION: n = A,T,C or G

<400> SEQUENCE: 245
yggmnnnnng ccaa                                                   14

<210> SEQ ID NO 246
<211> LENGTH: 40
<212> TYPE: DNA
<213> ORGANISM: Artificial Sequence
<220> FEATURE:
<223> OTHER INFORMATION: An oligonucleotide
```

<400> SEQUENCE: 246
aaccatggct tccaaggtgt acgaccccga gcaacgcaaa    40

<210> SEQ ID NO 247
<211> LENGTH: 40
<212> TYPE: DNA
<213> ORGANISM: Artificial Sequence
<220> FEATURE:
<223> OTHER INFORMATION: An oligonucleotide

<400> SEQUENCE: 247
cgcatgatca ctgggcctca gtggtgggct cgctgcaagc    40

<210> SEQ ID NO 248
<211> LENGTH: 40
<212> TYPE: DNA
<213> ORGANISM: Artificial Sequence
<220> FEATURE:
<223> OTHER INFORMATION: An oligonucleotide

<400> SEQUENCE: 248
aaatgaacgt gctggactcc ttcatcaact actatgattc    40

<210> SEQ ID NO 249
<211> LENGTH: 50
<212> TYPE: DNA
<213> ORGANISM: Artificial Sequence
<220> FEATURE:
<223> OTHER INFORMATION: An oligonucleotide

<400> SEQUENCE: 249
cgagaagcac gccgagaacg ccgtgatttt tctgcatggt aacgctgcct    50

<210> SEQ ID NO 250
<211> LENGTH: 40
<212> TYPE: DNA
<213> ORGANISM: Artificial Sequence
<220> FEATURE:
<223> OTHER INFORMATION: An oligonucleotide

<400> SEQUENCE: 250
ccagctacct gtggaggcac gtcgtgcctc acatcgagcc    40

<210> SEQ ID NO 251
<211> LENGTH: 40
<212> TYPE: DNA
<213> ORGANISM: Artificial Sequence
<220> FEATURE:
<223> OTHER INFORMATION: An oligonucleotide

<400> SEQUENCE: 251
cgtggctaga tgcatcatcc ctgatctgat cggaatgggt    40

<210> SEQ ID NO 252
<211> LENGTH: 40
<212> TYPE: DNA
<213> ORGANISM: Artificial Sequence
<220> FEATURE:
<223> OTHER INFORMATION: An oligonucleotide

<400> SEQUENCE: 252
aagtccggca agagcgggaa tgctctcatat cgcctcctgg    40

<210> SEQ ID NO 253
<211> LENGTH: 40
<212> TYPE: DNA

```
<213> ORGANISM: Artificial Sequence
<220> FEATURE:
<223> OTHER INFORMATION: An oligonucleotide

<400> SEQUENCE: 253
atcactacaa gtacctcacc gcttggttcg agctgctgaa                               40

<210> SEQ ID NO 254
<211> LENGTH: 40
<212> TYPE: DNA
<213> ORGANISM: Artificial Sequence
<220> FEATURE:
<223> OTHER INFORMATION: An oligonucleotide

<400> SEQUENCE: 254
ccttccaaag aaaatcatct ttgtgggcca cgactggggg                               40

<210> SEQ ID NO 255
<211> LENGTH: 40
<212> TYPE: DNA
<213> ORGANISM: Artificial Sequence
<220> FEATURE:
<223> OTHER INFORMATION: An oligonucleotide

<400> SEQUENCE: 255
gcttgtctgg cctttcacta ctcctacgag caccaagaca                               40

<210> SEQ ID NO 256
<211> LENGTH: 40
<212> TYPE: DNA
<213> ORGANISM: Artificial Sequence
<220> FEATURE:
<223> OTHER INFORMATION: An oligonucleotide

<400> SEQUENCE: 256
agatcaaggc catcgtccat gctgagagtg tcgtggacgt                               40

<210> SEQ ID NO 257
<211> LENGTH: 45
<212> TYPE: DNA
<213> ORGANISM: Artificial Sequence
<220> FEATURE:
<223> OTHER INFORMATION: An oligonucleotide

<400> SEQUENCE: 257
gatcgagtcc tgggacgagt ggcctgacat cgaggaggat atcgc                         45

<210> SEQ ID NO 258
<211> LENGTH: 40
<212> TYPE: DNA
<213> ORGANISM: Artificial Sequence
<220> FEATURE:
<223> OTHER INFORMATION: An oligonucleotide

<400> SEQUENCE: 258
cctgatcaag agcgaagagg gcgagaaaat ggtgcttgag                               40

<210> SEQ ID NO 259
<211> LENGTH: 40
<212> TYPE: DNA
<213> ORGANISM: Artificial Sequence
<220> FEATURE:
<223> OTHER INFORMATION: An oligonucleotide

<400> SEQUENCE: 259
aataacttct tcgtcgagac catgctccca agcaagatca                               40
```

```
<210> SEQ ID NO 260
<211> LENGTH: 45
<212> TYPE: DNA
<213> ORGANISM: Artificial Sequence
<220> FEATURE:
<223> OTHER INFORMATION: An oligonucleotide

<400> SEQUENCE: 260
tgcggaaact ggagcctgag gagttcgctg cctacctgga gccat              45

<210> SEQ ID NO 261
<211> LENGTH: 40
<212> TYPE: DNA
<213> ORGANISM: Artificial Sequence
<220> FEATURE:
<223> OTHER INFORMATION: An oligonucleotide

<400> SEQUENCE: 261
tcaaggagaa gggcgaggtt agacggccta ccctctcctg                    40

<210> SEQ ID NO 262
<211> LENGTH: 40
<212> TYPE: DNA
<213> ORGANISM: Artificial Sequence
<220> FEATURE:
<223> OTHER INFORMATION: An oligonucleotide

<400> SEQUENCE: 262
gcctcgcgag atccctctcg ttagggagg caagcccgac                     40

<210> SEQ ID NO 263
<211> LENGTH: 40
<212> TYPE: DNA
<213> ORGANISM: Artificial Sequence
<220> FEATURE:
<223> OTHER INFORMATION: An oligonucleotide

<400> SEQUENCE: 263
gtcgtccaga ttgtccgcaa ctacaacgcc taccttcggg                    40

<210> SEQ ID NO 264
<211> LENGTH: 40
<212> TYPE: DNA
<213> ORGANISM: Artificial Sequence
<220> FEATURE:
<223> OTHER INFORMATION: An oligonucleotide

<400> SEQUENCE: 264
ccagcgacga tctgcctaag atgttcatcg agtccgaccc                    40

<210> SEQ ID NO 265
<211> LENGTH: 40
<212> TYPE: DNA
<213> ORGANISM: Artificial Sequence
<220> FEATURE:
<223> OTHER INFORMATION: An oligonucleotide

<400> SEQUENCE: 265
tgggttcttt tccaacgcta ttgtcgaggg agctaagaag                    40

<210> SEQ ID NO 266
<211> LENGTH: 40
<212> TYPE: DNA
<213> ORGANISM: Artificial Sequence
<220> FEATURE:
<223> OTHER INFORMATION: An oligonucleotide
```

-continued

<400> SEQUENCE: 266
ttccctaaca ccgagttcgt gaaggtgaag ggcctccact                              40

<210> SEQ ID NO 267
<211> LENGTH: 40
<212> TYPE: DNA
<213> ORGANISM: Artificial Sequence
<220> FEATURE:
<223> OTHER INFORMATION: An oligonucleotide

<400> SEQUENCE: 267
tcagccagga ggacgctcca gatgaaatgg gtaagtacat                              40

<210> SEQ ID NO 268
<211> LENGTH: 49
<212> TYPE: DNA
<213> ORGANISM: Artificial Sequence
<220> FEATURE:
<223> OTHER INFORMATION: An oligonucleotide

<400> SEQUENCE: 268
caagagcttc gtggagcgcg tgctgaagaa cgagcagtaa ttctagagc                    49

<210> SEQ ID NO 269
<211> LENGTH: 29
<212> TYPE: DNA
<213> ORGANISM: Artificial Sequence
<220> FEATURE:
<223> OTHER INFORMATION: An oligonucleotide

<400> SEQUENCE: 269
gctctagaat tactgctcgt tcttcagca                                          29

<210> SEQ ID NO 270
<211> LENGTH: 40
<212> TYPE: DNA
<213> ORGANISM: Artificial Sequence
<220> FEATURE:
<223> OTHER INFORMATION: An oligonucleotide

<400> SEQUENCE: 270
cgcgctccac gaagctcttg atgtacttac ccatttcatc                              40

<210> SEQ ID NO 271
<211> LENGTH: 40
<212> TYPE: DNA
<213> ORGANISM: Artificial Sequence
<220> FEATURE:
<223> OTHER INFORMATION: An oligonucleotide

<400> SEQUENCE: 271
tggagcgtcc tcctggctga agtggaggcc cttcaccttc                              40

<210> SEQ ID NO 272
<211> LENGTH: 40
<212> TYPE: DNA
<213> ORGANISM: Artificial Sequence
<220> FEATURE:
<223> OTHER INFORMATION: An oligonucleotide

<400> SEQUENCE: 272
acgaactcgg tgttagggaa cttcttagct ccctcgacaa                              40

<210> SEQ ID NO 273
<211> LENGTH: 40
<212> TYPE: DNA

```
<213> ORGANISM: Artificial Sequence
<220> FEATURE:
<223> OTHER INFORMATION: An oligonucleotide

<400> SEQUENCE: 273
tagcgttgga aaagaaccca gggtcggact cgatgaacat                              40

<210> SEQ ID NO 274
<211> LENGTH: 40
<212> TYPE: DNA
<213> ORGANISM: Artificial Sequence
<220> FEATURE:
<223> OTHER INFORMATION: An oligonucleotide

<400> SEQUENCE: 274
cttaggcaga tcgtcgctgg cccgaaggta ggcgttgtag                              40

<210> SEQ ID NO 275
<211> LENGTH: 40
<212> TYPE: DNA
<213> ORGANISM: Artificial Sequence
<220> FEATURE:
<223> OTHER INFORMATION: An oligonucleotide

<400> SEQUENCE: 275
ttgcggacaa tctggacgac gtcgggcttg cctcccttaa                              40

<210> SEQ ID NO 276
<211> LENGTH: 40
<212> TYPE: DNA
<213> ORGANISM: Artificial Sequence
<220> FEATURE:
<223> OTHER INFORMATION: An oligonucleotide

<400> SEQUENCE: 276
cgagagggat ctcgcgaggc caggagaggg taggccgtct                              40

<210> SEQ ID NO 277
<211> LENGTH: 40
<212> TYPE: DNA
<213> ORGANISM: Artificial Sequence
<220> FEATURE:
<223> OTHER INFORMATION: An oligonucleotide

<400> SEQUENCE: 277
aacctcgccc ttctccttga atggctccag gtaggcagcg                              40

<210> SEQ ID NO 278
<211> LENGTH: 45
<212> TYPE: DNA
<213> ORGANISM: Artificial Sequence
<220> FEATURE:
<223> OTHER INFORMATION: An oligonucleotide

<400> SEQUENCE: 278
aactcctcag gctccagttt ccgcatgatc ttgcttggga gcatg                        45

<210> SEQ ID NO 279
<211> LENGTH: 40
<212> TYPE: DNA
<213> ORGANISM: Artificial Sequence
<220> FEATURE:
<223> OTHER INFORMATION: An oligonucleotide

<400> SEQUENCE: 279
gtctcgacga agaagttatt ctcaagcacc attttctcgc                              40
```

```
<210> SEQ ID NO 280
<211> LENGTH: 40
<212> TYPE: DNA
<213> ORGANISM: Artificial Sequence
<220> FEATURE:
<223> OTHER INFORMATION: An oligonucleotide

<400> SEQUENCE: 280
cctcttcgct cttgatcagg gcgatatcct cctcgatgtc                              40

<210> SEQ ID NO 281
<211> LENGTH: 43
<212> TYPE: DNA
<213> ORGANISM: Artificial Sequence
<220> FEATURE:
<223> OTHER INFORMATION: An oligonucleotide

<400> SEQUENCE: 281
aggccactcg tcccaggact cgatcacgtc cacgacactc tca                         43

<210> SEQ ID NO 282
<211> LENGTH: 42
<212> TYPE: DNA
<213> ORGANISM: Artificial Sequence
<220> FEATURE:
<223> OTHER INFORMATION: An oligonucleotide

<400> SEQUENCE: 282
gcatggacga tggccttgat cttgtcttgg tgctcgtagg ag                          42

<210> SEQ ID NO 283
<211> LENGTH: 40
<212> TYPE: DNA
<213> ORGANISM: Artificial Sequence
<220> FEATURE:
<223> OTHER INFORMATION: An oligonucleotide

<400> SEQUENCE: 283
tagtgaaagg ccagacaagc cccccagtcg tggcccacaa                              40

<210> SEQ ID NO 284
<211> LENGTH: 40
<212> TYPE: DNA
<213> ORGANISM: Artificial Sequence
<220> FEATURE:
<223> OTHER INFORMATION: An oligonucleotide

<400> SEQUENCE: 284
agatgatttt ctttggaagg ttcagcagct cgaaccaagc                              40

<210> SEQ ID NO 285
<211> LENGTH: 40
<212> TYPE: DNA
<213> ORGANISM: Artificial Sequence
<220> FEATURE:
<223> OTHER INFORMATION: An oligonucleotide

<400> SEQUENCE: 285
ggtgaggtac ttgtagtgat ccaggaggcg atatgagcca                              40

<210> SEQ ID NO 286
<211> LENGTH: 40
<212> TYPE: DNA
<213> ORGANISM: Artificial Sequence
<220> FEATURE:
<223> OTHER INFORMATION: An oligonucleotide
```

<400> SEQUENCE: 286
ttcccgctct tgccggactt acccattccg atcagatcag                        40

<210> SEQ ID NO 287
<211> LENGTH: 45
<212> TYPE: DNA
<213> ORGANISM: Artificial Sequence
<220> FEATURE:
<223> OTHER INFORMATION: An oligonucleotide

<400> SEQUENCE: 287
ggatgatgca tctagccacg ggctcgatgt gaggcacgac gtgcc                  45

<210> SEQ ID NO 288
<211> LENGTH: 40
<212> TYPE: DNA
<213> ORGANISM: Artificial Sequence
<220> FEATURE:
<223> OTHER INFORMATION: An oligonucleotide

<400> SEQUENCE: 288
tccacaggta gctggaggca gcgttaccat gcagaaaaat                        40

<210> SEQ ID NO 289
<211> LENGTH: 45
<212> TYPE: DNA
<213> ORGANISM: Artificial Sequence
<220> FEATURE:
<223> OTHER INFORMATION: An oligonucleotide

<400> SEQUENCE: 289
cacggcgttc tcggcgtgct tctcggaatc atagtagttg atgaa                  45

<210> SEQ ID NO 290
<211> LENGTH: 40
<212> TYPE: DNA
<213> ORGANISM: Artificial Sequence
<220> FEATURE:
<223> OTHER INFORMATION: An oligonucleotide

<400> SEQUENCE: 290
ggagtccagc acgttcattt gcttgcagcg agcccaccac                        40

<210> SEQ ID NO 291
<211> LENGTH: 40
<212> TYPE: DNA
<213> ORGANISM: Artificial Sequence
<220> FEATURE:
<223> OTHER INFORMATION: An oligonucleotide

<400> SEQUENCE: 291
tgaggcccag tgatcatgcg tttgcgttgc tcggggtcgt                        40

<210> SEQ ID NO 292
<211> LENGTH: 20
<212> TYPE: DNA
<213> ORGANISM: Artificial Sequence
<220> FEATURE:
<223> OTHER INFORMATION: An oligonucleotide

<400> SEQUENCE: 292
acaccttgga agccatggtt                                              20

<210> SEQ ID NO 293
<211> LENGTH: 10
<212> TYPE: DNA

```
<213> ORGANISM: Artificial Sequence
<220> FEATURE:
<223> OTHER INFORMATION: A Kozak sequence

<400> SEQUENCE: 293
aaccatggct                                                           10

<210> SEQ ID NO 294
<211> LENGTH: 12
<212> TYPE: DNA
<213> ORGANISM: Artificial Sequence
<220> FEATURE:
<223> OTHER INFORMATION: An oligonucleotide

<400> SEQUENCE: 294
taattctaga gc                                                        12

<210> SEQ ID NO 295
<211> LENGTH: 32
<212> TYPE: DNA
<213> ORGANISM: Artificial Sequence
<220> FEATURE:
<223> OTHER INFORMATION: A primer

<400> SEQUENCE: 295
gcgtagccat ggtaaagcgt gagaaaaatg tc                                  32

<210> SEQ ID NO 296
<211> LENGTH: 33
<212> TYPE: DNA
<213> ORGANISM: Artificial Sequence
<220> FEATURE:
<223> OTHER INFORMATION: A primer

<400> SEQUENCE: 296
ccgactctag attactaacc gccggccttc acc                                 33

<210> SEQ ID NO 297
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 297
atggtgaaac gcgaaaagaa cgtgatctac ggcccagaac cactgcatcc actggaagac     60
ctcaccgctg gtgagatgct cttccgagca ctgcgtaaac atagtcacct ccctcaagca    120
ctcgtggacg tcgtgggaga cgagagcctc tcctacaaag aattttttcga agctactgtg   180 ctgttggccc aaagcctcca taattgtggg tacaaaatga cgatgtggt gagcatttgt    240 gctgagaata cactcgctt ctttattcct gtaatcgctg cttggtacat cggcatgatt    300 gtcgccctg tgaatgaatc ttacatccca gatgagctgt gtaaggttat gggtattagc    360
aaacctcaaa tcgtctttac taccaaaaac atcttgaata aggtcttgga agtccagtct    420
cgtactaact tcatcaaacg catcattatt ctggataccg tcgaaaacat ccacggctgt    480
gagagcctcc ctaacttcat ctctcgttac agcgatggta atatcgctaa tttcaagccc    540
ttgcattttg atccagtcga gcaagtggcc gctattttgt gctcctccgg caccactggt    600
ttgcctaaag gtgtcatgca gactcaccag aatatctgtg tgcgtttgat ccacgctctc    660
gaccctcgtg tgggtactca attgatccct ggcgtgactg tgctggtgta tctgcctttc    720
tttcacgcct ttggtttctc tattaccctg ggctatttca tggtcggctt gcgtgtcatc    780
```

```
atgtttcgtc gcttcgacca agaagccttc ttgaaggcta ttcaagacta cgaggtgcgt    840
tccgtgatca acgtcccttc agtcattttg ttcctgagca aatctccttt ggttgacaag    900
tatgatctga gcagcttgcg tgagctgtgc tgtggcgctg ctcctttggc caagaagtg    960
gccgaggtcg ctgctaagcg tctgaacctc cctggtatcc gctgcggttt tggtttgact   1020
gagagcactt ctgctaacat ccatagcttg cgagacgagt ttaagtctgg tagcctgggt   1080
cgcgtgactc tcttatggc tgcaaagatc gccgaccgtg agaccggcaa agcactgggc    1140
ccaaatcaag tcggtgaatt gtgtattaag ggccctatgg tctctaaagg ctacgtgaac   1200
aatgtggagg ccactaaaga agccattgat gatgatggct ggctccatag cggcgacttc   1260
ggttactatg atgaggacga acacttctat gtggtcgatc gctacaaaga attgattaag   1320
tacaaaggct ctcaagtcgc accagccgaa ctggaagaaa ttttgctgaa gaacccttgt   1380
atccgcgacg tggccgtcgt gggtatccca gacttggaag ctggcgagtt gcctagcgcc   1440
tttgtggtga acaacccgg caaggagatc actgctaagg aggtctacga ctatttggcc    1500
gagcgcgtgt ctcacaccaa atatctgcgt ggcggcgtcc gcttcgtcga ttctattcca   1560
cgcaacgtta ccggtaagat cactcgtaaa gagttgctga agcaactcct cgaaaaagct   1620
ggcggc                                                              1626
```

<210> SEQ ID NO 298
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 298

```
Met Val Lys Arg Glu Lys Asn Val Ile Tyr Gly Pro Glu Pro Leu His
 1               5                  10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Val
```

```
            210                 215                 220
Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
            275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
                340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
            515                 520                 525

Arg Lys Glu Leu Leu Lys Gln Leu Leu Glu Lys Ala Gly Gly
530                 535                 540

<210> SEQ ID NO 299
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 299
atggtgaagc gtgagaaaaa tgtcatctat ggccctgagc ctctccatcc tttggaggat      60
ttgactgccg gcgaaatgct gtttcgtgct ctccgcaagc actctcattt gcctcaagcc     120
ttggtcgatg tggtcggcga tgaatctttg agctacaagg agttttttga ggcaaccgtc     180
ttgctggctc agtccctcca caattgtggc tacaagatga cgacgtcgt tagtatctgt     240
```

```
gctgaaaaca atacccgttt cttcattcca gtcatcgccg catggtatat cggtatgatc    300
gtggctccag tcaacgagag ctacattccc gacgaactgt gtaaagtcat gggtatctct    360
aagccacaga ttgtcttcac cactaagaat attctgaaca aagtcctgga agtccaaagc    420
cgcaccaact ttattaagcg tatcatcatc ttggacactg tggagaatat tcacggttgc    480
gaatctttgc ctaatttcat ctctcgctat tcagacggca acatcgcaaa ctttaaacca    540
ctccacttcg accctgtgga acaagttgca gccattctgt gtagcagcgg tactactgga    600
ctcccaaagg gagtcatgca gacccatcaa acatttgcg tgcgtctgat ccatgctctc     660
gatccacgct acggcactca gctgattcct ggtgtcaccg tcttggtcta cttgcctttc    720
ttccatgctt tcggctttca tattactttg ggttacttta tggtcggtct ccgcgtgatt    780
atgttccgcc gttttgatca ggaggctttc ttgaaagcca tccaagatta tgaagtccgc    840
agtgtcatca acgtgcctag cgtgatcctg tttttgtcta agagcccact cgtggacaag    900
tacgacttgt cttcactgcg tgaattgtgt tgcggtgccg ctccactggc taaggaggtc    960
gctgaagtgg ccgccaaacg cttgaatctt ccagggattc gttgtggctt cggcctcacc   1020
gaatctacca gcgctattat tcagtctctc cgcgatgagt ttaagagcgg ctctttgggc   1080
cgtgtcactc cactcatggc tgctaagatc gctgatcgcg aaactggtaa ggctttgggc   1140
ccgaaccaag tgggcgagct gtgtatcaaa ggccctatgg tgagcaaggg ttatgtcaat   1200
aacgttgaag ctaccaagga ggccatcgac gacgacggct ggttgcattc tggtgatttt   1260
ggatattacg acgaagatga gcattttttac gtcgtggatc gttacaagga gctgatcaaa   1320
tacaagggta gccaggttgc tccagctgag ttggaggaga ttctgttgaa aaatccatgc   1380
attcgcgatg tcgctgtggt cggcattcct gatctgaggg ccggcgaact gccttctgct   1440
ttcgttgtca agcagcctgg taaagaaatt accgccaaag aagtgtatga ttacctggct   1500
gaacgtgtga gccatactaa gtacttgcgt ggcggcgtgc gttttgttga ctccatccct   1560
cgtaacgtaa caggcaaaat tacccgcaag gagctgttga acaattgtt ggagaaggcc    1620 ggcggt                                                             1626
```

<210> SEQ ID NO 300
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 300

```
Met Val Lys Arg Glu Lys Asn Val Ile Tyr Gly Pro Glu Pro Leu His
  1               5                  10                  15

Pro Leu Glu Asp Leu Thr Ala Gly Glu Met Leu Phe Arg Ala Leu Arg
             20                  25                  30

Lys His Ser His Leu Pro Gln Ala Leu Val Asp Val Val Gly Asp Glu
         35                  40                  45

Ser Leu Ser Tyr Lys Glu Phe Phe Glu Ala Thr Val Leu Leu Ala Gln
     50                  55                  60

Ser Leu His Asn Cys Gly Tyr Lys Met Asn Asp Val Val Ser Ile Cys
 65                  70                  75                  80

Ala Glu Asn Asn Thr Arg Phe Phe Ile Pro Val Ile Ala Ala Trp Tyr
                 85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
```

```
            115                 120                 125
Lys Asn Ile Leu Asn Lys Val Leu Glu Val Gln Ser Arg Thr Asn Phe
    130                 135                 140
Ile Lys Arg Ile Ile Ile Leu Asp Thr Val Glu Asn Ile His Gly Cys
145                 150                 155                 160
Glu Ser Leu Pro Asn Phe Ile Ser Arg Tyr Ser Asp Gly Asn Ile Ala
                165                 170                 175
Asn Phe Lys Pro Leu His Phe Asp Pro Val Gln Val Ala Ala Ile
            180                 185                 190
Leu Cys Ser Ser Gly Thr Thr Gly Leu Pro Lys Gly Val Met Gln Thr
        195                 200                 205
His Gln Asn Ile Cys Val Arg Leu Ile His Ala Leu Asp Pro Arg Tyr
    210                 215                 220
Gly Thr Gln Leu Ile Pro Gly Val Thr Val Leu Val Tyr Leu Pro Phe
225                 230                 235                 240
Phe His Ala Phe Gly Phe His Ile Thr Leu Gly Tyr Phe Met Val Gly
                245                 250                 255
Leu Arg Val Ile Met Phe Arg Arg Phe Asp Gln Glu Ala Phe Leu Lys
            260                 265                 270
Ala Ile Gln Asp Tyr Glu Val Arg Ser Val Ile Asn Val Pro Ser Val
        275                 280                 285
Ile Leu Phe Leu Ser Lys Ser Pro Leu Val Asp Lys Tyr Asp Leu Ser
    290                 295                 300
Ser Leu Arg Glu Leu Cys Cys Gly Ala Ala Pro Leu Ala Lys Glu Val
305                 310                 315                 320
Ala Glu Val Ala Ala Lys Arg Leu Asn Leu Pro Gly Ile Arg Cys Gly
                325                 330                 335
Phe Gly Leu Thr Glu Ser Thr Ser Ala Ile Ile Gln Ser Leu Arg Asp
            340                 345                 350
Glu Phe Lys Ser Gly Ser Leu Gly Arg Val Thr Pro Leu Met Ala Ala
        355                 360                 365
Lys Ile Ala Asp Arg Glu Thr Gly Lys Ala Leu Gly Pro Asn Gln Val
    370                 375                 380
Gly Glu Leu Cys Ile Lys Gly Pro Met Val Ser Lys Gly Tyr Val Asn
385                 390                 395                 400
Asn Val Glu Ala Thr Lys Glu Ala Ile Asp Asp Gly Trp Leu His
                405                 410                 415
Ser Gly Asp Phe Gly Tyr Tyr Asp Glu Asp His Phe Tyr Val Val
                420                 425                 430
Asp Arg Tyr Lys Glu Leu Ile Lys Tyr Lys Gly Ser Gln Val Ala Pro
            435                 440                 445
Ala Glu Leu Glu Glu Ile Leu Leu Lys Asn Pro Cys Ile Arg Asp Val
        450                 455                 460
Ala Val Val Gly Ile Pro Asp Leu Glu Ala Gly Glu Leu Pro Ser Ala
465                 470                 475                 480
Phe Val Val Lys Gln Pro Gly Lys Glu Ile Thr Ala Lys Glu Val Tyr
                485                 490                 495
Asp Tyr Leu Ala Glu Arg Val Ser His Thr Lys Tyr Leu Arg Gly Gly
            500                 505                 510
Val Arg Phe Val Asp Ser Ile Pro Arg Asn Val Thr Gly Lys Ile Thr
        515                 520                 525
Arg Lys Glu Leu Leu Lys Gln Leu Leu Glu Lys Ala Gly Gly
    530                 535                 540
```

<210> SEQ ID NO 301
<211> LENGTH: 1626
<212> TYPE: DNA
<213> ORGANISM: Artificial Sequence
<220> FEATURE:
<223> OTHER INFORMATION: Sequence of a synthetic luciferase

<400> SEQUENCE: 301

```
atggtaaagc gtgagaaaaa tgtcatctat ggccctgagc ctctccatcc tttggaggat      60
ttgactgccg gcgaaatgct gtttcgtgct ctccgcaagc actctcattt gcctcaagcc     120
ttggtcgatg tggtcggcga tgaatctttg agctacaagg agttttttga ggcaaccgtc     180
ttgctggctc agtccctcca caattgtggc tacaagatga cgacgtcgt tagtatctgt      240
gctgaaaaca tacccgtttc ttcattcca gtcatcgccg catggtatat cggtatgatc     300
gtggctccag tcaacgagag ctacattccc gacgaactgt gtaaagtcat gggtatctct     360
aagccacaga ttgtcttcac cactaagaat attctgaaca agtcctgga agtccaaagc      420
cgcaccaact ttattaagcg tatcatcatc ttggacactg tggagaatat tcacggttgc     480
gaatctttgc ctaatttcat ctctcgctat tcagacggca acatcgcaaa ctttaaacca     540
ctccacttcg accctgtgga acaagttgca gccattctgt gtagcagcgg tactactgga     600
ctcccaaagg gagtcatgca gacccatcaa aacatttgcg tgcgtctgat ccatgctctc     660
gatccacgct acggcactca gctgattcct ggtgtcaccg tcttggtcta cttgcctttc     720
ttccatgctt tcggctttca tattactttg ggttacttta tggtcggtct ccgcgtgatt     780
atgttccgcc gttttgatca ggaggctttc ttgaaagcca tccaagatta tgaagtccgc     840
agtgtcatca acgtgcctag cgtgatcctg tttttgtcta agagcccact cgtggacaag     900
tacgacttgt cttcactgcg tgaattgtgt tgcggtgccg ctcccactgg ctaaggaggtc     960
gctgaagtgg ccgccaaacg cttgaatctt ccagggattc gttgtggctt cggcctcacc    1020
gaatctacca gtcgcgattat ccagactctc ggggatgagt ttaagagcgg ctctttgggc    1080
cgtgtcactc cactcatggc tgctaagatc gctgatcgcg aaactggtaa ggctttgggc    1140
ccgaaccaag tgggcgagct gtgtatcaaa ggccctatgg tgagcaaggg ttatgtcaat    1200
aacgttgaag ctaccaagga ggccatcgac gacgacggct ggttgcattc tggtgatttt    1260
ggatattacg acgaagatga gcattttac gtcgtggatc gttacaagga gctgatcaaa     1320
tacaagggta gccaggttgc tccagctgag ttggaggaga ttctgttgaa aaatccatgc    1380
attcgcgatg tcgctgtggt cggcattcct gatctggagg ccggcgaact gccttctgct    1440
ttcgttgtca gcagcctgg tacagaaatt accgccaaag aagtgtatga ttacctggct    1500
gaacgtgtga gccatactaa gtacttgcgt ggcggcgtgc gttttgttga ctccatccct    1560
cgtaacgtaa caggcaaaat tacccgcaag gagctgttga acaattgtt ggtgaaggcc    1620
ggcggt                                                               1626
```

<210> SEQ ID NO 302
<211> LENGTH: 542
<212> TYPE: PRT
<213> ORGANISM: Artificial Sequence
<220> FEATURE:
<223> OTHER INFORMATION: Sequence of a synthetic luciferase

<400> SEQUENCE: 302

```
Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
```

-continued

```
                    20                  25                  30
Lys His Ser His Leu Pro Gln Ala Leu Val Asp Val Val Gly Asp Glu
             35                  40                  45
Ser Leu Ser Tyr Lys Glu Phe Phe Glu Ala Thr Val Leu Leu Ala Gln
         50                  55                  60
Ser Leu His Asn Cys Gly Tyr Lys Met Asn Asp Val Val Ser Ile Cys
 65                  70                  75                  80
Ala Glu Asn Asn Thr Arg Phe Phe Ile Pro Val Ile Ala Ala Trp Tyr
                 85                  90                  95
Ile Gly Met Ile Val Ala Pro Val Asn Glu Ser Tyr Ile Pro Asp Glu
             100                 105                 110
Leu Cys Lys Val Met Gly Ile Ser Lys Pro Gln Ile Val Phe Thr Thr
         115                 120                 125
Lys Asn Ile Leu Asn Lys Val Leu Glu Val Gln Ser Arg Thr Asn Phe
130                 135                 140
Ile Lys Arg Ile Ile Ile Leu Asp Thr Val Glu Asn Ile His Gly Cys
145                 150                 155                 160
Glu Ser Leu Pro Asn Phe Ile Ser Arg Tyr Ser Asp Gly Asn Ile Ala
                 165                 170                 175
Asn Phe Lys Pro Leu His Phe Asp Pro Val Glu Gln Val Ala Ala Ile
             180                 185                 190
Leu Cys Ser Ser Gly Thr Thr Gly Leu Pro Lys Gly Val Met Gln Thr
         195                 200                 205
His Gln Asn Ile Cys Val Arg Leu Ile His Ala Leu Asp Pro Arg Tyr
210                 215                 220
Gly Thr Gln Leu Ile Pro Gly Val Thr Val Leu Val Tyr Leu Pro Phe
225                 230                 235                 240
Phe His Ala Phe Gly Phe His Ile Thr Leu Gly Tyr Phe Met Val Gly
                 245                 250                 255
Leu Arg Val Ile Met Phe Arg Arg Phe Asp Gln Glu Ala Phe Leu Lys
             260                 265                 270
Ala Ile Gln Asp Tyr Glu Val Arg Ser Val Ile Asn Val Pro Ser Val
         275                 280                 285
Ile Leu Phe Leu Ser Lys Ser Pro Leu Val Asp Lys Tyr Asp Leu Ser
         290                 295                 300
Ser Leu Arg Glu Leu Cys Cys Gly Ala Ala Pro Leu Ala Lys Glu Val
305                 310                 315                 320
Ala Glu Val Ala Ala Lys Arg Leu Asn Leu Pro Gly Ile Arg Cys Gly
                 325                 330                 335
Phe Gly Leu Thr Glu Ser Thr Ser Ala Ile Ile Gln Thr Leu Gly Asp
             340                 345                 350
Glu Phe Lys Ser Gly Ser Leu Gly Arg Val Thr Pro Leu Met Ala Ala
         355                 360                 365
Lys Ile Ala Asp Arg Glu Thr Gly Lys Ala Leu Gly Pro Asn Gln Val
         370                 375                 380
Gly Glu Leu Cys Ile Lys Gly Pro Met Val Ser Lys Gly Tyr Val Asn
385                 390                 395                 400
Asn Val Glu Ala Thr Lys Glu Ala Ile Asp Asp Gly Trp Leu His
                 405                 410                 415
Ser Gly Asp Phe Gly Tyr Tyr Asp Glu Asp Glu His Phe Tyr Val Val
             420                 425                 430
Asp Arg Tyr Lys Glu Leu Ile Lys Tyr Lys Gly Ser Gln Val Ala Pro
         435                 440                 445
```

```
Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465             470                 475                     480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly
    530                 535                 540
```

SYNTHETIC NUCLEIC ACID MOLECULE COMPOSITIONS AND METHODS OF PREPARATION

CROSS-REFERENCE TO RELATED APPLICATION

This application is a divisional of application Ser. No. 09/645,706, filed on Aug. 24, 2000, the specification of which is incorporated herein by reference in its entirety.

STATEMENT REGARDING FEDERALLY SPONSORED RESEARCH

The invention was made with government support under DMI-9402762 awarded by the National Science Foundation. The government has certain rights to the invention.

BACKGROUND OF THE INVENTION

Transcription, the synthesis of an RNA molecule from a sequence of DNA is the first step in gene expression. Sequences which regulate DNA transcription include promoter sequences, polyadenylation signals, transcription factor binding sites and enhancer elements. A promoter is a DNA sequence capable of specific initiation of transcription and consists of three general regions. The core promoter is the sequence where the RNA polymerase and its cofactors bind to the DNA. Immediately upstream of the core promoter is the proximal promoter which contains several transcription factor binding sites that are responsible for the assembly of an activation complex that in turn recruits the polymerase complex. The distal promoter, located further upstream of the proximal promoter also contains transcription factor binding sites. Transcription termination and polyadenylation, like transcription initiation, are site specific and encoded by defined sequences. Enhancers are regulatory regions, containing multiple transcription factor binding sites, that can significantly increase the level of transcription from a responsive promoter regardless of the enhancer's orientation and distance with respect to the promoter as long as the enhancer and promoter are located within the same DNA molecule. The amount of transcript produced from a gene may also be regulated by a post-transcriptional mechanism, the most important being RNA splicing that removes intervening sequences (introns) from a primary transcript between splice donor and splice acceptor sequences.

Natural selection is the hypothesis that genotype-environment interactions occurring at the phenotypic level lead to differential reproductive success of individuals and therefore to modification of the gene pool of a population. Some properties of nucleic acid molecules that are acted upon by natural selection include codon usage frequency, RNA secondary structure, the efficiency of intron splicing, and interactions with transcription factors or other nucleic acid binding proteins. Because of the degenerate nature of the genetic code, these properties can be optimized by natural selection without altering the corresponding amino acid sequence.

Under some conditions, it is useful to synthetically alter the natural nucleotide sequence encoding a polypeptide to better adapt the polypeptide for alternative applications. A common example is to alter the codon usage frequency of a gene when it is expressed in a foreign host cell. Although redundancy in the genetic code allows amino acids to be encoded by multiple codons, different organisms favor some codons over others. It has been found that the efficiency of protein translation in a non-native host cell can be substantially increased by adjusting the codon usage frequency but maintaining the same gene product (U.S. Pat. Nos. 5,096,825, 5,670,356, and 5,874,304).

However, altering codon usage may, in turn, result in the unintentional introduction into a synthetic nucleic acid molecule of inappropriate transcription regulatory sequences. This may adversely effect transcription, resulting in anomalous expression of the synthetic DNA. Anomalous expression is defined as departure from normal or expected levels of expression. For example, transcription factor binding sites located downstream from a promoter have been demonstrated to effect promoter activity (Michael et al., 1990; Lamb et al., 1998; Johnson et al., 1998; Jones et al., 1997). Additionally, it is not uncommon for an enhancer element to exert activity and result in elevated levels of DNA transcription in the absence of a promoter sequence or for the presence of transcription regulatory sequences to increase the basal levels of gene expression in the absence of a promoter sequence.

Thus, what is needed is a method for making synthetic nucleic acid molecules with altered codon usage without also introducing inappropriate or unintended transcription regulatory sequences for expression in a particular host cell.

SUMMARY OF THE INVENTION

The invention provides a synthetic nucleic acid molecule comprising at least 300 nucleotides of a coding region for a polypeptide, having a codon composition differing at more than 25% of the codons from a wild type nucleic acid sequence encoding a polypeptide, and having at least 3-fold fewer, preferably at least 5-fold fewer, transcription regulatory sequences than would result if the differing codons were randomly selected. Preferably, the synthetic nucleic acid molecule encodes a polypeptide that has an amino acid sequence that is at least 85%, preferably 90%, and most preferably 95% or 99% identical to the amino acid sequence of the naturally-occurring (native or wild type) polypeptide (protein) from which it is derived. Thus, it is recognized that some specific amino acid changes may also be desirable to alter a particular phenotypic characteristic of the polypeptide encoded by the synthetic nucleic acid molecule. Preferably, the amino acid sequence identity is over at least 100 contiguous amino acid residues. In one embodiment of the invention, the codons in the synthetic nucleic acid molecule that differ preferably encode the same amino acids as the corresponding codons in the wild type nucleic acid sequence.

The transcription regulatory sequences which are reduced in the synthetic nucleic acid molecule include, but are not limited to, any combination of transcription factor binding sequences, intron splice sites, poly(A) addition sites, enhancer sequences and promoter sequences. Transcription regulatory sequences are well known in the art.

It is preferred that the synthetic nucleic acid molecule of the invention has a codon composition that differs from that of the wild type nucleic acid sequence at more than 30%, 35%, 40% or more than 45%, e.g., 50%, 55%, 60% or more of the codons. Preferred codons for use in the invention are those which are employed more frequently than at least one other codon for the same amino acid in a particular organism and, more preferably, are also not low-usage codons in that organism and are not low-usage codons in the organism used to clone or screen for the expression of the synthetic nucleic acid molecule (for example, E. coli). Moreover, preferred codons for certain amino acids (i.e., those amino acids that have three or more codons,), may include two or more codons that are employed more frequently than the other (non-preferred) codon(s). The presence of codons in the synthetic nucleic acid molecule that are employed more frequently in one organism than in another organism results in a synthetic nucleic acid molecule which, when introduced into the cells of the organism that employs those codons more frequently, is expressed in those cells at a level that is greater than the expression of the wild type or parent nucleic acid sequence in those cells. For example, the synthetic nucleic acid molecule of the invention is expressed at a level that is at least about 110%, e.g., 150%, 200%, 500% or more (1000%, 5000%, or 10000%) of that of the wild type nucleic acid sequence in a cell or cell extract under identical conditions (such as cell culture conditions, vector backbone, and the like).

In one embodiment of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In one embodiment of the invention, the majority of the codons which differ are ones that are preferred codons in a desired host cell. Preferred codons for mammals (e.g., humans) and plants are known to the art (e.g., Wada et al., 1990). For example, preferred human codons include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, preferred "humanized" synthetic nucleic acid molecules of the invention have a codon composition which differs from a wild type nucleic acid sequence by having an increased number of the preferred human codons, e.g. CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the synthetic nucleic acid molecule of the invention may have an increased number of CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof, relative to the wild type nucleic acid sequence. Similarly, synthetic nucleic acid molecules having an increased number of codons that are employed more frequently in plants, have a codon composition which differs from a wild type or parent nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

The choice of codon may be influenced by many factors such as, for example, the desire to have an increased number of nucleotide substitutions or decreased number of transcription regulatory sequences. Under some circumstances (e.g. to permit removal of a transcription factor binding site) it may be desirable to replace a non-preferred codon with a codon other than a preferred codon or a codon other than the most preferred codon. Under other circumstances, for example, to prepare codon distinct versions of a synthetic nucleic acid molecule, preferred codon pairs are selected based upon the largest number of mismatched bases, as well as the criteria described above.

The presence of codons in the synthetic nucleic acid molecule that are employed more frequently in one organism than in another organism, results in a synthetic nucleic acid molecule which, when introduced into a cell of the organism that employs those codons, is expressed in that cell at a level which is greater than the level of expression of the wild type or parent nucleic acid sequence.

A synthetic nucleic acid molecule of the invention may encode a selectable marker protein or a reporter molecule. However, the invention applies to any gene and is not limited to synthetic reporter genes or synthetic selectable marker genes. In one embodiment of a synthetic nucleic acid molecule of the invention that is a reporter molecule, the synthetic nucleic acid molecule encodes a luciferase having a codon composition different than that of a wild type or parent Renilla luciferase or a beetle luciferase nucleic acid sequence. A synthetic click beetle luciferase nucleic acid molecule of the invention may optionally encode the amino acid valine at position 224 (i.e., it emits green light), or may optionally encode the amino acid histidine at position 224, histidine at position 247, isoleucine at position 346, glutamine at position 348 or combination thereof (i.e., it emits red light). Preferred synthetic luciferase nucleic acid molecules that are related to a wild type Renilla luciferase nucleic acid sequence include, but are not limited to, SEQ ID NO:21 (Rlucver2) or SEQ ID NO:22 (Rluc-final). Preferred synthetic luciferase nucleic acid molecules that are related to click beetle luciferase nucleic acid sequences include, but are not limited to, SEQ ID NO:7 (GRver5), SEQ ID NO:8 (GR6), SEQ ID NO:9 (GRver5.1), SEQ ID NO:14 (RDver5), SEQ ID NO:15 (RD7), SEQ ID NO:16 (RDver5.1), SEQ ID NO:17 (RDver5.2) or SEQ ID NO:18 (RD156-1H9).

The invention also provides an expression cassette. The expression cassette of the invention comprises a synthetic nucleic acid molecule of the invention operatively linked to a promoter that is functional in a cell. Preferred promoters are those functional in mammalian cells and those functional in plant cells. Optionally, the expression cassette may include other sequences, e.g., restriction enzyme recognition sequences and a Kozak sequence, and be a part of a larger polynucleotide molecule such as a plasmid, cosmid, artificial chromosome or vector, e.g., a viral vector.

Also provided is a host cell comprising the synthetic nucleic acid molecule of the invention, an isolated polypeptide (e.g., a fusion polypeptide encoded by the synthetic nucleic acid molecule of the invention), and compositions and kits comprising the synthetic nucleic acid molecule of the invention or the polypeptide encoded thereby in suitable container means and, optionally, instruction means. Preferred isolated polypeptides include, but are not limited to, those comprising SEQ ID NO:31 (GRver5.1), SEQ ID NO:226 (Rluc-final), or SEQ ID NO:223 (RD156-1H9).

The invention also provides a method to prepare a synthetic nucleic acid molecule of the invention by genetically altering a parent (either a wild type or another synthetic) nucleic acid sequence. The method may be used to prepare a synthetic nucleic acid molecule encoding a polypeptide comprising at least 100 amino acids. One embodiment of the invention is directed to the preparation of synthetic genes encoding reporter or selectable marker proteins. The method of the invention may be employed to alter the codon usage frequency and decrease the number of transcription regulatory sequences in any open reading frame or to decrease the number of transcription regulatory sites in a vector backbone.

Preferably, the codon usage frequency in the synthetic nucleic acid molecule is altered to reflect that of the host organism desired for expression of that nucleic acid molecule while also decreasing the number of potential transcription regulatory sequences relative to the parent nucleic acid molecule.

Thus, the invention provides a method to prepare a synthetic nucleic acid molecule comprising an open reading frame. The method comprises altering (e.g., decreasing or eliminating) a plurality of transcription regulatory sequences in a parent (wild type or a synthetic) nucleic acid sequence that encodes a polypeptide having at least 100 amino acids to yield a synthetic nucleic acid molecule which has a decreased number of transcription regulatory sequences and which preferably encodes the same amino acids as the parent nucleic acid molecule. The transcription regulatory sequences are selected from the group consisting of transcription factor binding sequences, intron splice sites, poly(A) addition sites, enhancer sequences and promoter sequences, and the resulting synthetic nucleic acid molecule has at least 3-fold fewer, preferably 5-fold fewer, transcription regulatory sequences relative to the parent nucleic acid sequence. The method also comprises altering greater than 25% of the codons in the synthetic nucleic acid sequence which has a decreased number of transcription regulatory sequences to yield a further synthetic nucleic acid molecule, wherein the codons that are altered encode the same amino acids as those in the corresponding position in the synthetic nucleic acid molecule which has a decreased number of transcription regulatory sequences and/or in the parent nucleic acid sequence. Preferably, the codons which are altered do not result in an increase in transcriptional regulatory sequences. Preferably, the further synthetic nucleic acid molecule encodes a polypeptide that has at least 85%, preferably 90%, and most preferably 95% or 99% contiguous amino acid sequence identity to the amino acid sequence of the polypeptide encoded by the parent nucleic acid sequence.

Alternatively, the method comprises altering greater than 25% of the codons in a parent nucleic acid sequence which encodes a polypeptide having at least 100 amino acids to yield a codon-altered synthetic nucleic acid molecule, wherein the codons that are altered encode the same amino acids as those present in the corresponding positions in the parent nucleic acid sequence. Then, a plurality of transcription regulatory sequences in the codon-altered synthetic nucleic acid molecule are altered to yield a further synthetic nucleic acid molecule. Preferably, the codons which are altered do not result in an increase in transcriptional regulatory sequences. Also, preferably, the further synthetic nucleic acid molecule encodes a polypeptide that has at least 85%, preferably 90%, and most preferably 95% or 99% contiguous amino acid sequence identity to the amino acid sequence of the polypeptide encoded by the parent nucleic acid sequence. Also provided is a synthetic (including a further synthetic) nucleic acid molecule prepared by the methods of the invention.

As described hereinbelow, the methods of the invention were employed with click beetle luciferase and *Renilla* luciferase nucleic acid sequences. While both of these nucleic acid molecules encode luciferase proteins, they are from entirely different families and are widely separated evolutionarily. These proteins have unrelated amino acid sequences, protein structures, and they utilize dissimilar chemical substrates. The fact that they share the name "luciferase" should not be interpreted to mean that they are from the same family, or even largely similar families. The methods produced synthetic luciferase nucleic acid molecules which exhibited significantly enhanced levels of mammalian expression without negatively effecting other desirable physical or biochemical properties (including protein half-life) and which were also largely devoid of known transcription regulatory elements.

The invention also provides at least two synthetic nucleic acid molecules that encode highly related polypeptides, but which synthetic nucleic acid molecules have an increased number of nucleotide differences relative to each other. These differences decrease the recombination frequency between the two synthetic nucleic acid molecules when those molecules are both present in a cell (i.e., they are "codon distinct" versions of a synthetic nucleic acid molecule). Thus, the invention provides a method for preparing at least two synthetic nucleic acid molecules that are codon distinct versions of a parent nucleic acid sequence that encodes a polypeptide. The method comprises altering a parent nucleic acid sequence to yield a first synthetic nucleic acid molecule having an increased number of a first plurality of codons that are employed more frequently in a selected host cell relative to the number of those codons present in the parent nucleic acid sequence. Optionally, the first synthetic nucleic acid molecule also has a decreased number of transcription regulatory sequences relative to the parent nucleic acid sequence. The parent nucleic acid sequence is also altered to yield a second synthetic nucleic acid molecule having an increased number of a second plurality of codons that are employed more frequently in the host cell relative to the number of those codons in the parent nucleic acid sequence, wherein the first plurality of codons is different than the second plurality of codons, and wherein the first and the second synthetic nucleic acid molecules preferably encode the same polypeptide. Optionally, the second synthetic nucleic acid molecule has a decreased number of transcription regulatory sequences relative to the parent nucleic acid sequence. Either or both synthetic molecules can then be further modified.

Clearly, the present invention has applications with many genes and across many fields of science including, but not limited to, life science research, agrigenetics, genetic therapy, developmental science and pharmaceutical development.

BRIEF DESCRIPTION OF THE FIGURES

FIG. 1. Codons and their corresponding amino acids.

Figure 2A:
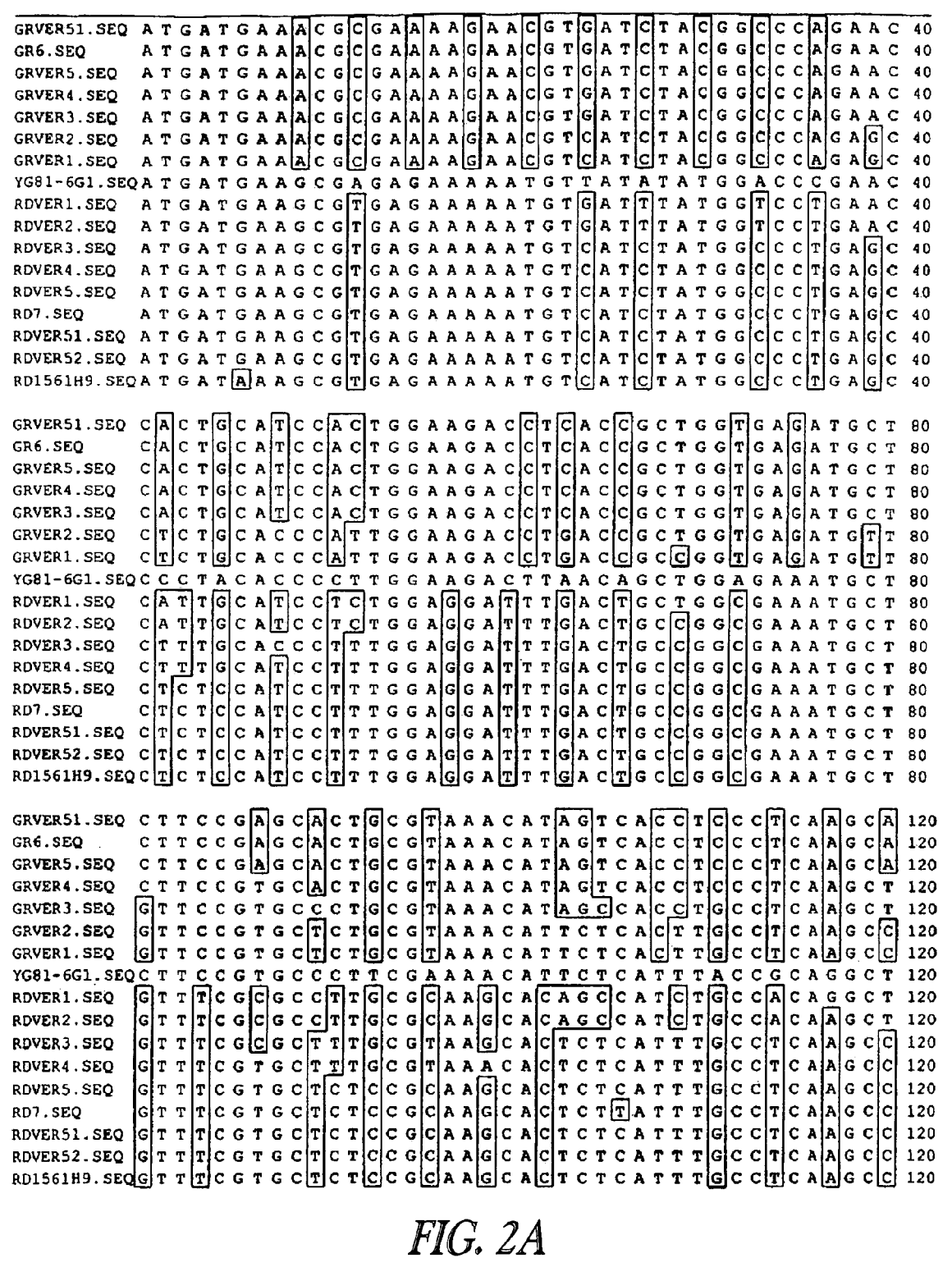
Figure 2B:
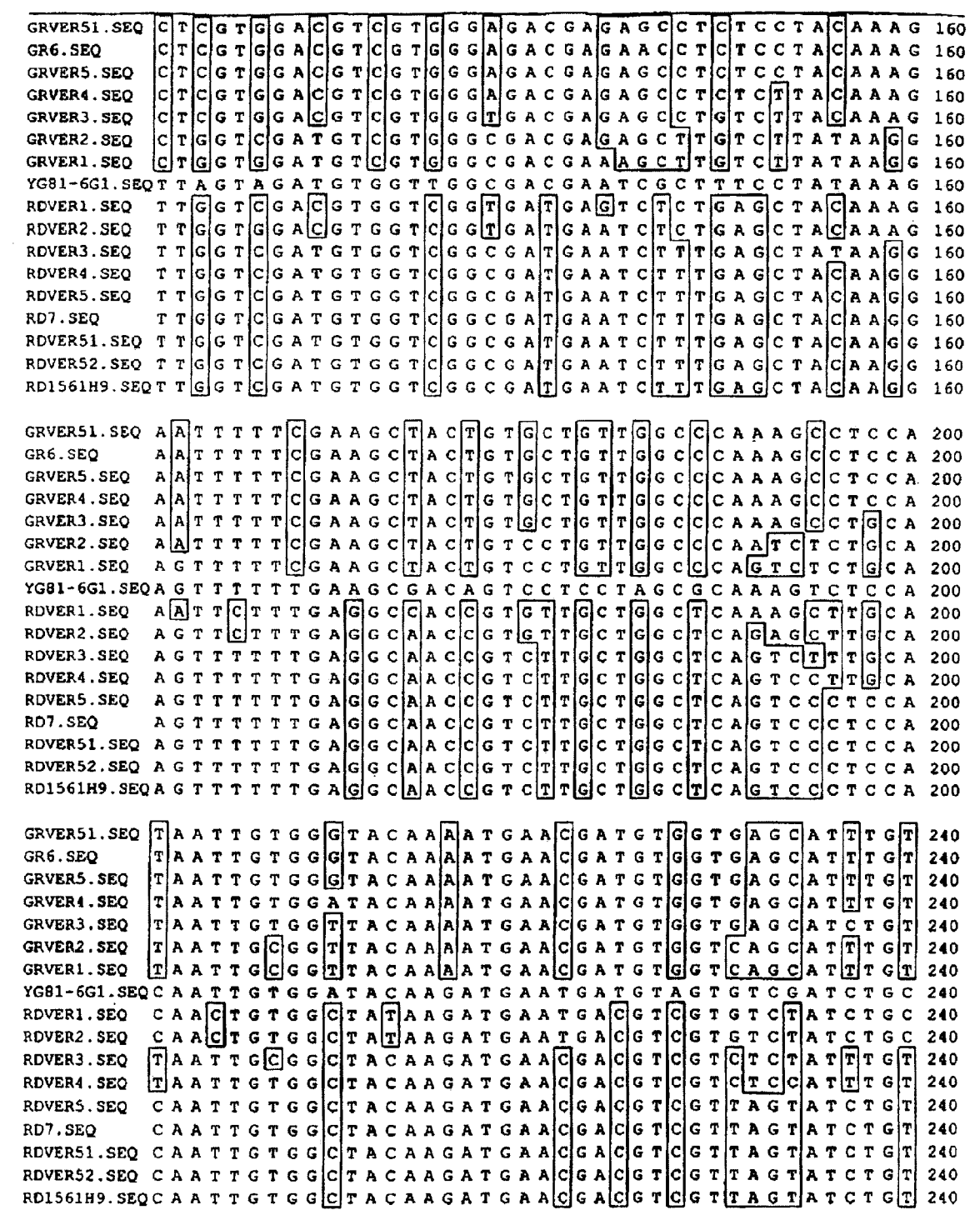
Figure 2F:
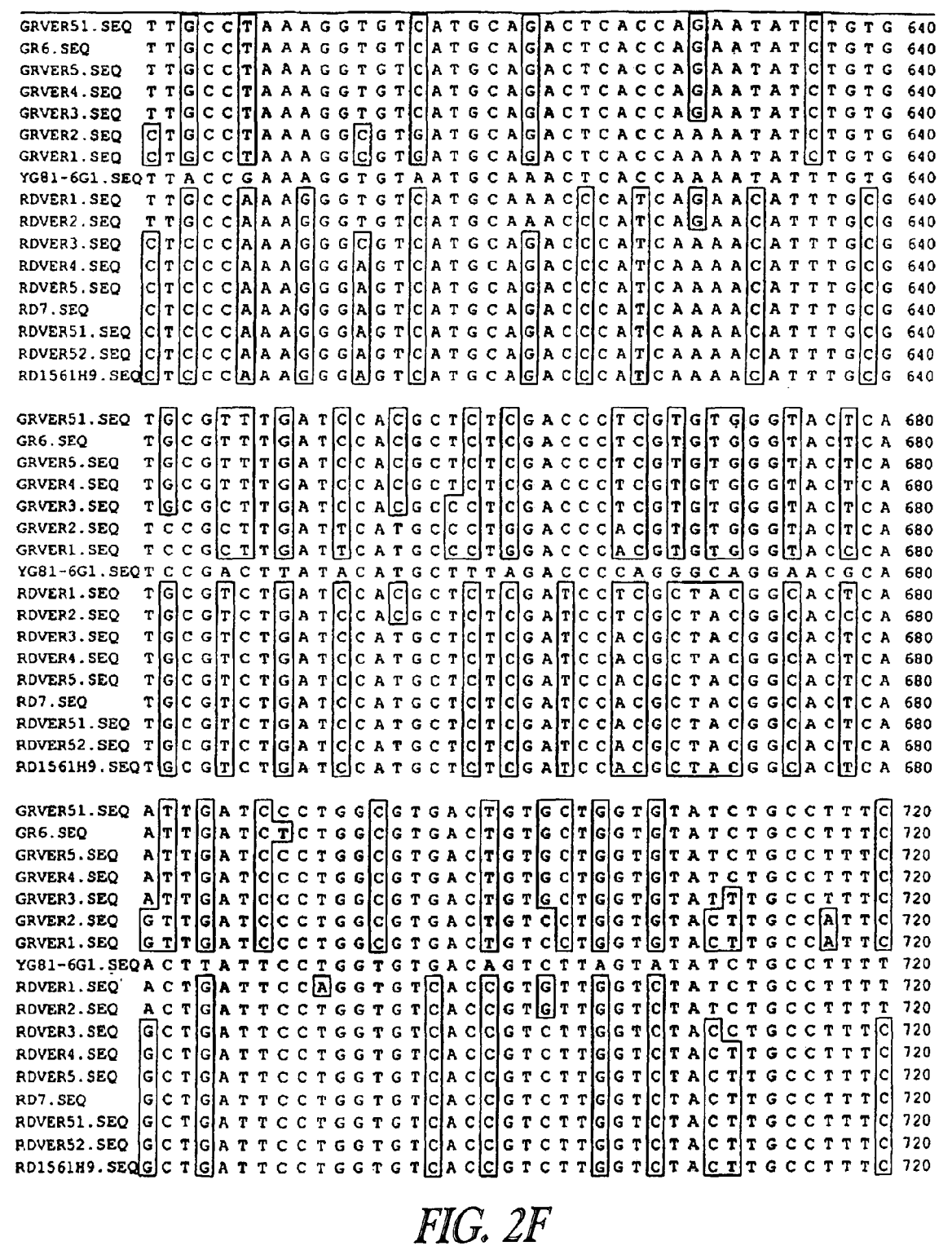
Figure 2H:
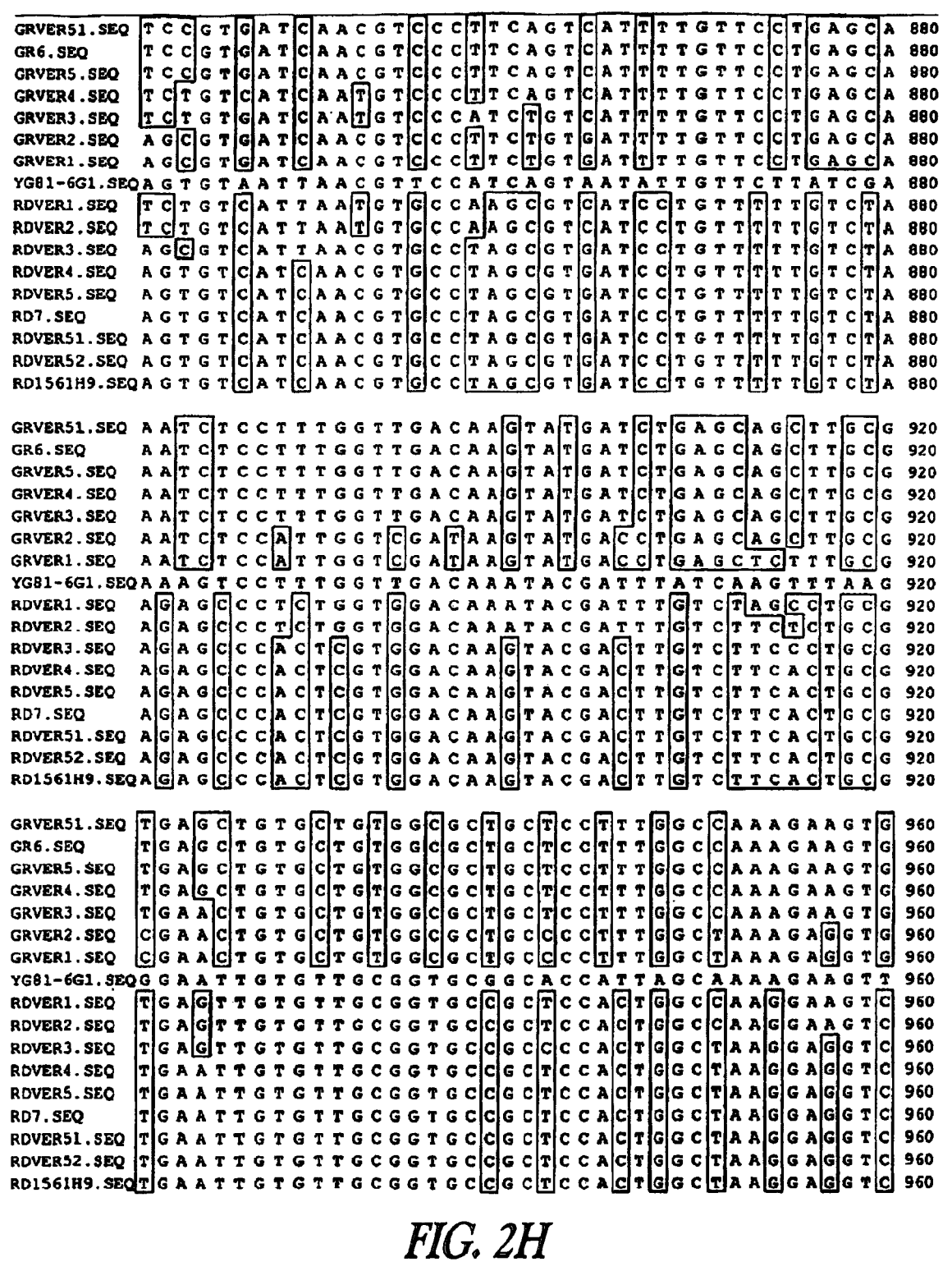
Figure 2J:
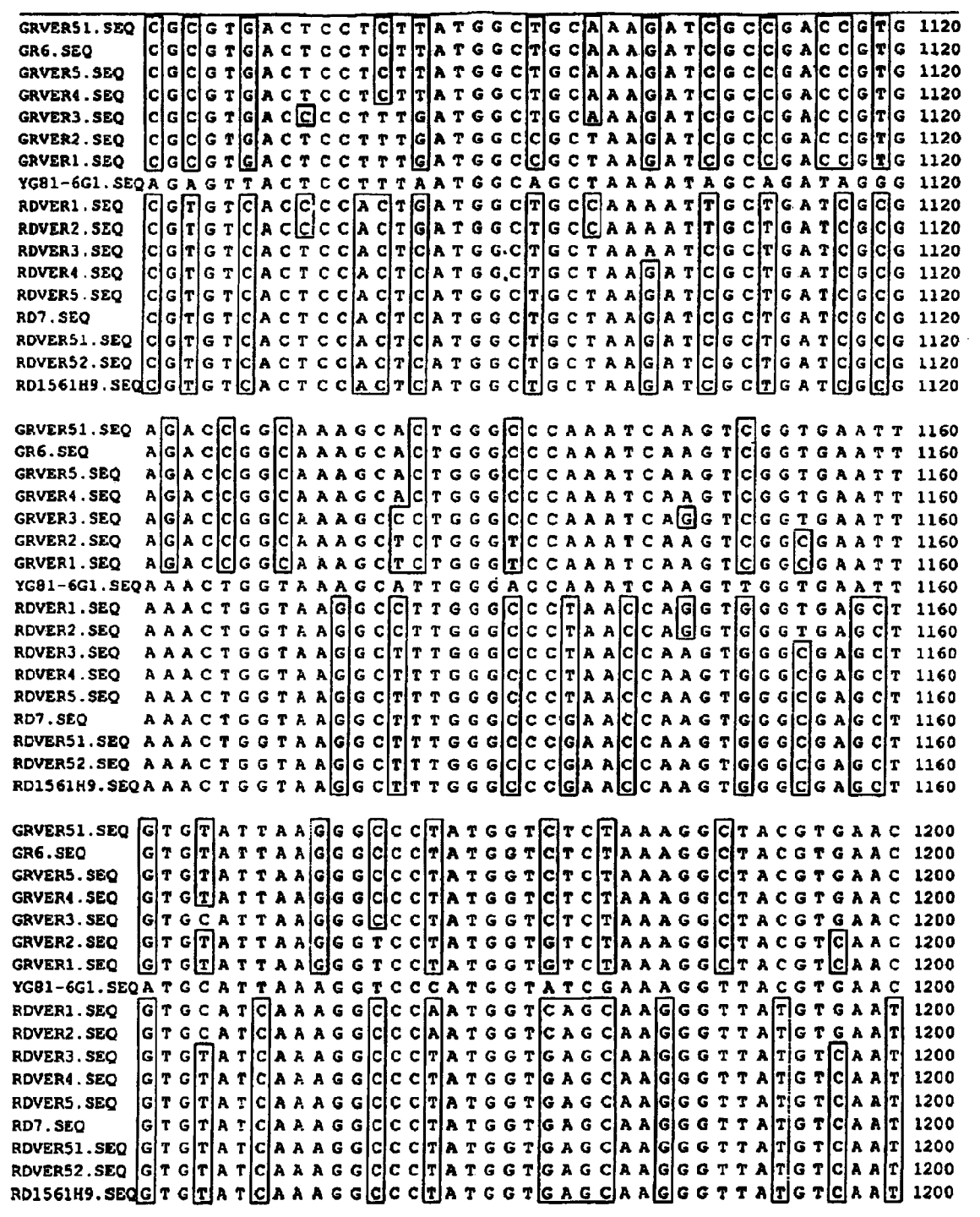
Figure 2M:
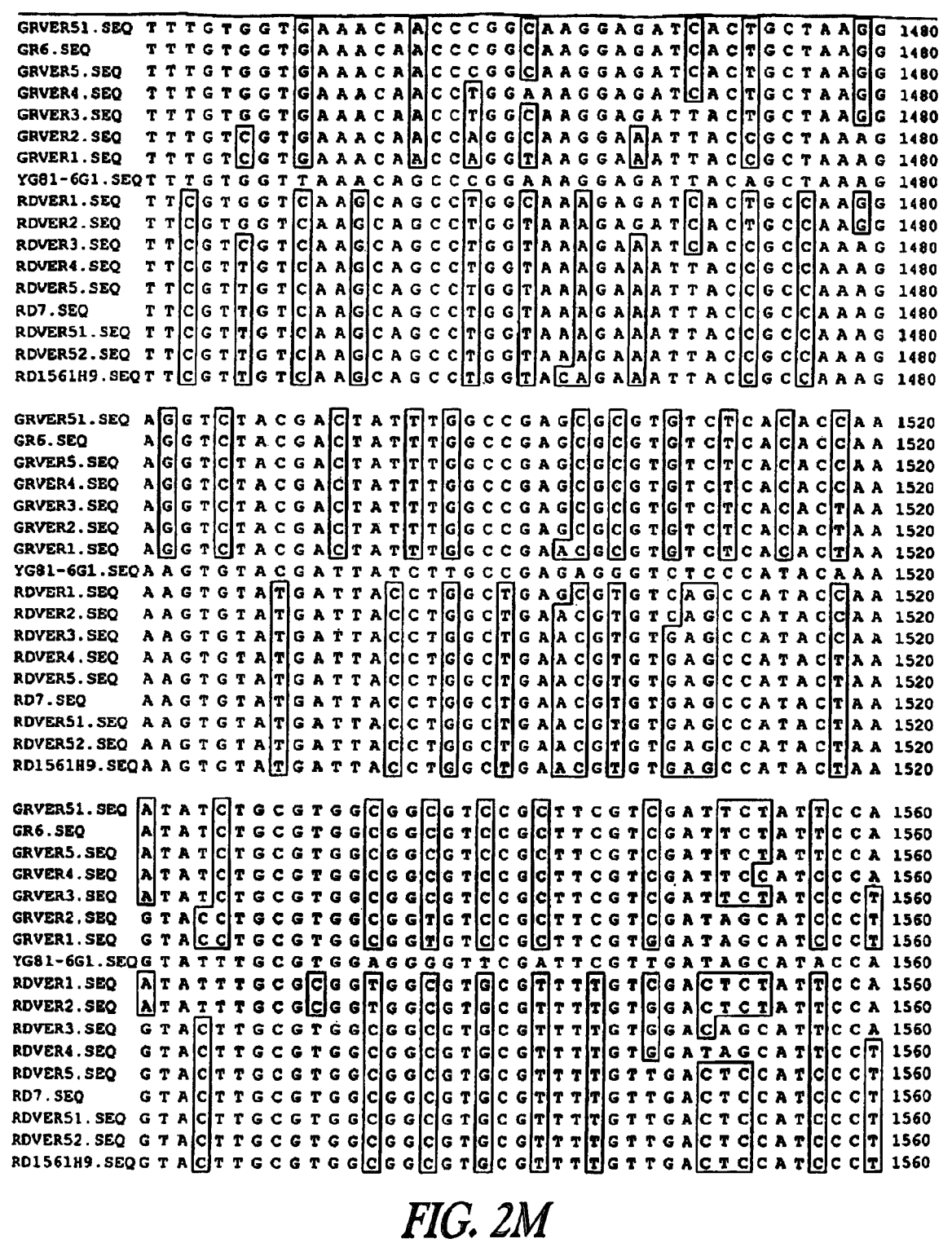
Figure 2N:
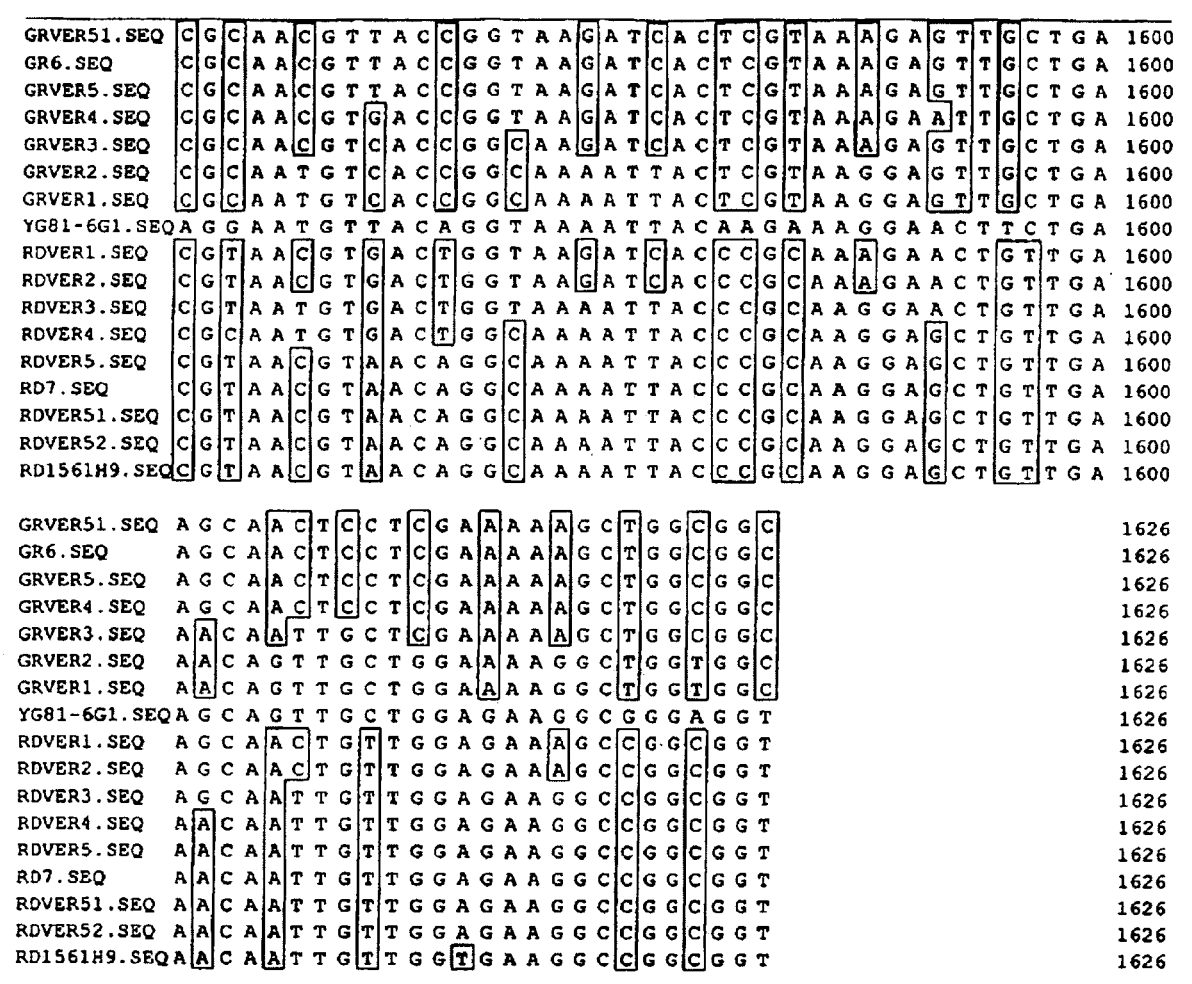

FIG. 2. A nucleotide sequence comparison of a yellow-green (YG) click beetle luciferase nucleic acid sequence (YG #81-6G01; SEQ ID NO:2) and various synthetic green (GR) click beetle luciferase nucleic acid sequences (GRver1, SEQ ID NO:3; GRver2, SEQ ID NO:4; GRver3, SEQ ID NO:5; GRver4, SEQ ID NO:6; GRver5, SEQ ID NO:7; GR6, SEQ ID NO:8; GRver5.1, SEQ ID NO:9) and various red (RD) click beetle luciferase nucleic acid sequences (RDver1, SEQ ID NO:10; RDver2, SEQ ID NO:11; RDver3, SEQ ID NO:12; RDver4, SEQ ID NO:13; RDver5, SEQ ID NO:14; RD7, SEQ ID NO:15; RDver5.1, SEQ ID NO:16; RDver5.2, SEQ ID NO:17; RD156-1H9, SEQ ID NO:18). The nucleotides enclosed in boxes are nucleotides that differ from the nucleotide present at the homologous position in SEQ ID NO:2.

FIG. 3. An amino acid sequence comparison of a YG click beetle luciferase amino acid sequence (YG#81-6G01, SEQ ID NO:24) and various synthetic GR click beetle luciferase amino acid sequences (GRver1, SEQ ID NO:25; GRver2, SEQ ID NO:26; GRver3, SEQ ID NO:27; GRver4, SEQ ID NO:28; GRver5, SEQ ID NO:29; GR6, SEQ ID NO:30; GRver5.1, SEQ ID NO:31) and various red (RD) click beetle luciferase amino acid sequences (RDver1, SEQ ID NO:32; RDver2, SEQ ID NO:33; RDver3, SEQ ID NO:34; RDver4, SEQ ID NO:218; RDver5, SEQ ID NO:219; RD7, SEQ ID NO:220; RDver5.1, SEQ ID NO:221; RDver5.2, SEQ ID NO:222; RD156-1H9, SEQ ID NO:223). All amino acid sequences are inferred from the corresponding nucleotide sequence. The amino acids enclosed in boxes are amino acids that differ from the amino acid present at the homologous position in SEQ ID NO:24.

FIG. 4. Codon usage in YG#81-6G01, GRver1, RDver1, GRver5, and RDver5, and humans (HUM) and relative codon usage in YG#81-6G01, GRver5, RDver5, and humans.

FIG. 5. Codon usage summaries for YG#81-6G01 (FIG. 5A), and GR/RD synthetic nucleic acid sequences, GRver1 (FIG. 5B), RDver1 (FIG. 5C), GRver2 (FIG. 5D), RDver2 (FIG. 5E), GRver3 (FIG. 5F), RDver3 (FIG. 5G), QRver4 (FIG. 5H), RDver4 (FIG. 5I), GRver5 (FIG. 5J), RDver5 (5K).

FIG. 6. Oligonucleotides employed to prepare synthetic GR/RD luciferase genes (SEQ ID Nos. 35-245).

FIG. 7. A nucleotide sequence comparison of a wild type *Renilla reniformis* luciferase nucleic acid sequence Genbank Accession No. M63501 (RELLUC, SEQ ID NO:19) and various synthetic *Renilla* luciferase nucleic acid sequences (Rlucver1, SEQ ID NO:20; Rlucver2, SEQ ID NO:21; Rluc-final, SEQ ID NO:22). The nucleotides enclosed in boxes are nucleotides that differ from the nucleotide present at the homologous position in SEQ ID NO:19.

FIG. 8. An amino acid sequence comparison of a wild type *Renilla reniformis* luciferase amino acid sequence (RELLUC, SEQ ID NO:224) and various synthetic *Renilla reniformis* luciferase amino acid sequences (Rlucver1, SEQ ID NO:225; Rlucver2, SEQ ID NO:226; Rluc-final, SEQ ID NO:227). All amino acid sequences are inferred from the corresponding nucleotide sequence. The amino acids enclosed in boxes are amino acids that differ from the amino acid present at the homologous position in SEQ ID NO:224.

FIG. 9. Codon usage in wild-type (A) versus synthetic (B) *Renilla* luciferase genes. For codon usage in selected organisms, see, e.g., Wada et al., 1990; Sharp et al., 1988; Aota et al., 1988; and Sharp et al., 1987, and for plant codons, Murray et al. 1989.

FIG. 10. Oligonucleotides employed to prepare synthetic *Renilla* luciferase gene (SEQ ID Nos. 246-292).

Figure 11C:
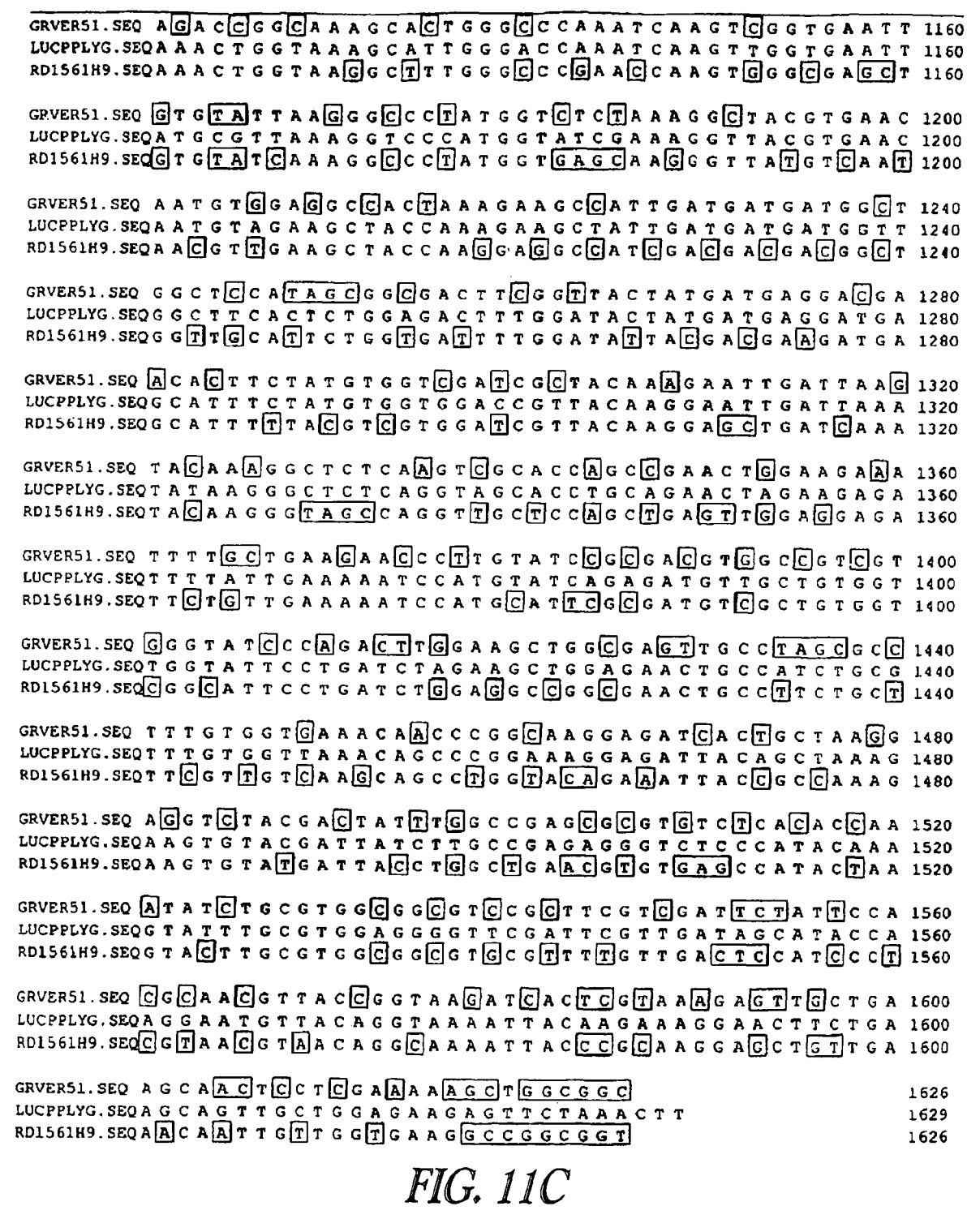

FIG. 11. A nucleotide sequence comparison of a wild type yellow-green (YG) click beetle luciferase nucleic acid sequence (LUCPPLYG, SEQ ID NO:1) and the synthetic green click beetle luciferase nucleic acid sequences (GRver5.1, SEQ ID NO:9) and the synthetic red click beetle luciferase nucleic acid sequences (RD156-1H9, SEQ ID NO:18). The nucleotides enclosed in boxes are nucleotides that differ from the nucleotide present at the homologous position in SEQ ID NO:1. Both synthetic sequences have a codon composition that differs from LUCPPLYG at more than 25% of the codons and have at least 3-fold fewer transcription regulatory sequences relative to a random selection of codons at the codons which differ.

FIG. 12. An amino acid sequence comparison of a wild type YG click beetle luciferase amino acid sequence (LUCPPLYG, SEQ ID NO:23) and the synthetic GR click beetle luciferase amino acid sequences (GRver5.1, SEQ ID NO:31) and the red (RD) click beetle luciferase amino acid sequences (RD156-1H9, SEQ ID NO:223). All amino acid sequences are inferred from the corresponding nucleotide sequence. The amino acids enclosed in boxes are amino acids that differ from the amino acid present at the homologous position in SEQ ID NO:23.

FIG. 18. Nucleotide and inferred amino acid sequence of click beetle luciferases in pGL3 vectors (GRver5.1 in pGL3, SEQ ID NO:297 encoding SEQ ID NO:298; RDver5.1 in pGL3, SEQ ID NO:299 encoding SEQ ID NO:300; and RD156-1H9 in pGL3, SEQ ID NO:301 encoding SEQ ID NO:302). To clone GRver5.1, RDver5.1, and RD156-1H9 nucleic acid sequences into pGL3 vectors, an oligonucleotide having an Nco I site at the initiation codon was employed, which resulted in an amino acid substitution at position 2 to valine.

DETAILED DESCRIPTION OF THE INVENTION

Definitions

Figure 13A:
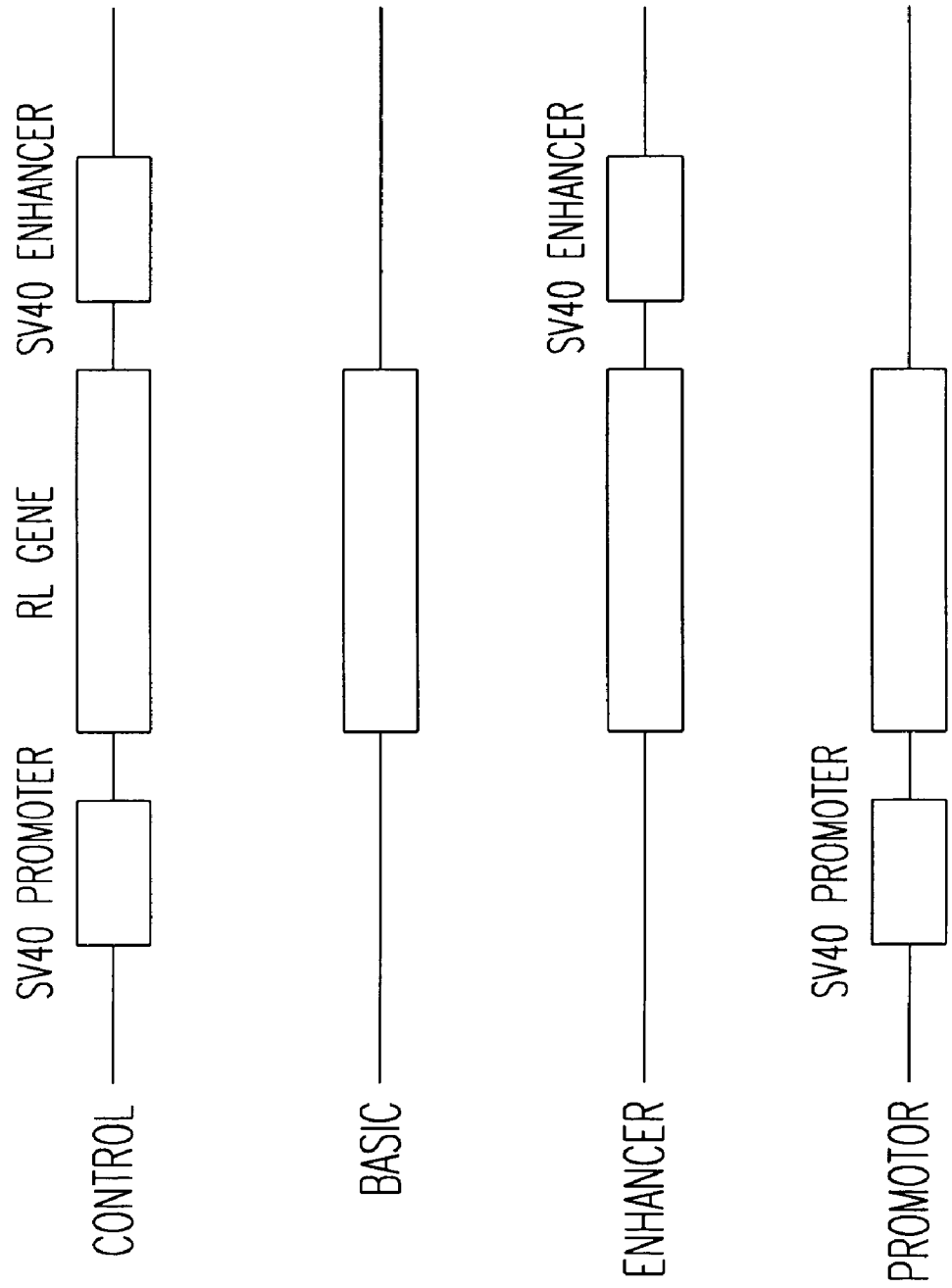
FIG. 13A illustrates the *Renilla* luciferase gene in the pGL3 vectors (Promega Corp.)

The term "gene" as used herein, refers to a DNA sequence that comprises coding sequences necessary for the production of a polypeptide or protein precursor. The polypeptide can be encoded by a full length coding sequence or by any portion of the coding sequence, as long as the desired protein activity is retained.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporation into a polypeptide chain, or a start or stop signal. FIG. 1 contains a codon table. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

By "protein" and "polypeptide" is meant any chain of amino acids, regardless of length or post-translational modification (e.g., glycosylation or phosphorylation). The synthetic genes of the invention may also encode a variant of a naturally-occurring protein or polypeptide fragment thereof. Preferably, such a protein polypeptide has an amino acid sequence that is at least 85%, preferably 90%, and most preferably 95% or 99% identical to the amino acid sequence of the naturally-occurring (native) protein from which it is derived.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "wild type" as used herein, refers to a gene or gene product that has the characteristics of that gene or gene product isolated from a naturally occurring source. A wild type gene is that which is most frequently observed in a population and is thus arbitrarily designated the "wild type" form of the gene. In contrast, the term "mutant" refers to a gene or gene product that displays modifications in sequence and/or functional properties (i.e., altered characteristics) when compared to the wild type gene or gene product. It is noted that naturally-occurring mutants can be isolated; these are identified by the fact that they have altered characteristics when compared to the wild type gene or gene product.

The terms "complementary" or "complementarity" are used in reference to a sequence of nucleotides related by the base-pairing rules. For example, for the sequence 5' "A-G-T" 3', is complementary to the sequence 3' "T-C-A" 5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon hybridization of nucleic acids.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as corn pared to the native form of the protein.

The terms "fusion protein" and "fusion partner" refer to a chimeric protein containing the protein of interest (e.g., luciferase) joined to an exogenous protein fragment (e.g., a fusion partner which consists of a non-luciferase protein). The fusion partner may enhance the solubility of protein as expressed in a host cell, may, for example, provide an affinity tag to allow purification of the recombinant fusion protein from the host cell or culture supernatant, or both. If desired, the fusion partner may be removed from the protein of interest by a variety of enzymatic or chemical means known to the art.

The terms "cell," "cell line," "host cell," as used herein, are used interchangeably, and all such designations include progeny or potential progeny of these designations. By "transformed cell" is meant a cell into which (or into an ancestor of which) has been introduced a DNA molecule comprising a synthetic gene. Optionally, a synthetic gene of the invention may be introduced into a suitable cell line so as to create a stably-transfected cell line capable of producing the protein or polypeptide encoded by the synthetic gene. Vectors, cells, and methods for constructing such cell lines are well known in the art, e.g. in Ausubel, et al. (infra). The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

Nucleic acids are known to contain different types of mutations. A "point" mutation refers to an alteration in the sequence of a nucleotide at a single base position from the wild type sequence. Mutations may also refer to insertion or deletion of one or more bases, so that the nucleic acid sequence differs from the wild-type sequence.

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

A "partially complementary" sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity). In this case, in the absence of non-specific binding, the probe will not hybridize to the second non-complementary target.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

"Probe" refers to an oligonucleotide designed to be sufficiently complementary to a sequence in a denatured nucleic acid to be probed (in relation to its length) to be bound under selected stringency conditions.

"Hybridization" and "binding" in the context of probes and denature melted nucleic acid are used interchangeably. Probes which are hybridized or bound to denatured nucleic acid are base paired to complementary sequences in the polynucleotide. Whether or not a particular probe remains base paired with the polynucleotide depends on the degree of complementarity, the length of the probe, and the stringency of the binding conditions. The higher the stringency, the higher must be the degree of complementarity and/or the longer the probe.

The term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the Tm (melting temperature) of the formed hybrid, the presence of other components (e.g., the presence or absence of polyethylene glycol), the molarity of the hybridizing strands and the G:C content of the nucleic acid strands.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989; Nucleic Acid Hybridization, A Practical Approach, IRL Press, Washington D.C., 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The Tm of a hybrid nucleic acid is often estimated using a formula adopted from hybridization assays in 1 M salt, and commonly used for calculating Tm for PCR primers: [(number of A+T)×2° C.+(number of G+C)×4° C.]. (C. R. Newton et al., *PCR*, 2nd Ed., Springer-Verlag (New York, 1997), p. 24). This formula was found to be inaccurate for primers longer than 20 nucleotides. (Id.) Another simple estimate of the $T_m$ value may be calculated by the equation: $T_m$=81.5+0.41(% G+C), when a nucleic acid is in aqueous solution at 1 M NaCl. (e.g., Anderson and Young, Quantitative Filter Hybridization, in *Nucleic Acid Hybridization*, 1985). Other more sophisticated computations exist in the art which take structural as well as sequence characteristics into account for the calculation of $T_m$. A calculated $T_m$ is merely an estimate; the optimum temperature is commonly determined empirically.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and antisense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

The term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

The term "recombinant DNA molecule" means a hybrid DNA sequence comprising at least two nucleotide sequences not normally found together in nature.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenlyation signal and optionally an enhancer sequence.

The term "a polynucleotide having a nucleotide sequence encoding a gene," means a nucleic acid sequence comprising the coding region of a gene, or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription (Maniatis et al., 1987). Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss et al., 1986; and Maniatis et al., 1987. For example, the SV40 early gene enhancer is very active in a wide variety of cell types from many mammalian species and has been widely used for the expression of proteins in mammalian cells (Dijkema et al., 1985). Two other examples of promoter/enhancer elements active in a broad range of mammalian cell types are those from the human elongation factor 1 gene (Uetsuki et al., 1989; Kim, et al., 1990; and Mizushima and Nagata, 1990) and the long terminal repeats of the Rous sarcoma virus (Gorman et al., 1982); and the human cytomegalovirus (Boshart et al., 1985).

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., Molecular Cloning: A Laboratory Manual, 2nd ed., Cold Spring Harbor Laboratory Press, New York, 1989, pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamH I/Bcl I restriction fragment and directs both termination and polyadenylation (Sambrook, supra, at 16.6-16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in situ" refers to cell culture. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of source (e.g., the American Type Culture Collection, Rockland, Md.). The method of transformation or transfection and the choice of expression vehicle will depend on the host system selected. Transformation and transfection methods are described, e.g., in Ausubel, et al., Current Protocols in Molecular Biology. John Wiley & Sons, New York. 1992. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

The term "enzyme" refers to molecules or molecule aggregates that are responsible for catalyzing chemical and biological reactions. Such molecules are typically proteins, but can also comprise short peptides, RNAs, ribozymes, antibodies, and other molecules. A molecule that catalyzes chemical and biological reactions is referred to as "having enzyme activity" or "having catalytic activity."

All amino acid residues identified herein are in the natural L-configuration. In keeping with standard polypeptide nomenclature (see *J. Biol. Chem.*, 243, 3557 (1969)), abbreviations for amino acid residues are as shown in the following Table of Correspondence.

| TABLE OF CORRESPONDENCE | | |
| --- | --- | --- |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

The term "sequence homology" means the proportion of base matches between two nucleic acid sequences or the proportion of amino acid matches between two amino acid sequences. When sequence homology is expressed as a percentage, e.g., 50%, the percentage denotes the proportion of matches over the length of sequence from one sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 100 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 85% identical when optimally aligned using the ALIGN program.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith and Waterman (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990), are based on the algorithm of Karlin and Altschul supra. To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. See http://www.ncbi.nlm.nih.gov. Alignment may also be performed manually by inspection The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) for the stated proportion of nucleotides over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 60%, preferably at least 65%, more preferably at least 70%, up to about 85%, and even more preferably at least 90 to 95%, more usually at least 99%, sequence identity as compared to a reference sequence over a comparison window of at least 20 nucleotide positions, frequently over a window of at least 20-50 nucleotides, and preferably at least 300 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the term "substantial identity" means that two peptide sequences, when optimally aligned, such as by the programs GAP or BESTFIT using default gap weights, share at least about 85% sequence identity, preferably at least about 90% sequence identity, more preferably at least about 95% sequence identity, and most preferably at least about 99% sequence identity.

The Synthetic Nucleic Acid Molecules and Methods of the Invention

The invention provides compositions comprising synthetic nucleic acid molecules, as well as methods for preparing those molecules which yield synthetic nucleic acid molecules that are efficiently expressed as a polypeptide or protein with desirable characteristics including reduced inappropriate or unintended transcription characteristics when expressed in a particular cell type.

Natural selection is the hypothesis that genotype-environment interactions occurring at the phenotypic level lead to differential reproductive success of individuals and hence to modification of the gene pool of a population. It is generally accepted that the amino acid sequence of a protein found in nature has undergone optimization by natural selection. However, amino acids exist within the sequence of a protein that do not contribute significantly to the activity of the protein and these amino acids can be changed to other amino acids with little or no consequence. Furthermore, a protein may be useful outside its natural environment or for purposes that differ from the conditions of its natural selection. In these circumstances, the amino acid sequence can be synthetically altered to better adapt the protein for its utility in various applications.

Likewise, the nucleic acid sequence that encodes a protein is also optimized by natural selection. The relationship between coding DNA and its transcribed RNA is such that any change to the DNA affects the resulting RNA. Thus, natural selection works on both molecules simultaneously. However, this relationship does not exist between nucleic acids and proteins. Because multiple codons encode the same amino acid, many different nucleotide sequences can encode an identical protein. A specific protein composed of 500 amino acids can theoretically be encoded by more than $10^{150}$ different nucleic acid sequences.

Natural selection acts on nucleic acids to achieve proper encoding of the corresponding protein. Presumably, other properties of nucleic acid molecules are also acted upon by natural selection. These properties include codon usage frequency, RNA secondary structure, the efficiency of intron splicing, and interactions with transcription factors or other nucleic acid binding proteins. These other properties may alter the efficiency of protein translation and the resulting phenotype. Because of the redundant nature of the genetic code, these other attributes can be optimized by natural selection without altering the corresponding amino acid sequence.

Under some conditions, it is useful to synthetically alter the natural nucleotide sequence encoding a protein to better adapt the protein for alternative applications. A common example is to alter the codon usage frequency of a gene when it is expressed in a foreign host. Although redundancy in the genetic code allows amino acids to be encoded by multiple codons, different organisms favor some codons over others. The codon usage frequencies tend to differ most for organisms with widely separated evolutionary histories. It has been found that when transferring genes between evolutionarily distant organisms, the efficiency of protein translation can be substantially increased by adjusting the codon usage frequency (see U.S. Pat. Nos. 5,096,825, 5,670,356 and 5,874,304).

Because of the need for evolutionary distance, the codon usage of reporter genes often does not correspond to the optimal codon usage of the experimental cells. Examples include β-galactosidase (β-gal) and chloramphenicol acetyltransferase (cat) reporter genes that are derived from *E. coli* and are commonly used in mammalian cells; the β-glucuronidase (gus) reporter gene that is derived from *E. coli* and commonly used in plant cells; the firefly luciferase (luc) reporter gene that is derived from an insect and commonly used in plant and mammalian cells; and the *Renilla* luciferase, and green fluorescent protein (gfp) reporter genes which are derived from coelenterates and are commonly used in plant and mammalian cells. To achieve sensitive quantitation of reporter gene expression, the activity of the gene product must not be endogenous to the experimental host cells. Thus, reporter genes are usually selected from organisms having unique and distinctive phenotypes. Consequently, these organisms often have widely separated evolutionary histories from the experimental host cells.

Previously, to create genes having a more optimal codon usage frequency but still encoding the same gene product, a synthetic nucleic acid sequence was made by replacing existing codons with codons that were generally more favorable to the experimental host cell (see U.S. Pat. Nos. 5,096,825, 5,670,356 and 5,874,304.) The result was a net improvement in codon usage frequency of the synthetic gene. However, the optimization of other attributes was not considered and so these synthetic genes likely did not reflect genes optimized by natural selection.

In particular, improvements in codon usage frequency are intended only for optimization of a RNA sequence based on its role in translation into a protein. Thus, previously described methods did not address how the sequence of a synthetic gene affects the role of DNA in transcription into RNA. Most notably, consideration had not been given as to how transcription factors may interact with the synthetic DNA and consequently modulate or otherwise influence gene transcription. For genes found in nature, the DNA would be optimally transcribed by the native host cell and would yield an RNA that encodes a properly folded gene product. In contrast, synthetic genes have previously not been optimized for transcriptional characteristics. Rather, this property has been ignored or left to chance.

This concern is important for all genes, but particularly important for reporter genes, which are most commonly used to quantitate transcriptional behavior in the experimental host cells. Hundreds of transcription factors have been identified in different cell types under different physiological conditions, and likely more exist but have not yet been identified. All of these transcription factors can influence the transcription of an introduced gene. A useful synthetic reporter gene of the invention has a minimal risk of influencing or perturbing intrinsic transcriptional characteristics of the host cell because the structure of that gene has been altered. A particularly useful synthetic reporter gene will have desirable characteristics under a new set and/or a wide variety of experimental conditions. To best achieve these characteristics, the structure of the synthetic gene should have minimal potential for interacting with transcription factors within a broad range of host cells and physiological conditions, Minimizing potential interactions between a reporter gene and a host cell's endogenous transcription factors increases the value of a reporter gene by reducing the risk of inappropriate transcriptional characteristics of the gene within a particular experiment, increasing applicability of the gene in various environments, and increasing the acceptance of the resulting experimental data.

In contrast, a reporter gene comprising a native nucleotide sequence, based on a genomic or cDNA clone from the original host organism, may interact with transcription factors when expressed in an exogenous host. This risk stems from two circumstances. First, the native nucleotide sequence contains sequences that were optimized through natural selection to influence gene transcription within the native host organism. However, these sequences might also influence transcription when the gene is expressed in exogenous hosts, i.e., out of context, thus interfering with its performance as a reporter gene. Second, the nucleotide sequence may inadvertently interact with transcription factors that were not present in the native host organism, and thus did not participate in its natural selection. The probability of such inadvertent interactions increases with greater evolutionary separation between the experimental cells and the native organism of the reporter gene.

These potential interactions with transcription factors would likely be disrupted when using a synthetic reporter gene having alterations in codon usage frequency. However, a synthetic reporter gene sequence, designed by choosing codons based only on codon usage frequency, is likely to contain other unintended transcription factor binding sites since the synthetic gene has not been subjected to the benefit of natural selection to correct inappropriate transcriptional activities. Inadvertent interactions with transcription factors could also occur whenever the encoded amino acid sequence is artificially altered, e.g., to introduce amino acid substitutions. Similarly, these changes have not been subjected to natural selection, and thus may exhibit undesired characteristics.

Thus, the invention provides a method for preparing synthetic nucleic acid sequences that reduce the risk of undesirable interactions of the nucleic acid with transcription factors when expressed in a particular host cell, thereby reducing inappropriate or unintended transcriptional characteristics. Preferably, the method yields synthetic genes containing improved codon usage frequencies for a particular host cell and with a reduced occurrence of transcription factor binding sites. The invention also provides a method of preparing synthetic genes containing improved codon usage frequencies with a reduced occurrence of transcription factor binding sites and additional beneficial structural attributes. Such additional attributes include the absence of inappropriate RNA splicing junctions, poly(A) addition signals, undesirable restriction sites, ribosomal binding sites, and secondary structural motifs such as hairpin loops.

Also provided is a method for preparing two synthetic genes encoding the same or highly similar proteins ("codon distinct" versions). Preferably, the two synthetic genes have a reduced ability to hybridize to a common polynucleotide probe sequence, or have a reduced risk of recombining when present together in living cells. To detect recombination, PCR amplification of the reporter sequences using primers complementary to flanking sequences and sequencing of the amplified sequences may be employed.

To select codons for the synthetic nucleic acid molecules of the invention, preferred codons have a relatively high codon usage frequency in a selected host cell, and their introduction results in the introduction of relatively few transcription factor binding sites, relatively few other undesirable structural attributes, and optionally a characteristic that distinguishes the synthetic gene from another gene encoding a highly similar protein. Thus, the synthetic nucleic acid product obtained by the method of the invention is a synthetic gene with improved level of expression due to improved codon usage frequency, a reduced risk of inappropriate transcriptional behavior due to a reduced number of undesirable transcription regulatory sequences, and optionally any additional characteristic due to other criteria that may be employed to select the synthetic sequence.

The invention may be employed with any nucleic acid sequence, e.g., a native sequence such as a cDNA or one which has been manipulated in vitro, e.g., to introduce specific alterations such as the introduction or removal of a restriction enzyme recognition site, the alteration of a codon to encode a different amino acid or to encode a fusion protein, or to alter GC or AT content (% of composition) of nucleic acid molecules. Moreover, the method of the invention is useful with any gene, but particularly useful for reporter genes as well as other genes associated with the expression of reporter genes, such as selectable markers. Preferred genes include, but are not limited to, those encoding lactamase ($\beta$-gal), neomycin resistance (Neo), CAT, GUS, galactopyranoside, GFP, xylosidase, thymidine kinase, arabinosidase and the like. As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene.

Exemplary marker genes include, but are not limited to, a neo gene, a $\beta$-gal gene, a gus gene, a cat gene, a gpt gene, a hyg gene, a hisD gene, a ble gene, a mprt gene, a bar gene, a nitrilase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a $\beta$-lactamase gene, a xylE gene, an $\alpha$-amylase gene, a tyrosinase gene, a luciferase (luc) gene, (e.g., a *Renilla reniformis* luciferase gene, a firefly luciferase gene, or a click beetle luciferase (*Pyrophorus plagiophthalamus*) gene), an aequorin gene, or a green fluorescent protein gene. Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA, and proteins that are inserted or trapped in the cell membrane.

The method of the invention can be performed by, although it is not limited to, a recursive process. The process includes assigning preferred codons to each amino acid in a target molecule, e.g., a native nucleotide sequence, based on codon usage in a particular species, identifying potential transcription regulatory sequences such as transcription factor binding sites in the nucleic acid sequence having preferred codons, e.g., using a database of such binding sites, optionally identifying other undesirable sequences, and substituting an alternative codon (i.e., encoding the same amino acid) at positions where undesirable transcription factor binding sites or other sequences occur. For codon distinct versions, alternative preferred codons are substituted in each version. If necessary, the identification and elimination of potential transcription factor or other undesirable sequences can be repeated until a nucleotide sequence is achieved containing a maximum number of preferred codons and a minimum number of undesired sequences including transcription regulatory sequences or other undesirable sequences. Also, optionally, desired sequences, e.g., restriction enzyme recognition sites, can be introduced. After a synthetic nucleic acid molecule is designed and constructed, its properties relative to the parent nucleic acid sequence can be determined by methods well known to the art. For example, the expression of the synthetic and target nucleic acid molecules in a series of vectors in a particular cell can be compared.

Thus, generally, the method of the invention comprises identifying a target nucleic acid sequence, such as a vector backbone, a reporter gene or a selectable marker gene, and a host cell of interest, for example, a plant (dicot or monocot), fungus, yeast or mammalian cell. Preferred host cells are mammalian host cells such as CHO, COS, 293, Hela, CV-1 and NIH3T3 cells. Based on preferred codon usage in the host cell(s) and, optionally, low codon usage in the host cell(s), e.g., high usage mammalian codons and low usage *E. coli* and mammalian codons, codons to be replaced are determined. For codon distinct versions of two synthetic nucleic acid molecules, alternative preferred codons are introduced to each version. Thus, for amino acids having more than two codons, one preferred codon is introduced to one version and another preferred codon is introduced to the other version. For amino acids having six codons, the two codons with the largest number of mismatched bases are identified and one is introduced to one version and the other codon is introduced to the other version. Concurrent, subsequent or prior to selecting codons to be replaced, desired and undesired sequences, such as undesired transcriptional regulatory sequences, in the target sequence are identified. These sequences can be identified using databases and software such as EPD, NNPD, REBASE, TRANSFAC, TESS, GenePro, MAR (www.ncgr.org/MARsearch) and BCM Gene Finder, further described herein. After the sequences are identified, the modification(s) are introduced. Once a desired synthetic nucleic acid sequence is obtained, it can be prepared by methods well known to the art (such as PCR with overlapping primers), and its structural and functional properties compared to the target nucleic acid sequence, including, but not limited to, percent homology, presence or absence of certain sequences, for example, restriction sites, percent of codons changed (such as an increased or decreased usage of certain codons) and expression rates.

As described below, the method was used to create synthetic reporter genes encoding *Renilla reniformis* luciferase, and two click beetle luciferases (one emitting green light and the other emitting red light). For both systems, the synthetic genes support much greater levels of expression than the corresponding native or parent genes for the protein. In addition, the native and parent genes demonstrated anomalous transcription characteristics when expressed in mammalian cells, which were not evident in the synthetic genes. In particular, basal expression of the native or parent genes is relatively high. Furthermore, the expression is induced to very high levels by an enhancer sequence in the absence of known promoters. The synthetic genes show lower basal expression and do not show the anomalous enhancer behavior. Presumably, the enhancer is activating transcriptional elements found in the native genes that are absent in the synthetic genes. The results clearly show that the synthetic nucleic acid sequences exhibit superior performance as reporter genes.

Exemplary Uses of the Molecules of the Invention

The synthetic genes of the invention preferably encode the same proteins as their native counterpart (or nearly so), but have improved codon usage while being largely devoid of known transcription regulatory elements in the coding region. (It is recognized that a small number of amino acid changes may be desired to enhance a property of the native counterpart protein, e.g. to enhance luminescence of a luciferase.) This increases the level of expression of the protein the synthetic gene encodes and reduces the risk of anomalous expression of the protein. For example, studies of many important events of gene regulation, which may be mediated by weak promoters, are limited by insufficient reporter signals from inadequate expression of the reporter proteins. The synthetic luciferase genes described herein permit detection of weak promoter activity because of the large increase in level of expression, which enables increased detection sensitivity. Also, the use of some selectable markers may be limited by the expression of that marker in an exogenous cell. Thus, synthetic selectable marker genes which have improved codon usage for that cell, and have a decrease in other undesirable sequences, (e.g., transcription factor binding sites), can permit the use of those markers in cells that otherwise were undesirable as hosts for those markers.

Promoter crosstalk is another concern when a co-reporter gene is used to normalize transfection efficiencies. With the enhanced expression of synthetic genes, the amount of DNA containing strong promoters can be reduced, or DNA containing weaker promoters can be employed, to drive the expression of the co-reporter. In addition, there may be a reduction in the background expression from the synthetic reporter genes of the invention. This characteristic makes synthetic reporter genes more desirable by minimizing the sporadic expression from the genes and reducing the interference resulting from other regulatory pathways.

The use of reporter genes in imaging systems, which can be used for in vivo biological studies or drug screening, is another use for the synthetic genes of the invention. Due to their increased level of expression, the protein encoded by a synthetic gene is more readily detectable by an imaging system. In fact, using a synthetic *Renilla* luciferase gene, luminescence in transfected CHO cells was detected visually without the aid of instrumentation.

In addition, the synthetic genes may be used to express fusion proteins, for example fusions with secretion leader sequences or cellular localization sequences, to study transcription in difficult-to-transfect cells such as primary cells, and/or to improve the analysis of regulatory pathways and genetic elements. Other uses include, but are not limited to, the detection of rare events that require extreme sensitivity (e.g., studying RNA recoding), use with IRES, to improve the efficiency of in vitro translation or in vitro transcription-translation coupled systems such as TNT (Promega Corp., Madison, Wis.), study of reporters optimized to different host organisms (e.g., plants, fungus, and the like), use of multiple genes as co-reporters to monitor drug toxicity, as reporter molecules in multiwell assays, and as reporter molecules in drug screening with the advantage of minimizing possible interference of reporter signal by different signal transduction pathways and other regulatory mechanisms.

Additionally, uses for the nucleic acid molecules of the invention include fluorescence activated cell sorting (FACS), fluorescent microscopy, to detect and/or measure the level of gene expression in vitro and in vivo, (e.g., to determine promoter strength), subcellular localization or targeting (fusion protein), as a marker, in calibration, in a kit, (e.g., for dual assays), for in vivo imaging, to analyze regulatory pathways and genetic elements, and in multi-well formats.

With respect to synthetic DNA encoding luciferases, the use of synthetic click beetle luciferases provides advantages such as the measurement of dual reporters. As *Renilla* luciferase is better suited for in vivo imaging (because it does not depend on ATP or $Mg^{2+}$ for reaction, unlike firefly luciferase, and because coelenterazine is more permeable to the cell membrane than luciferin), the synthetic *Renilla* luciferase gene can be employed in vivo. Further, the synthetic *Renilla* luciferase has improved fidelity and sensitivity in dual luciferase assays, e.g., for biological analysis or in drug screening platform.

Demonstration of the Invention Using Luciferase Genes

The reporter genes for click beetle luciferase and *Renilla* luciferase were used to demonstrate the invention because the reaction catalyzed by the protein they encode are significantly easier to quantify than the product of most genes. However, for the purposes of demonstrating the present invention they represent genes in general.

Although the click beetle luciferase and *Renilla* luciferase genes share the name "luciferase", this should not be interpreted to mean that they originate from the same family of genes. The two luciferase proteins are evolutionarily distinct; they have fundamentally different traits and physical structures, they use vastly different substrates (FIG. 17), and they evolved from completely different families of genes. The click beetle luciferase is 61 kD in size, uses luciferin as a substrate and evolved from the CoA synthetases. The *Renilla* luciferase originates from the sea pansy *Renilla Reniformis*, is 35 kD in size, uses coelenterazine as a substrate and evolved from the αβ hydrolases. The only shared trait of these two enzymes is that the reaction they catalyze results in light output. They are no more similar for resulting in light output than any other two enzymes would be, for example, simply because the reaction they catalyze results in heat.

Bioluminescence is the light produced in certain organisms as a result of luciferase-mediated oxidation reactions. The luciferase genes, e.g., the genes from luminous beetles, sea pansy, and, in particular, the luciferase from *Photinus pyralis* (the common firefly of North America), are currently the most popular luminescent reporter genes. Reference is made to Bronstein et al. (1994) for a review of luminescent reporter gene assays and to Wood (1995) for a review of the evolution of beetle bioluminescence. See FIG. 17 for an illustration of the reactions catalyzed by each of firefly and click beetle luciferases (17A) and *Renilla* luciferase (17B).

Figure 17A:
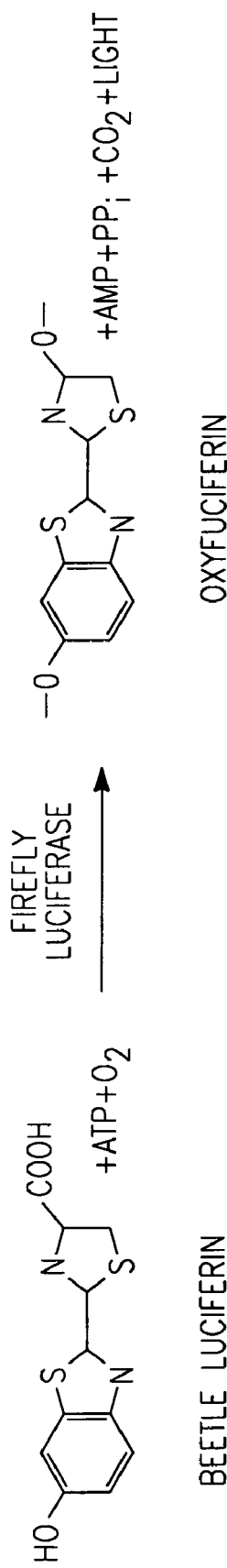
FIGS. 17A-B. Illustrates the reactions catalyzed by firefly and click beetle (17A), and *Renilla* (17B) luciferases.
Figure 17B:
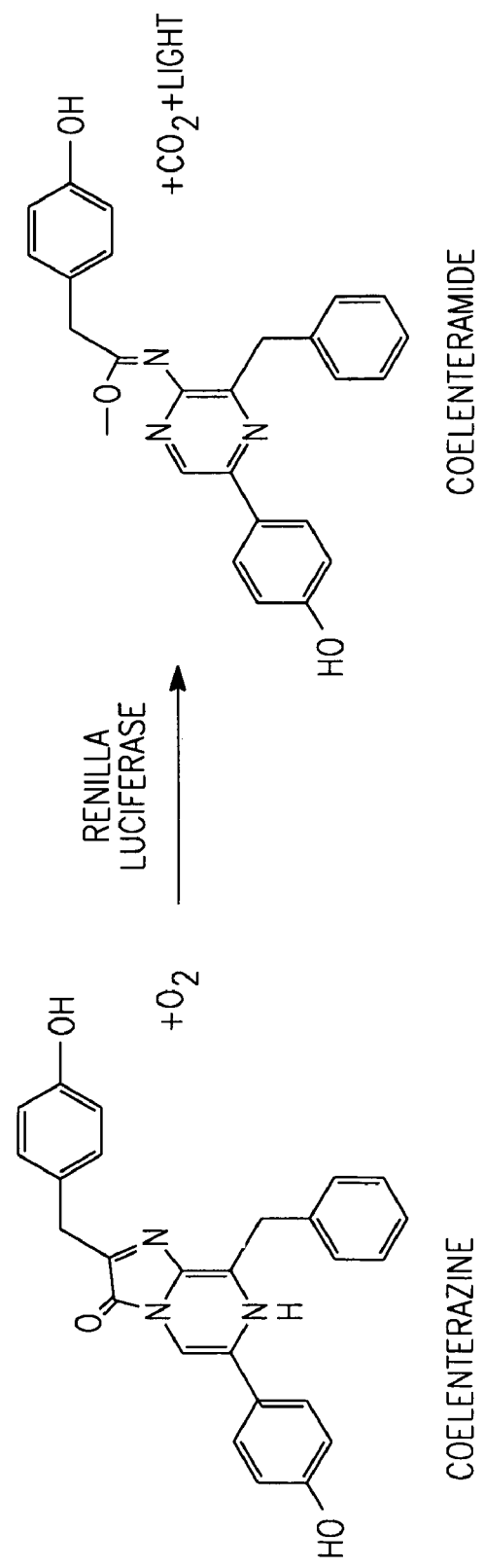

Firefly luciferase and *Renilla* luciferase are highly valuable as genetic reporters due to the convenience, sensitivity and linear range of the luminescence assay. Today, luciferase is used in virtually every type of experimental biological system, including, but not limited to, prokaryotic and eukaryotic cell culture, transgenic plants and animals, and cell-free expression systems. The firefly luciferase enzyme is derived from a specific North American beetle, *Photinus pyralis*. The firefly luciferase enzyme and the click beetle luciferase enzyme are monomeric proteins (61 kDa) which generate light through monooxygenation of beetle luciferin utilizing ATP and $O_2$ (FIG. 17A). The *Renilla* luciferase is derived from the sea pansy *Renilla reniformis*. The *Renilla* luciferase enzyme is a 36 kDa monomeric protein that utilizes $O_2$ and coelenterazine to generate light (FIG. 17B).

The gene encoding firefly luciferase was cloned from *Photinus pyralis*, and demonstrated to produce active enzyme in *E. coli* (de Wet et al., 1987). The cDNA encoding firefly luciferase (luc) continues to gain favor as the gene of choice for reporting genetic activity in animal, plant and microbial cells. The firefly luciferase reaction, modified by the addition of CoA to produce persistent light emission, provides an extremely sensitive and rapid in vitro assay for quantifying firefly luciferase expression in small samples of transfected cells or tissues.

To use firefly luciferase or click beetle luciferase as a genetic reporter, extracts of cells expressing the luciferase are mixed with substrates (beetle luciferin, $Mg^{2+}$ ATP, and $O_2$), and luminescence is measured immediately. The assay is very rapid and sensitive, providing gene expression data with little effort. The conventional firefly luciferase assay has been further improved by including coenzyme A in the assay reagent to yield greater enzyme turnover and thus greater luminescence intensity (Promega Luciferase Assay Reagent, Cat.# E1500, Promega Corporation, Madison, Wis.). Using this reagent, luciferase activity can be readily measured in luminometers or scintillation counters. Firefly and click beetle luciferase activity can also be detected in living cells in culture by adding luciferin to the growth medium. This in situ luminescence relies on the ability of beetle luciferin to diffuse through cellular and peroxisomal membranes and on the intracellular availability of ATP and $O_2$ in the cytosol and peroxisome.

Further, although reporter genes are widely used to measure transcription events, their utility can be limited by the fidelity and efficiency of reporter expression. For example, in U.S. Pat. No. 5,670,356, a firefly luciferase gene (referred to as luc+) was modified to improve the level of luciferase expression. While a higher level of expression was observed, it was not determined that higher expression had improved regulatory control.

The invention will be further described by the following nonlimiting examples.

EXAMPLE 1

Synthetic Click Beetle (RD and GR) Luciferase Nucleic Acid Molecules

LucPplYG is a wild-type click beetle luciferase that emits yellow-green luminescence (Wood, 1989). A mutant of LucPplYG named YG#81-6G01 was envisioned. YG#81-6G01 lacks a peroxisome targeting signal, has a lower KM for luciferin and ATP, has increased signal stability and increased temperature stability when compared to the wild type (PCT/WO9914336). YG #81-6G01 was mutated to emit green luminescence by changing Ala at position 224 to Val (A224V is a green-shifting mutation), or to emit red luminescence by simultaneously introducing the amino acid substitutions A224H, S247H, N3461, and H348Q (red-shifting mutation set) (PCT/WO9518853)

Using YG #81-6G01 as a parent gene, two synthetic gene sequences were designed. One codes for a luciferase emitting green luminescence (GR) and one for a luciferase emitting red luminescence (RD). Both genes were designed to 1) have optimized codon usage for expression in mammalian cells, 2) have a reduced number of transcriptional regulatory sites including mammalian transcription factor binding sites, splice sites, poly(A) addition sites and promoters, as well as prokaryotic (*E. coli*) regulatory sites, 3) be devoid of unwanted restriction sites, e.g., those which are likely to interfere with standard cloning procedures, and 4) have a low DNA sequence identity compared to each other in order to minimize genetic rearrangements when both are present inside the same cell. In addition, desired sequences, e.g., a Kozak sequence or restriction enzyme recognition sites, may be identified and introduced.

Not all design criteria could be met equally well at the same time. The following priority was established for reduction of transcriptional regulatory sites: elimination of transcription factor (TF) binding sites received the highest priority, followed by elimination of splice sites and poly(A) addition sites, and finally prokaryotic regulatory sites. When removing regulatory sites, the strategy was to work from the lesser important to the most important to ensure that the most important changes were made last. Then the sequence was rechecked for the appearance of new lower priority sites and additional changes made as needed. Thus, the process for designing the synthetic GR and RD gene sequences, using computer programs described herein, involved 5 optionally iterative steps that are detailed below 1. Optimized codon usage and changed A224V to create GRver1, separately changed A224H, S247H, H348Q and N346I to create RDver1. These particular amino acid changes were maintained throughout all subsequent manipulations to the sequence.
2. Removed undesired restriction sites, prokaryotic regulatory sites, splice sites, poly(A) sites thereby creating GRver2 and RDver2.
3. Removed transcription factor binding sites (first pass) and removed any newly created undesired sites as listed in step 2 above thereby creating GRver3 and RDver3.
4. Removed transcription factor binding sites created by step 3 above (second pass) and removed any newly created undesired sites as listed in step 2 above thereby creating GRver4 and RDver4.
5. Removed transcription factor binding sites created by step 4 above (third Pass) and confirmed absence of sites listed in step 2 above thereby creating GRver5 and RDver5.
6. Constructed the actual genes by PCR using synthetic oligonucleotides corresponding to fragments of GRver5 and RDver5 designed sequences (FIGS. 6 and 10) thereby creating GR6 and RD7. GR6, upon sequencing was found to have the serine residue at amino acid position 49 mutated to an asparagine and the proline at amino acid position 230 mutated to a serine (S49N, P230S). RD7, upon sequencing was found to have the histidine at amino acid position 36 mutated to a tyrosine (H36Y). These changes occurred during the PCR process.
7. The mutations described in step 6 above (S49N, P230S for GR6 and H36Y for RD7) were reversed to create GRver5.1 and RDver5.1.
8. RDver5.1 was further modified by changing the arginine codon at position 351 to a glycine codon (R351G) thereby creating RDver5.2 with improved spectral properties compared to RDver5.1.
9. RDver5.2 was further mutated to increase luminescence intensity thereby creating RD156-1H9 which encodes four additional amino acid changes (M2I, S349T, $K_{488}T$, E538V) and three silent single base changes (SEQ ID NO:18).

1. Optimize Codon Usage and Introduce Mutations Determining Luminescence Color

The starting gene sequence for this design step was YG #81-6G01 (SEQ ID NO:2).

a) Optimize Codon Usage:

The strategy was to adapt the codon usage for optimal expression in human cells and at the same time to avoid *E. coli* low-usage codons. Based on these requirements, the best two codons for expression in human cells for all amino acids with more than two codons were selected (see Wada et al., 1990). In the selection of codon pairs for amino acids with six codons, the selection was biased towards pairs that have the largest number of mismatched bases to allow design of GR and RD genes with minimum sequence identity (codon distinction):

```
Arg: CGC/CGT Leu: CTG/TTG Ser: TCT/AGC
Thr: ACC/ACT Pro: CCA/CCT Ala: GCC/GCT
Gly: GGC/GGT Val: GTC/GTG Ile: ATC/ATT
```

Based on this selection of codons, two gene sequences encoding the YG#81-6G01 luciferase protein sequence were computer generated. The two genes were designed to have minimum DNA sequence identity and at the same time closely similar codon usage. To achieve this, each codon in the two genes was replaced by a codon from the limited list described above in an alternating fashion (e.g., $Arg_{(n)}$ is CGC in gene 1 and CGT in gene 2, $Arg_{(n+1)}$ is CGT in gene 1 and CGC in gene 2).

For subsequent steps in the design process it was anticipated that changes had to be made to this limited optimal codon selection in order to meet other design criteria, however, the following low-usage codons in mammalian cells were not used unless needed to meet criteria of higher priority:

```
Arg: CGA Leu: CTA Ser: TCG
Pro: CCG Val: GTA Ile: ATA
```

Also, the following low-usage codons in *E. coli* were avoided when reasonable (note that 3 of these match the low-usage list for mammalian cells):

```
Arg: CGA/CGG/AGA/AGG
Leu: CTA Pro: CCC Ile: ATA
``` b) Introduce Mutations Determining Luminescence Color:

Into one of the two codon-optimized gene sequences was introduced the single green-shifting mutation and into the other were introduced the 4 red-shifting mutations as described above.

The two output sequences from this first design step were named GRver1 (version 1 GR) and RDver1 (version 1 RD). Their DNA sequences are 63% identical (594 mismatches), while the proteins they encode differ only by the 4 amino acids that determine luminescence color (see FIGS. 2 and 3 for an alignment of the DNA and protein sequences).

Tables 1 and 2 show, as an example, the codon usage for valine and leucine in human genes, the parent gene YG#81-6G01, the codon-optimized synthetic genes GRver1 and RDver1, as well as the final versions of the synthetic genes after completion of step 5 in the design process (GRver5 and RDver5). For a complete summary of the codon changes, see FIGS. 4 and 5.

TABLE 1

| Valine | | | | | | |
|---|---|---|---|---|---|---|
| Codon | Human | Parent | GR ver1 | RD ver1 | GR ver5 | RD ver5 |
| GTA | 4 | 13 | 0 | 0 | 1 | 1 |
| GTC | 13 | 4 | 25 | 24 | 21 | 26 |
| GTG | 24 | 12 | 25 | 25 | 25 | 17 |
| GTT | 9 | 20 | 0 | 0 | 3 | 5 |

TABLE 2

Leucine

| Codon | Human | Parent | GR ver1 | RD ver1 | GR ver5 | RD ver5 |
|---|---|---|---|---|---|---|
| CTA | 3 | 5 | 0 | 0 | 0 | 0 |
| CTC | 12 | 4 | 0 | 1 | 12 | 11 |
| CTG | 24 | 4 | 28 | 27 | 19 | 18 |
| CTT | 6 | 12 | 0 | 0 | 1 | 1 |
| TTA | 3 | 17 | 0 | 0 | 0 | 0 |
| TTG | 6 | 13 | 27 | 27 | 23 | 25 |

2. Remove Undesired Restriction Sites, Prokaryotic Regulatory Sites, Splice Sites and Poly(A) Addition Sites The starting gene sequences for this design step were GRver1 and RDver1.

a) Remove Undesired Restriction Sites.

To check for the presence and location of undesired restriction sites, the sequences of both synthetic genes were compared against a database of restriction enzyme recognition sequences (REBASE ver.712, http://www.neb.com/rebase) using standard sequence analysis software (GenePro ver 6.10, Riverside Scientific Ent.).

Specifically, the following restriction enzymes were classified as undesired:

BamH I, Xho I, Sfi I, Kpn I, Sac I, Mlu I, Nhe I, Sma I, Xho I, Bgl II, Hind III, Nco I, Nar I, Xba I, Hpa I, Sal I, other cloning sites commonly used: EcoR I, EcoR V, Cla I, eight-base cutters (commonly used for complex constructs), BstE II (to allow N-terminal fusions), Xcm I (can generate A/T overhang used for T-vector cloning).

To eliminate undesired restriction sites when found in a synthetic gene, one or more codons of the synthetic gene sequence were altered in accordance with the codon optimization guidelines described in 1a above.

b) Remove Prokaryotic (*E. coli*) Regulatory Sequences:

To check for the presence and location of prokaryotic regulatory sequences, the sequences of both synthetic genes were searched for the presence of the following consensus sequences using standard sequence analysis software (GenePro):

TATAAT (−10 Pribnow box of promoter)

AGGA or GGAG (ribosome binding site; only considered if paired with a methionine codon 12 or fewer bases downstream).

To eliminate such regulatory sequences when found in a synthetic gene, one or more codons of the synthetic gene at sequence were altered in accordance with the codon optimization guidelines described in 1a above.

c) Remove Splice Sites:

To check for the presence and location of splice sites, the DNA strand corresponding to the primary RNA transcript of each synthetic gene was searched for the presence of the following consensus sequences (see Watson et al., 1983) using standard sequence analysis software (GenePro):

splice donor site: AG|GTRAGT (exon|intron), the search was performed for AGGTRAG and the lower stringency GGTRAGT;

splice acceptor site: (Y)$_n$NCAG|G (intron|exon), the search was performed with n=1.

To eliminate splice sites found in a synthetic gene, one or more codons of the synthetic gene sequence were altered in accordance with the codon optimization guidelines described in 1a above. Splice acceptor sites were generally difficult to eliminate in one gene without introducing them into the other gene because they tended to contain one of the two only Gln codons (CAG); they were removed by placing the Gln codon CAA in both genes at the expense of a slightly increased sequence identity between the two genes.

d) Remove Poly(A) Addition Sites:

To check for the presence and location of poly(A) addition sites, the sequences of both synthetic genes were searched for the presence of the following consensus sequence using standard sequence analysis software (GenePro):

AATAAA.

To eliminate each poly(A) addition site found in a synthetic gene, one or more codons of the synthetic gene sequence were altered in accordance with the codon optimization guidelines described in 1a above. The two output sequences from this second design step were named GRver2 and RDver2. Their DNA sequences are 63% identical (590 mismatches) (FIGS. 2 and 3).

3. Remove Transcription Factor (TF) Binding Sites then Repeat Steps 2 a-d

The starting gene sequences for this design step were GRver2 and RDver2. To check for the presence, location and identity of potential TF binding sites, the sequences of both synthetic genes were used as query sequences to search a database of transcription factor binding sites (TRANSFAC v3.2). The TRANSFAC database (http://transfac.gbf.de/TRANSFAC/index:html) holds information on gene regulatory DNA sequences (TF binding sites) and proteins (TFs) that bind to and act through them. The SITE table of TRANSFAC Release 3.2 contains 4,401 entries of individual (putative) TF binding sites (including TF binding sites in eukaryotic genes, in artificial sequences resulting from mutagenesis studies and in vitro selection procedures based on random oligonucleotide mixtures or specific theoretical considerations, and consensus binding sequences (from Faisst and Meyer, 1992)).

The software tool used to locate and display these TF binding sites in the synthetic gene sequences was TESS (Transcription Element Search Software, http://agave.humgen.upenn.edu/tess/index.html). The filtered string-based search option was used with the following user-defined search parameters:

Factor Selection Attribute: Organism Classification

Search Pattern: Mammalia

Max. Allowable Mismatch %: 0

Min. element length: 5

Min. log-likelihood: 10

This parameter selection specifies that only mammalian TF binding sites (approximately 1,400 of the 4,401 entries in the database) that are at least 5 bases long will be included in the search. It further specifies that only TF binding sites that have a perfect match in the query sequence and a minimum log likelihood (LLH) score of 10 will be reported. The LLH scoring method assigns 2 to an unambiguous match, 1 to a partially ambiguous match (e.g., A or T match W) and 0 to a match against 'N'. For example, a search with parameters specified above would result in a "hit" (positive result or match) for TATAA (SEQ ID NO:240) (LLH=10), STRATG (SEQ ID NO:241) (LLH=10), and MTTNCNNMA (SEQ ID NO:242) (LLH=10) but not for TRATG (SEQ ID NO: 243) (LLH=9) if these four TF binding sites were present in the query sequence. A lower stringency test was performed at the end of the design process to re-evaluate the search parameters.

When TESS was tested with a mock query sequence containing known TF binding sites it was found that the program was unable to report matches to sites ending with the 3' end of the query sequence. Thus, an extra nucleotide was added to the 3' end of all query sequences to eliminate this problem.

The first search for TF binding sites using the parameters described above found about 100 transcription factor binding sites (hits) for each of the two synthetic genes (GRver2 and RDver2). All sites were eliminated by changing one or more codons of the synthetic gene sequences in accordance with the codon optimization guidelines described in 1a above. However, it was expected that some these changes created new TF binding sites, other regulatory sites, and new restriction sites. Thus, steps 2a-d were repeated as described, and 4 new restriction sites and 2 new splice sites were removed. The two output sequences from this third design step were named GRver3 and RDver3. Their DNA sequences are 66% identical (541 mismatches) (FIGS. 2 and 3).

4. Remove New Transcription Factor (TF) Binding Sites, then Repeat Steps 2 a-d

The starting gene sequences for this design step were GRver3 and RDver3. This fourth step is an iteration of the process described in step 3. The search for newly introduced TF binding sites yielded about 50 hits for each of the two synthetic genes. All sites were eliminated by changing one or more codons of the synthetic gene sequences in general accordance with the codon optimization guidelines described in 1a above. However, more high to medium usage codons were used to allow elimination of all TF binding sites. The lowest priority was placed on maintaining low sequence identity between the GR and RD genes. Then steps 2 a-d were repeated as described. The two output sequences from this fourth design step were named GRver4 and RDver4. Their DNA sequences are 68% identical (506 mismatches) (FIGS. 2 and 3).

5. Remove New Transcription Factor (TF) Binding Sites then Repeat Steps 2a-d

The starting gene sequences for this design step were GRver4 and RDver4. This fifth step is another iteration of the process described in step 3 above. The search for new TF binding sites introduced in step 4 yielded about 20 hits for each of the two synthetic genes. All sites were eliminated by changing one or more codons of the synthetic gene sequences in general accordance with the codon optimization guidelines described in 1a above. However, more high to medium usage codons were used (these are all considered "preferred") to allow elimination of all TF binding sites. The lowest priority was placed on maintaining low sequence identity between the GR and RD genes. Then steps 2a-d were repeated as described. Only one acceptor splice site could not be eliminated. As a final step the absence of all TF binding sites in both genes as specified in step 3 was confirmed. The two output sequences from this fifth and last design step were named GRver5 and RDver5. Their DNA sequences are 69% identical (504 mismatches) (FIGS. 2 and 3).

Additional Evaluation of GRver5 and RDver5
a) Use Lower Stringency Parameters for TESS:

The search for TF binding sites was repeated as described in step 3 above, but with even less stringent user-defined parameters:

setting LLH to 9 instead of 10 did not result in new hits;
setting LLH to 0 through 8 (incl.) resulted in hits for two additional sites, MAMAG (22 hits) and CTKTK (24 hits);
setting LLH to 8 and the minimum element length to 4, the search yielded (in addition to the two sites above) different 4-base sites for AP-1, NF-1, and c-Myb that are shortened versions of their longer respective consensus sites which were eliminated in steps 3-5 above.

It was not realistic to attempt complete elimination of these sites without introduction of new sites, so no further changes were made.

b) Search Different Database:

The Eukaryotic Promoter Database (release 45) contains information about reliably mapped transcription start sites (1253 sequences) of eukaryotic genes. This database was searched using BLASTN 1.4.11 with default parameters (optimized to find nearly identical sequences rapidly; see Altschul et al, 1990) at the National Center for Biotechnology Information site (http://www.ncbi.nlm.nih.gov/cgi-bin/BLAST). To test this approach, a portion of pGL3-Control vector sequence containing the SV40 promoter and enhancer was used as a query sequence, yielding the expected hits to SV40 sequences. No hits were found when using the two synthetic genes as query sequences.

Summary of GRver5 and RDver5 Synthetic Gene Properties

Both genes, which at this stage were still only "virtual" sequences in the computer, have a codon usage that strongly favors mammalian high-usage codons and minimizes mammalian and *E. coli* low-usage codons. FIG. 4 shows a summary of the codon usage of the parent gene and the various synthetic gene versions.

Both genes are also completely devoid of eukaryotic TF binding sites consisting of more than four unambiguous bases, donor and acceptor splice sites (one exception: GRver5 contains one splice acceptor site), poly(A) addition sites, specific prokaryotic (*E. coli*) regulatory sequences, and undesired restriction sites.

The gene sequence identity between GRver5 and RDver5 is only 69% (504 base mismatches) while their encoded proteins are 99% identical (4 amino acid mismatches), see FIGS. 2 and 3. Their identity with the parent sequence YG#81-6G1 is 74% (GRver5) and 73% (RDver5), see FIG. 2. Their base composition is 49.9% GC (GRver5) and 49.5% GC (RDver5), compared to 40.2% GC for the parent YG#81-6G01.

Construction of Synthetic Genes

The two synthetic genes were constructed by assembly from synthetic oligonucleotides in a thermocycler followed by PCR amplification of the full-length genes (similar to Stemmer et al. (1995) *Gene.* 164, pp. 49-53). Unintended mutations that interfered with the design goals of the synthetic genes were corrected.

a) Design of Synthetic Oligonucleotides:

The synthetic oligonucleotides were mostly 40mers that collectively code for both complete strands of each designed gene (1,626 bp) plus flanking regions needed for cloning (1,950 bp total for each gene; FIG. 6). The 5' and 3' boundaries of all oligonucleotides specifying one strand were generally placed in a manner to give an average offset/overlap of 20 bases relative to the boundaries of the oligonucleotides specifying the opposite strand.

The ends of the flanking regions of both genes matched the ends of the amplification primers (pRAMtailup: 5'-gtactgagacgacgccagcccaagcttaggcctgagtg SEQ ID NO:229, and pRAMtaildn: 5'-ggcatgagcgtgaactgactgaactagcggccgccgag SEQ ID NO:230) to allow cloning of the genes into our *E. coli* expression vector pRAM (WO99/14336).

A total of 183 oligonucleotides were designed (FIG. 6): fifteen oligonucleotides that collectively encode the upstream and downstream flanking sequences (identical for both genes; SEQ ID NOs: 35-49) and 168 oligonucleotides (4×42) that encode both strands of the two genes (SEQ ID NOs: 50-217).

All 183 oligonucleotides were run through the hairpin analysis of the OLIGO software (OLIGO 4.0 Primer Analysis Software© 1989-1991 by Wojciech Rychlik) to identify potentially detrimental intra-molecular loop formation. The guidelines for evaluating the analysis results were set according to recommendations of Dr. Sims (Sigma-Genosys Custom Gene Synthesis Department): oligos forming hairpins with $\Delta G<-10$ have to be avoided, those forming hairpins with $\Delta G \leqq -7$ involving the 3' end of the oligonucleotide should also be avoided, while those with an overall $\Delta G \leqq -5$ should not pose a problem for this application. The analysis identified 23 oligonucleotides able to form hairpins with a $\Delta G$ between −7.1 and −4.9. Of these, 5 had blocked or nearly blocked 3' ends (0-3 free bases) and were re-designed by removing 1-4 bases at their 3' end and adding it to the adjacent oligonucleotide.

The 40mer oligonucleotide covering the sequence complementary to the poly(A) tail had a very low complexity 3' end (13 consecutive T bases). An additional 40mer was designed with a high complexity 3' end but a consequently reduced overlap with one of its complementary oligonucleotides (11 instead of 20 bases) on the opposite strand.

Even though the oligos were designed for use in a thermocycler-based assembly reaction, they could also be used in a ligation-based protocol for gene construction. In this approach, the oligonucleotides are annealed in a pairwise fashion and the resulting short double-stranded fragments are ligated using the sticky overhangs. However, this would require that all oligonucleotides be phosphorylated.

b) Gene Assembly and Amplification

In a first step, each of the two synthetic genes was assembled in a separate reaction from 98 oligonucleotides. The total volume for each reaction was 50 µl:
 0.5 µM oligonucleotides (=0.25 pmoles of each oligo)
 1.0 U Taq DNA polymerase
 0.02 U Pfu DNA polymerase
 2 mM $MgCl_2$
 0.2 mM dNTPs (each)
 0.1% gelatin
 Cycling conditions: (94° C. for 30 seconds, 52° C. for 30 seconds, and 72° C. for 30 seconds)×55 cycles.

In a second step, each assembled synthetic gene was amplified in a separate reaction. The total volume for each reaction was 50 µl:
 2.5 l assembly reaction
 5.0 U Taq DNA polymerase
 0.1 U Pfu DNA polymerase
 1 M each primer (pRAMtailup, pRAMtaildn)
 2 mM $MgCl_2$
 0.2 mM dNTPs (each)
 Cycling conditions: (94° C. for 20 seconds, 65° C. for 60 seconds, 72° C. for 3 minutes)×30 cycles.

The assembled and amplified genes were subcloned into the pRAM vector and expressed in E. coli, yielding 1-2% luminescent GR or RD clones. Five GR and five RD clones were isolated and analyzed further. Of the five GR clones, three had the correct insert size, of which one was weakly luminescent and one had an altered restriction pattern. Of the five RD clones, two had the correct size insert with an altered restriction pattern and one of those was weakly luminescent. Overall, the analysis indicated the presence of a large number of mutations in the genes, most likely the result of errors introduced in the assembly and amplification reactions.

c) Corrective Assembly and Amplification

To remove the large number of mutations present in the full-length synthetic genes we performed an additional assembly and amplification reaction for each gene using the proof-reading DNA polymerase Tli. The assembly reaction contained, in addition to the 98 GR or RD oligonucleotides, a small amount of DNA from the corresponding full-length clones with mutations described above. This allows the oligos to correct mutations present in the templates.

The following assembly reaction was performed for each of the synthetic genes. The total volume for each reaction was 50 µl:
 0.5 µM oligonucleotides (=0.25 pmoles of each oligo)
 0.016 pmol plasmid (mix of clones with correct insert size)
 2.5 U Tli DNA polymerase
 2 mM $MgCl_2$
 0.2 mM dNTPs (each)
 0.1% gelatin
 Cycling conditions: 94° C. for 30 seconds, then (94° C. for 30 seconds, 52° C. for 30 seconds, 72° C. for 30 seconds) for 55 cycles, then 72° C. for 5 minutes.

The following amplification reaction was performed on each of the assembly reactions. The total volume for each amplification reaction was 50 µl:
 1-5 µl of assembly reaction
 40 pmol each primer (pRAMtailup, pRAMtaildn)
 2.5 U Tli DNA polymerase
 2 mM $MgCl_2$
 0.2 mM dNTPs (each)
 Cycling conditions: 94° C. for 30 seconds, then (94° C. for 20 seconds, 65° C. for 60 seconds and 72° C. for 3 minutes) for 30 cycles, then 72° C. for 5 minutes.

The genes obtained from the corrective assembly and amplification step were subcloned into the pRAM vector and expressed in E. coli, yielding 75% luminescent GR or RD clones. Forty-four GR and 44 RD clones were analyzed with our screening robot (WO99/14336). The six best GR and RD clones were manually analyzed and one best GR and RD clone was selected (GR6 and RD7). Sequence analysis of GR6 revealed two point mutations in the coding region, both of which resulted in an amino acid substitution (S49N and P230S). Sequence analysis of RD7 revealed three point mutations in the coding region, one of which resulted in an amino acid substitution (H36Y). It was confirmed that none of the silent point mutations introduced any regulatory or restriction sites conflicting with the overall design criteria for the synthetic genes.

d) Reversal of Unintended Amino Acid Substitutions

The unintended amino acid substitutions present in the GR6 and RD7 synthetic genes were reversed by site-directed mutagenesis to match the GRver5 and RDver5 designed sequences, thereby creating GRver5.1 and RDver5.1. The DNA sequences of the mutated regions were confirmed by sequence analysis.

e) Improve Spectral Properties

The RDver5.1 gene was further modified to improve its spectral properties by introducing an amino change (R351G), thereby creating RDver5.2 pGL3 Vectors with RD and GR Genes

The parent click beetle luciferase YG#81-6G1 ("YG"), and the synthetic click beetle luciferase genes GRver5.1 ("GR"), RDver5.2 ("RD"), and RD156-1H9 were cloned into the four pGL3 reporter vectors (Promega Corp.):
 pGL3-Basic=no promoter, no enhancer
 pGL3-Control=SV40 promoter, SV40 enhancer
 pGL3-Enhancer=SV40 enhancer (3' to luciferase coding sequences)
 pGL3-Promoter=SV40 promoter.

The primers employed in the assembly of GR and RD synthetic genes facilitated the cloning of those genes into pRAM vectors. To introduce the genes into pGL3 vectors (Promega Corp., Madison, Wis.) for analysis in mammalian cells, each gene in a pRAM vector (pRAM RDver5.1, pRAM GRver5.1, and pRAM RD156-1H9) was amplified to introduce an Nco I site at the 5' end and an Xba I site at the 3' end of the gene. The primers for pRAM RDver5.1 and pRAM GRver5.1 were:

GR→5' GGA TCC CAT GGT GAA GCG TGA GAA 3' (SEQ ID NO: 231)
or
RD→5' GGA TCC CAT GGT GAA ACG CGA 3' (SEQ ID NO: 232)
and
5' CTA GCT TTT TTT TCT AGA TAA TCA TGA AGA C 3' (SEQ ID NO: 233)

The primers for pRAM RD156-1H9 were:

5' GCG TAG CCA TGG TAA AGC GTG AGA AAA ATG TC 3' (SEQ ID NO: 295)
and
5' CCG ACT CTA GAT TAC TAA CCG CCG GCC TTC ACC 3' (SEQ ID NO: 296)

The PCR included:
  100 ng DNA plasmid
  1 µM primer upstream
  1 µM primer downstream
  0.2 mM dNTPs
  1× buffer (Promega Corp.)
  5 units Pfu DNA polymerase (Promega Corp.)
  Sterile nanopure $H_2O$ to 50 µl The cycling parameters were: 94° C. for 5 minutes; (94° C. for 30 seconds; 55° C. for 1 minute; and 72° C. for 3 minutes)×15 cycles. The purified PCR product was digested with Nco I and Xba I, ligated with pGL3-control that was also digested with Nco I and Xba I, and the ligated products introduced to E. coli. To insert the luciferase genes into the other pGL3 reporter vectors (basic, promoter and enhancer), the pGL3-control vectors containing each of the luciferase genes was digested with Nco I and Xba I, ligated with other pGL3 vectors that also were digested with Nco I and Xba I, and the ligated products introduced to E. coli. Note that the polypeptide encoded by GRver5.1 and RDver5.1 (and RD156-1H9, see below) nucleic acid sequences in pGL3 vectors has an amino acid substitution at position 2 to valine as a result of the Nco I site at the initiation codon in the oligonucleotide.

Because of internal Nco I and Xba I sites, the native gene in YG #81-6G01 was amplified from a Hind III site upstream to a Hpa I site downstream of the coding region and which included flanking sequences found in the GR and RD clones. The upstream primer (5'-CAA AAA GCT TGG CAT TCC GGT ACT GTT GGT AAA GCC ACC ATG GTG AAG CGA GAG-3'; SEQ ID NO:234) and a downstream primer (5'-CAA TTG TTG TTG TTA ACT TGT TTA TT-3'; SEQ ID NO:235) were mixed with YG#81-6G01 and amplified using the PCR conditions above. The purified PCR product was digested with Nco I and Xba I, ligated with pGL3-control that was also digested with Hind III and Hpa I, and the ligated products introduced into E. coli. To insert YG#81-6G01 into the other pGL3 reporter vectors (basic, promoter and enhancer), the pGL3-control vectors containing YG#81-6G01 were digested with Nco I and Xba I, ligated with the other pGL3 vectors that also were digested with Nco I and Xba I, and the ligated products introduced to E. coli. Note that the clone of YG#81-6G01 in the pGL3 vectors has a C instead of an A at base 786, which yields a change in the amino acid sequence at residue 262 from Phe to Leu (FIG. 2 shows the sequence of YG#81-6G01 prior to introduction into pGL3 vectors). To determine whether the altered amino acid at position 262 affected the enzyme biochemistry, the clone of YG#81-6G01 was mutated to resemble the original sequence. Both clones were then tested for expression in E. coli, physical stability, substrate binding, and luminescence output kinetics. No significant differences were found.

Partially purified enzymes expressed from the synthetic genes and the parent gene were employed to determine Km for luciferin and ATP (see Table 3).

TABLE 3

| Enzyme | $K_M(LH_2)$ | $K_M(ATP)$ |
| --- | --- | --- |
| YG parent | 2 µM | 17 µM |
| GR | 1.3 µM | 25 µM |
| RD | 24.5 µM | 46 µM |

In vitro eukaryotic transcription/translation reactions were also conducted using Promega's TNT T7 Quick system according to manufacturer's instructions. Luminescence levels were 1 to 37-fold and 1 to 77-fold higher (depending on the reaction time) for the synthetic GR and RD genes, respectively, compared to the parent gene (corrected for luminometer spectral sensitivity).

To test whether the synthetic click beetle luciferase genes and the wild type click beetle gene have improved expression in mammalian cells, each of the synthetic genes and the parent gene was cloned into a series of pGL3 vectors and introduced into CHO cells (Table 8). In all cases, the synthetic click beetle genes exhibited a higher expression than the native gene. Specifically, expression of the synthetic GR and RD genes was 1900-fold and 40-fold higher, respectively, than that of the parent (transfection efficiency normalized by comparison to native Renilla luciferase gene). Moreover, the data (basic versus control vector) show that the synthetic genes have reduced basal level transcription.

Further, in experiments with the enhancer vector where the percentage of activity in reference to the control is compared between the native and synthetic gene, the data showed that the synthetic genes have reduced risk of anomalous transcription characteristics. In particular, the parent gene appeared to contain one or more internal transcriptional regulatory sequences that are activated by the enhancer in the vector, and thus is not suitable as a reporter gene while the synthetic GR and RD genes showed a clean reporter response (transfection efficiency normalized by comparison to native Renilla luciferase gene). See Table 9.

The clone names and their corresponding SEQ ID numbers for nucleotide sequence and amino acid sequence are listed below in Table 4.

TABLE 4

| Clone name | Luciferase Type | SEQ ID NO. | SEQ ID NO. |
| --- | --- | --- | --- |
| LUCPPLYG | Wild type YG Click Beetle | 1 | 23 |
| YG#81-6G01 | Mutant YG Click Beetle | 2 | 24 |
| GRver1 | Synthetic Green Click Beetle | 3 | 25 |
| GRver2 | Synthetic Green Click Beetle | 4 | 26 |
| GRver3 | Synthetic Green Click Beetle | 5 | 27 |
| GRver4 | Synthetic Green Click Beetle | 6 | 28 |
| GRver5 | Synthetic Green Click Beetle | 7 | 29 |
| GR6 | Synthetic Green Click Beetle | 8 | 30 |
| GRver5.1 | Synthetic Green Click Beetle | 9 | 31 |
| RDver1 | Synthetic Red Click Beetle | 10 | 32 |
| RDver2 | Synthetic Red Click Beetle | 11 | 33 |
| RDver3 | Synthetic Red Click Beetle | 12 | 34 |
| RDver4 | Synthetic Red Click Beetle | 13 | 218 |

TABLE 4-continued

| Clone name | Luciferase Type | SEQ ID NO. | SEQ ID NO. |
|---|---|---|---|
| RDver5 | Synthetic Red Click Beetle | 14 | 219 |
| RD7 | Synthetic Red Click Beetle | 15 | 220 |
| RDver5.1 | Synthetic Red Click Beetle | 16 | 221 |
| RDver5.2 | Synthetic Red Click Beetle | 17 | 222 |
| RD156-1H9 | Synthetic Red Click Beetle | 18 | 223 |
| RELLUC | Wild type Renilla | 19 | 224 |
| Rlucver1 | Synthetic Renilla | 20 | 225 |
| Rlucver2 | Synthetic Renilla | 21 | 226 |
| Rluc-final | Synthetic Renilla | 22 | 227 |

EXAMPLE 2

Evolution of the RD Luciferase Gene

RDver5.2 was mutated to increase its luminescence intensity, thereby creating RD156-1H9 which carries four additional amino acid changes (M2I, S349T, K488T, E538V) and three silent point mutations (SEQ ID NO:18).

a) Site-Directed Mutagenesis:

The initial strategy was to use site-directed mutagenesis. There are four amino acid differences between the GR and RD synthetic genes with H348Q providing the greatest contribution to red color. Thus, this substitution may also cause structural changes in the protein that could lead to low light output. Optimization of positions near this area could increase light output. The following positions were selected for mutagenesis:

1. S344 (at the edge of the binding pocket for luciferin)—randomize this codon.
2. A245 (strictly conserved but closest to 348 and at the edge of the active site pocket)—randomize this codon.
3. I347 (not conserved, next to 348 in sequence)—mutate to hydrophobic amino acids only.
4. S349 (not conserved, next to 348 in sequence)—mutate to S, T, A, P only.

Oligonucleotides designed to mutate the above positions were used in a site-directed mutagenesis experiment (WO99/14336) and the resulting mutants were screened for luminescence intensity. There was little variation in light intensity and only about 25% were luminescent. For more detailed analysis, clones were picked and analyzed with the screening robot (PCT/WO99/14336). None of the clones had a luminescence intensity (LI) higher than RDver5.2, but four of the clones had slightly lower composite Km for luciferin and ATP (Km).

b) Directed Evolution:

Protocols and procedures used for the directed evolution are detailed in see PCT/WO9914336. DNA from the four clones with lower Km was combined and three libraries of random mutants were produced. The libraries were screened with the robot and clones with the highest LI values were selected. These clones were shuffled together and another robotic screen was completed with an incubation temperature of 46° C. The three clones with the highest LI values were RD156-0B4, RD156-1A5, and RD156-1H9.

c) Analysis:

The three clones with the highest LI values were selected for manual analysis to confirm that their luminescence intensity was higher than that of RDver5.2 and to ensure that their spectral properties were not compromised. One of the clones was slightly green-shifted, all others maintained the spectral properties of RDver5.2 (Table 5).

TABLE 5

| Clone | Peak (nm) | Width (nm) |
|---|---|---|
| RD156-0B4 | 616 | 68 |
| RD156-1A5 | 614 | 70 |
| RD156-1H9 | 618 | 69 |
| RDver5.2 (prep #1) | 617 | 70 |
| RDver5.2 (prep #2) | 618 | 69 |

The Km values for luciferin and the luminescence intensity relative to RDver5.2 were determined for all three clones in several independent experiments. All cells samples were processed with CCLR lysis buffer (E1483, Promega Corp., Madison, Wis.) and diluted 1:10 into buffer (25 mM HEPES pH 7.8, 5% glycerol, 1 mg/ml BSA, 150 mM NaCl). Table 7 summarizes the results (Lum: luminescence values were normalized to optical density; measurements for independent experiments are separated by forward slashes) from expression in bacterial cells. RD156-1H9, the clone with the highest luminescence intensity (5 to 10-fold increase) also has an about 2-fold higher Km for luciferin.

TABLE 6

| Clone | Km Luciferin [µM] | Lum (normalized to RDver5.2) |
|---|---|---|
| RD156-0B4 | 8/10 | 2.2/2.5 |
| RD156-1A5 | 13/13 | 3.1/5.6 |
| RD156-1H9 | 20/23/23 | 4/10.9/7.5 |
| RDver5.2 (prep #1) | 12/14/14 | |
| RDver5.2 (prep #2) | 40/50 | |
| GRver5.1 (prep #1) | 0.5 | 64 |
| GRver5.1 (prep #2) | 3 | |

Table 7 shows a comparison between the luminescence intensities of RD156-1H9, GRver5.1 and RDver5.2 normalized to GRver5.1 with and without correction for the spectral sensitivity of the luminometer photomultiplier tube. With correction, the luminescence intensity of clone RD156-1H9 was only about 2-fold lower than that of GRver5.1. The luciferin K for clone RD156-1H9 is approximately 40-fold higher than GRver5.1. RD156-1H9 is thermostable at 50° C. for at least 2 hours.

TABLE 7

| Name | No Correction | With Correction |
|---|---|---|
| RDver5.2 | 0.016 | 0.06 |
| GRver5.1 | 1.000 | 1.00 |
| RD156-1H9 | 0.116 | 0.45 |

Tables 8 and 9 show a comparison of luciferase expression levels in CHO cells. Table 8 shows the expression levels only from the control vectors in comparison to the firefly luciferase gene (RLU=relative light units). Table 9 shows a comparison of the expression levels in all four pGL3 vectors calculated as a percent of the expression level in pGL3-control.

TABLE 8

| Synthetic Click Beetle Gene Expression | |
|---|---|
| Control vector | rlu |
| YG#81-6G01 | 177 |
| GRver5.1 | 343,417 |
| RDver5.1 | 7,161 |

TABLE 8-continued

Synthetic Click Beetle Gene Expression

| Control vector | rlu |
|---|---|
| RD156-1H9 | 20,802 |
| FireFly | 488,016 |

TABLE 9

Synthetic Click Beetle Gene Expression

| Vector | Percent of control vector |
|---|---|
| YG-control | 100 |
| RD-control | 100 |
| GR-control | 100 |
| RD156-1H9 control | 100 |
| YG-basic | 3.3 |
| RD-basic | 1.0 |
| GR-basic | 0.2 |
| RD156-1H9 basic | 0.3 |
| YG-promoter | 4.2 |
| RD-promoter | 15.1 |
| GR-promoter | 5.7 |
| RD156-1H9 promoter | 15.5 |
| YG-enhancer | 51.5 |
| RD-enhancer | 2.8 |
| GR-enhancer | 1.4 |
| RD156-1H9 enhancer | 0.3 |

EXAMPLE 3

Synthetic *Renilla* Luciferase Nucleic Acid Molecule

The synthetic *Renilla* luciferase genes prepared include 1) an introduced Kozak sequence, 2) codon usage optimized for mammalian (human) expression, 3) a reduction or elimination of unwanted restriction sites, 4) removal of prokaryotic regulatory sites (ribosome binding site and TATA box), 5) removal of splice sites and poly(A) addition sites, and 6) a reduction or elimination of mammalian transcriptional factor binding sequences.

The process of computer-assisted design of synthetic *Renilla* luciferase genes by iterative rounds of codon optimization and removal of transcription factor binding sites and other regulatory sites as well as restriction sites can be described in three steps:

1. Using the wild type *Renilla* luciferase gene as the parent gene, codon usage was optimized, one amino acid was changed (T→A) to generate a Kozak consensus sequence, and undesired restriction sites were eliminated thereby creating synthetic gene Rlucver1.
2. Remove prokaryotic regulatory sites, splice sites, poly(A) sites and transcription factor (TF) binding sites (first pass). Then remove newly created TF binding sites. Then remove newly created undesired restriction enzyme sites, prokaryotic regulatory sites, splice sites, and poly(A) sites without introducing new TF binding sites. This thereby created Rlucver2.
3. Change 3 bases of Rlucver2 thereby creating Rluc-final.
4. The actual gene was then constructed from synthetic oligonucleotides corresponding to the Rluc-final designed sequence. All mutations resulting from the assembly or PCR process were corrected. This gene is Rluc-final (SEQ ID NO:22) and encodes the amino acid sequence of SEQ ID NO:227.

Codon Selection

Starting with the *Renilla reniformis* luciferase sequence in Genbank (Accession No. M63501, SEQ ID NO:19), codons were selected based on codon usage for optimal expression in human cells and to avoid *E. coli* low-usage codons. The best codon for expression in human cells (or the best two codons if found at a similar frequency) was chosen for all amino acids with more than one codon (Wada et al., 1990):

| | |
|---|---|
| Arg: CGC | Lys: AAG |
| Leu: CTG | Asn: AAC |
| Ser: TCT/AGC | Gln: CAG |
| Thr: ACC | His: CAC |
| Pro: CCA/CCT | Glu: GAG |
| Ala: GCC | Asp: GAC |
| Gly: GGC | Tyr: TAC |
| Val: GTG | Cys: TGC |
| Ile: ATC/ATT | Phe: TTC |

In cases where two codons were selected for one amino acid, they were used in an alternating fashion. To meet other criteria for the synthetic gene, the initial optimal codon selection was modified to some extent later. For example, introduction of a Kozak sequence required the use of GCT for Ala at amino acid position 2 (see below).

The following low-usage codons in mammalian cells were not used unless needed: Arg: CGA, CGU; Leu: CTA, UUA; Ser: TCG; Pro: CCG; Val: GTA; and Ile: ATA. The following low-usage codons in *E. coli* were also avoided when reasonable (note that 3 of these match the low-usage list for mammalian cells): Arg: CGA/CGG/AGA/AGG, Leu: CTA; Pro: CCC; Ile: ATA.

Introduction of Kozak Sequences

The Kozak sequence: 5' aaccATGGCT 3' (SEQ ID NO: 293) (the Nco I site is underlined, the coding region is shown in capital letters) was introduced to the synthetic *Renilla* luciferase gene. The introduction of the Kozak sequence changes the second amino acid from Thr to Ala (GCT).

Removal of Undesired Restriction Sites

REBASE ver. 808 (updated Aug. 1, 1998; Restriction Enzyme Database; www.neb.com/rebase) was employed to identify undesirable restriction sites as described in Example 1. The following undesired restriction sites (in addition to those described in Example 1) were removed according to the process described in Example 1: EcoICR 1, NdeI, NsiI, SphI, SpeI, XmaI, PstI.

The version of *Renilla* luciferase (Rluc) which incorporates all these changes is Rlucver1.

Removal of Prokaryotic (*E. coli*) Regulatory Sequences, Splice Sites, and Poly(A) Sites The priority and process for eliminating transcription regulation sites was as described in Example 1.

Removal of TF Binding Sites

The same process, tools, and criteria were used as described in Example 1, however, the newer version 3.3 of the TRANSFAC database was employed.

After removing prokaryotic regulatory sequences, splice sites and poly(A) sites from Rlucver1, the first search for TF binding sites identified about 60 hits. All sites were eliminated with the exception of three that could not be removed without altering the amino acid sequence of the synthetic *Renilla* gene:

1. site at position 63 composed of two codons for W (T GGTGG), for CAC-binding protein T00076;
2. site at position 522 composed of codons for KMV (A ANATG GTN), for myc-DF1 T00517;
3. site at position 885 composed of codons for EMG (G ARATG GGN), for myc-DF1 T00517.

The subsequent second search for (newly introduced) TF binding sites yielded about 20 hits. All new sites were eliminated, leaving only the three sites described above. Finally, any newly introduced restriction sites, prokaryotic regulatory sequences, splice sites and poly(A) sites were removed without introducing new TF binding sites if possible.

Rlucver2 was obtained (SEQ ID Nos. 21 and 226).

As in Example 1, lower stringency search parameters were specified for the TESS filtered string search to further evaluate the synthetic *Renilla* gene.

With the LLH reduced from 10 to 9 and the minimum element length reduced from 5 to 4, the TESS filtered string search did not show any new hits. When, in addition to the parameter changes listed above, the organism classification was expanded from "mammalia" to "chordata", the search yielded only four more TF binding sites. When the Min LLH was further reduced to between 8 and 0, the search showed two additional 5-base sites (MAMAG and CTKTK) which combined had four matches in Rlucver2, as well as several 4-base sites. Also as in Example 1, Rlucver2 was checked for hits to entries in the EPD (Eukaryotic Promoter Database, Release 45). Three hits were determined (one to *Mus musculus* promoter H-2L^d (*Cell*, 44, 261 (1986), one to Herpes Simplex Virus type 1 promoter b'g'2.7 kb, and one to *Homo sapiens* DHFR promoter (*J. Mol. Biol.*, 176, 169 (1984)). However, no further changes were made to Rlucver2.

Summary of Properties for Rlucver2
- All 30 low usage codons were eliminated. The introduction of a Kozak sequence changed the second amino acid from Thr to Ala;
- base composition: 55.7% GC (Renilla wild-type parent gene: 36.5%);
- one undesired restriction site could not be eliminated: EcoR V at position 488;
- the synthetic gene had no prokaryotic promoter sequence but one potentially functional ribosome binding site (RBS) at positions 867-73 (about 13 bases upstream of a Met codon) could not be eliminated;
- all poly(A) addition sites were eliminated;
- splice sites: 2 donor splice sites could not be eliminated (both share the amino acid sequence MGK);
- TF sites: all sites with a consensus of >4 unambiguous bases were eliminated (about 280 TF binding sites were removed) with 3 exceptions due to the preference to avoid changes to the amino acid sequence.

Synthetic *Renilla* luciferase sequences are shown in FIGS. 7 and 8. A codon usage comparison is shown in FIG. 9.

When introduced into pGL3, Rluc-final has a Kozak sequence (CACCATGGCT). The changes in Rluc-final relative to Rlucver2 were introduced during gene assembly. One change was at position 619, a C to an A, which eliminated a eukaryotic promoter sequence and reduced the stability of a hairpin structure in the corresponding oligonucleotide employed to assemble the gene. Other changes included a change from CGC to AGA at positions 218-220 (resulted in a better oligonucleotide for PCR).

Gene Assembly Strategy

The gene assembly protocol employed for the synthetic *Renilla* luciferase was similar to that described in Example 1. The oligonucleotides employed are shown in FIG. 10.

Sense Strand primer:
(SEQ ID NO: 236)
5' AACCATGGCTTCCAAGGTGTACGACCCCGAGCAACGCAAA 3'

Anti-sense Strand primer:
(SEQ ID NO: 237)
5' GCTCTAGAATTACTGCTCGTTCTTCAGCACGCGCTCCACG 3'

The resulting synthetic gene fragment was cloned into a pRAM vector using Nco I and Xba I. Two clones having the correct size insert were sequenced. Four to six mutations were found in the synthetic gene from each clone. These mutations were fixed by site-directed mutagenesis (Gene Editor from Promega Corp., Madison, Wis.) and swapping the correct regions between these two genes. The corrected gene was confirmed by sequencing.

Other Vectors

To prepare an expression vector for the synthetic *Renilla* luciferase gene in a pGL-3 control vector backbone, 5 µg of pGL3-control was digested with Nco I and Xba I in 50 µl final volume with 2 µl of each enzyme and 5 µl 10× buffer B (nanopure water was used to fill the volume to 50 µl). The digestion reaction was incubated at 37° C. for 2 hours, and the whole mixture was run on a 1% agarose gel in 1XTAE. The desired vector backbone fragment was purified using Qiagen's QIAquick gel extraction kit.

The native *Renilla* luciferase gene fragment was cloned into pGL3-control vector using two oligonucleotides, Nco I-RL-F and Xba I-RL-R, to PCR amplify native *Renilla* luciferase gene using pRL-CMV as the template. The sequence for Nco I-RL-F is 5'-CGCTAGCCATGGCTTC-GAAAGTTTATGATCC-3' (SEQ ID NO:238); the sequence for Xba I-RL-R is 5' GGCCAGTAACTCTAGAATTAT-TGTT-3' (SEQ ID NO:239). The PCR reaction was carried out as follows:

Reaction mixture (for 100 µl):

| DNA template (Plasmid) | 1.0 µl (1.0 ng/µl final) |
| 10 X Rec. Buffer | 10.0 µl (Stratagene Corp.) |
| dNTPs (25 mM each) | 1.0 µl (final 250 µM) |
| Primer 1 (10 µM) | 2.0 µl (0.2 µM final) |
| Primer 2 (10 µM) | 2.0 µl (0.2 µM final) |
| Pfu DNA Polymerase | 2.0 µl (2.5 U/µl, Stratagene Corp.) |
| | 82.0 µl double distilled water |

PCR Reaction: heat 94° C. for 2 minutes; (94° C. for 20 seconds; 65° C. for 1 minute; 72° C. for 2 minutes; then 72° C. for 5 minutes)×25 cycles, then incubate on ice. The PCR amplified fragment was cut from a gel, and the DNA purified and stored at −20° C.

To introduce native *Renilla* luciferase gene fragment into pGL3-control vector, 5 µg of the PCR product of the native *Renilla* luciferase gene (RAM-RL-synthetic) was digested with Nco I and Xba I. The desired *Renilla* luciferase gene fragment was purified and stored at −20° C.

Then 100 ng of insert and 100 ng of pGL3-control vector backbone were digested with restriction enzymes Nco I and Xba I and ligated together. Then 2 µl of the ligation mixture was transformed into JM109 competent cells. Eight ampicillin resistance clones were picked and their DNA isolated. DNA from each positive clone of pGL3-control-native and pGL3-control-synthetic was purified. The correct sequences for the native gene and the synthetic gene in the vectors were confirmed by DNA sequencing.

To determine whether the synthetic *Renilla* luciferase gene has improved expression in mammalian cells, the gene was cloned into the mammalian expression vector pGL3-control vector under the control of SV40 promoter and SV40 early enhancer (FIG. 13A). The native *Renilla* luciferase gene was also cloned into the pGL-3 control vector so that the expression from synthetic gene and the native gene could be compared. The expression vectors were then transfected into four common mammalian cell lines (CHO, NIH3T3, Hela and CV-1; Table 10), and the expression levels compared between the vectors with the synthetic gene versus the native gene. The amount of DNA used was at two different levels to ascertain that expression from the synthetic gene is consistently increased at different expression levels. The results show a 70-600 fold increase of expression for the synthetic *Renilla* luciferase gene in these cells (Table 10).

TABLE 10

Enhanced Synthetic *Renilla* Gene Expression

| Cell Type | Amount Vector | Fold Expression Increase |
|---|---|---|
| CHO | 0.2 µg | 142 |
|  | 2.8 µg | 145 |
| NIH3T3 | 0.2 µg | 326 |
|  | 2.0 µg | 593 |
| HeLa | 0.2 µg | 185 |
|  | 1.0 µg | 103 |
| CV-1 | 0.2 µg | 68 |
|  | 2.0 µg | 72 |

Figure 14:
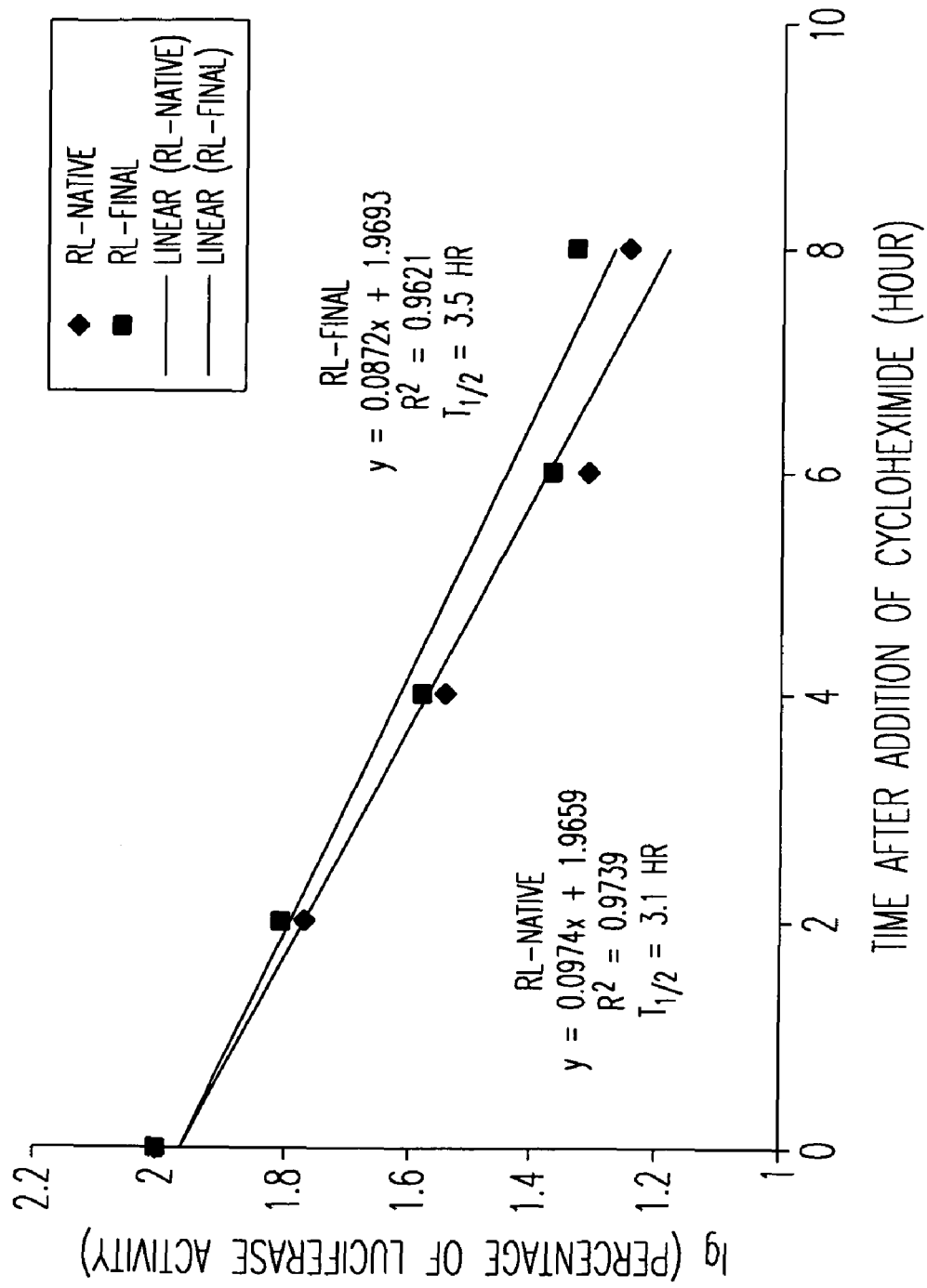
FIG. 14. Half-life of synthetic (Rluc-final) and native *Renilla* luciferases in CHO cells.

One important advantage of luciferase reporter is its short protein half-life. The enhanced expression could also result from extended protein half-life and, if so, this gives an undesired disadvantage of the new gene. This possibility is ruled out by a cycloheximide chase ("CHX Chase") experiment (FIG. 14), which demonstrated that there was no increase of protein half-life resulted from the humanized *Renilla* luciferase gene.

Figure 13B:
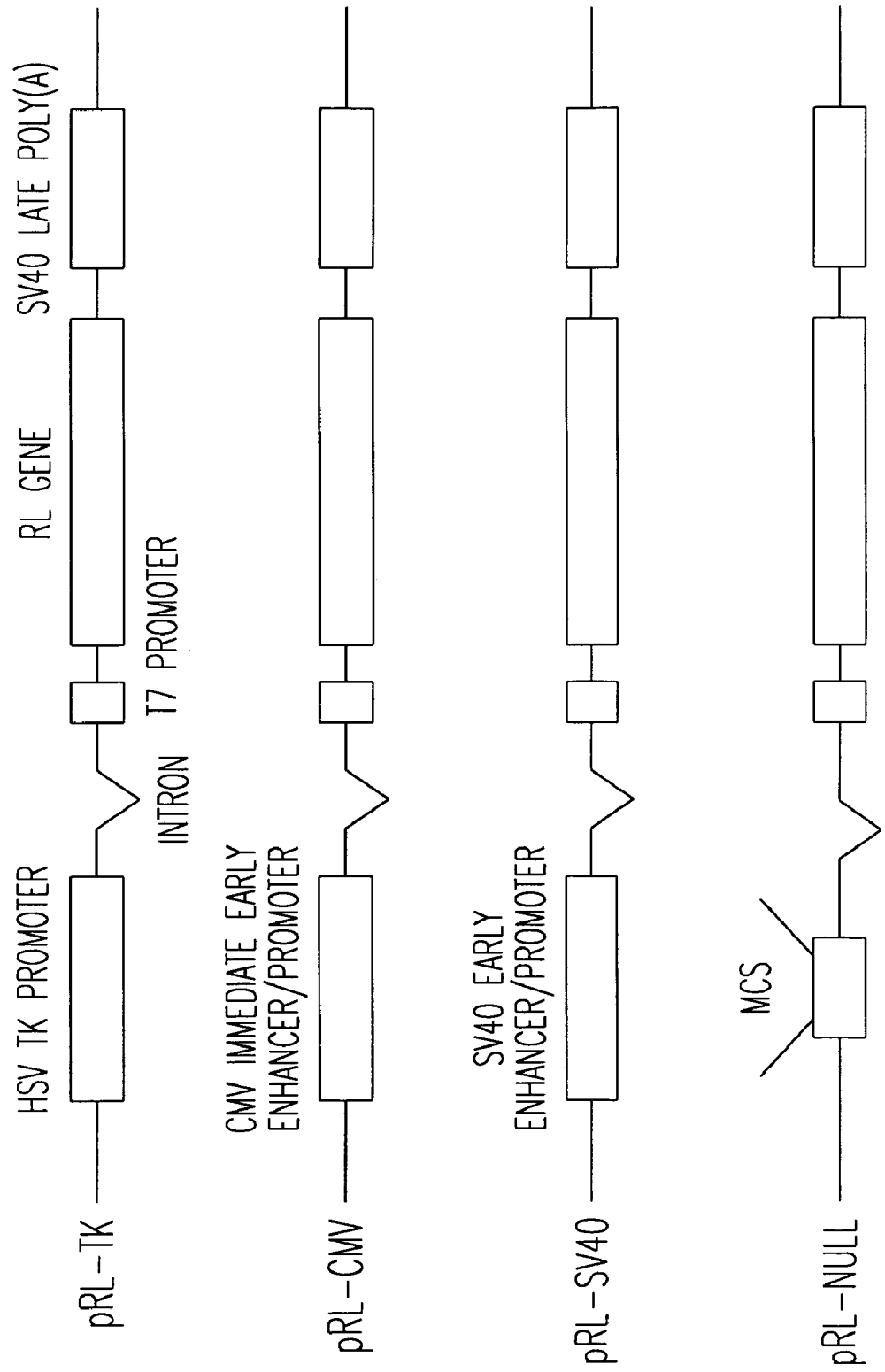
FIG. 13B illustrates the *Renilla* luciferase co-reporter vector series. pRL-TK has the herpes simplex virus (HSV) tk promoter; pRL-SV40 has the SV40 virus early enhancer/promoter; pRL-CMV has the cytomegalovirus (CMV) enhancer and immediate early promoter; pRL-null has MCS (multiple cloning sites) but no promoter or enhancer; pRL-TK(Int⁻) has HSV/tk promoter without an intron that is present in the other plasmids; pR-GL3B has the pGL-3 Basic backbone (Promega Corp.); pR-GL3 TK has the pGL3-Basic backbone with an HSV tk promoter.
Figure 13C:
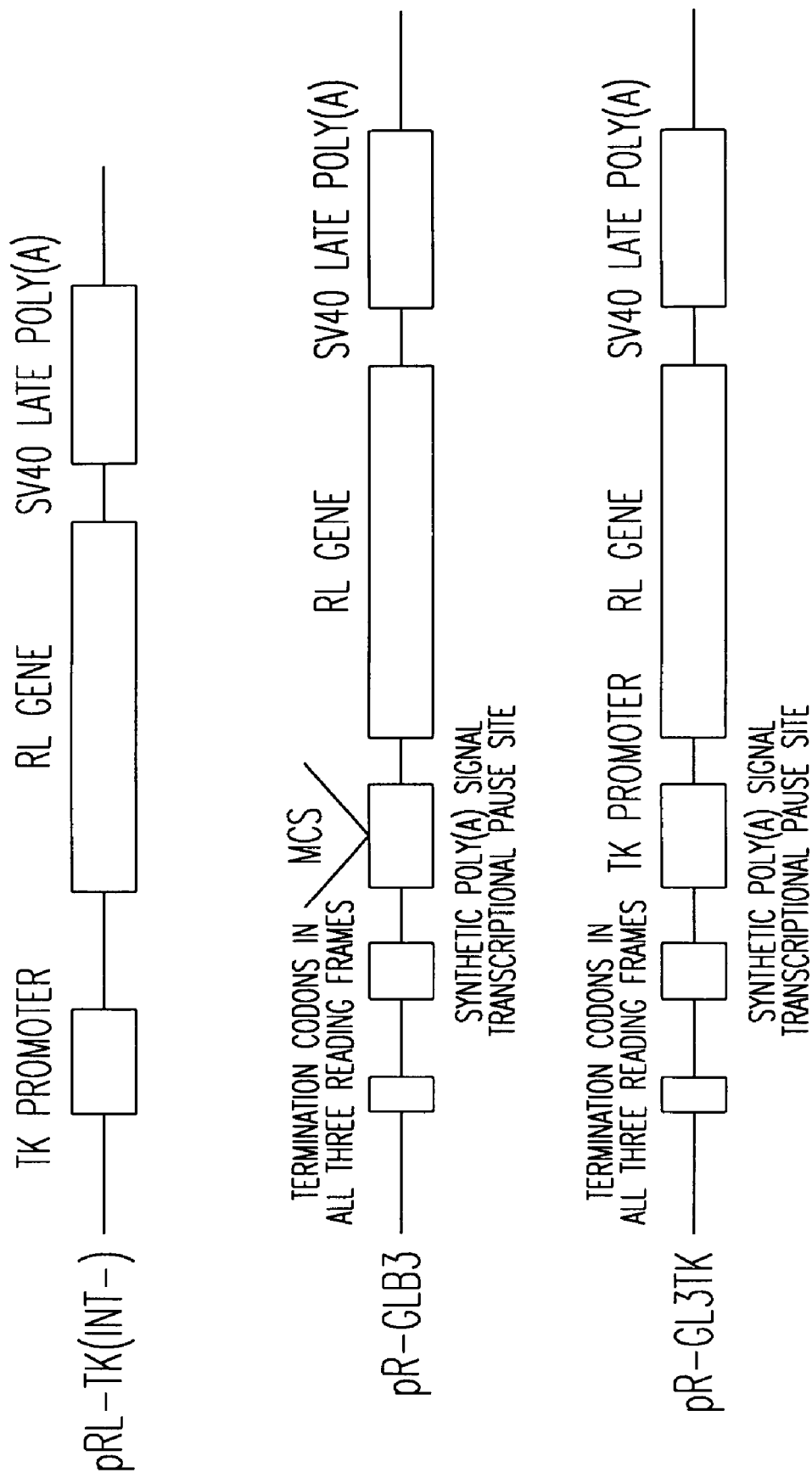
FIG. 13. pRL vector series. All of the vectors contain the *Renilla* wild type or synthetic gene as further described herein.

To ensure that the increase in expression is not limited to one expression vector backbone, is promoter specific and/or cell specific, a synthetic *Renilla* gene (Rluc-final) as well as native *Renilla* gene were cloned into different vector backbones and under different promoters (FIG. 13B). The synthetic gene always exhibited increased expression compared to its wild-type counterpart (Table 11).

TABLE 11

*Renilla* Gene Expression: native v. synthetic (Rluc-final)

| Vector | NIH-3T3 | HeLa | CHO |
|---|---|---|---|
| pRL-tk, native | 3,834.6 | 922.4 | 7,671.9 |
| pRL-tk, synthetic | 13,252.5 | 9,040.2 | 41,743.5 |
| pRL-CMV, native | 168,062.2 | 842,482.5 | 153,539.5 |
| pRL-CMV, synthetic | 2,168,129 | 8,440,306 | 2,532,576 |
| pRL-SV40, native | 224,224.4 | 346,787.6 | 85,323.6 |
| pRL-SV40, synthetic | 1,469,588 | 2,632,510 | 1,422,830 |
| pRL-null, native | 2,853.8 | 431.7 | 2,434 |
| pRL-null, synthetic | 9,151.17 | 2,439 | 28,317.1 |
| pRGL3b, native | 12 | 21.8 | 17 |
| pRGL3b, synthetic | 130.5 | 212.4 | 1,094.5 |
| pRGL3-tk, native | 27.9 | 155.5 | 186.4 |
| pRGL3-tk, synthetic | 6,778.2 | 8,782.5 | 9,685.9 |
| pRL-tk no intron, native | 31.8 | 165 | 93.4 |
| pRL-tk no intron, synthetic | 6,665.5 | 6,379 | 21,433.1 |

TABLE 12

*Renilla* Luciferase Expression in Mammalian Cells

| | Percent of control vector | | |
|---|---|---|---|
| Vector | CHO cells | NIH3T3 cells | HeLa cells |
| pRL-control native | 100 | 100 | 100 |
| pRL-control synthetic | 100 | 100 | 100 |
| pRL-basic native | 4.1 | 5.6 | 0.2 |
| pRL-basic synthetic | 0.4 | 0.1 | 0.0 |
| pRL-promoter native | 5.9 | 7.8 | 0.6 |
| pRL-promoter synthetic | 15.0 | 9.9 | 1.1 |
| pRL-enhancer native | 42.1 | 123.9 | 52.7 |
| pRL-enhancer synthetic | 2.6 | 1.5 | 5.4 |

(Vector BACKBONES Illustrated in FIG. 13a)

With reduced spurious expression the synthetic gene should exhibit less basal level transcription in a promoterless vector. The synthetic and native *Renilla* luciferase genes were cloned into the pGL3-basic vector to compare the basal level of transcription. Because the synthetic gene itself has increased expression efficiency, the activity from the promoterless vector cannot be compared directly to judge the difference in basal transcription, rather, this is taken into consideration by comparing the percentage of activity from the promoterless vector in reference to the control vector (expression from the basic vector divided by the expression in the fully functional expression vector with both promoter and enhancer elements). The data demonstrate that the synthetic *Renilla* luciferase has a lower level of basal transcription than the native gene (Table 12)

It is well known to those skilled in the art that an enhancer can substantially stimulate promoter activity. To test whether the synthetic gene has reduced risk of inappropriate transcriptional characteristics, the native and synthetic gene were introduced into a vector with an enhancer element (pGL3-enhancer vector). Because the synthetic gene has higher expression efficiency, the activity of both cannot be compared directly to compare the level of transcription in the presence of the enhancer, however, this is taken into account by using the percentage of activity from enhancer vector in reference to the control vector (expression in the presence of enhancer divided by the expression in the fully functional expression vector with both promoter and enhancer elements). Such results show that when native gene is present, the enhancer alone is able to stimulate transcription from 42-124% of the control, however, when the native gene is replaced by the synthetic gene in the same vector, the activity only constitutes 1-5% of the value when the same enhancer and a strong SV40 promoter are employed. This clearly demonstrates that synthetic gene has reduced risk of spurious expression (Table 12).

Figure 15A:
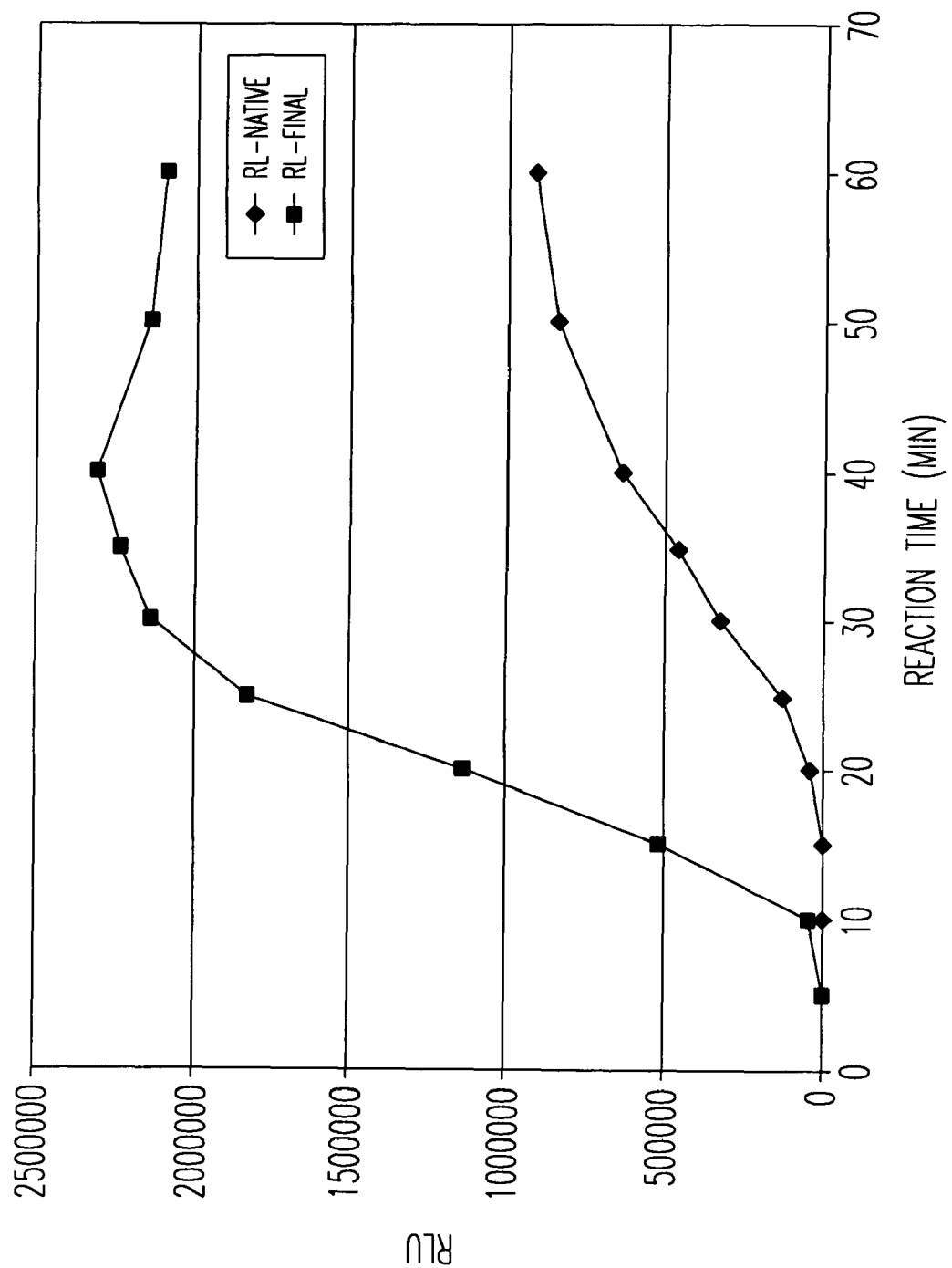
FIGS. 15A-B. In vitro transcription/translation of *Renilla* luciferase nucleic acid sequences. A) t=0-60 minutes; B) linear range.
Figure 15B:
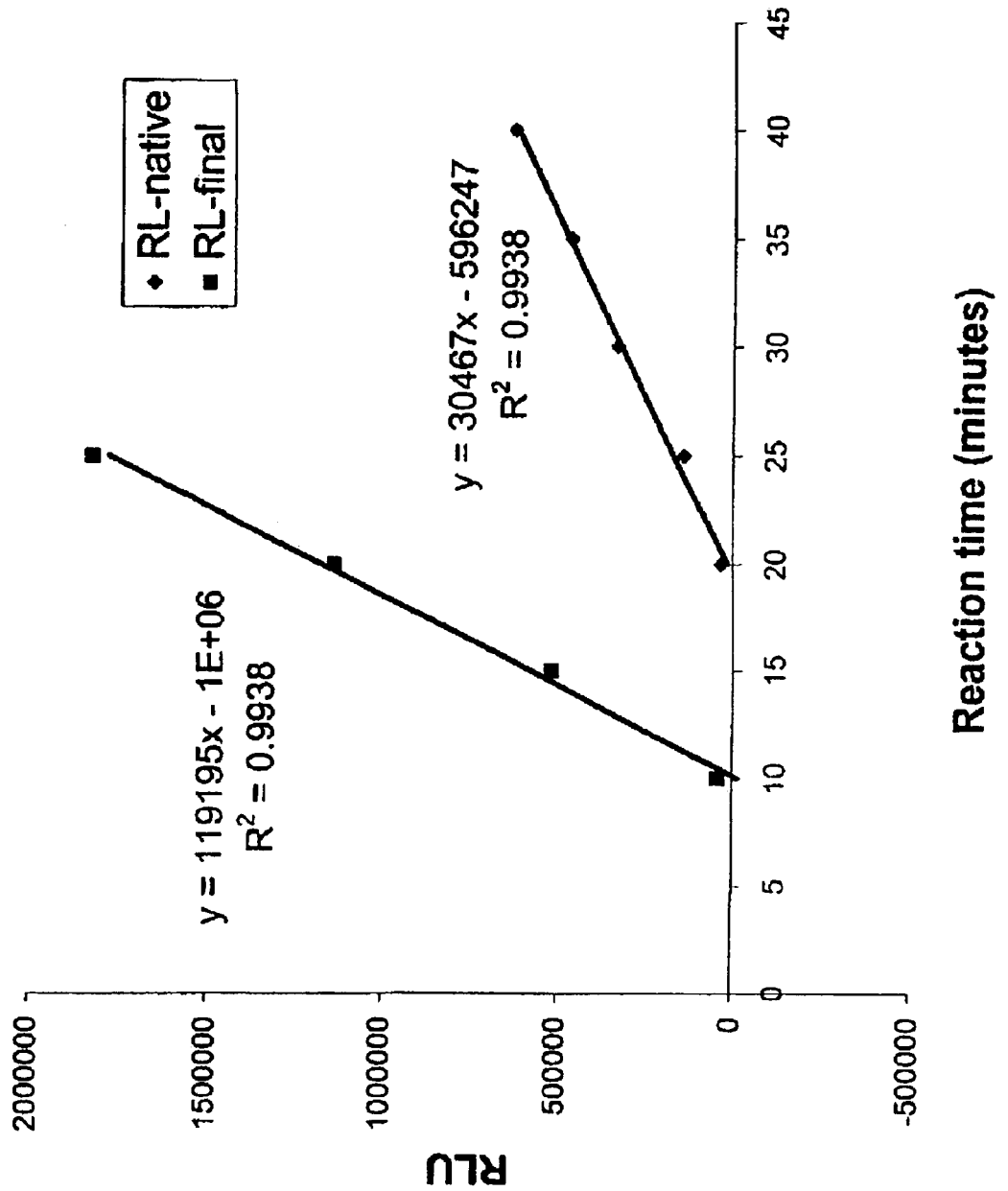
Figure 15C:
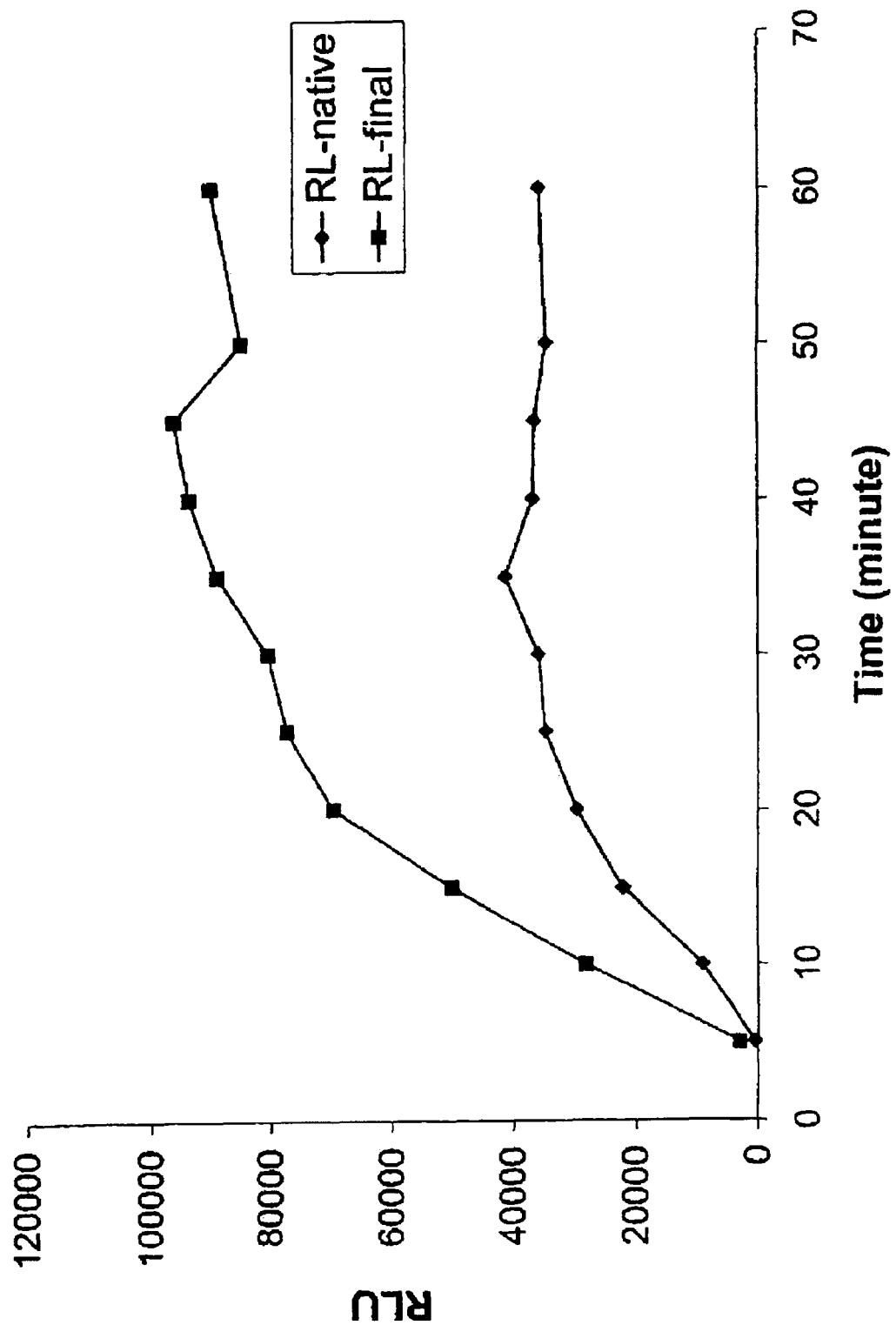
FIGS. 15C-D. In vitro translation of native and synthetic (Rluc-final) *Renilla* luciferase RNAs in a rabbit reticulocyte lysate. RNA was quantitated and the same amount was employed as in the translation reaction shown in FIGS. 15A-B. C) t=0-60 minutes; D) linear range.
Figure 15D:
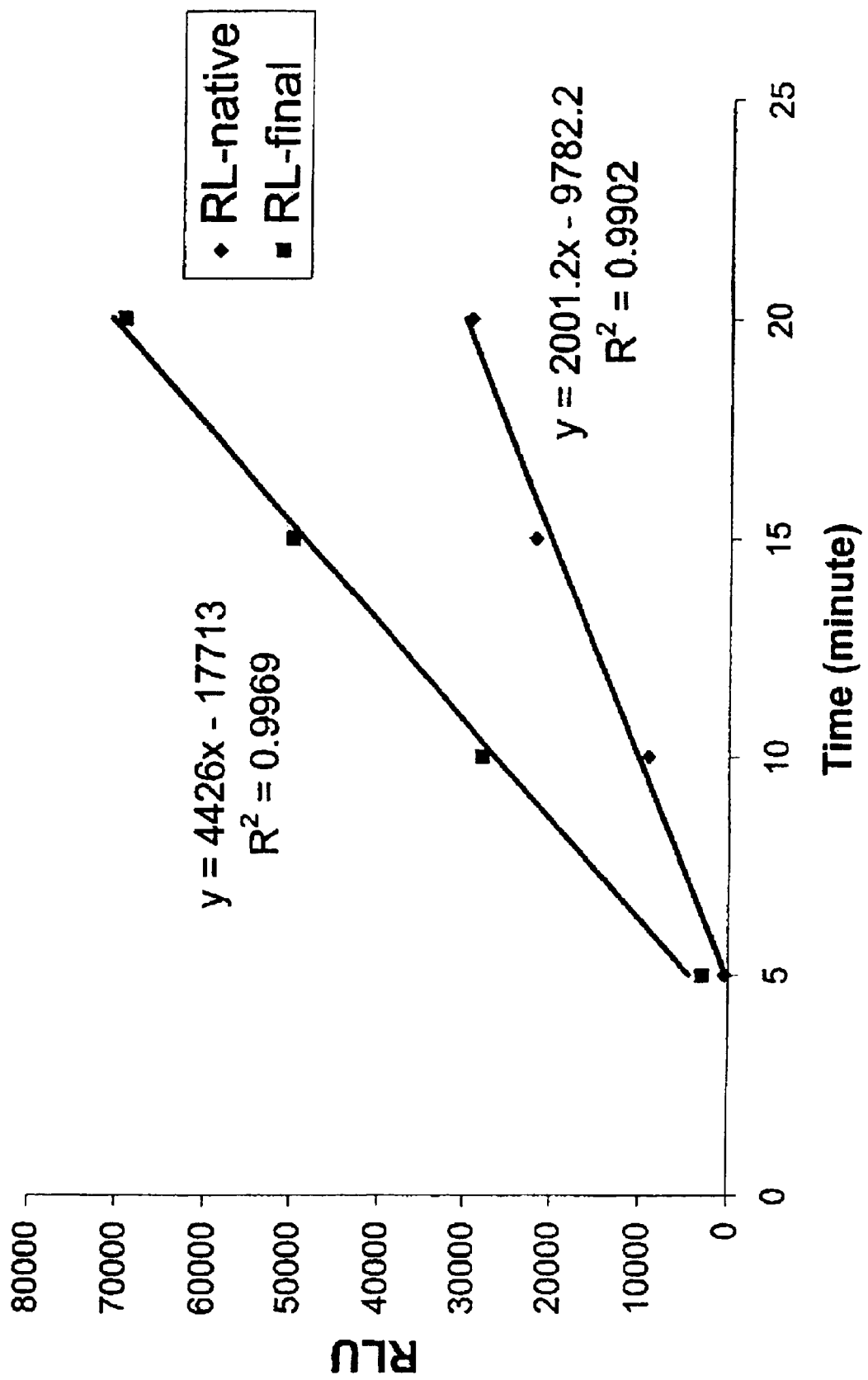
Figure 15E:
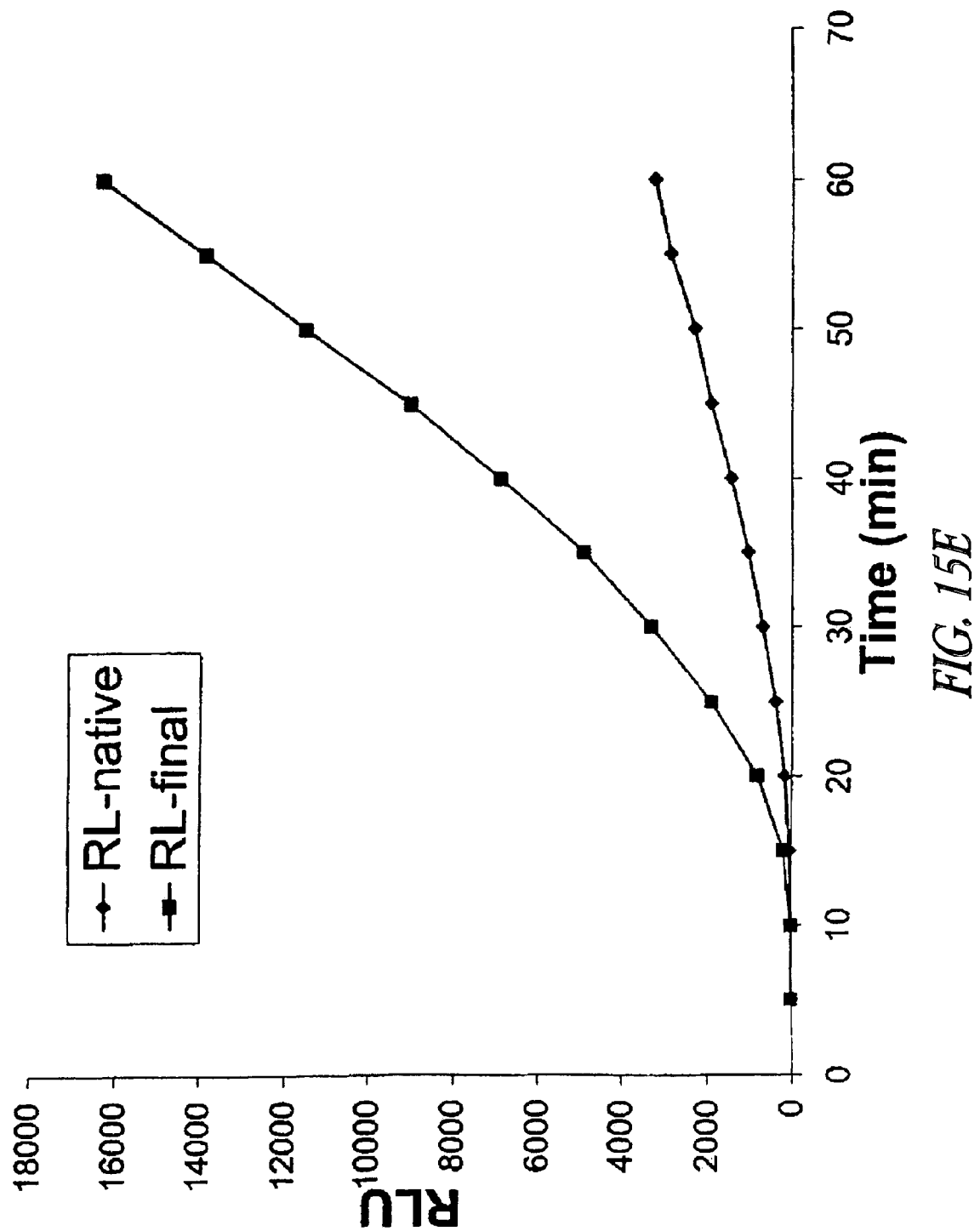
FIGS. 15E-F. Translation of native and synthetic (Rluc-final) *Renilla* RNAs in a wheat germ extract. E) t=0-60 minutes; F) linear range.
Figure 15F:
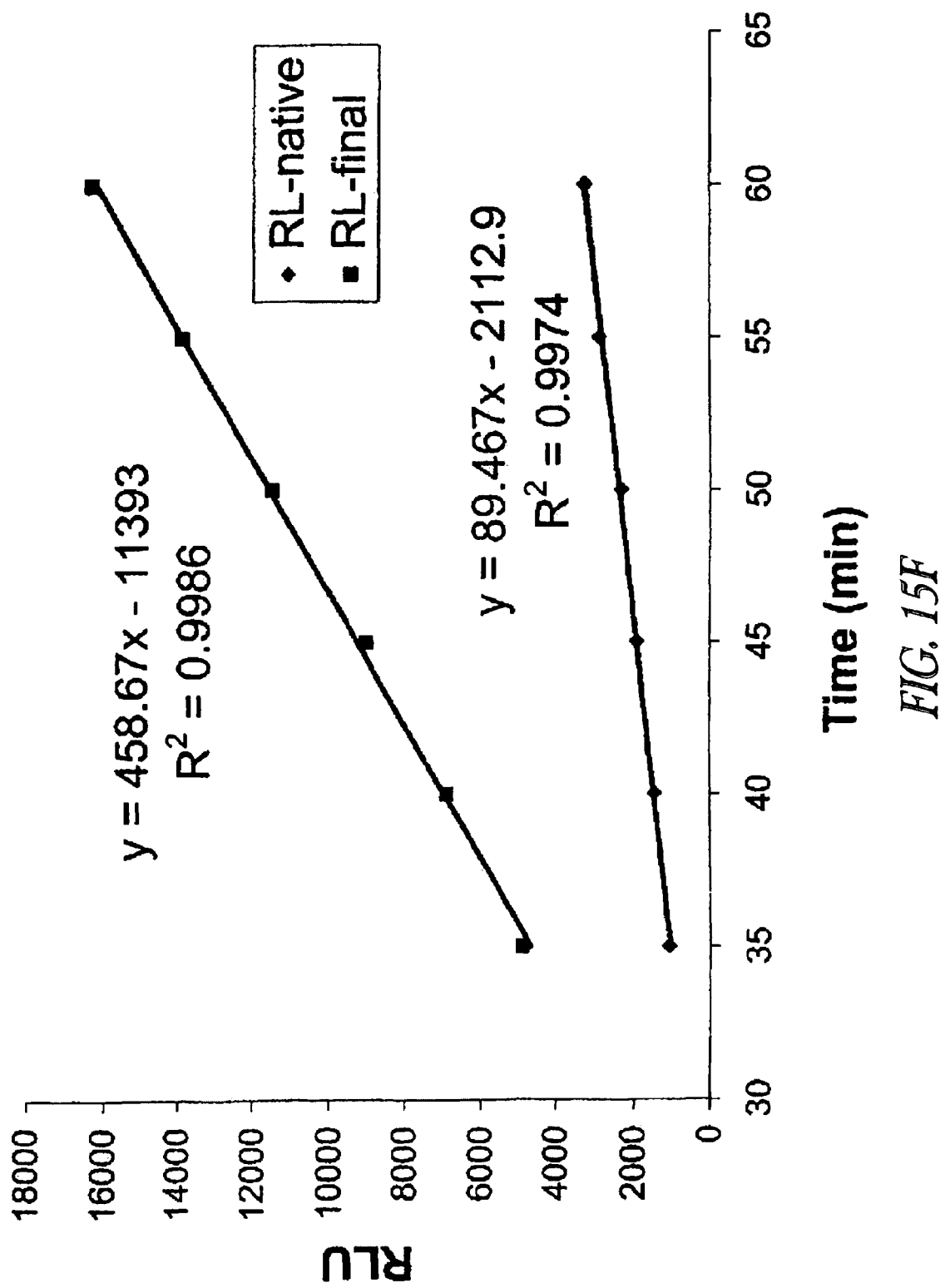

The synthetic *Renilla* gene (Rluc-final) was used in in vitro systems to compare translation efficiency with the native gene. In a T7 quick coupled transcription/translation system (Promega Corp., Madison, Wis.), pRL-null native plasmid (having the native *Renilla* luciferase gene under the control of the T7 promoter) or the same amount of pRL-null-synthetic plasmid (having the synthetic *Renilla* luciferase gene under the control of the T7 promoter) was added to the TNT reaction mixture and luciferase activity measured every 5 minutes up to 60 minutes. Dual Luciferase assay kit (Promega Corp.) was used to measure *Renilla* luciferase activity. The data showed that improved expression was obtained from the synthetic gene (FIG. 15A,B). To further evidence the increased translation efficiency of the synthetic gene, RNA was prepared by an in vitro transcription system, then purified. pRL-null (native or synthetic) vectors were linearized with BamH I. The DNA was purified by multiple phenol-chloroform extraction followed by ethanol precipitation. An in vitro T7 transcription system was employed by prepare RNAs. The DNA template was removed by using RNase-free DNase, and RNA was purified by phenol-chloroform extraction followed by multiple isopropanol precipitations. The same amount of purified RNA, either for the synthetic gene or the native gene, was then added to a rabbit reticulocyte lysate (FIG. 15 C, D) or wheat germ lysate (FIG. 15 E, F). Again, the synthetic *Renilla* luciferase gene RNA produced more luciferase than the native one. These data suggest that the translation efficiency is improved by the synthetic sequence. To determine why the synthetic gene was highly expressed in wheat germ, plant codon usage was determined. The lowest usage codons in higher plants coincided with those in mammals.

Reporter gene assays are widely used to study transcriptional regulation events. This is often carried out in co-transfection experiments, in which, along with the primary reporter construct containing the testing promoter, a second control reporter under a constitutive promoter is transfected into cells as an internal control to normalize experimental variations including transfection efficiencies between the samples. Control reporter signal, potential promoter cross talk between the control reporter and primary reporter, as well as potential regulation of the control reporter by experimental conditions, are important aspects to consider for selecting a reliable co-reporter vector.

As described above, vector constructs were made by cloning synthetic *Renilla* luciferase gene into different vector backbones under different promoters. All the constructs showed higher expression in the three mammalian cell lines tested (Table 11). Thus, with better expression efficiency, the synthetic *Renilla* luciferase gives out higher signal when transfected into mammalian cells.

Figure 16A:
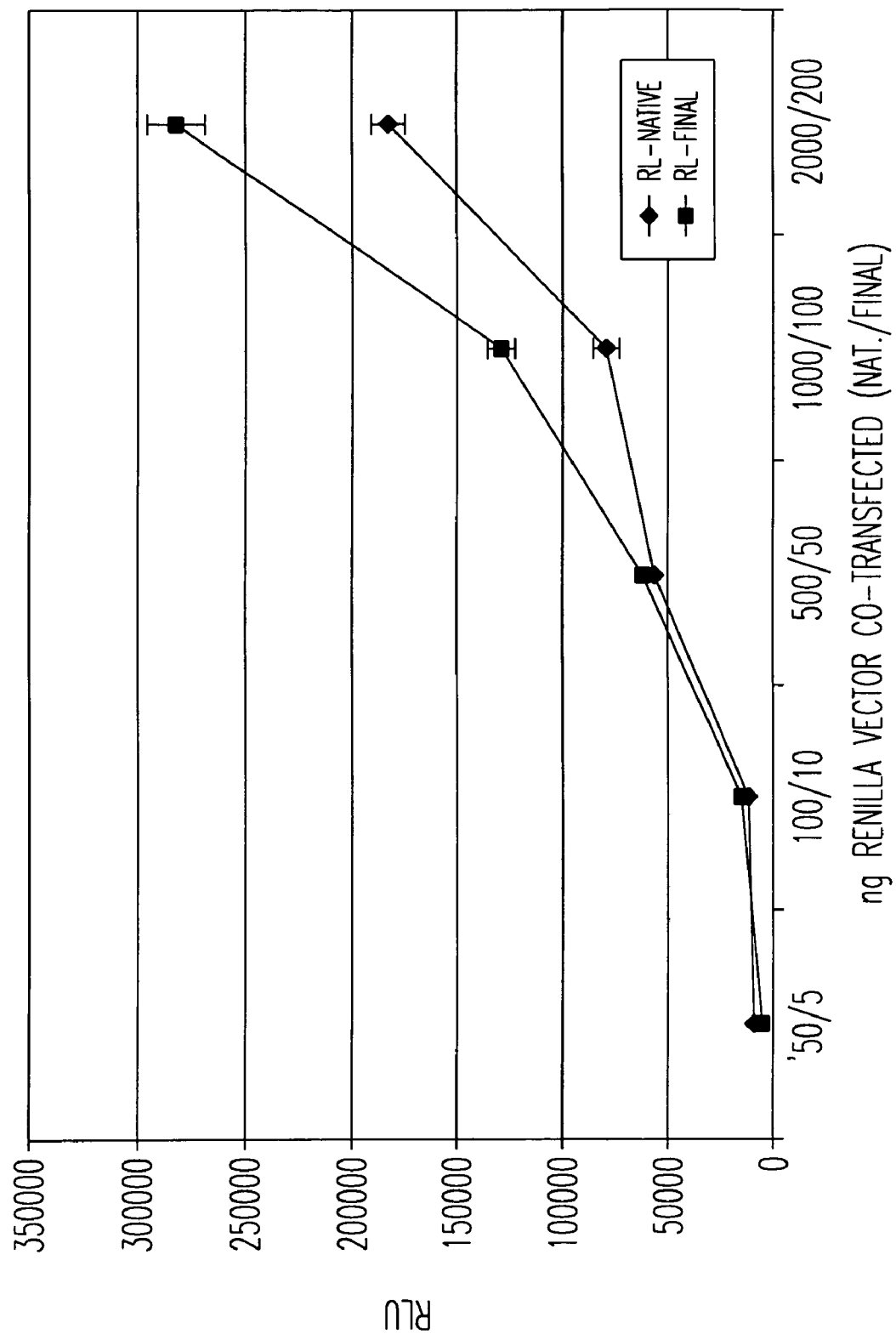
FIG. 16. High expression from a synthetic *Renilla* nucleic acid sequence reduces the risk of promoter interference in a co-transfection assay. CHO cells were co-transfected with a constant amount (50 ng) of firefly luciferase expression vector (pGL3 control vector, with SV40 promoter and enhancer; Luc+) and a pRL vector having a native (0 ng, 50 ng, 100 ng, 500 ng, 1 μg or 2 μg) or synthetic (0 ng, 5 ng, 10 ng, 50 ng, 100 ng or 200 ng) *Renilla* luciferase gene.
Figure 16B:
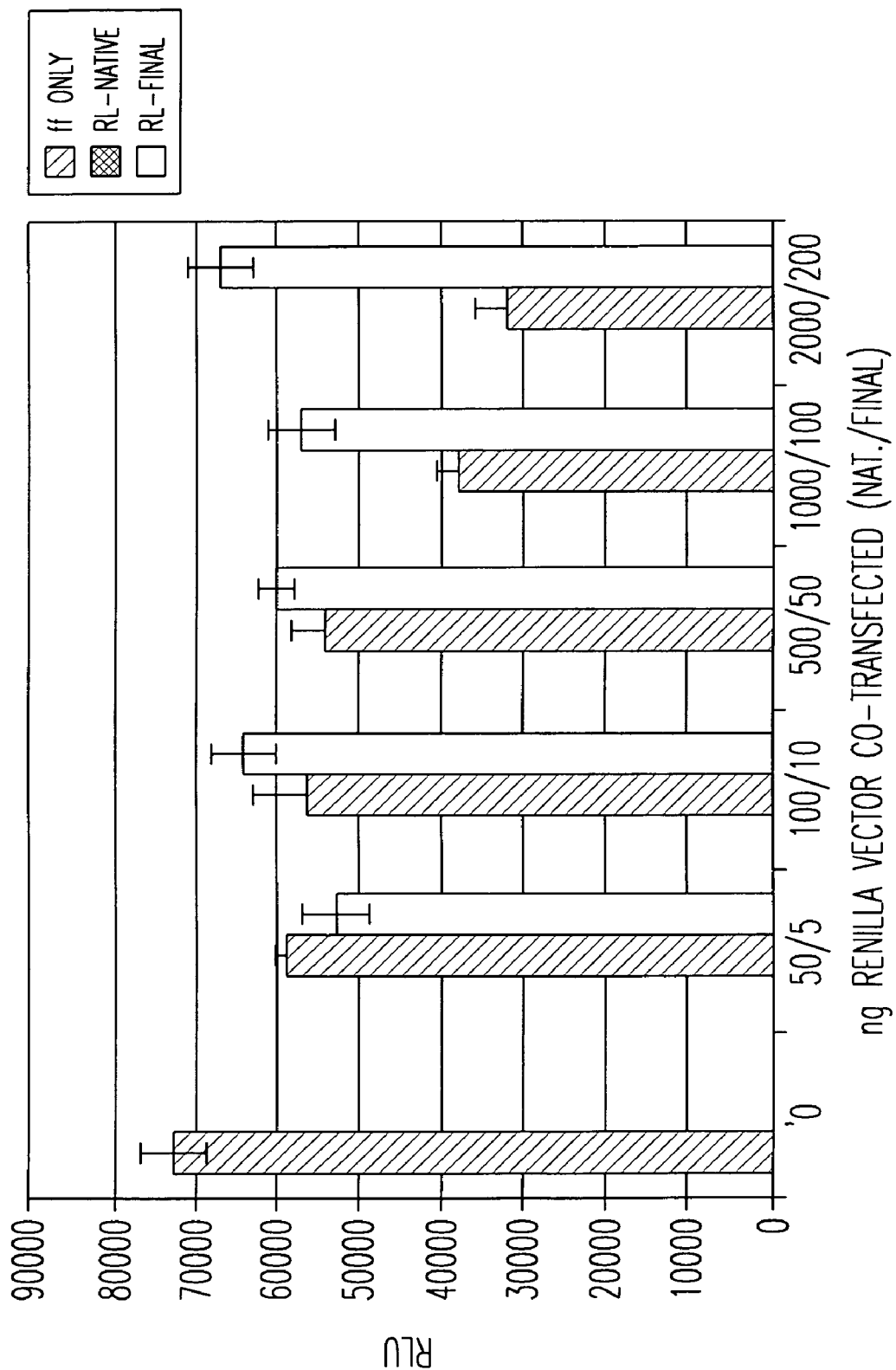

Because a higher signal is obtained, less promoter activity is required to achieve the same reporter signal, this reduced risk of promoter interference. CHO cells were transfected with 50 ng pGL3-control (firefly luc+) plus one of 5 different amounts of native pRL-TK plasmid (50, 100, 500, 1000, or 2000 ng) or synthetic pRL-TK (5, 10, 50, 100, or 200 ng). To each transfection, pUC19 carrier DNA was added to a total of 3 µg DNA. Shown in FIG. 16 is the experiment demonstrating that 10 fold less pRL-TK DNA gives similar or more signal as the native gene, with reduced risk of inhibiting expression from the primary reporter pGL3-control.

Experimental treatment sometimes may activate cryptic sites within the gene and cause induction or suppression of the co-reporter expression, which would compromise its function as co-reporter for normalization of transfection efficiencies. One example is that TPA induces expression of co-reporter vectors harboring the wild-type gene when transfecting MCF-7 cells. 500 ng pRL-TK (native), 5 µg native and synthetic pRG-B, 2.5 µg native and synthetic pRG-TK were transfected per well of MCF-7 cells. 100 ng/well pGL3-control (firefly luc+) was co-transfected with all RL plasmids. Carrier DNA, pUC19, was used to bring the total DNA transfected to 5.1 µg/well. 15.3 µl TransFast Transfection Reagent (Promega Corp., Madison, Wis.) was added per well. Sixteen hours later, cells were trypsinized, pooled and split into six wells of a 6-well dish and allowed to attach to the well for 8 hours. Three wells were then treated with the 0.2 nM of the tumor promoter, TPA (phorbol-12-myristate-13-acetate, Calbiochem #524400-S), and three wells were mock treated with 20 µl DMSO. Cells were harvested with 0.4 ml Passive Lysis Buffer 24 hours post TPA addition. The results showed that by using the synthetic gene, undesirable change of co-reporter expression by experimental stimuli can be avoided (Table 13). This demonstrates that using synthetic gene can reduce the risk of anomalous expression.

TABLE 13

TPA Induction

| Vector | Rlu | Fold Induction |
| --- | --- | --- |
| pRL-tk untreated (native) | 184 | |
| pRL-tk TPA treated (native) | 812 | 4.4 |
| pRG-B untreated (native) | 1 | |
| pRG-B TPA treated (native) | 8 | 8.0 |
| pRG-B untreated (final) | 132 | |
| pRG-B TPA treated (final) | 195 | 1.47 |
| pRG-tk untreated (native) | 44 | |
| pRG-tk TPA treated (native) | 192 | 4.36 |
| pRG-tk untreated (final) | 12,816 | |
| pRG-tk TPA treated (final) | 11,347 | 0.88 |

REFERENCES

Altschul et al., *Nucl. Acids Res.*, 25, 3389 (1997).
Aota et al., *Nucl. Acids Res.*, 16, 315 (1988).
Boshart et al., *Cell*, 41, 521 (1985).
Bronstein et al., *Cal. Biochem.*, 219, 169 (1994).
Corpet et al., *Nucl. Acids Res.*, 16, 881 (1988).
deWet et al., *Mol. Cell. Biol.*, 7, 725 (1987).
Dijkema et al., *EMBO J.*, 4, 761 (1985).
Faist and Meyer, *Nucl. Acids Res.*, 20, 26 (1992).
Gornan et al., *Proc. Natl. Acad. Sci. USA*, 79, 6777 (1982).
Higgins et al., *Gene*, 73, 237 (1985).
Higgins et al., *CABIOS*, 5, 151 (1989).
Huang et al., *CABIOS*, 8, 155 (1992).
Itolcik et al., *PNAS*, 94, 12410 (1997).
Johnson et al., *Mol. Reprod. Devel.*, 50, 377 (1998).
Jones et al., *Mol. Cell. Biol.*, 17, 6970 (1997).
Karlin and Altschul, *Proc. Natl. Acad. Sci. USA*, 87, 2264 (1990).
Karlin and Altschul, *Proc. Natl. Acad. Sci. USA*, 90, 5873 (1993).
Keller et al., *J. Cell Biol.*, 84, 3264 (1987).
Kim et al., *Gene*, 91, 217 (1990).
Lamb et al., *Mol. Reprod. Devel.*, 51, 218 (1998).
Mariatis et al., *Science*, 236, 1237 (1987).
Michael et al., *EMBO. J.*, 9, 481 (1990).
Mizushima and Nagata, *Nucl. Acids Res.*, 18, 5322 (1990).
Murray et al., *Nucl. Acids Res.*, 17, 477 (1989).
Myers and Miller, *CABIOS*, 4, 11 (1988).
Needleman and Wunsen, *J. Mol. Biol.*, 48, 443 (1970).
Pearson and Lipman, *Proc. Natl. Acad. Sci. USA*, 85, 2444 (1988).
Pearson et al., *Meth. Mol. Biol.*, 24, 307 (1994).
Sharp et al., *Nucl. Acids Res.*, 16, 8207 (1988).
Sharp et al., *Nucl. Acids Res.*, 15, 1281 (1987).
Smith and Waterman, *Adv. Appl. Math.*, 2, 482 (1981).
Stemmer et al., *Gene*, 164, 49 (1995).
Uetsuki et al., *J. Biol. Chem.*, 264, 5791 (1989).
Voss et al., *Trends Biochem. Sci.*, 11, 287 (1986).
Wada et al., *Nucl. Acids Res.*, 18, 2367 (1990).
Watson et al, eds. *Recombinant DNA: A Short Course*, Scientific American Books, W. H. Freeman and Company, New York (1983).
Wood, K. *Photochemistry and Photobiology*, 62, 662 (1995).
Wood, K. *Science* 244, 700 (1989)

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A synthetic nucleic acid molecule comprising at least 300 nucleotides of a coding region for a luciferase, having a codon composition differing at more than 25% of the codons from a wild type nucleic acid sequence encoding the luciferase, and having at least 3-fold fewer transcription regulatory sequences relative to the average number of such sequences resulting from random selections of codons at the codons which differ, wherein the transcription regulatory sequences are selected from the group consisting of transcription factor binding sequences, intron splice sites, poly(A) addition sites and promoter sequences, wherein the luciferase encoded by the synthetic nucleic acid molecule has at least 85% sequence identity to the luciferase encoded by the wild type nucleic acid sequence, wherein the majority of the codons which differ in the synthetic nucleic acid molecule are those which are employed more frequently in mammals, and wherein the synthetic nucleic acid molecule has at least 99% sequence identity to SEQ ID NO: 22.

2. The synthetic nucleic acid molecule of claim 1 wherein the synthetic nucleic acid molecule has at least 5-fold fewer transcription regulatory sequences.

3. The synthetic nucleic acid molecule of claim 1 wherein the codon composition of the synthetic nucleic acid molecule differs from the wild type nucleic acid sequence at more than 35% of the codons.

4. The synthetic nucleic acid molecule of claim 1 wherein the codon composition of the synthetic nucleic acid molecule differs from the wild type nucleic acid sequence at more than 45% of the codons.

5. The synthetic nucleic acid molecule of claim 1 wherein the codon composition of the synthetic nucleic acid molecule differs from the wild type nucleic acid sequence at more than 55% of the codons.

6. The synthetic nucleic acid molecule of claim 1 wherein the wild type nucleic acid sequence encodes a *Renilla* luciferase.

7. The synthetic nucleic acid molecule of claim 1 wherein the majority of codons which differ in the synthetic nucleic acid molecule are those which are preferred codons in humans.

8. The synthetic nucleic acid molecule of claim 1 wherein the synthetic nucleic acid molecule comprises SEQ ID NO: 21 (Rlucver2) or SEQ ID NO:22 (Rluc-final).

9. The synthetic nucleic acid molecule of claim 7 wherein the majority of codons are CGC, CTG, TCT, AGC, ACC, CCA, CCT, GCC, GGC, GTG, ATC, ATT, AAG, AAC, CAG, CAC, GAG, GAC, TAC, TGC and TTC.

10. The synthetic nucleic acid molecule of claim 7 wherein the majority of codons are CGC, CTG, TCT, ACC, CCA, GCC, GGC, GTC, and ATC or codons CGT, TTG, AGC, ACT, CCT, GCT, GGT, GTG and ATT.

11. The synthetic nucleic acid molecule of claim 1 wherein the synthetic nucleic acid molecule is capable of being expressed in a mammalian host cell at a level which is greater than that of the wild type nucleic acid sequence.

12. The synthetic nucleic acid molecule of claim 1 wherein the synthetic nucleic acid molecule has an increased number of CTG or TTG leucine-encoding codons.

13. The synthetic nucleic acid molecule of claim 1 wherein the synthetic nucleic acid molecule has an increased number of GTG or GTC valine-encoding codons.

14. The synthetic nucleic acid molecule of claim 1 wherein the synthetic nucleic acid molecule has an increased number of GGC or GGT glycine-encoding codons.

15. The synthetic nucleic acid molecule of claim 1 wherein the synthetic nucleic acid molecule an increased number of ATC or ATT isoleucine-encoding codons.

16. The synthetic nucleic acid molecule of claim 1 wherein the synthetic nucleic acid molecule has an increased number of CCA or CCT proline-encoding codons.

17. The synthetic nucleic acid molecule of claim 1 wherein the synthetic nucleic acid molecule has an increased number of CGC or CGT arginine-encoding codons.

18. The synthetic nucleic acid molecule of claim 1 wherein the synthetic nucleic acid molecule has an increased number of AGC or TCT serine-encoding codons.

19. The synthetic nucleic acid molecule of claim 1 wherein the synthetic nucleic acid molecule has an increased number of ACC or ACT threonine-encoding codons.

20. The synthetic nucleic acid molecule of claim 1 wherein the synthetic nucleic acid molecule has an increased number of GCC or GCT alanine-encoding codons.

21. The synthetic nucleic acid molecule of claim 1 wherein the codons in the synthetic nucleic acid molecule encode the same amino acids as the corresponding codons in the wild type nucleic acid sequence.

22. A plasmid comprising the synthetic nucleic acid molecule of claim 1.

23. An expression vector comprising the synthetic nucleic acid molecule of claim 1 linked to a promoter functional in a cell.

24. The expression vector of claim 23 wherein the synthetic nucleic acid molecule is operatively linked to a Kozak consensus sequence.

25. The expression vector of claim 23 wherein the promoter is functional in a mammalian cell.

26. The expression vector of claim 23 wherein the promoter is functional in a human cell.

27. The expression vector of claim 23 wherein the promoter is functional in a plant cell.

28. The expression vector of claim 23 wherein the expression vector further comprises a multiple cloning site.

29. The expression vector of claim 28 wherein the expression vector comprises a multiple cloning site positioned between the promoter and the synthetic nucleic acid molecule.

30. The expression vector of claim 28 wherein the expression vector comprises a multiple cloning site positioned downstream from the synthetic nucleic acid molecule.

31. An isolated host cell comprising the expression vector of claim 23.

32. A reporter gene expression kit comprising, in suitable container means, the expression vector of claim 23.

33. The synthetic nucleic acid molecule of claim 1 wherein the synthetic nucleic acid molecule is expressed at a level which is at least 110% of that of the wild type nucleic acid sequence in a cell or cell extract under identical conditions.

34. The synthetic nucleic acid molecule of claim 1 wherein the polypeptide encoded by the synthetic nucleic acid molecule has at least 90% contiguous sequence identity to the polypeptide encoded by the wild type nucleic acid sequence.

35. The synthetic nucleic acid molecule of claim 1 wherein the polypeptide encoded by the synthetic nucleic acid molecule is identical in amino acid sequence to the polypeptide encoded by the wild type nucleic acid sequence.

36. A synthetic nucleic acid molecule comprising at least 300 nucleotides having at least 99% sequence identity to SEQ ID NO: 22 and encoding a polypeptide having luciferase activity and at least 90% identity to the wild-type *Renilla* luciferase.

37. The synthetic nucleic acid molecule of claim 36, wherein the synthetic nucleic acid molecule is SEQ ID NO:22.

38. The synthetic nucleic acid molecule of claim 36, wherein the synthetic nucleic acid molecule is SEQ ID NO: 21.

* * * * *